US011904002B2

(12) United States Patent
Artomov et al.

(10) Patent No.: US 11,904,002 B2
(45) Date of Patent: Feb. 20, 2024

(54) CONSTRUCTION AND METHODS OF USE OF A THERAPEUTIC CANCER VACCINE LIBRARY COMPRISING FUSION-SPECIFIC VACCINES

(71) Applicant: BostonGene Corporation, Waltham, MA (US)

(72) Inventors: Maksym Artomov, Kirkwood, MO (US); Feliks Frenkel, Moscow (RU); Igor Golubev, Moscow (RU); Olga Zolotareva, Moscow (RU)

(73) Assignee: BostonGene Corporation, Waltham, MA (US)

( * ) Notice: Subject to any disclaimer, the term of this patent is extended or adjusted under 35 U.S.C. 154(b) by 0 days.

(21) Appl. No.: 16/671,574

(22) Filed: Nov. 1, 2019

(65) Prior Publication Data

US 2020/0054728 A1 Feb. 20, 2020

Related U.S. Application Data

(63) Continuation of application No. 16/108,739, filed on Aug. 22, 2018, now abandoned, which is a continuation of application No. PCT/US2017/026723, filed on Apr. 7, 2017.

(60) Provisional application No. 62/319,774, filed on Apr. 7, 2016.

(51) Int. Cl.
| | |
|---|---|
| *A61K 38/16* | (2006.01) |
| *A61K 39/00* | (2006.01) |
| *G01N 33/574* | (2006.01) |
| *A61K 39/39* | (2006.01) |
| *C40B 40/10* | (2006.01) |

(52) U.S. Cl.
CPC ......... *A61K 39/0011* (2013.01); *A61K 39/00* (2013.01); *A61K 39/39* (2013.01); *G01N 33/574* (2013.01); *A61K 2039/53* (2013.01); *A61K 2039/55533* (2013.01); *A61K 2039/585* (2013.01); *C07K 2319/00* (2013.01); *C40B 40/10* (2013.01)

(58) Field of Classification Search
CPC ............... A61K 39/0011; A61K 39/00; A61K 2039/585; G01N 33/574; C07K 2319/00; C40B 40/10
See application file for complete search history.

(56) References Cited

U.S. PATENT DOCUMENTS

| | | | | |
|---|---|---|---|---|
| 5,840,839 A | * | 11/1998 | Wang ................ | C07K 14/4748 530/325 |
| 2006/0008468 A1 | | 1/2006 | Chiang et al. | |
| 2011/0293637 A1 | * | 12/2011 | Hacohen ............ | A61K 39/0011 424/173.1 |
| 2014/0296081 A1 | * | 10/2014 | Diehn ................. | C12Q 1/6886 506/2 |
| 2014/0323329 A1 | * | 10/2014 | Rhodes ............... | C12Q 1/6886 435/6.12 |
| 2015/0079119 A1 | * | 3/2015 | Johnston ........... | A61K 39/0011 424/185.1 |
| 2015/0140041 A1 | * | 5/2015 | Vitiello .............. | A61K 35/17 424/277.1 |
| 2015/0203589 A1 | | 7/2015 | Iavarone et al. | |
| 2016/0069895 A1 | | 3/2016 | Delamarre et al. | |
| 2018/0153975 A1 | * | 6/2018 | Fritsch .............. | A61K 39/0011 |
| 2018/0155688 A1 | * | 6/2018 | Seet ................... | A61K 39/0011 |
| 2019/0030147 A1 | | 1/2019 | Artomov et al. | |
| 2019/0307868 A1 | | 10/2019 | Rooney | |

FOREIGN PATENT DOCUMENTS

WO WO 03/084467 * 10/2003

OTHER PUBLICATIONS

Englehard (1994) Annu. Rev. Immunol. 12: 181.*
Rammenesee et al. (1993) Annu. Rev. Immunol. 11: 213.*
Pinilla-Ibarz et al., Blood, 95:1781-1787, 2000.*
Tomlins et al., Science, 310:644-648, 2005.*
Consumer Genome Atlas Research Network, Nature, 507:315-320, 2014.*
Parker et al, Chin J Cancer, 32:594-603, 2013.*
International Search Report and Written Opinion for International Application No. PCT/US2017/026723 dated Jul. 14, 2017.

* cited by examiner

*Primary Examiner* — Mark Halvorson
(74) *Attorney, Agent, or Firm* — Wolf, Greenfield & Sacks, P.C.

(57) ABSTRACT

Methods described herein relate to constructing therapeutic fusion-specific vaccine libraries, selecting a therapeutic fusion-specific vaccine for a cancer patient, and/or constructing a de novo therapeutic fusion-specific vaccine for patients having a gene fusion that is absent from a fusion-specific vaccine library.

6 Claims, 8 Drawing Sheets

Specification includes a Sequence Listing.

| Patient ID | Patient Data | Library Data | Data Matching |
|---|---|---|---|
| 602 | 604 | 606 | 608 |
| | | | |
| | | | |

FIG. 6.

CONSTRUCTION AND METHODS OF USE OF A THERAPEUTIC CANCER VACCINE LIBRARY COMPRISING FUSION-SPECIFIC VACCINES

RELATED APPLICATIONS

This application claims priority under 35 U.S.C. § 120 and is a continuation of U.S. patent application Ser. No. 16/108,739, filed Aug. 22, 2018, entitled "CONSTRUCTION AND METHODS OF USE OF A THERAPEUTIC CANCER VACCINE LIBRARY COMPRISING FUSION-SPECIFIC VACCINES", which is a continuation of and claims priority under 35 U.S.C. § 120 to international PCT Application, PCT/US2017/026723, filed Apr. 7, 2017, entitled "CONSTRUCTION AND METHODS OF USE OF A THERAPEUTIC CANCER VACCINE LIBRARY COMPRISING FUSION-SPECIFIC VACCINES", which claims the benefit under 35 U.S.C. § 119(e) of the filing date of U.S. provisional patent application Ser. No. 62/319,774, entitled "CONSTRUCTION AND METHODS OF USE OF A THERAPEUTIC CANCER VACCINE LIBRARY COMPRISING FUSION-SPECIFIC VACCINES," filed Apr. 7, 2016, the entire contents of which are incorporated herein by reference.

FIELD OF THE INVENTION

The methods described herein are directed toward the field of immunotherapy for cancer patients.

BACKGROUND

Recent advances in personalized genomic sequencing and cancer genomic sequencing technologies have made it possible to obtain patient-specific information. This information can be used to prepare patient-specific medicines including patient-specific cancer vaccines that are developed based on the genome of the patient and the mutation information gathered from the patient's biological sample.

SUMMARY

Provided herein, inter alia, are methods for constructing therapeutic fusion-specific vaccine libraries, selecting a therapeutic fusion-specific vaccine for a cancer patient, and/or constructing a de novo therapeutic fusion-specific vaccine for patients having a gene fusion that is absent from a fusion-specific vaccine library.

In some embodiments, the method provides compositions for providing therapeutic fusion-specific vaccine libraries that can be used as sources of vaccines for many cancer patients.

In some aspects, the specification provides a method for constructing a therapeutic fusion-specific vaccine library for a cancer patient, the method comprising (a) identifying one or more tumor-specific gene fusions from publicly available data, (b) identifying one or more fusion junction sequences, wherein the fusion junction sequences comprise nucleic acid sequences and/or amino acid sequences corresponding to one or more tumor-specific gene fusions, (c) obtaining information relating to interaction between fusion junction sequences with one or more HLA alleles, and (d) selecting at least one fusion junction sequence for the therapeutic fusion-specific vaccine library.

In some aspects, the specification provides a method for selecting a therapeutic fusion-specific vaccine for a cancer patient, the method comprising (a) determining the presence of one or more tumor-specific gene fusions in a biological sample from the cancer patient, (b) obtaining information relating to one or more HLA alleles of the cancer patient, (c) analyzing a library of fusion-specific vaccines, wherein each fusion-specific vaccine in the library comprises one or more fusion junction sequences having a nucleic acid sequences and/or an amino acid sequence corresponding to one or more tumor-specific gene fusions, and (d) selecting at least one fusion-specific vaccine in the library as the therapeutic fusion-specific vaccine for the cancer patient by selecting the fusion-specific vaccine comprising (i) one or more fusion junction sequences corresponding to one or more tumor-specific gene fusions of the cancer patient, and (ii) one or more fusion junction sequences that bind one or more HLA alleles of the cancer patient.

In some aspects, the specification provides a method for constructing a de novo therapeutic fusion-specific vaccine for a cancer patient, the method comprising (a) determining the presence of one or more tumor-specific gene fusions in a biological sample from the cancer patient, (b) obtaining information relating to one or more HLA alleles of the cancer patient, (c) determining that the cancer patient's fusion junction sequence is not present in the library of fusion-specific vaccines, and (d) constructing at least one fusion-specific vaccine as the de novo therapeutic fusion-specific vaccine for the cancer patient by constructing the fusion-specific vaccine comprising (i) one or more fusion junction sequences corresponding to one or more tumor-specific gene fusions of the cancer patient, and (ii) one or more fusion junction sequences that bind one or more HLA alleles of the cancer patient.

In some embodiments, the method further comprises administering the therapeutic fusion-specific vaccine to the cancer patient.

In some embodiments, the biological sample is a tissue sample or fluid sample taken from the cancer patient. In some embodiments, the biological sample is analyzed by DNA sequencing, RNA sequencing, and/or protein sequencing. In some embodiments, one or more tumor-specific gene fusions are identified in the biological sample. In some embodiments, information relating to one or more HLA alleles of the cancer patient are obtained by analysis of the biological sample.

In some embodiments, the fusion-specific vaccine comprises one or more nucleic acid sequences corresponding to one or more tumor-specific gene fusions. In some embodiments, the fusion-specific vaccine comprises one or more peptides having amino acid sequences corresponding to one or more tumor-specific gene fusions. In some embodiments, the fusion-specific vaccine comprises one or more peptides selected from Table A.

In some embodiments, the fusion-specific vaccine comprises 1, 2, 3, 4, 5, 6, 7, 8, 9, 10, 11, 12, 13, 14, 15, 16, 17, 18, 19, or 20 peptides corresponding to one or more tumor-specific gene fusions. In some embodiments, the fusion-specific vaccine comprises 20 or more peptides corresponding to one or more tumor-specific gene fusions.

In some embodiments, the fusion-specific vaccine comprises one or more peptides that bind to one or more HLA alleles of the cancer patient with an $IC_{50}$ less than 500 nM. In some embodiments, the fusion-specific vaccine comprises one or more peptides that bind to one or more HLA alleles of the cancer patient with an $IC_{50}$ less than 250 nM. In some embodiments, the fusion-specific vaccine comprises one or more peptides that bind to one or more HLA alleles of the cancer patient with an $IC_{50}$ less than 100 nM. In some embodiments, the fusion-specific vaccine comprises one or more peptides that bind to one or more HLA alleles of the cancer patient with an $IC_{50}$ less than 50 nM.

In some embodiments, the library of fusion-specific vaccines comprises at least 2-10 fusion-specific vaccines having distinct fusion junction sequences. In some embodiments, the library of fusion-specific vaccines comprises at least 5-10 fusion-specific vaccines corresponding to distinct fusion junction sequences. In some embodiments, the library of fusion-specific vaccines comprises at least 10-50 fusion-specific vaccines corresponding to distinct fusion junction sequences. In some embodiments, the library of fusion-specific vaccines comprises at least 50-100 fusion-specific vaccines corresponding to distinct fusion junction sequences. In some embodiments, the library of fusion-specific vaccines comprises 100 or more fusion-specific vaccines corresponding to distinct fusion junction sequences.

In some embodiments, the fusion-specific vaccine comprises one or more peptides having 8-10 amino acids. In some embodiments, the fusion-specific vaccine comprises one or more peptides having 10-25 amino acids. In some embodiments, the fusion-specific vaccine comprises one or more peptides having 25-50 amino acids. In some embodiments, the fusion-specific vaccine comprises one or more peptides having 50-100 amino acids. In some embodiments, the fusion-specific vaccine comprises one or more peptides having 100 or more amino acids. In some embodiments, the fusion-specific vaccine comprises a combination of two or more peptides having numbers of amino acids described herein.

In some embodiments, the fusion-specific vaccine comprises one or more peptides having an amino acid sequence corresponding to a one or more tumor-specific gene fusions and one or more addition amino acid sequences. In some embodiments, the fusion-specific vaccine comprises two or more peptides having an amino acid sequence corresponding to two or more tumor-specific gene fusions and one or more addition amino acid sequences.

In some embodiments, the fusion-specific vaccine comprises one or more peptides having a modification. In some embodiments, the fusion-specific vaccine comprises one or more adjuvants. In some embodiments, the fusion-specific vaccine comprises the peptide having a concentration of 100 ng-10 mg.

In some embodiments, the fusion-specific vaccine is administered once to the cancer patient. In some embodiments, the cancer patient is treated with two or more doses of the fusion-specific vaccine.

In some embodiments, the library of fusion-specific vaccines comprises peptides having an amino acid sequence corresponding to gene fusions that are present in a type of cancer. In some embodiments, the type of cancer is melanoma, skin cancer, head and neck cancer, breast cancer, lung cancer, ovarian cancer, cervical cancer, prostate cancer, thyroid cancer, kidney cancer, liver cancer, pancreatic cancer, gastric cancer, testicular cancer, brain tumor, glioma, glioblastoma, solitary fibrous tumor, bladder cancer, colorectal cancer, renal cell carcinoma, sarcoma, myeloma, leukemia, and/or lymphoma. In some embodiments, the type of cancer is a metastatic tumor. In some embodiments, the type of cancer is any tumor type.

In some embodiments, the cancer patient is administered dendritic cells or other antigen presenting cells that have been pulsed with at least one fusion junction peptide having a sequence from the fusion-specific vaccine library. In some embodiments, the cancer patient is administered dendritic cells or other antigen presenting cells comprising at least one fusion junction peptide having a sequence from the fusion-specific vaccine library. In some embodiments, autologous T-cells can be collected from the cancer patient, stimulated ex vivo with fusion junction sequences, and stimulated autologous T-cells are transfused into the cancer patient.

BRIEF DESCRIPTION OF DRAWINGS

The following drawings form part of the present specification and are included to further demonstrate certain aspects of the present disclosure, which can be better understood by reference to one or more of these drawings in combination with the detailed description of specific embodiments presented herein.

FIG. 6 shows a non-limiting example of a data structure for storing data associated with one or more patients, in accordance with some embodiments of the present methods.

DETAILED DESCRIPTION

Figure 1:
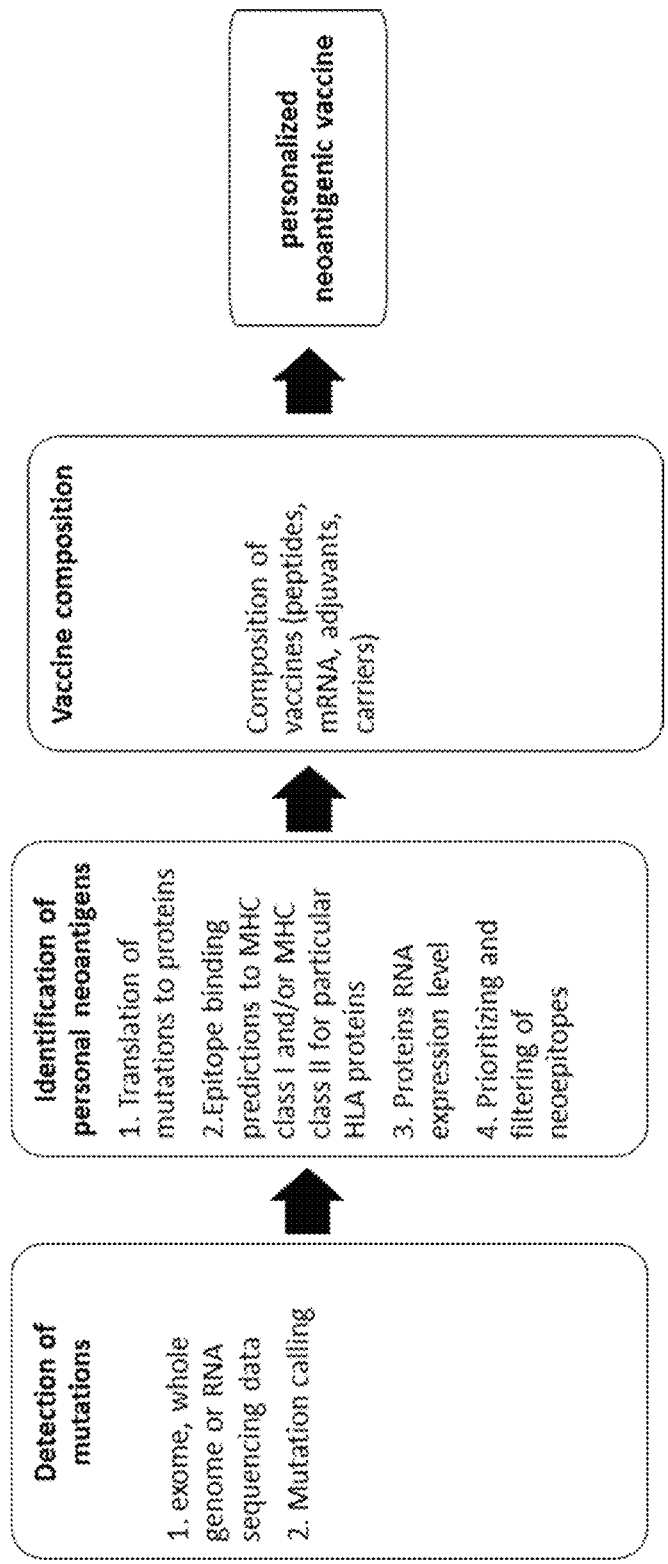
FIG. 1 illustrates a non-limiting example of a typical strategy for generating personalized neoantigenic vaccines including 3 steps: (1) detection of mutations from sequencing data and mutation calling; (2) identification of personal neoantigens; and (3) vaccine composition.

Applicant has recognized that patient-specific medicines, such as patient-specific vaccines, although effective, can be very expensive. As illustrated in FIG. 1, generating a patient specific vaccine typically involves a series of steps that are tailored for each individual patient, including detecting mutations from patient sequence data, identifying patient-specific neoantigens, and designing and synthesizing a patient-specific vaccine composition. In contrast, Applicant has developed methods and compositions for providing simple vaccine libraries that can be used as sources of vaccines for many cancer patients. Applicant has recognized that many cancers involve gene fusions, regardless of whether the cancers also include point mutations or other genetic rearrangements. Applicant has developed a method involving a vaccine library comprising a plurality of fusion junction sequences corresponding to the protein products of gene fusions associated with cancers in many patients. Aspects of the application are based, at least in part, on the recognition that gene fusions are present in many cancers and that a library of fusion-specific vaccines can be generated to represent a significant percentage of cancers without requiring de novo construction of personalized cancer vaccines for patients having cancers associated with these gene fusions.

Accordingly, aspects of the application relate to methods and compositions for providing fusion-specific cancer vaccines to patients without resorting to personalized vaccine development for each patient. In some embodiments, a library of fusion-specific vaccines is provided and a patient is evaluated to determine whether the patient will be responsive to at least one of the vaccines in the library. In some embodiments, the presence of one or more cancer-associated gene fusions is identified in the patient. In some embodiments, the HLA genotype of the patient is evaluated to determine whether the patient will be responsive to one or more fusion-specific vaccines corresponding to a cancer-associated gene fusion identified in the patient. In some embodiments, if the patient is determined to be responsive to at least one fusion-specific vaccine in the library, then one or more of the vaccines is administered to the patient. In some embodiments, if the patient is determined not to be responsive to at least one fusion-specific vaccine in the library, then a personalized vaccine can be prepared de novo for the patient.

A Fusion-Specific Vaccine Library

Figure 2:
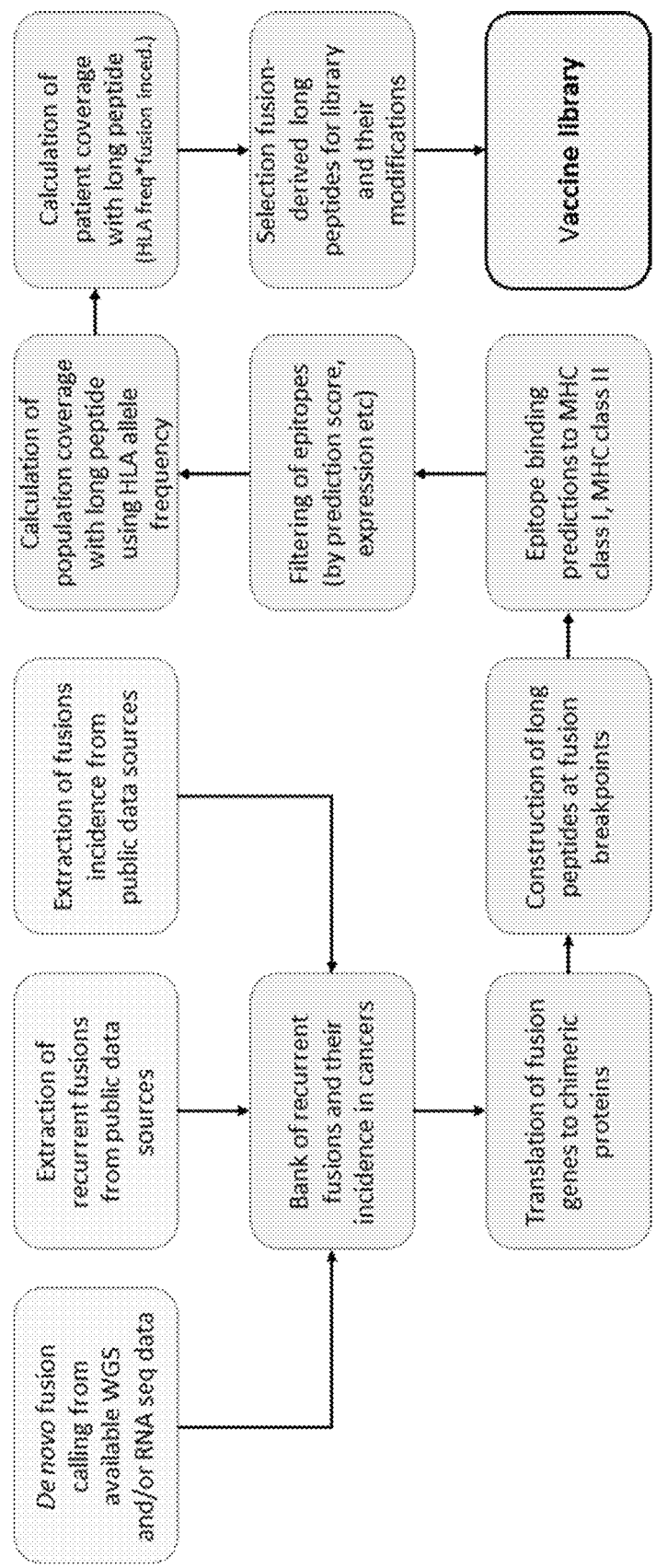
FIG. 2 illustrates a non-limiting example of a strategy for constructing a vaccine library comprising (1) screening of publicly available databases containing cancer sample sequences, information relating to genomic aberrations in cancer, and/or information relating to gene fusions in cancer; (2) extracting gene fusion incidence data; (3) analyzing fusion breakpoint peptides and MHC interaction; (4) selecting fusion breakpoint peptides based on affinity for MHC proteins; (5) calculating population coverage of selected peptides; and (6) incorporation of selected peptides into vaccine library.

In some aspects, the specification provides a method for constructing a therapeutic fusion-specific vaccine library for a cancer patient, including (a) identifying one or more tumor-specific gene fusions from publicly available data, (b) identifying one or more fusion junction sequences, wherein the fusion junction sequences comprise nucleic acid sequences and/or amino acid sequences corresponding to one or more tumor-specific gene fusions, (c) obtaining information relating to interaction between fusion junction sequences with one or more HLA alleles, and (d) selecting at least one fusion junction sequence for the therapeutic fusion-specific vaccine library. For example, FIG. 2 illustrates a non-limiting embodiment for constructing a vaccine library that includes screening publicly available databases containing cancer sample sequences, information relating to genomic aberrations in cancer, and/or information relating to gene fusions in cancer; extracting gene fusion incidence data; analyzing fusion breakpoint peptides and MHC interaction; selecting fusion breakpoint peptides based on affinity for MHC proteins; calculating population coverage of selected peptides; and incorporation of selected peptides into vaccine library. It should be appreciated that one or more of these steps may be omitted or modified depending on the vaccine library being developed. For example, sequence and related information can be obtained from any suitable source including public, private, customized, or other libraries containing cancer-related sequence information. In some embodiments, gene fusion incidence data does not need to be used. In some embodiments, population coverage does not need to be calculated. Accordingly, in some embodiments, a library can be designed by i) selecting fusion peptides of interest (e.g., based on one or more criteria, for example the types of cancer to be covered, the target patient population, the geographic region, the size and range of peptides to be included in the library, etc., or any combination thereof), and ii) obtaining or calculating MHC interaction information for those peptides. In some embodiments, the library can by synthesized or assembled using any suitable synthetic techniques (e.g., any suitable peptide chemistry, recombinant expression techniques, or any combination thereof).

Figure 3:
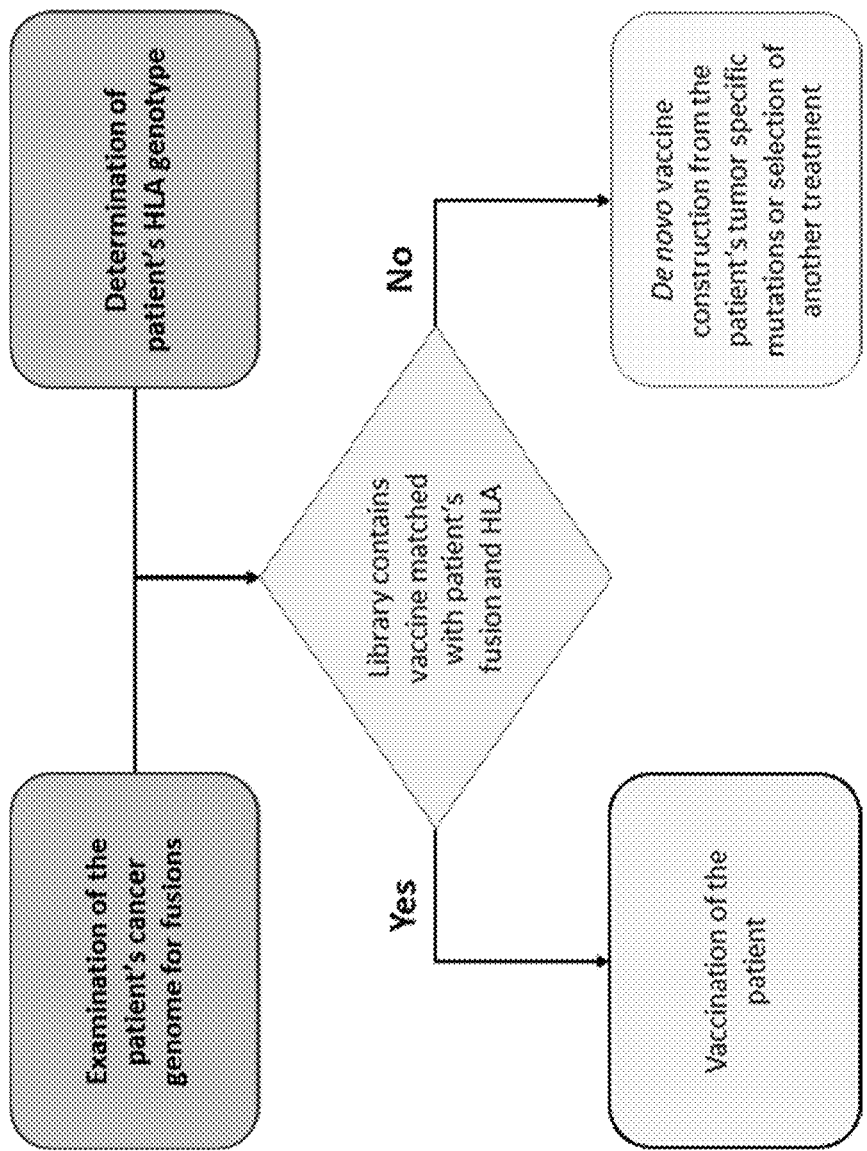
FIG. 3 illustrates a non-limiting scheme for selecting patients for treatment with a vaccine library comprising (1) examining patient's cancer genome for gene fusions; (2) determining patient's HLA genotype; (3) matching vaccine library to patient's gene fusion and HLA type, and (4) administering a vaccine from the vaccine library to the patient or de novo vaccine construction from the patient's tumor specific mutations or selection of another treatment.

In some aspects, the specification provides a method for selecting a therapeutic fusion-specific vaccine for a cancer patient, the method comprising (a) determining the presence of one or more tumor-specific gene fusions in a biological sample from the cancer patient, (b) obtaining information relating to one or more HLA alleles of the cancer patient, (c) analyzing a library of fusion-specific vaccines, wherein each fusion-specific vaccine in the library comprises one or more fusion junction sequences having a nucleic acid sequences and/or an amino acid sequence corresponding to one or more tumor-specific gene fusions, and (d) selecting at least one fusion-specific vaccine in the library as the therapeutic fusion-specific vaccine for the cancer patient by selecting the fusion-specific vaccine comprising (i) one or more fusion junction sequences corresponding to one or more tumor-specific gene fusions of the cancer patient, and (ii) one or more fusion junction sequences that bind one or more HLA alleles of the cancer patient. FIG. 3 illustrates a non-limiting example of a method of selecting a vaccine for a patient from a vaccine library described in this application. In some embodiments, i) a patient's cancer genome (e.g., the genome of a cancer in the patient, for example obtained from a biopsy or other sample obtained from cancer tissue in the patient) is analyzed to detect the presence of one or more gene fusions, ii) the patient's HLA genotype is determined (e.g., by sequencing one or more HLA loci of the patient, or obtained from whole genome sequence data for the patient, and iii) the library and the patient's HLA genotype are evaluated to determine with the library contains one or more peptides that match the patient's HLA genotype (e.g., based on one or more matching criteria that can be selected by the user, for example by a physician or a healthcare organization). If the library contains one or more peptides that are suitable for the patient (e.g., that correspond to one or more tumor specific mutations/neoantigens and that are HLA matched, for example based on specified HLA match criteria), then a vaccine containing one or more of those peptides can be selected from the library and administered to the patient. In the event that the library does not contain any peptides that are suitable for the patient (e.g., based on the tumor specific mutations in the patient that are not represented in the library and/or based on a failure to meet the specified HLA match criteria) then a de novo vaccine can be designed and synthesized for the patient (e.g., based on the patient's tumor specific mutations/neoantigens and/or HLA type) and/or a different therapy can be selected for the patient.

In some aspects, the specification provides a method for constructing a de novo therapeutic fusion-specific vaccine for a cancer patient, the method comprising (a) determining the presence of one or more tumor-specific gene fusions in a biological sample from the cancer patient, (b) obtaining information relating to one or more HLA alleles of the cancer patient, (c) determining that the cancer patient's fusion junction sequence is not present in the library of fusion-specific vaccines, and (d) constructing at least one fusion-specific vaccine as the de novo therapeutic fusion-specific vaccine for the cancer patient by constructing the fusion-specific vaccine comprising (i) one or more fusion junction sequences corresponding to one or more tumor-specific gene fusions of the cancer patient, and (ii) one or more fusion junction sequences that bind one or more HLA alleles of the cancer patient.

In some embodiments, the fusion-specific vaccine comprises one or more nucleic acid sequences corresponding to one or more tumor-specific gene fusions. In some embodiments, the fusion-specific vaccine comprises one or more peptides having amino acid sequences corresponding to one or more tumor-specific gene fusions. In some embodiments, the fusion-specific vaccine comprises one or more peptides selected from Table A. In some embodiments, one or more of the peptides listed in Table A is included in a peptide vaccine library. In some embodiments, one or more peptides in a peptide vaccine library consists of or includes a fragment of a peptide listed in Table A. In some embodiments, a fragment includes at least one amino acid (e.g., at least 2, 3, 4, 5 or more amino acids) from the N-terminal portion of a fusion peptide and at least one amino acid (e.g., at least 2, 3, 4, 5 or more amino acids) from the C-terminal portion of a fusion peptide. A vaccine library can include a plurality separate receptacles each containing a different peptide or a different combination of two or more peptides. Accordingly, a library can be a collection of receptacles, for example, wells, vials, tubes, or other containers capable of storing one or more different peptides, for example in the form of dry preparations (e.g., powder or crystalline form), liquid preparations (e.g., aqueous, organic, or other solutions), suspensions, or a combination thereof in different containers. In some embodiments, the receptacles are separate. In some embodiments, the receptacles are connected (e.g., in the form of an array, for example a 2D array). Receptacles can be made of any suitable material (e.g., glass, plastic, polymer, or other suitable material). In some embodiments, different peptides may be provided in different solutions (e.g., different salt concentrations, different pHs, etc.) depending on their solubility properties. Peptides in receptacles in a library can be provided at any suitable concentration (for example, nanomolar (e.g., from 1-1,000 nM), micromolar (e.g., from 1-1,000 μM), millimolar (e.g., 1-1,000 mM), or molar (e.g., 1M or higher)). Different peptides may be provided at different concentrations. In some embodiments, a peptide in a library is in a solution without an adjuvant or other agent, and an adjuvant or other agent may be added when the vaccine is prepared. However, in some embodiments, a peptide preparation in a library may also contain an adjuvant and/or other agent (e.g., a solubilizing or stabilizing agent, a therapeutic agent, or other agent).

Once a suitable combination of peptides has been determined or selected for a patient as described in this application, a vaccine can be prepared for the patient by retrieving (e.g., using a pipette or other suitable device for transferring the peptide(s)) from the appropriate library receptacles an appropriate amount of the one or more peptides that were identified to be suitable for that patient. The resulting combination of peptide(s) can be transferred to one or more suitable containers (e.g., syringes, infusion pumps, etc.) for administration to the patient. During this process, a peptide solution from the library may be diluted (e.g., around 5×, 10×, 100×, or other dilution) in a physiologically acceptable buffer for administration to a patient. An adjuvant also may be added at this stage. This procedure can be followed for a plurality of patients, for example at a hospital or other medical center.

Accordingly, in some embodiments a library can include a plurality (e.g., all, or a subset of) the peptides in Table A and a vaccine can be selected from that library based on the criteria described in this application. However, other libraries can be used (e.g., containing one or more of the peptides listed in Table A, and/or one or more other neoantigenic peptides) as described in this application.

TABLE A

Peptides for vaccine library.

| SEQ ID NO. | Long peptide for vaccine | Exons | Fusion name |
|---|---|---|---|
| 1 | AIKSKNVDVNVKDEETEVKSEEGPGWTILR | E5:E5 | ACBD6/RRP15 |
| 2 | EAPLNPKANREKMTQDPLLGMLDGREDLER | E3:E7 | ACTB/GLI1 |
| 3 | EAPLNPKANREKMTQPISGIPSPDESPKRA | E3:E5 | |
| 4 | EAPLNPKANREKMTQLKSELDMLVGKCREE | E3:E6 | |
| 5 | PRAVFPSIVGRPRHQLKSELDMLVGKCREE | E2:E6 | |
| 6 | QTKVLSASQAFAAQRDSITQHKVCAPENYL | E5:E14 | AGPAT5/MCPH1 |
| 7 | NDKLQKELNVLKSEQDLIRDQGFRGDGGST | E8:E9 | AKAP9/BRAF |
| 8 | QERERDPQQEQERERIDDVIDEIISLESSY | E7:E5 | ASPSCR1/TFE3 |
| 9 | QERERDPQQEQERERLPVSGNLLDVYSSQG | E7:E6 | |
| 10 | SSQKAHGILARRPSYRTHG | E3:E10 | ATF1/EWSR1 |
| 11 | MSVPTPIYQTSSGQYSSFRQDHPSSMGVYG | E4:E8 | |
| 12 | RNVQDFKRASEEITKTTQDGLDWLIST | E10:E11 | ATG4C/FBXO38 |
| 13 | TPAQLYTLQPKLPITVYRRKHQELQAMQME | E7:E20 | ATIC/ALK |

TABLE A-continued

Peptides for vaccine library.

| SEQ ID NO. | Long peptide for vaccine | Exons | Fusion name |
|---|---|---|---|
| 14 | TQLPHIPVAVRVGCLQYYRTDSDNQAILSE | E9:E21 | BBS9/PKD1L1 |
| 15 | KTRVYRDTAEPNWNEKPFSGQ | E15:E2 | BCR/ABL1 |
| 16 | RKQTGVFGVKIAVVTKSPSAASSI | E18:E2 | |
| 17 | EITPRRQSMTVKKGESYTFLISSDYERAEW | E8:E12 | |
| 18 | KLQTVHSIPLTINKEAGSIEALQRPVASDF | E13:E2 | |
| 19 | KTRVYRDTAEPNWNELDPQALQDRDWQRTV | E15:E17 | |
| 20 | QWSHQQRVGDLFQKLNLRARSNKDAKDPTT | E4:E6 | |
| 21 | SRDALVSGALESTKATKAKPFSGQ | E2:E2 | |
| 22 | SNKDAKDPTTKNSLEKALQRPVASDFEPQG | E6:E2 | |
| 23 | ASEETYLSHLEALLLKPFSGQ | E3:E2 | |
| 24 | EITPRRQSMTVKKGEKPFSGQ | E8:E2 | |
| 25 | KLQTVHSIPLTINKEGEKLRVLGYNHNGEW | E13:E3 | |
| 26 | GVATDIQALKAAFDVRPSPCEDRHWPGLAL | E19:E1 | |
| 27 | GVATDIQALKAAFDVKALQRPVASDFEPQG | E19:E2 | |
| 28 | QIWPNDGEGAFHGDAGEKLRVLGYNHNGEW | E1:E3 | |
| 29 | LNVIVHSATGFKQSSSEKLRVLGYNHNGEW | E14:E3 | |
| 30 | LNVIVHSATGFKQSSKALQRPVASDFEPQG | E14:E2 | |
| 31 | KLQTVHSIPLTINKEEALQRPVASDFEPQG | E13:E2 | |
| 32 | QIWPNDGEGAFHGDAEALQRPVASDFEPQG | E1:E2 | |
| 33 | QIWPNDGEGAFHGDADYELLTENDMLPNMR | E1:E19 | BCR/JAK2 |
| 34 | QIWPNDGEGAFHGDAVLQERIPWVPPECIE | E1:E17 | |
| 35 | APNVHINTIEPVNIDNDLRLQMEAQRICLS | E8:E9 | BRAF/AKAP9 |
| 36 | RYVKSCLQKKQRKPFSSALPGPDMSMKPSA | E10:E2 | BRD3/NUTM1 |
| 37 | SSSESSSSDSEDSETASALPGPDMSMKPSA | E11:E2 | |
| 38 | SEFREGVRKIAREQKVYRRKHQELQAMQME | E17:E20 | CARS/ALK |
| 39 | LQEENRDLRKASVTIEDPKWEFPRKNLVLG | E1:E12 | CCDC6/RET |
| 40 | EEEFLTNELSRKLMQEDPKWEFPRKNLVLG | E2:E12 | |
| 41 | SRHSLEQKPTDAPPKVWHRRLKNQKSAKEG | E6:E35 | CD74/ROS1 |
| 42 | SRHSLEQKPTDAPPKAGVPNKPGIPKLLEG | E6:E32 | |
| 43 | SRHSLEQKPTDAPPKDDFWIPETSFILTII | E6:E34 | |
| 44 | VHPDALNRFGKTALQLHVHACLLTRKQEDC | E2:E3 | CDKN2D/WDFY2 |
| 45 | VHPDALNRFGKTALQLHVHACLLTRKQEDC | E2:E3 | |
| 46 | VHPDALNRFGKTALQLHVHACLLTRKQEDC | E2:E3 | |
| 47 | LAENITQERDSLMCLDLIRDQGFRGDGGST | E16:E9 | CEP89/BRAF |
| 48 | TQEEEDEILPRKDYEKTLGRRDSSDDWEIP | E2:E11 | CLCN6/BRAF |
| 49 | EERSVLNNQLLEMKKSTLPTQEEIENLPAF | E20:E36 | CLIP1/ROS1 |
| 50 | RKEEEQATETQPIVYVYRRKHQELQAMQME | E31:E20 | CLTC/ALK |
| 51 | AMPYFIQVMKEYLTKGVYRRKHQELQAMQM | E30:E20 | |
| 52 | AMPYFIQVMKEYLTKCTAGSTRSCKPCRWS | E30:E20 | |
| 53 | CVAYERGQCDLELINLPVSGNLLDVYSSQG | E17:E6 | CLTC/TFE3 |
| 54 | GKAGERGVPGPPGAVGDPIPEELYEMLSDH | E26:E2 | COL1A1/PDGFB |
| 55 | GPSGPRGLPGPPGAPGDPIPEELYEMLSDH | E7:E2 | |
| 56 | GAPGAKGARGSAGPPGDPIPEELYEMLSDH | E37:E2 | |
| 57 | GPSGPAGPTGARGAPGDPIPEELYEMLSDH | E34:E2 | |
| 58 | GPPGPAGPAGPPGPIGDPIPEELYEMLSDH | E36:E2 | |
| 59 | GPPGPRGRTGDAGPVGDPIPEELYEMLSDH | E47:E2 | |
| 60 | GPAGPPGFPGAVGAKGDPIPEELYEMLSDH | E16:E2 | |
| 61 | GPRGANGAPGNDGAKGDPIPEELYEMLSDH | E31:E2 | |
| 62 | GKPGRPGERGPPGPQGDPIPEELYEMLSDH | E10:E2 | |
| 63 | YDEKSTGGISVPGPMGDPIPEELYEMLSDH | E6:E2 | |
| 64 | GPQGPGGPPGPKGNSGDPIPEELYEMLSDH | E19:E2 | |
| 65 | GLPGTAGLPGMKGHRGDPIPEELYEMLSDH | E11:E2 | |
| 66 | GNPGADGQPGAKGANGDPIPEELYEMLSDH | E18:E2 | |
| 67 | KRHVWFGESMTDGFQGDPIPEELYEMLSDH | E49:E2 | |
| 68 | RTCRDLKMCHSDWKSGGPHSRGAL | E48:E2 | |
| 69 | GFQGPPGEPGEPGASGDPIPEELYEMLSDH | E8:E2 | |
| 70 | GEPGSPGENGAPGQMGDPIPEELYEMLSDH | E13:E2 | |
| 71 | GHRGFSGLQGPPGPPGDPIPEELYEMLSDH | E45:E2 | |
| 72 | GPIGPPGPAGAPGDKGDPIPEELYEMLSDH | E33:E2 | |
| 73 | GQAGVMGFPGPKGAAGDPIPEELYEMLSDH | E25:E2 | |

TABLE A-continued

Peptides for vaccine library.

| SEQ ID NO. | Long peptide for vaccine | Exons | Fusion name |
|---|---|---|---|
| 74 | PPGPPGPPGPPGLGGGDPIPEELYEMLSDH | E5:E2 | |
| 75 | GKDGEAGAQGPPGPAGDPIPEELYEMLSDH | E27:E2 | |
| 76 | GQRGERGFPGLPGPSGDPIPEELYEMLSDH | E40:E2 | |
| 77 | GPPGLAGPPGESGREGDPIPEELYEMLSDH | E41:E2 | |
| 78 | GPAGPVGPVGARGPAGDPIPEELYEMLSDH | E44:E2 | |
| 79 | GVPGDLGAPGPSGARGDPIPEELYEMLSDH | E30:E2 | |
| 80 | GLPGERGRPGAPGPAGDPIPEELYEMLSDH | E14:E2 | |
| 81 | GPAGEKGSPGADGPAGDPIPEELYEMLSDH | E39:E2 | |
| 82 | GARGNDGATGAAGPPGDPIPEELYEMLSDH | E15:E2 | |
| 83 | GEPGPPGPAGAAGPAGDPIPEELYEMLSDH | E17:E2 | |
| 84 | GAPGSKGDTGAKGEPGDPIPEELYEMLSDH | E20:E2 | |
| 85 | GAEGSPGRDGSPGAKGDPIPEELYEMLSDH | E42:E2 | |
| 86 | GEAGRPGEAGLPGAKGDPIPEELYEMLSDH | E23:E2 | |
| 87 | GFPGAAGRVGPPGPSGDPIPEELYEMLSDH | E38:E2 | |
| 88 | GPAGPPGEAGKPGEQGDPIPEELYEMLSDH | E29:E2 | |
| 89 | GEQGPSGASGPAGPRGDPIPEELYEMLSDH | E46:E2 | |
| 90 | GPVGPAGKSGDRGETGDPIPEELYEMLSDH | E43:E2 | |
| 91 | GERGAAGLPGPKGDRGDPIPEELYEMLSDH | E32:E2 | |
| 92 | THGQEEGQVEGQDEDRWTW | E1:E2 | COL1A1/USP6 |
| 93 | THGQEEGQVEGQDEDTKNTIK | E1:E1 | |
| 94 | TLLLLAVTLCLATCQYWPKWEGLDSTLFHE | E1:E3 | COL1A2/PLAG1 |
| 95 | TLLLLAVTLCLATCQCCLLVLPWPYLAPRM | E1:E2 | |
| 96 | APSALSSSPLLTAPHRK | E5:E7 | CREB3L2/FUS |
| 97 | APSALSSSPLLTAPHVTMAKINPP | E5:E6 | |
| 98 | ELSEPGDGEALMYHTALGTKDHVMTPNRII | E1:E8 | |
| 99 | ELSEPGDGEALMYHTALGTKDHVMTP | E1:E8 | |
| 100 | TRAFEQLMTDLTLSRLQGSLRKQVVNLSP | E1:E2 | CRTC3/MAML2 |
| 101 | SPPWDQDRRMMFPPPGILTNVI | E20:E10 | CTAGE5/SIP1 |
| 102 | PPPSGIATLVSGIAGVYRRKHQELQAMQME | E26:E20 | DCTN1/ALK |
| 103 | DCVLVLLLMPRLICKCTAGSTRSCKPCRWS | E16:E20 | |
| 104 | RHLVFPLLEFLSVKELVMYQIPFARVVCLV | E1:E3 | EIF3E/RSPO2 |
| 105 | RHLVFPLLEFLSVKEVRGGEMLIALN | E1:E2 | |
| 106 | NKYIMSNSGDYEILYLYRRKHQELQAMQME | E20:E20 | EML4/ALK |
| 107 | ILRGTFNDGFQIEVQCTAGSTRSCKPCRWS | E15:E20 | |
| 108 | HTDGNEQLSVMRYSIVYRRKHQELQAMQME | E18:E20 | |
| 109 | VTKTADKHKDVIINQVSPTPEPHLPLSLIL | E6:E19 | |
| 110 | SEDHVASVKKSVSSKVYRRKHQELQAMQME | E2:E20 | |
| 111 | IILWDHDLNPEREIECTAGSTRSCKPCRWS | E14:E20 | |
| 112 | WSKTTVEPTPGKGPKVYRRKHQELQAMQME | E13:E20 | |
| 113 | VTKTADKHKDVIINQVYRRKHQELQAMQME | E6:E20 | |
| 114 | STSTQSKSSSGSAHFGPPRMQWRSPPG | E10:E2 | EPC1/PHF1 |
| 115 | ECEQAERLGAVDESLRKYIFKPRTV | E5:E5 | ERO1L/FERMT2 |
| 116 | ALRMEEDSIRLPAHLPKNRGIAIPVDLDSQ | E2:E35 | ETV6/ITPR2 |
| 117 | IHTQPEVILHQNHEEGRKHPYSWECMCQKY | E4:E16 | ETV6/JAK2 |
| 118 | IHTQPEVILHQNHEEVLQERIPWVPPECIE | E4:E17 | |
| 119 | VSPPEEHAMPIGRIADYELLTENDMLPNMR | E5:E19 | |
| 120 | VSPPEEHAMPIGRIADKSNLLVFRTNGVSD | E5:E12 | |
| 121 | VSPPEEHAMPIGRIADVQHIKRRDIVLKRE | E5:E15 | ETV6/NTRK3 |
| 122 | IHTQPEVILHQNHEEGPVAVISGEEDSASP | E4:E14 | |
| 123 | VSPPEEHAMPIGRIAGPVAVISGEEDSASP | E5:E14 | |
| 124 | IHTQPEVILHQNHEEDVQHIKRRDIVLKRE | E4:E15 | |
| 125 | APSQYSQQSSSYGQQIAIAPNGALQLASPG | E7:E5 | EWSR1/ATF1 |
| 126 | APSQYSQQSSSYGQQKKLLENVAERRKNM | E7:E7 | |
| 127 | GMGSAGERGGFNKPGEKF | E9:E4 | |
| 128 | GGMSRGGRGGGRGGMGKILKDLSSEDTRGR | E8:E4 | |
| 129 | APSQYSQQSSSYGQQIAITQGGAIQLANNG | E7:E7 | EWSR1/CREB1 |
| 130 | NKPGGPMDEGPDLDLVFKKEVYLHTSPHLK | E10:E2 | EWSR1/DDIT3 |
| 131 | LPPREGRGMPPPLRGVFKKEVYLHTSPHLK | E13:E2 | |
| 132 | APSQYSQQSSSYGQQMFKKEVYLHTSPHLK | E7:E2 | |

TABLE A-continued

Peptides for vaccine library.

| SEQ ID NO. | Long peptide for vaccine | Exons | Fusion name |
|---|---|---|---|
| 133 | APSQYSQQSSSYGQQTAQPSPSTVPKTEDQ | E7:E9 | EWSR1/ERG |
| 134 | APSQYSQQSSSYGQQNPYQILGPTSSRLAN | E7:E10 | |
| 135 | NKPGGPMDEGPDLDLDLPYEPPRRSAWTGH | E10:E8 | |
| 136 | APSQYSQQSSSYGQQSSGQIQLWQFLLELL | E7:E11 | |
| 137 | APSQYSQQSSSYGQQNLPYEPPRRSAWTGH | E7:E8 | |
| 138 | APSQYSQQSSSYGQQRDIKQEPGMYREGPT | E7:E12 | EWSR1/ETV1 |
| 139 | NKPGGPMDEGPDLDLDPVGDGLFKDGKNPS | E10:E2 | EWSR1/FEV |
| 140 | APSQYSQQSSSYGQQNPVGDGLFKDGKNPS | E7:E2 | |
| 141 | GGMSRGGRGGGRGGMGIPVTASLPPLEWPL | E8:E3 | EWSR1/NFATC2 |
| 142 | YEDPPTAKAAVEWFDDMPCVQAQYSPSPPG | E12:E3 | EWSR1/NR4A3 |
| 143 | APSQYSQQSSSYGQQRPMDEGPDLDLGPPV | E7:E10 | |
| 144 | GMGSAGERGGFNKPGGPPVDPDEDSDNSAI | E9:E11 | |
| 145 | LPPREGRGMPPPLRGDMPCVQAQYSPSPPG | E13:E3 | |
| 146 | NKPGGPMDEGPDLDLDMPCVQAQYSPSPPG | E10:E3 | |
| 147 | YEDPPTAKAAVEWFDEPTAEEGSPASPGPE | E12:E2 | |
| 148 | APSQYSQQSSSYGQQKPTAEEGSPASPGPE | E7:E2 | |
| 149 | APSQYSQQSSSYGQQSGRDGISTSKRQKS | E7:E5 | EWSR1/PBX1 |
| 150 | GGMSRGGRGGGRGGMGRKRRNFNKQATEIL | E8:E5 | |
| 151 | APSQYSQQSSSYGQQNVKWGKLRDYQVRGL | E7:E5 | EWSR1/SMARCA5 |
| 152 | GGMSRGGRGGGRGGMGGTNLGKKKQHICHI | E8:E6 | EWSR1/SP3 |
| 153 | YGQTAYATSYGQPPTEGTSTGYTTPTAPQA | E4:E5 | EWSR1/WT1 |
| 154 | AYPAYGQQPAATAPTSSAGERGGFNKPG | E5:E9 | |
| 155 | AYPAYGQQPAATAPTSYSSTQPTSYDQSSY | E5:E7 | |
| 156 | APSQYSQQSSSYGQQNEKKDIDHETVVEEQ | E7:E2 | EWSR1/YY1 |
| 157 | GGMSRGGRGGGRGGMGRHRPWG | E8:E5 | EWSR1/ZNF444 |
| 158 | LRLQDYEEKTKKAERDDFWIPETSFILTII | E10:E34 | EZR/ROS1 |
| 159 | TSSLHGSSLHRPSTEDLIRDQGFRGDGGST | E2:E9 | FAM131B/BRAF |
| 160 | MGCIGSRTVGSTTGLSATPPASLPG | E1:E10 | |
| 161 | STEQTRTDFSWDGINDLIRDQGFRGDGGST | E3:E9 | |
| 162 | MASSGERTPSNALDPRWRSLW | E1:E17 | FBXL18/RNF216 |
| 163 | RLSEARLSQRDLSPTDLIRDQGFRGDGGST | E13:E9 | FCHSD1/BRAF |
| 164 | ATLCTARPSPTLPEQDWPKWEGLDSTLFHE | E2:E3 | FGFR1/PLAG1 |
| 165 | ATLCTARPSPTLPEQGCLLVLPWPYLAPRM | E2:E2 | |
| 166 | LVEDLDRIVALTSNQGLLESSAEKAPVSVS | E17:E7 | FGFR1/TACC1 |
| 167 | ARDIHHIDYYKKTTNLDAKKSPLALLAQTC | E14:E2 | FGFR1/ZNF703 |
| 168 | LVEDLDRVLTVTSTDNVMEQFNPGLRNLIN | E17:E2 | FGFR3/BAIAP2L1 |
| 169 | LVEDLDRVLTVTSTDFKESALRKQSLYLKF | E17:E8 | FGFR3/TACC3 |
| 170 | LVEDLDRVLTVTSTDVPGPPPGVPAPGGPP | E17:E10 | |
| 171 | LVEDLDRVLTVTSTDVKATQEENRELRSRC | E17:E11 | |
| 172 | RKAGDFHRNDSIYEEPQQVVQKKPAQEETE | E8:E4 | FHIT/HMGA2 |
| 173 | YFKDKGDSNSSAGWKVMGLLTNHGGVPHQP | E1:E8 | FOXO1/PAX3 |
| 174 | QYNSSSGGGGGGGGGVAIAPNGALQLASPG | E5:E5 | FUS/ATF1 |
| 175 | EPRGRGGGRGGRGGMGPSGPPAFAAHPSEQ | E6:E5 | FUS/CREB3L2 |
| 176 | EPRGRGGGRGGRGGMGNCRDQALWS | E6:E6 | |
| 177 | EPRGRGGGRGGRGGMGPQWTTCICRPPLRA | E6:E5 | |
| 178 | EPRGRGGGRGGRGGMGCLPSGPPAFAAHPS | E6:E5 | |
| 179 | QYNSSSGGGGGGGGGAPVDHLHLPPTPPSS | E5:E5 | |
| 180 | QYNSSSGGGGGGGGGETAGIRPSGPDRGGE | E5:E6 | |
| 181 | GGMGGSDRGGFNKFGAPVDHLHLPPTPPSS | E7:E5 | |
| 182 | QYNSSSGGGGGGGGGGVFKKEVYLHTSPHLK | E5:E2 | FUS/DDIT3 |

TABLE A-continued

Peptides for vaccine library.

| SEQ ID NO. | Long peptide for vaccine | Exons | Fusion name |
|---|---|---|---|
| 183 | EPRGRGGGRGGRGGMGVQEGSVSSYITTPE | E6:E2 | |
| 184 | GGMGGSDRGGFNKFGVFKKEVYLHTSPHLK | E7:E2 | |
| 185 | GYGQSSYSSYGQSQNMFKKEVYLHTSPHLK | E3:E2 | |
| 186 | FNRGGGNGRGGRGRGVFKKEVYLHTSPHLK | E11:E2 | |
| 187 | IESVADYFKQIGIIKTDPTAEMAAESLPFS | E9:E3 | |
| 188 | NKFGGPRDQGSRHDSVFKKEVYLHTSPHLK | E8:E2 | |
| 189 | EPRGRGGGRGGRGGMGGSDRGGFNKFG | E6:E7 | FUS/ERG |
| 190 | GGMGGSDRGGFNKFGDLPYEPPRRSAWTGH | E7:E8 | |
| 191 | NKFGGPRDQGSRHDSAAQPSPSTVPKTEDQ | E8:E9 | |
| 192 | QYNSSSGGGGGGGGGDLPYEPPRRSAWTGH | E5:E8 | |
| 193 | GGMGGSDRGGFNKFGDPYQILGPTSSRLAN | E7:E10 | |
| 194 | GGMGGSDRGGFNKFGGSGQIQLWQFLLELL | E7:E11 | |
| 195 | EPRGRGGGRGGRGGMGQWPDPALAVPPGAP | E6:E11 | |
| 196 | FDDPPSAKAAIDWFDDPVGDGLFKDGKNPS | E10:E2 | FUS/FEV |
| 197 | RAENACVPPFTIEVKKTLGRRDSSDDWEIP | E2:E11 | GATM/BRAF |
| 198 | PLEGDMSSPNSTGIQIMFETFNTPAMYVAI | E6:E4 | GLI1/ACTB |
| 199 | MIPHPQSRGPFPTCQIMFETFNTPAMYVAI | E5:E4 | |
| 200 | GKPRNVALITGITGQPLHICQP | E1:E22 | GMDS/PDE8B |
| 201 | EDGEKAAREVKLLLLGSTTGLSATPPASLP | E1:E10 | GNAI1/BRAF |
| 202 | QKLMGQIHQLRSELQEDPKWEFPRKNLVLG | E7:E12 | GOLGA5/RET |
| 203 | GARLAAKYLDKELAGSTLPTQEEIENLPAF | E4:E36 | GOPC/ROS1 |
| 204 | GASCKDTSGEIKVLQVWHRRLKNQKSAKEG | E8:E35 | |
| 205 | LINIMIEPQATRKAQDAIRSHSESASPSAL | E16:E8 | HACL1/RAF1 |
| 206 | EVLRNLSSPGWENISSLLFVSKFFEHHPIP | E4:E7 | HERPUD1/BRAF |
| 207 | MTVDHLKMLHTAGGKAFNNPRPGQLGRLLP | E4:E13 | HEY1/NCOA2 |
| 208 | VVASTISGKSQIEETVYRRKHQELQAMQME | E28:E20 | HIP1/ALK |
| 209 | KKHYELAGVAEGWEEVYRRKHQELQAMQME | E30:E20 | |
| 210 | HGATTCLRAPPEPADLYRRKHQELQAMQME | E21:E20 | |
| 211 | SDSAQGSDVSLTACKDDFWIPETSFILTII | E9:E34 | HLA-A/ROS1 |
| 212 | EATGEKRPGRPRKWVTVKVPQKNS | E3:E13 | HMGA2/ALDH2 |
| 213 | PKGSKNKSPSKAAQKVHQERLYQEYNFSKA | E2:E6 | HMGA2/CCNB1IP1 |
| 214 | EATGEKRPGRPRKWNFFRLNYLEVCH | E3:E4 | HMGA2/COX6C |
| 215 | EATGEKRPGRPRKWVVVSTTVNVDGHVLA | E3:E8 | HMGA2/EBF1 |
| 216 | EATGEKRPGRPRKWLQKHDKEDFPASWRS | E3:E9 | HMGA2/FHIT |
| 217 | EATGEKRPGRPRKWGSVKSAGPTTAREQV | E3:E4 | HMGA2/LHFP |
| 218 | PRKWPQQVVQKKPAQSWYLG | E4:E12 | HMGA2/NFIB |
| 219 | EATGEKRPGRPRKWSWYLG | E3:E12 | |
| 220 | EATGEKRPGRPRKWVILTNQITTHLSGAL | E3:E8 | HMGA2/RAD51B |
| 221 | EATGEKRPGRPRKWLSASLAVVHMEPAMN | E3:E9 | HMGA2/WIF1 |
| 222 | EATGEKRPGRPRKWGTKPASYMP | E3:E10 | |
| 223 | EATGEKRPGRPRKWAEYFYEFLSLRSLDK | E3:E3 | |
| 224 | EATGEKRPGRPRKWLFKLVSHVLENRMGW | E3:E4 | |
| 225 | PRKWPQQVVQKKPAQGTKPASYMP | E4:E10 | |
| 226 | MESQRGRNCNEKPTNVR | E1:E4 | HNRNPA2B1/ETV1 |
| 227 | KANAARSQLETYKRQEDPKWEFPRKNLVLG | E11:E12 | HOOK3/RET |
| 228 | SRSPPAENEVSTPMQKKKGGRGLMTENTMR | E7:E3 | IL6R/ATP8B2 |
| 229 | SVEGVVRILLEHYYKAWKKRWFILRSGRMS | E2:E2 | INTS4/GAB2 |
| 230 | SFRAIIRDLNSLFTPDCRLLWDYVYQLLSD | E18:E6 | JAK2/ETV6 |

TABLE A-continued

Peptides for vaccine library.

| SEQ ID NO. | Long peptide for vaccine | Exons | Fusion name |
|---|---|---|---|
| 231 | NIIFQFTKCCPPKPKETGSDFSMFEALRDT | E11:E25 | JAK2/PCM1 |
| 232 | SPKDFNKYFLTFAVEEAESGNISQKSDEED | E10:E37 | |
| 233 | PPITPSSSFRSSTPTGPPRMQWRSPPG | E3:E2 | JAZF1/PHF1 |
| 234 | PPITPSSSFRSSTPTEPTQIYRFLRTRNLI | E3:E2 | JAZF1/SUZ12 |
| 235 | DLAEIGIAVGNNDVKEDPKWEFPRKNLVLG | E15:E12 | KIF5B/RET |
| 236 | VRSKNMARRGHSAQIDPLCDELCRTVIAAA | E24:E11 | |
| 237 | LRKLFVQDLATRVKKEDPKWEFPRKNLVLG | E22:E12 | |
| 238 | FLENNLEQLTKVHKQEDPKWEFPRKNLVLG | E23:E12 | |
| 239 | VRSKNMARRGHSAQIDVAEEAGCPLSCAVS | E24:E8 | |
| 240 | ENEKELAACQLRISQEDPKWEFPRKNLVLG | E16:E12 | |
| 241 | EILTRAHEREFGSVDVYRRKHQELQAMQME | E9:E20 | KLC1/ALK |
| 242 | TLEGELHDLRGQVAKTLTAHLETRWRRRTK | E2:E10 | LMNA/NTRK1 |
| 243 | TSSGAGFFLPQHDSSVWHRRLKNQKSAKEG | E16:E35 | LRIG3/ROS1 |
| 244 | RGGRGGREFADFEYRDLIRDQGFRGDGGST | E9:E9 | LSM14A/BRAF |
| 245 | RKDEELTSSQRDLAVRDLKLDNILLDAEGH | E6:E12 | MBOAT2/PRKCE |
| 246 | QKKKAKSQQYKGHKKRTGWAPPTFLLYQFA | E16:E1 | MBTD1/CXorf67 |
| 247 | SHHSSHKKRKNKNRHRPPQDAMAQPPRLSR | E5:E2 | MEAF6/PHF1 |
| 248 | VLHPMDAAQRSQHIKKTLGRRDSSDDWEIP | E4:E11 | MKRN1/BRAF |
| 249 | KNLLEFAETLQFIDSFLNTSSNHENSDLEM | E9:E11 | MYB/NFIB |
| 250 | AFTVPKNRSLASPLQSWYLG | E15:E12 | |
| 251 | AFTVPKNRSLASPLQPNGSGQVVGKVPGHF | E15:E9 | |
| 252 | AFTVPKNRSLASPLQSSQLELHLHLHRCHF | E15:E8 | |
| 253 | LMSTENELKGQQVLPLRICDWTMNQNGRHL | E8:E11 | |
| 254 | AFTVPKNRSLASPLQPTQPQAHLKPIDMWD | E15:E10 | |
| 255 | AFTVPKNRSLASPLQLRICDWTMNQNGRHL | E15:E11 | |
| 256 | LMSTENELKGQQVLPPNGSGQVVGKVPGHF | E8:E9 | |
| 257 | FQENGPPLLKKIKQESWYLG | E13:E12 | |
| 258 | FQENGPPLLKKIKQELRICDWTMNQNGRHL | E13:E11 | |
| 259 | LMSTENELKGQQVLPSWYLG | E8:E12 | |
| 260 | EALNHRIVQQAKEMTVWHRRLKNQKSAKEG | E23:E35 | MYO5A/ROS1 |
| 261 | FDSKRREGKQLSLHEATSKSQIMSLWGLVS | E2:E2 | NAB2/STAT6 |
| 262 | DSASLSGESLDGHLQAEQMGKDGRGYVPAT | E5:E17 | |
| 263 | QVARESTYLSSLKGSRQPPSPRSCLCGVWS | E3:E2 | |
| 264 | QVARESTYLSSLKGSRPQVYPPHSHSIPPY | E3:E19 | |
| 265 | DSASLSGESLDGHLQGTNHFLPQSSRCLPW | E5:E18 | |
| 266 | PEELGGPPLKKLKQEGPTTSYPRAPDAYHG | E4:E18 | |
| 267 | FDSKRREGKQLSLHECLCTA | E2:E6 | |
| 268 | QVARESTYLSSLKGSRDQPLPTPELQMPTM | E3:E18 | |
| 269 | PEELGGPPLKKLKQEGVPGRLRRLLLQLG | E4:E3 | |
| 270 | QVARESTYLSSLKGSRPHLQMPPSLGQMSL | E3:E20 | |
| 271 | DSASLSGESLDGHLQGSPQIENIQPFSAKD | E5:E16 | |
| 272 | QVARESTYLSSLKGSS | E3:E17 | |
| 273 | PEELGGPPLKKLKQEATSKSQIMSLWGLVS | E4:E2 | |
| 274 | PEELGGPPLKKLKQESIYQRDPLKLVATFR | E4:E4 | |
| 275 | FDSKRREGKQLSLHEFRHLPMPFHWKQEEL | E2:E5 | |
| 276 | VGRLSPCVPAKPPLAAEQMGKDGRGYVPAT | E6:E17 | |
| 277 | VGRLSPCVPAKPPLAGNLQVPDHVSVGSGL | E6:E2 | |
| 278 | VGRLSPCVPAKPPLAGSPQIENIQPFSAKD | E6:E16 | |
| 279 | PEELGGPPLKKLKQEFLFSVSSELQGGTWV | E4:E1 | |
| 280 | VGRLSPCVPAKPPLAGTNHFLPQSSRCLPW | E6:E18 | |
| 281 | PSRKPLDSRVLNAVKYYGTAANDIGDTTNR | E4:E13 | NACC2/NTRK2 |
| 282 | KGETITGLLQEFDVQEALSVVSEDQSLFEC | E3:E4 | NDRG1/ERG |
| 283 | DVDLAEVKPLVEKGEEALSVVSEDQSLFEC | E2:E4 | |
| 284 | PIAMALANVVPCSQWVFTKYGKCYMFNSGE | E27:E2 | NF1/ACCN1 |
| 285 | PPTWPKPLVPAIPICSSAGERGGFNKPGGP | E2:E9 | NFATC2/EWSR1 |

TABLE A-continued

Peptides for vaccine library.

| SEQ ID NO. | Long peptide for vaccine | Exons | Fusion name |
|---|---|---|---|
| 286 | MRRQQEGFKGTFPDALPVSGNLLDVYSSQG | E9:E6 | NONO/TFE3 |
| 287 | GEVDADCMDVNVRGPAGPSRTGYLHPPSPG | E30:E14 | NOTCH1/GABBR2 |
| 288 | KCGSGPVHISGQHLVVYRRKHQELQAMQME | E5:E20 | NPM1/ALK |
| 289 | VAPPTTAASSVEEPEGHRESNSRLPGPPEG | E5:E11 | NTN1/ACLY |
| 290 | FMDNPFEFNPEDPIPDKLKCTKEEHLCTQR | E9:E8 | NTRK1/TPM3 |
| 291 | PQYFRQGHNCHKPDTYCRLLWDVYQLLSD | E14:E6 | NTRK3/ETV6 |
| 292 | MDRDLSYNLLEDLPSFSV | E1:E12 | NUP107/LGR5 |
| 293 | SNPMNPTIGNGLSPQNSIRHNLSLHSKFIR | E7:E2 | PAX3/FOXO1 |
| 294 | SNPMNPTIGNGLSPQFTADLDQFDQLLPTL | E7:E14 | PAX3/NCOA1 |
| 295 | YQLSETSYQPTSIPQGLPELELEAIDNQFG | E6:E15 | |
| 296 | SNPMNPTIGNGLSPQPGSELDNLEEILDDL | E7:E12 | PAX3/NCOA2 |
| 297 | PSNHMNPVSNGLSPQNSIRHNLSLHSKFIR | E7:E2 | PAX7/FOXO1 |
| 298 | LGRNLSTHQTYPVVAGREMVGPTLPGYPPH | E8:E10 | PAX8/PPARG |
| 299 | AGSPDTESPVLVNDYRENVIEYKHCLITKN | E36:E11 | PCM1/JAK2 |
| 300 | AGSPDTESPVLVNDYEIELSSLREALSFVS | E36:E9 | |
| 301 | LEKIIKCNRSTEISSVLQERIPWVPPECIE | E24:E17 | |
| 302 | KKRNSTQLKSRVKNINKSNLLVFRTNGVSD | E23:E12 | |
| 303 | NSELTPSESLATTDDEIELSSLREALSFVS | E26:E9 | |
| 304 | RQIKAIMKEVIPFLKEDPKWEFPRKNLVLG | E29:E12 | PCM1/RET |
| 305 | GVACEPLPDRYTVSEESNGWK | E13:E4 | PLXND1/TMCC1 |
| 306 | LQPMAGTCPAPEIHAIERLEVSSLAQTSSA | E12:E4 | |
| 307 | DSERLQYEKKLKSTKCTAGSTRSCKPCRWS | E8:E20 | PPFIBP1/ALK |
| 308 | YKKMQDTVVLAQGKKVYRRKHQELQAMQME | E12:E20 | PPFIBP1/ALK |
| 309 | LVCKMKGEGVEIVDRVWHRRLKNQKSAKEG | E9:E35 | PPFIBP1/ROS1 |
| 310 | KEPVKIAAPELHKGDVQTHLENPTRYHLQQ | E1:E4 | PRCC/TFE3 |
| 311 | PQEIAPDASFIDDEAVQTHLENPTRYHLQQ | E4:E4 | |
| 312 | DSEEDEPTKKKTILQLPVSGNLLDVYSSQG | E2:E6 | |
| 313 | KEPVKIAAPELHKGDIDDVIDEIISLESSY | E1:E5 | |
| 314 | KLWGIDRDSYRRILMEDPKWEFPRKNLVLG | E7:E12 | PRKAR1A/RET |
| 315 | SPWPLLGSAQGQFSAVHPNVSQGCQGGCAT | E1:E2 | PTPRK/RSPO3 |
| 316 | TGLPGPPLITRTKCAVHPNVSQGCQGGCAT | E7:E2 | |
| 317 | FGEKLFSGVLMDLSKSTLPTQEEIENLPAF | E1:E36 | PWWP2A/ROS1 |
| 318 | ATSILEYPIEPSGVLGPASVISNDDDSASP | E6:E16 | QKI/NTRK2 |
| 319 | EASSLKYLAEEFSIPEPTGEPSPKRPRGRP | E7:E2 | RAD51B/HMGA2 |
| 320 | EASSLKYLAEEFSIPKAEATGEKRPRGRPR | E7:E3 | RAD51B/HMGA2 |
| 321 | HMVSTTLPVDSRMIESTANPETPNSTISRE | E7:E2 | RAF1/DAZL |
| 322 | DGYQGSQTFHGAPLTVYRRKHQELQAMQME | E18:E20 | RANBP2/ALK |
| 323 | ASYDDPYKKAVAMSKR | E2:E5 | RBM14/PACS1 |
| 324 | DSMENQVSVDAFKILDMEAQQVNEAESARE | E11:E8 | RET/GOLGA5 |
| 325 | DSMENQVSVDAFKILKCERLLLYLYCHELS | E11:E17 | RET/TRIM33 |
| 326 | EHRKELGPYVFREAQVNKLELELESAKQKF | E22:E24 | RGS22/SYCP1 |
| 327 | FIQKIRYTNARDRNQDLIRDQGFRGDGGST | E3:E9 | RNF130/BRAF |
| 328 | TVQGSNIFERTEVLADDFWIPETSFILTII | E4:E34 | SDC4/ROS1 |
| 329 | TVQGSNIFERTEVLAAGVPNKPGIPKLLEG | E4:E32 | |

TABLE A-continued

Peptides for vaccine library.

| SEQ ID NO. | Long peptide for vaccine | Exons | Fusion name |
|---|---|---|---|
| 330 | GQESDDFELSGSGDLDDFWIPETSFILTII | E2:E34 | |
| 331 | GQESDDFELSGSGDLVWHRRLKNQKSAKEG | E2:E35 | |
| 332 | GQESDDFELSGSGDLAGVPNKPGIPKLLEG | E2:E32 | |
| 333 | PGHMHTQVPPYPQPQLYRRKHQELQAMQME | E19:E20 | SEC31A/ALK |
| 334 | GTLPAASELPASQRTVYRRKHQELQAMQME | E20:E20 | |
| 335 | GTLPAASELPASQRTVLQERIPWVPPECIE | E20:E17 | SEC31A/JAK2 |
| 336 | MAATDLERFSNSYNNSQAPSPGLGS | E1:E19 | SEPT8/AFF4 |
| 337 | VPPATMSGSMMGSDMLPVSGNLLDVYSSQG | E9:E6 | SFPQ/TFE3 |
| 338 | VPPATMSGSMMGSDMIDDVIDEIISLESSY | E9:E5 | |
| 339 | RQREESYSRMGYMDPIDDVIDEIISLESSY | E7:E5 | |
| 340 | LEDMRSNNVEDCKMMVIHPKTDEQRCRLQE | E17:E4 | SLC26A6/PRKAR2A |
| 341 | VCSLDILSSAFQLVGDDFWIPETSFILTII | E4:E34 | SLC34A2/ROS1 |
| 342 | VCSLDILSSAFQLVGAGVPNKPGIPKLLEG | E4:E32 | |
| 343 | ILPYTLASLYHREKQLIAMDSAITLWQFLL | E4:E2 | SLC45A3/ELK4 |
| 344 | LSSIRPPRLEGENTQDLIRDQGFRGDGGST | E10:E9 | SND1/BRAF |
| 345 | LSSIRPPRLEGENTQKTLGRRDSSDDWEIP | E10:E11 | |
| 346 | PTANLDQKDKQFVAKDLIRDQGFRGDGGST | E9:E9 | |
| 347 | SKKEVPIHRVADISGKTLGRRDSSDDWEIP | E14:E11 | |
| 348 | SKKEVPIHRVADISGDLIRDQGFRGDGGST | E14:E9 | |
| 349 | YSHKLFNGSMEAFIKRPRGQRDSSYYWEIE | E12:E10 | SRGAP3/RAF1 |
| 350 | KQTLGEGERAECGTTRMQFEVTANQPHLQP | E11:E8 | |
| 351 | GPPQPPQQRPYGYDQEWVSKSPSHLSCVIN | E10:E4 | SS18/SSX1 |
| 352 | GPPQPPQQRPYGYDQLNILR | E10:E5 | |
| 353 | QYPGQQGYPGQQQGYVEHPQMTFGRLHRII | E9:E5 | |
| 354 | QYPGQQGYPGQQQGYGFKVTLPPFMCNKQA | E9:E4 | |
| 355 | GPPQPPQQRPYGYDQIMPKKPAEDENDSKG | E10:E6 | |
| 356 | TAPSAQQQRPYGYEQIMPKKPAEDENDSKG | E10:E6 | SS18L1/SSX1 |
| 357 | GDGMPVGPVPPGFFQRENVIEYKHCLITKN | E5:E11 | SSBP2/JAK2 |
| 358 | ETCEHSSEAKAFHDYRENVIEYKHCLITKN | E4:E11 | |
| 359 | NITLGEPPGFLHSWWCEKMSLNINTV | E3:E11 | |
| 360 | HPQMTFGRLHRIIPKGQYGNYQQ | E5:E11 | SSX1/SS18 |
| 361 | YPKKPKDEAFRSHYKQFEEGLLDRCPAPGP | E16:E7 | STAT6/NAB2 |
| 362 | TELNQGDMKPPSYDSVYRRKHQELQAMQME | E3:E20 | STRN/ALK |
| 363 | CTEKGTWRESTLTCTVLLQIL | E6:E2 | SUSD1/ROD1 |
| 364 | RFAKKMDKMVQKKNAIGQNGKDWIPLSSTK | E1:E3 | TCEA1/PLAG1 |
| 365 | HEGLSPTPFMNSNLMDMPCVQAQYSPSPPG | E5:E3 | TCF12/NR4A3 |
| 366 | GYKILIPKGSYGRVKVS | E7:E8 | TECTA/TBCEL |
| 367 | SYLPGGTTGLQLPSTPVDREPVDREPVVCH | E5:E8 | TFE3/ASPSCR1 |
| 368 | SPMALLTIGSSSEKEPVDREPVDREPVVCH | E4:E8 | |
| 369 | QPPYTGAQTQAGQIEVYRRKHQELQAMQME | E6:E20 | TFG/ALK |
| 370 | KNVMSAFGLTDDQVSVYRRKHQELQAMQME | E5:E20 | |
| 371 | EPPGEPGPSTNIPENVYRRKHQELQAMQME | E4:E20 | |
| 372 | QAPPQQPQQYGIQYSDMPCVQAQYSPSPPG | E7:E3 | TFG/NR4A3 |
| 373 | KNVMSAFGLTDDQVSDTNSTSGDPVEKKDE | E5:E10 | TFG/NTRK1 |
| 374 | MALNSEALSVVSEDQSLFEC | E2:E4 | TMPRSS2/ERG |
| 375 | MALNSPSGSEQLVDGLAY | E2:E3 | |
| 376 | FLVGAALAAGLLWKFRTLLMNAVWPKAGRW | E4:E5 | |
| 277 | FLVGAALAAGLLWKFRSLISCE | E4:E4 | |
| 378 | DGVSHCPGGEDENRCGSLISCE | E5:E4 | |
| 379 | MALNSVIPGSLETRGKPC | E2:E2 | |
| 380 | VCTQPKSPSGTVCTSRSLISCE | E3:E4 | |

TABLE A-continued

Peptides for vaccine library.

| SEQ ID NO. | Long peptide for vaccine | Exons | Fusion name |
|---|---|---|---|
| 381 | VCTQPKSPSGTVCTSSYSRIFGDPRKAVLT | E3:E2 | |
| 382 | MALNSLRYLTMMSSLYQTIR | E2:E6 | TMPRSS2/ETV1 |
| 383 | VCTQPKSPSGTVCTSRGSLFPQKLLNAETS | E3:E2 | |
| 384 | KGEPHHELPPGSTKRVPASVQLHTAVEMHH | E8:E9 | TP53/NTRK1 |
| 385 | DAQAGKEPGGSRAHSSPGQCAAAHGGGDAP | E10:E9 | |
| 386 | QPKKKPLDGEYFTLQSRPVCSCTRRWRCTT | E9:E9 | |
| 387 | ERSVAKLEKTIDDLEVYRRKHQELQAMQME | E7:E20 | TPM3/ALK |
| 388 | ERSVAKLEKTIDDLEDTNSTSGDPVEKKDE | E7:E10 | TPM3/NTRK1 |
| 389 | ERSVAKLEKTIDDLEVWHRRLKNQKSAKEG | E8:E35 | TPM3/ROS1 |
| 390 | LQKLEEAEKAADESESTLPTQEEIENLPAF | E2:E36 | |
| 391 | PRMQGPIQQPSISHQEDPKWEFPRKNLVLG | E9:E12 | TRIM24/RET |
| 392 | QLEEKQQQPTRELLQEDPKWEFPRKNLVLG | E3:E12 | |
| 393 | KKGKTAQGLSPVDQREDPKWEFPRKNLVLG | E16:E12 | |
| 394 | VISAENWKPATKTDQGLLKMTEYKLVVVGA | E3:E2 | UBE2L3/KRAS |
| 395 | RNELLGDDGNSSENQSNKVPVVQHPHHVHP | E4:E5 | VTI1A/TCF7L2 |
| 396 | MRSYKQEMGKLETDFSNKVPVVQHPHHVHP | E3:E5 | |
| 397 | MRSYKQEMGKLETDFYLQMKWPLLDVQAGS | E3:E4 | |
| 398 | MVANVEKQLEEAKELSNKVPVVQHPHHVHP | E2:E5 | |
| 399 | LRDNLTLWTSDMQGDAYPALGPGVTANPGT | E5:E2 | YWHAE/FAM22A |
| 400 | LRDNLTLWTSDMQGDAYPVLGPGVTANPGT | E5:E2 | YWHAE/NUTM2B |
| 401 | IKTLEGEFSVTMWSSGPMDEGPDLDLGPPV | E1:E10 | YY1/EWSR1 |
| 402 | FGSTRGSLDKPDSFMGEYSVGNKHRDPFEA | E10:E7 | ZC3H7B/BCOR |
| 403 | QCKTETQESQAFQERGSTTGLSATPPASLP | E3:E10 | ZSCAN30/BRAF |

In some embodiments, the fusion-specific vaccine library comprises 2 or more (e.g., 2-5, 5-10, 10-25, 25-50, 50-100, 100-500, 500-1,000 or more) different fusion junction sequences that can be used as therapeutic vaccines for treating cancer.

In some embodiments, a method was developed for constructing a fusion-specific vaccine library from publicly available data such as but not limited to whole genome sequencing (WGS) data and/or RNA-sequencing data. In some embodiments, sources of publicly available data are databases such as but not limited to COSMIC (cancer.sanger.ac.uk/cosmic/), TCGA Fusion Gene Data Portal (54.84.12.177/PanCanFusV2/), and/or FusionCancer Database (donglab.ecnu.edu.cn/databases/FusionCancer/).

In some embodiments, neoantigenic peptides having amino acid sequences corresponding to the gene fusion junction can be generated. In some embodiments, a library of recurrent fusion-derived neoantigenic peptide vaccines can be constructed containing all cancer-associated neoantigenic peptides or subsets thereof. In some embodiments, a library can contain 2 or more different fusion peptides (e.g., 2-5, 5-10, 10-25, 25-50, 50-100, 100-500, 500-1,000 or more different fusion peptides).

In some embodiments, methods are disclosed for construction of a fusion-derived neoantigenic vaccine library, selection of patients and/or peptides for vaccination, and subsequent treating of patients with neoantigenic vaccines.

In some embodiments, methods for identifying recurrent fusion derived neoepitopes and constructing a vaccine library include several steps (FIG. 2). In some embodiments, methods comprise screening publicly available databases containing information regarding tumor whole genome sequencing (WGS) and/or RNA-sequencing data. In some embodiments, fusion genes and fusion transcripts can be de novo discovered using WGS and/or RNA-sequencing data. In some embodiments, methods integrate publicly available fusion-detection algorithms followed by heuristic filtering.

In some embodiments, methods comprise screening one or more publicly available databases containing information relating to annotated fusion genes, fusion transcripts, breakpoint coordinates of tumor-specific fusion genes, fusion proteins, and/or any resources containing information about recurrent fusions and their presence in tumor(s). In some embodiments, methods comprise screening peer-review articles. In some embodiments, methods comprise screening proprietary databases and/or patient sequence information.

In some embodiments, methods comprise further validation of fusion genes detected by screening publicly available databases containing WGS and/or RNA-sequencing data.

In some embodiments, methods comprise extracting fusion incidence data in cancer(s) from public data sources (e.g., cancer.org and/or cancer.net), proprietary information resources (e.g., uptodate.com) and/or peer-reviewed literature.

In some embodiments, methods comprise translating recurrent fusions to chimeric proteins, identifying long peptides at fusion breakpoints, and predicting peptide binding affinity to MHC class I proteins and/or MHC class II proteins using bioinformatics algorithms. In some embodiments, methods comprise determining peptide binding affinity to MHC proteins using biochemical techniques in vitro.

In some embodiments, methods comprise generating a set of T-cell epitopes by selection of fusion-derived neoepitopes having an $IC_{50}$ less than 500 nM. In some embodiments, the epitopes can bind HLA proteins and be recognized by T-cells. In some embodiments, $IC_{50}$ thresholds for MHC class I-peptide interaction are used for selecting peptides. In some embodiments, MHC class II-peptide interaction are used for selecting peptides.

In some embodiments, methods comprise determining a binding affinity of peptide-HLA class I major genes comprising HLA-A, HLA-B, and/or HLA-C. In some embodiments, methods comprise determining a binding affinity of peptide-HLA class I minor genes comprising HLA-E, HLA-F, and/or HLA-G. In some embodiments, methods comprise determining a binding affinity of peptide-HLA class II genes comprising HLA-DMA, HLA-DMB, HLA-DOA, HLA-DOB, HLA-DPA1, HLA-DPB1, HLA-DQA1, HLA-DQA2, HLA-DQB1, HLA-DQB2, and/or HLA-DR. In some embodiments, methods comprise determining a binding affinity of the peptide to any antigen presenting protein.

In some embodiments, population coverage for each long peptide is calculated based on HLA allele frequency, wherein the HLA protein can bind to the fusion-derived neoepitopes with $IC_{50}$<500 nM. In some embodiments, patient coverage is calculated based on HLA allele frequency and gene fusion incidence rates in tumors. In some embodiments, the patient coverage is the percentage of patients having a particular tumor or tumors comprising a fusion-derived neoantigen included in the library. In some embodiments, patients having a particular tumor or tumors comprising a fusion-derived neoantigen included in the library are vaccinated with one or more fusion-specific vaccines from the library.

In some embodiments, fusion-specific vaccines from the library comprise fusion-derived long peptides having 25-30 amino acids. In some embodiments, fusion-specific vaccines from the library comprise fusion-derived long peptides having 30-50 amino acids. In some embodiments, fusion-specific vaccines from the library comprise fusion-derived long peptides having 50-100 amino acids. In some embodiments, fusion-specific vaccines from the library comprise fusion-derived long peptides encompassing the entire fusion protein.

In some embodiments, fusion-derived neoantigens can be modified by anchor residues, with additional amino acid sequences like T-helper epitopes that can be included in polypeptide for enhancing of in vivo processing, binding to MHC, and/or immunogenicity.

In some embodiments, fusion-derived long peptides in the library are characterized by their association with particular fusion genes from which peptides are derived. In some embodiments, fusion-derived long peptides in the library are characterized by listing the HLA proteins that can effectively present neoepitopes derived from the fusion-derived long peptide. In some embodiments, fusion-derived long peptides in the library are characterized by the population coverage of the fusion-derived long peptide.

In some embodiments, a vaccine library contains fusion-derived long peptides or polypeptides constructed of fusion-derived neoepitopes at the fusion breakpoint. In some embodiments, fusion-derived long peptides or polypeptides in the library are described by cancer types. In some embodiments, fusion-derived long peptides or polypeptides in the library are described by short peptides derived from long peptides, wherein the short peptides interact with MHC class I and/or MHC class II proteins. In some embodiments, fusion-derived long peptides or polypeptides in the library are described by the population coverage.

In some embodiments, the interactions between short peptides and MHC proteins are characterized by an $IC_{50}$, wherein the short peptides bind to MHC proteins with an $IC_{50}$<500 nM. In some embodiments, fusion-derived peptides are formulated with an appropriate carrier or adjuvant. In some embodiments, fusion-derived neoantigens are DNA and/or RNA. In some embodiments, a single vaccine can contain one or more long peptides. In some embodiments, a fusion-derived long peptide can produce several shorter peptides that bind to MHC proteins. In some embodiments, a vaccine targets one or more neoantigens. In some embodiments, a vaccine library targets more neoantigens than the number of vaccines in the library.

Peptide Length

In some embodiments, a fusion-derived peptide in a vaccine has a length of 7-11 amino acids. In some embodiments, the peptide has a length of 7 amino acids. In some embodiments, the peptide has a length of 8 amino acids. In some embodiments, the peptide has a length of 9 amino acids. In some embodiments, the peptide has a length of 10 amino acids. In some embodiments, the peptide has a length of 11 amino acids. In some embodiments the peptide length is 25 or more amino acids, 50 or more amino acids, 75 or more amino acids, or 100 or more amino acids. In some embodiments, the peptides are processed to a shorter length intracellularly. In some embodiments the neoantigenic fusion-derived peptides in the library can include, but are not limited to, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100 or more amino acids. In some embodiments, long peptides in the library correspond to shorter peptides that bind to MHC proteins. In some embodiments, a peptide in a vaccine can be of any suitable length that is sufficient to be immunogenic in a patient.

Peptide Synthesis and Modification

In some embodiments, fusion-derived peptides are in neutral (uncharged) forms or in forms that are salts. Methods for synthesizing peptides are well known in the art. In one embodiment, the peptides provided herein are synthesized using an appropriate solid-state synthetic procedure (see for example, Steward and Young, Solid Phase Peptide Synthesis, Freemantle, San Francisco, Calif. (1968); Merrifield (1967) Recent Progress in Hormone Res 23: 451). However, any other suitable synthetic technique may be used. In some embodiments, one or more peptides provided herein are synthesized by expressing the peptides through standard molecular biological techniques. In some embodiments, one or more peptides provided herein are isolated from natural sources.

In some embodiments, fusion-derived peptides are modified. Modifications should not reduce biological activity of peptides and their ability to induce tumor-specific immune responses. Modifications include but are not limited to phosphorylation, glycosylation, and oxidation. In some embodiments, peptides described herein are linked to one or more additional moieties (e.g., that help promote or stimulate an immune response, stabilize or solubilize the peptide, etc., or any combination thereof).

In some embodiments, fusion-derived peptides are modified for enhancing their in vivo processing, binding to MHC, and/or immunogenicity. In some embodiments, fusion-derived peptide modifications include modification to anchor residues. In some embodiments, anchor residues are position 2 and position 8 in peptides comprising 9-10 amino acid residues. In some embodiments, peptide modifications comprise adding amino acid sequences like T-helper epitopes upstream or downstream.

In some embodiments, fusion-derived neoantigens comprise polypeptides consisting of repeating fusion-derived neoantigenic short peptides.

Patient Selection

In some embodiments, a patient is eligible for treatment with one or more fusion-specific vaccines from the library when the patient's tumor biopsy comprises one or more gene fusions corresponding to fusion-derived peptides or fusion-derived neoantigens present in the library.

In some embodiments, a patient is eligible for treatment with fusion-specific vaccines from the library when the long peptide in the library can bind to the HLA alleles of the patient and be presented to the patient's immune system. In some embodiments, long peptides in the library are characterized by the HLA alleles which can bind the long peptide derivatives and present them to the immune system.

In some embodiments, the long peptide or polypeptide at the point of junction must be able to produce neoantigens for a particular patient. In some embodiments, the patient is eligible for vaccination if at least one HLA allele of the patient matches the HLA allele of the particular fusion-derived neoantigen. In some embodiments, up to six HLA alleles of the patient match the HLA alleles of the particular fusion-derived neoantigen.

In some embodiments, a method of selecting a patient for vaccination with a therapeutic fusion-specific vaccine from a fusion-specific vaccine library is based on one or more factors (e.g., as illustrated in FIG. 3). In some embodiments, selecting a patient for vaccination with a therapeutic peptide vaccine from a fusion-specific vaccine library is based on genetic analysis of a patient's tumor sample (e.g., biopsy) and normal tissue sample. In some embodiments, genetic analysis is performed using one or more techniques that detects fusion genes, fusion transcripts, and/or fusion proteins in a patient's tumor. In some embodiments, genetic analysis is performed with whole genome sequencing, RNA sequencing, proteome sequencing, fluorescence in situ hybridization, pyrosequencing, qPCR, Sanger sequencing, or any known analysis method that allows identification of fusion genes or/and transcripts presented in a tumor sample and absent in a normal tissue sample.

In some embodiments, one or more gene fusions found with WGS and/or RNA sequencing are validated with in vitro techniques. In some embodiments, fusions identified by screening public and proprietary databases for information about the presence of a particular fusion in a particular cancer type are validated with in vitro techniques.

In some embodiments, selecting a patient for vaccination with a therapeutic peptide vaccine from a fusion-specific vaccine library is based on measuring the expression level of the fusion gene or transcript. In some embodiments, the expression level of the fusion gene or transcript is measured by RNA sequencing and/or any technique that measures the expression level of the fusion transcript(s) and/or the corresponding chimeric protein(s). In some embodiments, the fusion is expressed.

In some embodiments, selecting a patient for vaccination with a therapeutic fusion-specific vaccine from a fusion-specific vaccine library is based on the patient's HLA genotype. In some embodiments, the patient is HLA genotyped using one or more serological tests, PCR, WGS, WES, RNA sequencing, and/or any other technique that determines the patient's HLA genes and/or HLA proteins. In some embodiments, the patient's HLA genotyping can be performed in silico with patient's tumor sequencing data comprising transcriptome, exome, and/or genome sequencing data. In some embodiments, HLA genotyping should have at least a 4-digit resolution for matching a patient's HLA alleles to vaccines in the library. However, other thresholds can be used for HLA matching.

In some embodiments, selecting a patient for vaccination with a therapeutic fusion-specific vaccine from fusion-specific vaccine library is based on matching of patient's HLA alleles with HLA alleles that bind to fusion-derived long peptides in the vaccine library. In some embodiments, HLA proteins can bind to peptides derived from the fusion gene detected in a patient's tumor and bind to short peptides derived from long peptides presented in the library. In some embodiments, the patient is eligible for vaccination if at least one HLA allele of the patient matches the HLA allele of the particular fusion-derived peptide. In some embodiments, up to six HLA alleles of the patient matches the HLA alleles of the particular fusion-derived peptide.

In some embodiments, a patient is selected for vaccination with a therapeutic fusion-specific vaccine from the fusion-specific vaccine library if one or more of the fusion-derived long peptide(s) in library are found in the patient's tumor biopsy as part of the expressed fusion protein (e.g., a fusion gene or fusion transcript) and not found in normal tissue(s). In some embodiments, a patient is selected for vaccination with a therapeutic fusion-specific vaccine from the fusion-specific vaccine library if the patient has one or more HLA proteins that can effectively bind and present to the immune system one or more fusion-derived neoantigens that are present in the library. In some embodiments, at least one HLA allele of the patient must match one of the HLA alleles that bind to the fusion-derived neoantigens in the vaccine library.

In some embodiments, long peptides in a library might not bind to a patient's HLA proteins, whereas shorter peptides may bind to one or more of the patient's HLA proteins, and the patient is eligible for vaccination. For example, 30-mer peptides (peptides that are 30 amino acids long) cannot bind to MHC class I proteins, but derivatives of the 30-mer peptides, such as 8-mer, 9-mer, 10-mer, and/or 11-mer peptides will bind to the patient's HLA proteins and can be used to vaccinate the patient.

In some embodiments, a patient may have multiple HLA proteins that match multiple tumor-specific recurrent fusion-derived long peptides present in the library.

In some embodiments, protein mass spectrometry can be used for identifying fusion-derived peptides bound to a patient's HLA proteins. In some embodiments, peptides are eluted from HLA molecules on cancer cells and then analyzed with mass spectrometry and matched with peptides in the vaccine library.

In some embodiments, no appropriate vaccine in the library matches a particular patient and a "de novo" method for identifying tumor-specific chimeric protein-derived neoepitopes in a patient can be used and a patient-specific personalized vaccine composition can be generated.

In some embodiments, patient tumor-specific chimeric protein-derived neoepitopes (e.g., neoantigens) can be determined by sequencing RNA and/or DNA isolated from the patient's tumor biopsy sample(s) and/or normal tissue sample(s).

In some embodiments, fusion transcripts which are present in a tumor sample and absent from normal tissue are identified using established bioinformatical algorithms. In some embodiments, false positive fusion transcripts are filtered out using WGS data, homology of fused genes at RNA level, or other available approaches. In some embodiments, false positive fusion transcripts identified with in silico fusion detection are filtered out using publicly available fusion genes and fusion transcripts and chimeric proteins databases.

In some embodiments, in vitro validation of in silico detected fusion transcripts is performed using qPCR and/or Sanger sequencing with DNA and/or RNA isolated from patient's tumor sample(s) and normal tissue sample(s).

In some embodiments, a set of patient tumor-specific fusion-derived peptides corresponding to a chimeric protein's breakpoint is generated. In some embodiments, a peptide represents one or more novel tumor-specific sequences that are not presented in normal tissues and contains at least one amino acid of one fusion partner, for example from the N-terminal side or from the C-terminal side of the breakpoint, and several amino acids of the other fusion partner (e.g., from the C-terminal side or from the N-terminal side of the breakpoint).

In some embodiments, the patient is HLA genotyped using one or more in vitro techniques such as serological tests or in silico techniques based on WGS, WES or RNA sequencing data.

In some embodiments, binding affinity (or any other parameter characterizing peptide-MHC interaction process) is predicted by means of highly validated bioinformatical algorithms that can be found elsewhere including iedb.org, or cbs.dtu.dk/services/. In some embodiments, the expression level of all identified fusion transcripts corresponding to the patient's tumor-specific fusion-derived peptides are measured using RNA sequencing data or any available technique for measuring expression level of fusion transcript and/or corresponding chimeric protein. In some embodiments, the patient's tumor-specific fusion-derived neoepitopes are expression products of the fusion gene transcript and have $IC_{50}$ to patient's HLA proteins less than 500, less than 250, less than 150, or less than 50 nM.

In some embodiments, a patient's tumor-specific vaccine composition comprises 1, 2, 3, 4, 5, 6, 7, 8, 9, 10, 11, 12, 13, 14, 15, 16, 17, 18, 19, 20 or any appropriate number of patient tumor-specific fusion-derived peptides, wherein the composition optionally comprises one or more DNA or RNA constructs encoding such peptides.

In some embodiments, a variety of bioinformatical algorithms and pipelines have been established for identifying tumor-specific fusions and generating corresponding neoepitopes.

Peptide Selection

In some embodiments, gene fusion peptides are selected based on $IC_{50}$ for HLA proteins. In some embodiments, gene fusion peptides having an $IC_{50}$ of more than 500 nM are considered non-binding. In some embodiments, peptides with an $IC_{50}$ of less than 500 nM are considered binding. In some embodiments, peptide vaccine compositions comprise gene fusion peptides having $IC_{50}$ less than 500 nM, less than 450 nM, less than 400 nM, less than 350 nM, less than 300 nM, less than 250 nM, less than 200 nM, less than 150 nM, less than 100 nM, less than 50 nM, less than 25 nM, less than 10 nM, or less than 1 nM for one or more HLA proteins of a patient are selected for a vaccine for that patient (e.g., one or more of these concentration thresholds can be used for determining peptide matches for a patient). However, other $IC_{50}$ thresholds (e.g., higher, lower, or intermediate concentrations) can be used to determine whether a peptide is a match for a patient.

In some embodiments, a gene fusion peptide $IC_{50}$ is predicted using established computational methods. In some embodiments, computational methods include NetMHC (e.g., cbs.dtu.dk/services/NetMHC/) and NetMHCpan (e.g., cbs.dtu.dk/services/NetMHCpan/). In some embodiments, a gene fusion peptide $IC_{50}$ is determined in vitro using one or more biochemical assays. Methods described herein are not limited by the techniques used to identify the gene fusion peptide $IC_{50}$.

In some embodiments, binding of gene fusion peptides to HLA proteins is determined from biological samples by eluting peptides from HLA proteins and analyzing them using mass spectrometry.

In some embodiments, gene fusion peptides are selected based on patient coverage. In some embodiments, gene fusion peptides having patient coverage greater than 5%, greater than 10%, greater than 20%, greater than 30%, greater than 40%, greater than 50%, greater than 60%, greater than 70%, greater than 80%, or greater than 90% are selected.

In some embodiments, the vaccine library can be expanded with the same methods described herein to incorporate new recurrent fusion data as it emerges.

Biological Samples

Methods provided herein detect gene fusions in biological samples. Biological samples, as used herein, refer to samples taken or derived from a patient. These samples may be tissue samples or they may be fluid samples (e.g., a bodily fluid). Examples of biological fluid samples are whole blood, plasma, serum, urine, sputum, phlegm, saliva, tears, and other bodily fluids. In some embodiments, the biological sample is a whole blood sample, or a sample of white blood cells from a subject. In some embodiments, the biological sample is a tumor, a fragment of a tumor, a tumor biopsy, or a tumor cell(s).

Treatment

Other aspects of the specification relate to methods of treatment for a patient with cancer. Cancer includes, but is not limited to: melanoma, skin cancer, head and neck cancer, breast cancer, lung cancer, ovarian cancer, cervical cancer, prostate cancer, thyroid cancer, kidney cancer, liver cancer, pancreatic cancer, gastric cancer, testicular cancer, brain tumor, glioma, glioblastoma, solitary fibrous tumor, bladder cancer, colorectal cancer, renal cell carcinoma, sarcoma, myeloma, leukemia, and/or lymphoma.

In some embodiments, the treatment is regimented to modulate the patient's immune system to induce a response against a tumor comprising a gene fusion. In some embodiments, treatment comprises administering a peptide vaccine one or more times to a patient. In some embodiments, an initial vaccine can be administered followed by one or more booster administrations. In some embodiments, a vaccine can be administered once or more daily, weekly, monthly, or at other time intervals or other frequencies. The frequency of administration and the duration of a treatment (e.g., once, one week, 1-4 weeks, 1-12 months or longer) can depend on the severity of the disease, the effectiveness of the vaccine, and/or the health of the patient. In some embodiments, treatment comprises administering a peptide vaccine at day 1, 4, 8, 15, and 21 and at week 12, 20, 30, and 40.

In some embodiments, vaccines can be administered intravenously (i.v.), intradermally (i.d.), parenterally, intraperitoneally (i.p.), subcutaneously (s.c.), intramuscularly (i.m.), orally, sublingually, intranasally, rectally, or intravaginally. The treatment is not limited to the method of vaccine administration.

In some embodiments, treatment comprises therapeutic or prophylactic vaccination of a patient with a tumor or at risk of developing cancer, and inducing antitumor immune responses in the patient. In some embodiments, treatment comprises preventive vaccination of the patient against a tumor by one or more peptides from the library or vaccine composition identified with methods described herein.

In some embodiments, treatment comprises treating a patient with a fusion-derived peptide or vaccine composition in combination with one or more additional therapies. In some embodiments, an additional therapy is an FDA approved therapy. In some embodiments, an additional therapy is an experimental therapy that is not yet approved. In some embodiments, vaccination of a patient is combined with one or more targeted therapies, chemotherapies, radiation, immunotherapy, or with hematopoietic stem cell transplantation. In some embodiments, any other suitable therapy for a particular tumor and patient may be combined with vaccination. In some embodiments, suitable therapies that can be combined with vaccination include but are not limited to immunotherapies, for example checkpoint blockade therapies, for example, but not limited to, anti-PD1 (e.g., nivolumab (Opdivo®), pembrolizumab (Keytruda®), pidilizumab etc), anti-CTLA4 (e.g., ipilimumab (Yervoy®), tremelimumab), or other checkpoint inhibitors such as BMS-936559, MPDL3280A, MEDI4736, MSB0010718C, IMP321, MGA271.

One aspect of the specification provides methods for treating a patient having a tumor and eliciting an antitumor immune response in the patient by administering dendritic cells (or other antigen presenting cells) that have been pulsed with at least one fusion-derived peptide (or coding mRNA or DNA) from the vaccine library. The dendritic cells (or other antigen presenting cells) pulsed in this manner comprise at least one fusion-derived peptide (or coding mRNA or DNA) from the vaccine library.

In some embodiments, the vaccine composition comprises at least two distinct peptides wherein each peptide corresponds to the amino acid sequence at the point of junction and each peptide is equal to or less than 50 amino acids in length.

In some embodiments, peptides or vaccine compositions are administered at concentrations sufficient to induce an antitumor immune response in the patient. Concentrations of peptides and vaccine components and dosing regimens can be easily determined by anyone skilled in the art.

In some embodiments, treatment comprises administering a vaccine having a peptide concentration of 1-10 mg per injection. In some embodiments, peptide doses per patient for one vaccination are 100 ng or more (e.g., 100-500 ng, 500-1,000 ng, or more), 1 µg or more (e.g., 1-10 µg, 10-100 µg, 100-500 µg, 500-1,000 µg, or more), 1 mg or more (e.g., 1-10 mg, 10-50 mg, 50-100 mg, or more), or 100 mg or more. In some embodiments, peptide doses per patient are adjusted depending on patient condition, patient weight, cancer stage and severity. In some embodiments, peptide doses and treatment regimen can vary depending on a patient's response to therapy. In some embodiments, peptide doses and treatment regimen can vary depending on a patient's condition.

The concentration of peptides provided in the pharmaceutical formulations can vary widely, e.g., from less than about 0.1%, usually at or at least about 2% to as much as 20% to 50% or more by weight, and will be selected primarily by fluid volumes, viscosities, etc., in accordance with the particular mode of administration selected.

In some embodiments, the peptide concentration in the vaccine (e.g., for each peptide, or the combined total peptide concentration) is around 1 nM, around 250 nM, around 500 nM, around 750 nM, around 1 µM, around 250 µM, around 500 µM, around 750 µM, around 1 mM, around 250 mM, around 500 mM, around 750 mM, or around 1M, or more or an intermediate concentration. In some embodiments, the peptide dose per patient is around 1 ng, around 250 ng, around 500 ng, around 750 ng, around 1 µg, around 250 µg, around 500 µg, around 750 µg, around 1 mg, around 250 mg, around 500 mg, around 750 mg, around 1,000 mg, or more or an intermediate amount.

In some embodiments, an initial dose is (e.g., for therapeutic or prophylactic administration) from about 1.0 µg to about 50,000 µg of peptide for a 70 kg patient, followed by subsequent doses (e.g., boosting doses) of from about 1.0 µg to about 10,000 µg of peptide pursuant to a regimen (e.g., a boosting regimen) over weeks to months depending upon the patient's response and condition. However, in some embodiments, subsequent doses can be the same as the initial dose. It should be appreciated that equivalent dosages for patients in different weight ranges can be calculated. In some embodiments, a typical dose (e.g., daily dose) is at least 0.1 µg/kg, at least 1 µg/kg, at least 10 µg/kg, at least 25 µg/kg, at least 50 µg/kg, at least 100 µg/kg, at least 250 µg/kg, at least 500 µg/kg, at least 750 µg/kg, at least 1 mg/kg, at least 10 mg/kg, or more or an intermediate range between any of these values.

In some embodiments, DNA or mRNA encoding a fusion-derived peptide or polypeptide is administered to a patient. In some embodiments, DNA or mRNA encoding a fusion-derived peptide or polypeptide is incorporated into a vector. In some embodiments, DNA or mRNA comprises additional sequences including but not limited to a T-helper sequence. In some embodiments, DNA or mRNA comprises standard regulatory sequences that ensure expression in a particular cell type. In some embodiments, DNA or mRNA comprises additional sequences encoding proteins such as IL-2 or GM-CSF that can increase a patient's immune response. In some embodiments, DNA or mRNA is transfected into mammalian cells with techniques including but not limited to electroporation.

In some embodiments, autologous T-cells can be collected from a patient and stimulated ex vivo with fusion-derived peptides and/or DNA or RNA encoding the fusion-derived peptides. In some embodiments, autologous T-cells can be collected from a patient and stimulated ex vivo with fusion-derived peptides and/or DNA or RNA encoding the fusion-derived peptides and the stimulated T-cells are infused into the patient.

In some embodiments, DNA or RNA encoding the fusion-derived peptides comprises attenuated viral vectors. In some embodiments, viral vectors comprise BCG, vaccinia, and/or fowlpox.

In some embodiments, the library can be used for treating subjects diagnosed with cancer, wherein the subject is human. In some embodiments, the subject can be a mouse, cat, dog, horse, primate, or any animal.

Use of a Therapeutic Fusion-Specific Vaccine for Treating Cancer

To practice the method disclosed herein, an effective amount of the pharmaceutical composition (e.g., vaccine) described herein can be administered to a subject (e.g., a human) in need of the treatment via a suitable route (e.g., intravenous administration, subcutaneous, intradermal, or other route).

The subject to be treated by the methods described herein can be a human patient having cancer. Examples of cancer includes, but is not limited to, melanoma, skin cancer, head and neck cancer, breast cancer, lung cancer, ovarian cancer, cervical cancer, prostate cancer, thyroid cancer, kidney cancer, liver cancer, pancreatic cancer, gastric cancer testicular cancer, brain tumor, glioma, glioblastoma, solitary fibrous tumor, bladder cancer, colorectal cancer, renal cell carcinoma, sarcoma, myeloma, leukemia, and/or lymphoma.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having a cancer. A subject having a cancer can be identified by routine medical examination, e.g., laboratory tests, PET scan, biopsy, PET scans, CT scans, or ultrasounds. A subject having a cancer might show one or more symptoms of the disorder, e.g., unexplained weight loss, fever, fatigue, pain, skin changes, unusual bleeding or discharge, and/or thickening or lumps in parts of the body. A subject at risk for a cancer can be a subject having one or more of the risk factors for that disorder. For example, risk factors associated with cancer include (a) viral infection (e.g., herpes virus infection), (b) age, (c) family history, (d) heavy alcohol consumption, (e) obesity, and (f) tobacco use.

"An effective amount" as used herein refers to the amount of each active agent required to confer therapeutic effect on the subject, either alone or in combination with one or more other active agents. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

Empirical considerations, such as the half-life, generally will contribute to the determination of the dosage. For example, antibodies that are compatible with the human immune system, such as humanized antibodies or fully human antibodies, may be used to prolong half-life of the peptide and to prevent the peptide being attacked by the host's immune system. Frequency of administration may be determined and adjusted over the course of therapy, and is generally, but not necessarily, based on treatment and/or suppression and/or amelioration and/or delay of a cancer. Alternatively, sustained continuous release formulations of a fusion-specific vaccine may be appropriate. Various formulations and devices for achieving sustained release are known in the art.

In one example, dosages for a fusion-specific vaccine as described herein may be determined empirically in individuals who have been given one or more administration(s) of a fusion-specific vaccine. Individuals are given incremental dosages of the fusion-specific vaccine. To assess efficacy of the fusion-specific vaccine, an indicator of a cancer (such as tumor formation or tumor growth) can be followed.

In some embodiments, dosing frequency is once every week, every 2 weeks, every 4 weeks, every 5 weeks, every 6 weeks, every 7 weeks, every 8 weeks, every 9 weeks, or every 10 weeks; or once every month, every 2 months, or every 3 months, or longer. The progress of this therapy is easily monitored by conventional techniques and assays. The dosing regimen (including the fusion-specific vaccine used) can vary over time. For repeated administrations over several days or longer, depending on the condition, the treatment is sustained until a desired suppression of symptoms occurs or until sufficient therapeutic levels are achieved to alleviate a cancer, or a symptom thereof.

For the purpose of the present disclosure, the appropriate dosage of a fusion-specific vaccine will depend on the specific fusion-specific vaccine(s) (or compositions thereof) employed, the type and severity of cancer, whether the fusion-specific vaccine is administered for preventive or therapeutic purposes, previous therapy, the patient's clinical history and response to the antagonist, and the discretion of the attending physician. Typically the clinician will administer a fusion-specific vaccine, until a dosage is reached that achieves the desired result. Administration of a fusion-specific vaccine can be continuous or intermittent, depending, for example, upon the recipient's physiological condition, whether the purpose of the administration is therapeutic or prophylactic, and other factors known to skilled practitioners. The administration of a fusion-specific vaccine may be essentially continuous over a preselected period of time or may be in a series of spaced dose, e.g., either before, during, or after developing cancer.

As used herein, the term "treating" refers to the application or administration of a composition including one or more active agents to a subject, who has a cancer, a symptom of a cancer, or a predisposition toward a cancer, with the purpose to cure, heal, alleviate, relieve, alter, remedy, ameliorate, improve, or affect the disorder, the symptom of the disease, or the predisposition toward a cancer.

Alleviating a cancer includes delaying the development or progression of the disease, or reducing disease severity. Alleviating the disease does not necessarily require curative results. As used therein, "delaying" the development of a disease (such as lung cancer) means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a cancer includes initial onset and/or recurrence.

In some embodiments, the fusion-specific vaccine described herein is administered to a subject in need of the treatment at an amount sufficient to induce a immunological response against a tumor by at least 5% (e.g., 15%, 30%, 40%, 50%, 60%, 70%, 80%, 90% or greater). In other embodiments, the fusion-specific vaccine is administered in an amount effective in reducing tumor metastasis. Alternatively, the fusion-specific vaccine is administered in an amount effective in reducing tumor formation or tumor growth.

Conventional methods, known to those of ordinary skill in the art of medicine, can be used to administer the pharmaceutical composition to the subject, depending upon the type of disease to be treated or the site of the disease. This composition can also be administered via other conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods.

Injectable compositions may contain various carriers such as vegetable oils, dimethylactamide, dimethyformamide, ethyl lactate, ethyl carbonate, isopropyl myristate, ethanol, and polyols (glycerol, propylene glycol, liquid polyethylene glycol, and the like). For intravenous injection, water soluble antibodies can be administered by the drip method, whereby a pharmaceutical formulation containing the antibody and a physiologically acceptable excipients is infused. Physiologically acceptable excipients may include, for example, 5% dextrose, 0.9% saline, Ringer's solution or other suitable excipients. Intramuscular preparations, e.g., a sterile formulation of a suitable soluble salt form of the antibody, can be dissolved and administered in a pharmaceutical excipient such as Water-for-Injection, 0.9% saline, or 5% glucose solution.

In one embodiment, a fusion-specific vaccine is administered via site-specific or targeted local delivery techniques. Examples of site-specific or targeted local delivery techniques include various implantable depot sources of the fusion-specific vaccine or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing a polynucleotide, expression vector, or subgenomic polynucleotides can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338. Therapeutic compositions containing a polynucleotide are administered in a range of about 100 ng to about 200 mg of DNA for local administration in a gene therapy protocol. In some embodiments, concentration ranges of about 500 ng to about 50 mg, about 1 µg to about 2 mg, about 5 µg to about 500 µg, and about 20 µg to about 100 µg of DNA or more can also be used during a gene therapy protocol.

The therapeutic polynucleotides and polypeptides described herein can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581.

It is also apparent that an expression vector can be used to direct expression of any of the fusion-specific vaccines described herein. The particular dosage regimen, i.e., dose, timing and repetition, used in the method described herein will depend on the particular subject and that subject's medical history.

In some embodiments, more than one fusion-specific vaccine may be administered to a subject in need of the treatment. The fusion-specific vaccine can correspond to the same tumor junction sequence or different tumor junction sequences. At least one, at least two, at least three, at least four, at least five different fusion-specific vaccines can be co-administered. Generally, those fusion-specific vaccines have complementary activities that do not adversely affect each other. Fusion-specific vaccines can also be used in conjunction with other agents that serve to enhance and/or complement the effectiveness of the agents.

Treatment efficacy can be assessed by methods well-known in the art, e.g., monitoring tumor growth or formation in a patient subjected to the treatment.

Combination Therapy

Also provided herein are combined therapies using any of the fusion-specific vaccines described herein and another anti-cancer therapeutic agent, such as those described herein. The term combination therapy, as used herein, embraces administration of these agents (e.g., a fusion-specific vaccine and an anti-cancer therapeutic agent) in a sequential manner, that is, wherein each therapeutic agent is administered at a different time, as well as administration of these therapeutic agents, or at least two of the agents, in a substantially simultaneous manner. In some embodiments, combination therapies include two or more therapeutic agents (e.g., vaccines or other agents) combined in the same composition. However, in many embodiments, different therapeutic agents are provided in separate compositions. Sequential or substantially simultaneous administration of each agent can be affected by any appropriate route including, but not limited to, oral routes, intravenous routes, intramuscular, subcutaneous routes, and direct absorption through mucous membrane tissues. The agents can be administered by the same route or by different routes. For example, a first agent (e.g., a fusion-specific vaccine) can be administered orally, and a second agent (e.g., an anti-cancer agent) can be administered intravenously.

As used herein, the term "sequential" means, unless otherwise specified, characterized by a regular sequence or order, e.g., if a dosage regimen includes the administration of a fusion-specific vaccine and an anti-cancer agent, a sequential dosage regimen could include administration of the fusion-specific vaccine before, simultaneously, substantially simultaneously, or after administration of the anti-cancer agent, but both agents will be administered in a regular sequence or order. The term "separate" means, unless otherwise specified, to keep apart one from the other. The term "simultaneously" means, unless otherwise specified, happening or done at the same time, i.e., the agents of the invention are administered at the same time. The term "substantially simultaneously" means that the agents are administered within minutes of each other (e.g., within 10 minutes of each other) and intends to embrace joint administration as well as consecutive administration, but if the administration is consecutive it is separated in time for only a short period (e.g., the time it would take a medical practitioner to administer two agents separately). As used herein, concurrent administration and substantially simultaneous administration are used interchangeably. Sequential administration refers to temporally separated administration of the agents described herein.

Combination therapy can also embrace the administration of the agents described herein (e.g., a fusion-specific vaccine and an anti-cancer agent) in further combination with other biologically active ingredients (e.g., a different anti-cancer agent) and non-drug therapies (e.g., surgery).

It should be appreciated that any combination of a fusion-specific vaccine and another anti-cancer agent (e.g., a chemotherapeutic agent) may be used in any sequence for treating a cancer. The combinations described herein may be selected on the basis of a number of factors, which include but are not limited to the effectiveness of inducing an immune response, reducing tumor formation or tumor growth, and/or alleviating at least one symptom associated with the cancer, or the effectiveness for mitigating the side effects of another agent of the combination. For example, a combined therapy described herein may reduce any of the side effects associated with each individual members of the combination, for example, a side effect associated with the anti-cancer agent.

In some embodiments, another anti-cancer therapeutic agent is a chemotherapy, a radiation therapy, a surgical therapy and/or an immunotherapy. Examples of the chemotherapeutic agents include, but are not limited to, Carboplatin or Cisplatin, Docetaxel, Gemcitabine, Nab-Paclitaxel, Paclitaxel, Pemetrexed, and Vinorelbine. Examples of radiation therapy include, but are not limited to, ionizing radiation, gamma-radiation, neutron beam radiotherapy, electron beam radiotherapy, proton therapy, brachytherapy, and systemic radioactive isotopes and radiosensitizers. Examples of a surgical therapy include, but are not limited to, a curative surgery (e.g., tumor removal surgery), a preventive surgery, a laparoscopic surgery, and a laser surgery. Examples of an immunotherapy include, but are not limited to, a PD-1 inhibitor or a PD-L1 inhibitor, adoptive cell transfer, and therapeutic cancer vaccines.

Additional examples of chemotherapy include, but are not limited to, Platinating agents, such as Carboplatin, Oxaliplatin, Cisplatin, Nedaplatin, Satraplatin, Lobaplatin, Triplatin, Tetranitrate, Picoplatin, Prolindac, Aroplatin and other derivatives; Topoisomerase I inhibitors, such as Camptothecin, Topotecan, irinotecan/SN38, rubitecan, Belotecan, and other derivatives; Topoisomerase II inhibitors, such as Etoposide (VP-16), Daunorubicin, a doxorubicin agent (e.g., doxorubicin, doxorubicin HCl, doxorubicin analogs, or doxorubicin and salts or analogs thereof in liposomes), Mitoxantrone, Aclarubicin, Epirubicin, Idarubicin, Amrubicin, Amsacrine, Pirarubicin, Valrubicin, Zorubicin, Teniposide and other derivatives; Antimetabolites, such as Folic family (Methotrexate, Pemetrexed, Raltitrexed, Aminopterin, and relatives); Purine antagonists (Thioguanine, Fludarabine, Cladribine, 6-Mercaptopurine, Pentostatin, clofarabine and relatives) and Pyrimidine antagonists (Cytarabine, Floxuridine, Azacitidine, Tegafur, Carmofur, Capecitabine, Gemcitabine, hydroxyurea, 5-Fluorouracil (5FU), and relatives); Alkylating agents, such as Nitrogen mustards (e.g., Cyclophosphamide, Melphalan, Chlorambucil, mechlorethamine, Ifosfamide, mechlorethamine, Trofosfamide, Prednimustine, Bendamustine, Uramustine, Estramustine, and relatives); nitrosoureas (e.g., Carmustine, Lomustine, Semustine, Fotemustine, Nimustine, Ranimustine, Streptozocin, and relatives); Triazenes (e.g., Dacarbazine, Altretamine, Temozolomide, and relatives); Alkyl sulphonates (e.g., Busulfan, Mannosulfan, Treosulfan, and relatives); Procarbazine; Mitobronitol, and Aziridines (e.g., Carboquone, Triaziquone, ThioTEPA, triethylenemalamine, and relatives); Antibiotics, such as Hydroxyurea, Anthracyclines (e.g., doxorubicin agent, daunorubicin, epirubicin and other derivatives); Anthracenediones (e.g., Mitoxantrone and relatives); Streptomyces family (e.g., Bleomycin, Mitomycin C, Actinomycin, Plicamycin); and Ultraviolet light.

Pharmaceutical Compositions

In some embodiments, methods are provided for constructing a fusion-derived vaccine library which can be used for treating a patient having cancer and eliciting an immune response in the patient. In some embodiments, the vaccine comprises fusion-derived long peptides or polypeptides comprising neoantigens peptides matched to patients HLA and which can induce an antitumor immune response in the patient. In some embodiments, the immune response can be detected by analyzing IFN-γ production or tumor killing activity of T-cells in vitro.

In some embodiments, the vaccine comprises one fusion-derived long peptide at a breakpoint or several shorter derivatives of the long peptide. In some embodiments, the vaccine comprises 1, 2, 3, 4, 5, 6, 7, 8, 9, 10, 11, 12, 13, 14, 15, 16, 17, 18, 19, or 20 neoantigenic peptides that can be bound by the patient's HLA class I and/or class II proteins. It should be appreciated that the vaccine comprising one or more neoantigenic peptides may further comprise one or more additional therapeutic agents. Alternatively, or in addition, on or more additional therapeutic agents may be administered separately In some embodiments, a vaccine comprises two or more different peptides that are selected for a patient, wherein the peptide are mixed together in a single vaccine composition for administration to the patient. However, in some embodiments, two or more different peptides can be administered separately to a patient. It should be appreciated that a vaccine can contain any suitable concentration of each of the two or more peptides. In some embodiments, the concentration of each peptide in the vaccine is identical or similar. However, in some embodiments, different peptides can be provided at different concentrations.

In some embodiments, the vaccine comprises fusion-derived long peptides or polypeptides that are processed into shorter neoantigenic peptides which can be bound to at least one HLA class I protein of the patient. In some embodiments, the vaccine comprises fusion-derived long peptides or polypeptides that are processed into shorter neoantigenic peptides which can be bound to one or more, two or more, three or more, four or more, five or more, or six HLA class I protein of the patient. In some embodiments, peptides can bind to HLA class II proteins and induce helper T-cell response.

In some embodiments, a vaccine comprises several different fusion-derived long peptides or polypeptides corresponding to several different fusion genes present in the patient's tumor. In some embodiments, compositions comprises one or more, or two or more neoantigenic fusion-derived peptides.

In some embodiments, vaccine compositions comprises any adjuvant that can be used to activate an immune response in a patient. In some embodiments, an adjuvant can be any substance or any compound incorporated into a vaccine composition that increases the immune response of the patient to the fusion-derived peptides. Examples of adjuvants include, but are not limited to, poly-ICLC, Poly (I:C), GM-CSF, BCG, monophosphoryl lipid A, MF59, Freund's adjuvants, Montanide IMS, Montanide ISA 206, Montanide ISA-51, Montanide ISA 50V, Aluminium salts, Alhydrogel, Rehydrogel HPA, PLGA, MPL1, ASO4, ASO1B, ASO2A, P3CSK4, CpG-ODN, Imiquimod ISS, ONTAK, LipoVac, Amplivax, CpG7909, dSLIM, IC30, IC31, SRL172, virus particles, YF-17D, AS15, OK-432, IMP321, OM-174, cytokines, and other adjuvants that can be found in the field using any source (e.g., peer-reviewed literature or medical guidelines).

In some embodiments, fusion-derived peptides are administered separately from one or more adjuvant(s). In some embodiments, fusion-derived peptides are administered along with one or more adjuvant(s). In some embodiments, vaccine compositions comprise one or more adjuvants and one or more fusion-derived peptides.

In some embodiments, vaccine compositions comprise different carriers such as polysaccharides, polypeptides, proteins, liposomes, or antigen presenting cells. In some embodiments, peptides might be combined with carriers that increase their immunogenicity, biological activity, and/or stability. In some embodiments, carriers include, but are not limited to, proteins such as bovine serum albumin (BSA), human serum albumin, immunoglobulins, transferrin, insulin; and/or carbohydrates such as lactose, cellulose, starch. In some embodiments, carriers are proteins such as diphtheria toxoid, tetanus toxoid, influenza virus proteins, and/or herpes virus proteins. In some embodiments, vaccine compositions comprise any carriers that are safe and acceptable for patients.

In some embodiments, vaccine compositions comprise at least one or more autologous antigen presenting cells (APC) pulsed with respective fusion-derived peptides from library. Pulsing APC cells may be performed in any manner known in the field. See, for example, Boczkowski et al, J Exp. Med. 1996 Aug. 1; 184(2): 465-72; see also: O'Neill and Bhardwaj, Adoptive Immunotherapy: Methods and Protocols, 2005, Volume 109 pp 97-112, which are incorporated by reference herein for this purpose. In some embodiments, vaccine compositions comprise at least one or more autologous antigen presenting cells (APC) comprising fusion-derived peptides from library. In some embodiments, APCs can be dendritic cells, macrophages, B-cells, or any professional antigen presenting cell. In some embodiments, APCs can be loaded with DNA or mRNA encoding respective fusion-derived peptide(s) of a vaccine library. In some embodiments, vaccine compositions comprise autologous peripheral blood mononuclear cells (PBMC).

In another aspect, vaccine compositions comprise components directed to the personal needs of a particular patient. In some embodiments, the personal needs of a particular patient include but are not limited to allergies, previous treatments, and/or comorbidities.

In some embodiments, fusion-derived peptides from a library can be combined with any other tumor-specific neoantigens for a particular patient that are not included in the vaccine library. In some embodiments, fusion-derived peptides from a library can be combined with tumor-specific neoantigens for a particular patient that have been identified de novo from WGS, WES, or RNA sequencing data.

In some embodiments, vaccine compositions can be prepared in sterilized water. In some embodiments, vaccine compositions can be prepared in buffered solutions such as but not limited to 0.9% saline.

One or more of the fusion-specific vaccines provided herein can be mixed with a pharmaceutically acceptable carrier (excipient), including buffer, to form a pharmaceutical composition for use in treating cancer. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

For example, a pharmaceutical composition described herein contains one or more fusion-specific vaccines that correspond to one or more tumor-specific gene fusions. In one example, a pharmaceutical composition described herein contains more than one fusion-specific vaccines that recognize a tumor-specific gene fusion. In another example, the pharmaceutical composition comprises at least two fusion-specific vaccines that correspond to different tumor-specific gene fusions. Alternatively or in addition, the pharmaceutical composition comprises one or more peptide vaccines or other anticancer agents. It should be appreciated that any of the pharmaceutical compositions provided herein may be administered alone, separately or in a combination.

The pharmaceutical compositions to be used in the present methods can comprise pharmaceutically acceptable carriers, excipients, or stabilizers in the form of lyophilized formulations or aqueous solutions. (Remington: The Science and Practice of Pharmacy $20^{th}$ Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™ (polysorbate), PLURONICS™ (poloxamers) or polyethylene glycol (PEG). Pharmaceutically acceptable excipients are further described herein.

In some examples, the pharmaceutical composition described herein comprises liposomes containing the fusion-specific vaccine, which can be prepared by methods known in the art, such as described in Epstein, et al., Proc. Natl. Acad. Sci. USA 82:3688 (1985); Hwang, et al., Proc. Natl. Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized p hosphatidyletnanolamine (PEG-PE). Liposomes are extruded through filters of defined pore size to yield liposomes with the desired diameter.

The active ingredients (e.g., a fusion-specific vaccine) may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are known in the art, see, e.g., Remington, The Science and Practice of Pharmacy 20th Ed. Mack Publishing (2000).

In other examples, the pharmaceutical composition described herein can be formulated in sustained-release format. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions to be used for in vivo administration must be sterile. This is readily accomplished by, for example, filtration through sterile filtration membranes. However, other sterilization techniques, including but not limited to heat, chemical, and/or radiation based sterilization techniques may be used. Therapeutic vaccine compositions are generally placed into a container having a sterile access port, for example, an intravenous solution bag or vial having a stopper pierceable by a hypodermic injection needle.

The pharmaceutical compositions described herein can be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient can be mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described herein containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g., Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 .im, particularly 0.1 and 0.5 .im, and have a pH in the range of 5.5 to 8.0.

The emulsion compositions can be those prepared by mixing a fusion-specific vaccine with Intralipid™ (a lipid emulsion) or the components thereof (soybean oil, egg phospholipids, glycerol and water).

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect.

Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Kits for Use in Treating Cancer

The present disclosure also provides kits for use in alleviating cancer. Such kits can include one or more containers comprising a fusion-specific vaccine. In some embodiments, the kit can comprise instructions for use in accordance with any of the methods described herein. The included instructions can comprise a description of administration of the fusion-specific vaccine to treat, delay the onset, or alleviate a cancer according to any of the methods described herein. The kit may further comprise a description of selecting an individual suitable for treatment based on identifying whether that individual has cancer. In still other embodiments, the instructions comprise a description of administering a fusion-specific vaccine to an individual having, suspected of having, or at risk for a cancer.

The instructions relating to the use of a fusion-specific vaccine generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a cancer. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is a fusion-specific vaccine.

Kits may optionally provide additional components such as buffers and interpretive information. Normally, the kit comprises a container and a label or package insert(s) on or associated with the container. In some embodiments, the invention provides articles of manufacture comprising contents of the kits described herein.

Without further elaboration, it is believed that one skilled in the art can, based on the description herein, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Computational Methods

It should be appreciated that the various aspects and concepts of the present methods described herein may be implemented in any of numerous ways, and are not limited to any particular implementation technique. Examples of specific implementations are described below for illustrative purposes only, but the aspects of the methods described herein are not limited to these illustrative implementations.

Figure 5:
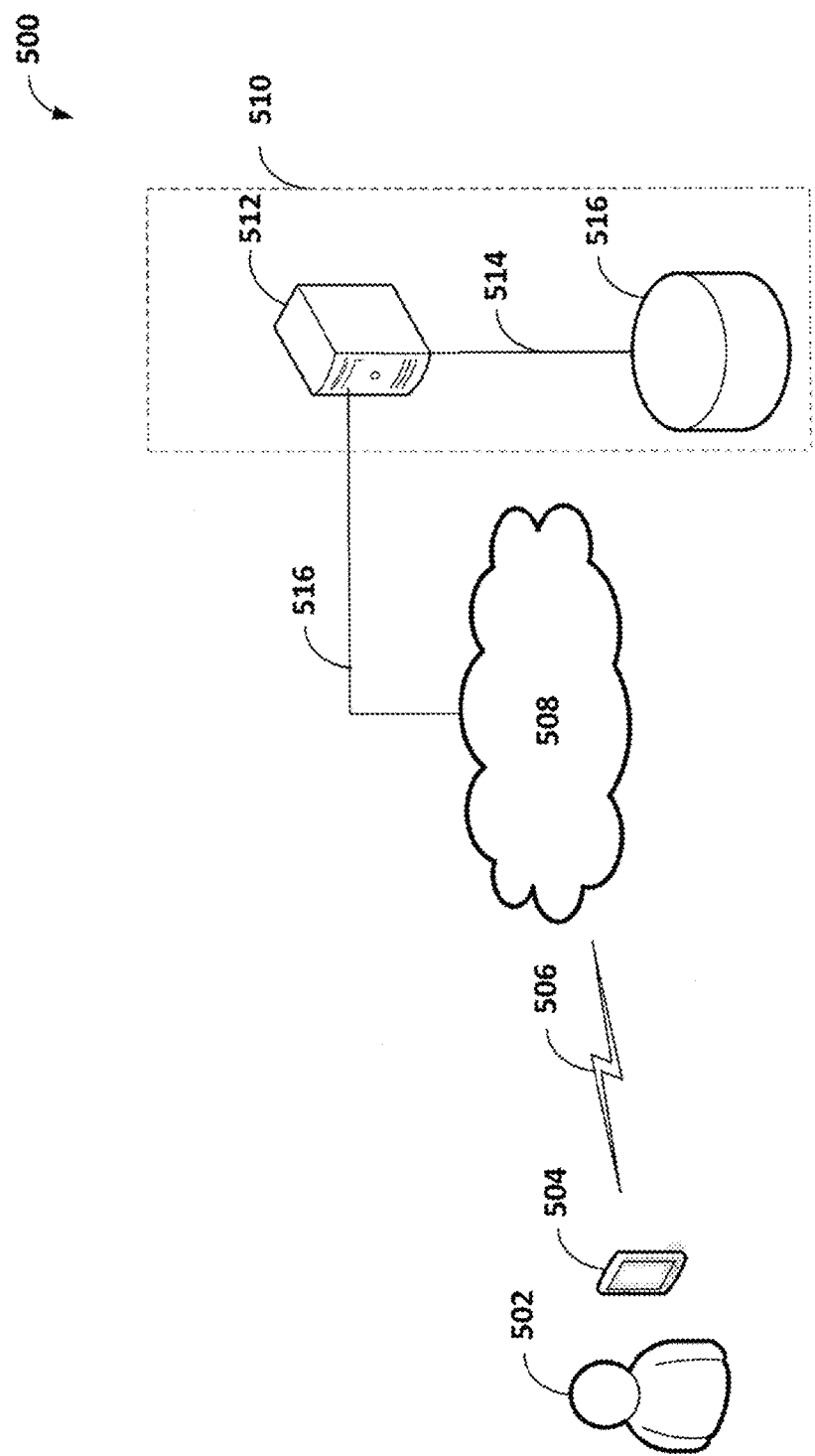
FIG. 5 shows a non-limiting example of an environment in which embodiments of the present methods may operate.

FIG. 5 shows a non-limiting illustrative environment 500 in which embodiments of the present methods may operate. In the illustrative environment, healthcare provider 502 may use any device 504 to obtain information from system 510. Healthcare provider 502 may obtain information from system 510 one time or multiple times. Information between healthcare provider 502 and system 510 may be initiated in any suitable way.

In some embodiments, device 504 may be any suitable device that healthcare provider 502 may use to obtain information from system 510. For instance, device 504 may be a dedicated mobile phone (e.g., a cellular phone), a mobile smart phone, a personal digital assistant (PDA), a laptop computer, a tablet computer, or any other mobile device capable of supporting an exchange of information through a communications medium (e.g., a wired or wireless communications medium). In some embodiments, healthcare provider 502 is not limited to obtaining information by using a mobile device and may use any device capable of obtaining information. For instance, healthcare provider 502 may obtain information from 510 by using a telephone connected to landline, a desktop computer connected to a network such as the Internet, or using any other device capable of communicating with system 510. It should also be recognized that if healthcare provider 502 obtains information from system 510, healthcare provider 502 is not limited to using the same device. Thus, healthcare provider 502 may obtain information using one or a plurality of different devices, each of which may be any suitable device capable of obtaining information.

Information may be any suitable information relating to patient data and/or library data. Information is not limited by the type of communications infrastructure or communications medium used to obtain the information. For example, information may be patient information such as but not limited to a patient's identity, cancer type, gene fusion, and/or HLA allele information. As another example, information may be library information such as but not limited to peptide sequence information, peptide-HLA affinities, sequences of DNA and/or RNA encoding peptide sequence information, and/or gene fusion information.

In the illustrated embodiment, device 504 communicates with system 510 through a communication medium 508. Communication medium 508 may be any suitable network or other type of communication medium. For example, communication medium 508 may be a cellular network, a local area network, a circuit-switched telephone network, a public-switched telephone network, the Internet, some combination of any of the foregoing, or any other communication medium capable of supporting telecommunications.

In the illustrated embodiment, device 504 is communicatively coupled to communication medium 508 via wireless connection 506 and system 510 is communicatively coupled to communication medium 508 using a wired connection 516. This is merely for illustration, as device 504 and system 510 each may be communicatively coupled to communication medium 508 in any suitable way including wired and/or wireless connections.

System 510 comprises one or more computers (e.g., servers) each configured to perform processing related to supporting matching patient data and library data. In the illustrated embodiment, system 510 comprises a single server 512, though in other embodiments any suitable number of servers may be used and distributed in any manner. For instance, in some embodiments, system 510 may comprise at least ten, at least one hundred, at least one thousand, or at least ten thousand servers. For embodiments in which system 510 comprises multiple servers, the servers need not be located in the same physical location and may be distributed across multiple physical locations.

Each server, such as server 512, may be configured (alone or in combination with one or more other servers) to support one or more applications and may be configured to execute any other programs. For example, one or more of the servers may be configured to execute programs for supporting functionality related to patient data, library data, patient and library matching, and/or any other functions used in embodiments of the present methods.

As previously discussed, a healthcare provider, such as healthcare provider 502, may conduct one or multiple analyses with system 510. Multiple analyses may take place over any suitable time period of any suitable length. In some embodiments, system 510 calculates HLA-peptide affinities. In some embodiments, system 510 calculates HLA-peptide matching and a healthcare provider obtains this information. In some embodiments, a healthcare provider receives matched HLA-peptide information from system 510.

As discussed herein, system 510 may obtain any suitable data associated with one or more healthcare providers (e.g., information identifying healthcare provider 502, patient information, library information, patient and library matching information, etc.). System 510 may obtain any of the above-described data, associated with one or more healthcare providers, in any suitable way. For example, system 510 may extract this data from information collected from healthcare provider 502. In this case, system 510 may store at least a portion of the obtained data on one or more storage devices 516 so that it may be retrieved from the one or more storage devices for subsequent use as discussed herein.

Storage device(s) 516 may be any suitable storage device(s) or article(s) of manufacture capable of storing information. For example, storage device(s) 516 may be any non-transitory computer readable storage medium or media such as a computer memory (RAM and/or ROM), one or more hard disk drives, one or more optical disks (CDs and/or DVDs), one or more magnetic tapes, one or more flash memories, one or more circuit configurations in Field Programmable Gate Arrays and/or any other suitable device(s).

In the illustrated embodiment, storage device(s) 516 are shown as being part of system 510 and as being connected to server 512 by wired connection 514. It should be appreciated that all embodiments are not limited in this respect. For example, in other embodiments, storage device(s) 516 may be connected to server 512 using any suitable type of connection or communication medium, and may be internal or external to system 510. When storage device(s) 516 are external to system 510, the system may be communicatively coupled to storage device(s) 516 to obtain information from them in any suitable manner.

While FIG. 5 shows only a single healthcare provider using a single device 504, it should be recognized that embodiments of the present method are not limited in this respect and that system 510 may be configured to service any number of healthcare providers (e.g., hundreds, thousands, or greater) who may be using any number of devices (e.g., hundreds, thousands, or greater). Data associated with one or more patients made by each healthcare provider may be stored on at least one storage device (e.g., storage device 516 and/or on devices that the healthcare provider(s) use).

Regardless of where data associated with one or more patients involving one or more healthcare providers may be stored, such data may be stored in any suitable form. FIG. 6 shows a non-limiting example of a data structure 600 that may be used to store data associated with one or more patients in accordance with one embodiment. While in the illustrated embodiment data structure 600 is shown in the form of a table, this is not a limitation of the present method, as any suitable data structure may be used to store the data.

Data structure 600 may store any suitable data associated with one or more patients between any of one or more healthcare providers and system 510. In one non-limiting example described herein, data structure 600 may store patient identification data 602, patient data 604, library data 606, and/or data matching 608. In some embodiments, patient identification data 602 comprises information relating to patient identification such as name and date of birth. In some embodiments, patient data 604 comprises information relating to a patient's cancer type, gene fusion information, and/or HLA allele information. In some embodiments, library data 606 comprises information relating to peptide sequence, peptide-HLA affinity, sequences of DNA and/or RNA encoding peptides, gene fusion sequences, gene fusion cancer types, and $IC_{50}$. In some embodiments, data matching 608 comprises information relating to peptide population coverage, allele coverage, and information matching peptides to HLA alleles, peptides to gene fusions, and/or peptides to cancer types. However, it should be recognized that these examples are not limiting, and that data structure 600 may store any other data associated with one or more patients.

For each patient, data structure 600 may store one or more data records. A data record may store any suitable data associated with a patient and may store such data in any suitable format (e.g., in one or more fields). Each field may store any suitable amount of data and any suitable type of data and, for example, may store alphanumeric data representing the data directly, or a pointer to another location where data may be stored. In some instances, data structure 600 may store the same type of data record for each patient, but this is not a limitation on the data structure or other aspects of the methods described herein, as in other embodiments, data structure 600 may store one type of data record for one patient and another type of data record for another patient. For example, a data record for one patient may store a different amount of data than another data record for another patient.

Data structure 600 may store any suitable number of data records. In FIG. 6, data structure 600 is shown as storing four data records, but it should be appreciated that the data structure may store many more (e.g., hundreds, thousands, millions, etc.) data records.

Each data record in data structure 600 is shown as having four fields; however, this is for purposes of illustration only and is not a limitation of the present methods as any suitable number of fields may be used. For instance, any suitable number of fields may be used to store information identifying the patient, and any suitable number of fields may be used to store data associated with the patient.

Figure 7:
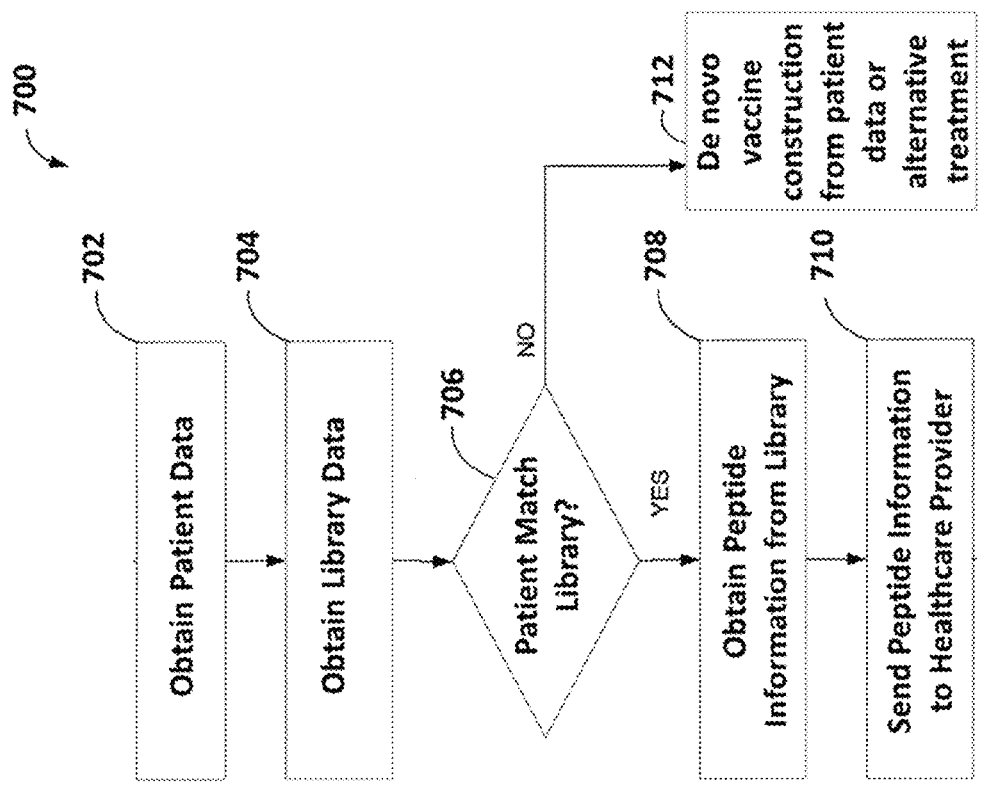
FIG. 7 shows flow chart of an illustrative process for matching patient data and library data, in accordance with some embodiments of the present methods.

FIG. 7 shows a flow chart of an illustrative process for matching patient data and library data, in accordance with some embodiments of the present method.

Process 700 begins in act 702, where patient data may be received from a healthcare provider. The patient data may be received by a system, such as system 510, and may be received in any suitable way. Next, process 700 proceeds to act 704, where library information is obtained.

After the library information is obtained in act 704, process 700 proceeds to decision block 706, where it is determined whether patient information obtained in act 702 matches library information obtained in act 704. For example, it may be determined, in decision block 706, whether the patient is a candidate for treatment with one or more peptide vaccines from the library. As disclosed herein, such data may include patient allele data, peptide sequence information, and/or any of the other types of data described herein.

If it is determined, in decision block 706, that library data does not match data associated with one or more patients, process 700 proceeds to act 712, where a patient may be identified as a candidate for de novo vaccine generation and treatment or a candidate for alternative treatment.

If it is determined in decision block 706 that library data matches patient data, process 700 proceeds to act 708, where at least a portion of the library data may be retrieved. The data to retrieve may be any suitable data and may be determined in any suitable way. After peptide library data associated with one or more patients is retrieved in act 708, process 700 proceeds to act 710, where peptide information is sent to the healthcare provider.

Figure 8:
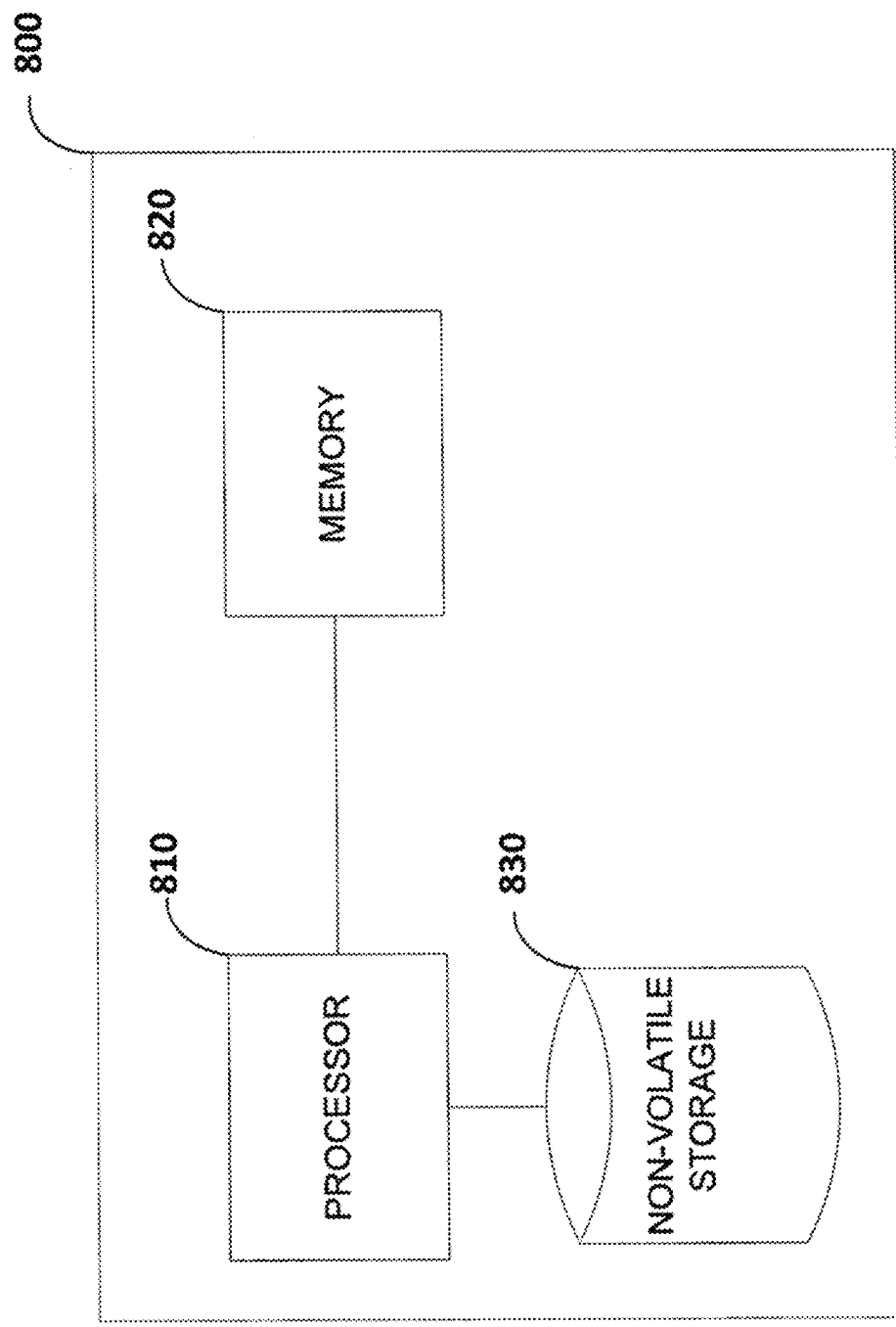
FIG. 8 shows a block diagram of an illustrative computer system that may be used in implementing aspects of the present methods.

An illustrative implementation of a computer system 810 that may be used in connection with any of the embodiments of the method described herein is shown in FIG. 8. The computer system 800 may include one or more processors 810 and one or more articles of manufacture that comprise non-transitory computer-readable storage media (e.g., memory 820 and one or more non-volatile storage media 830). Processor 810 may control writing data to and reading data from memory 820 and non-volatile storage device 830 in any suitable manner, as the aspects of the method described herein are not limited in this respect. To perform any of the functionality described herein, processor 810 may execute one or more processor-executable instructions stored in one or more non-transitory computer-readable storage media (e.g., memory 820), which may serve as non-transitory computer-readable storage media storing processor-executable instructions for execution by processor 810.

The terms "program" or "software" are used herein in a generic sense to refer to any type of computer code or set of processor-executable instructions that can be employed to program a computer or other processor to implement various aspects of embodiments as discussed herein. Additionally, it should be appreciated that according to one aspect, one or more computer programs that when executed perform methods described herein need not reside on a single computer or processor, but may be distributed in a modular fashion among different computers or processors to implement various aspects of the present method.

Programs for Fusion Detection in RNA Sequence and/or WGS Data

In some embodiments, any one of the more than 30 publicly available programs for fusion detection can be used (programs available at omicstools (omictools.com/gene-fusion-detection-category). In some embodiments, more than one program for fusion detection is used. In some embodiments, the results from different fusion detection programs may significantly diverge.

In some embodiments, fusion detection programs are alignment-based programs that map reads to a reference and infer breakpoint positions from discordantly aligned reads. The majority of existing programs are alignment-based programs. However, alignment-based programs may differ in references (genome, transcriptome or both) or aligners, e.g., STAR (ncbi.nlm.nih.gov/pmc/articles/PMC3530905/), TopHat2 (ncbi.nlm.nih.gov/pmc/articles/PMC4053844/) or bowtie2 (ncbi.nlm.nih.gov/pmc/articles/PMC3322381/) and therefore give very diverse results.

In some embodiments, de novo assembly-based programs perform transcriptome assembly and align obtained sequences to a reference transcriptome and thus find chimeric transcripts. In some embodiments, the de novo assembly-based program JAFFA (genomemedicine.biomedcentral.com/articles/10.1186/s13073-015-0167-x) can be used in 'assembly' mode.

In some embodiments, fusion detection programs are a hybrid of alignment-based and de-novo assembly-based approaches. In some embodiments, the hybrid approach first aligns reads to known transcriptome similar to the alignment-based approach. In some embodiments, the hybrid approach re-assembles unaligned reads and fragments spanning a breakpoint to new sequences. In some embodiments, the hybrid approach re-assembles unaligned reads and fragments spanning a breakpoint to new sequences using TRUP (ncbi.nlm.nih.gov/pmc/articles/PMC4300615/).

In some embodiments, fusion callers may be used for de novo assembly. In some embodiments, fusion callers consume a lot of resources and time. In some embodiments, fusion callers and alignment-based tools gave the same results.

In some embodiments, a program has filters that influence the results produced by the program. In some embodiments, a program has its own set of filters with specific default values. In some embodiments, a program has a filter for low fusion coverage that filters out low frequency junction or spanning reads. In some embodiments, a program has a filter for homology that filters out fusion partners with long homological regions. In some embodiments, a program has a filter for minimal distance between fusion partners that filters out potential read through transcripts. In some embodiments, a program has a promiscuity filter that filters out fusions containing partner transcripts which are presented in many other fusions. In some embodiments, a program generates a program-specific list of frequent false-positives.

In some embodiments, multiple fusion detection programs are used to determine a gene fusion recurrence rate. In some embodiments, four fusion detection programs are used to identify gene fusions. In some embodiments, a gene fusion is detected by two out of four fusion detection programs. In some embodiments, the fusion detection programs used are ChimeraScan (ncbi.nlm.nih.gov/pmc/articles/PMC3187648/), SOAP-fuse (ncbi.nlm.nih.gov/pmc/articles/PMC4054009/), and Integrate (genome.cshlp.org/content/early/2015/11/10/gr.186114.114.abstract).

Algorithm for Calculating Fusion-Derived Peptide Lengths

In some embodiments, fusion-derived peptide lengths are calculated from gene fusions. In some embodiments, computational algorithm (1) is used for calculating fusion-derived peptide lengths, $$S(X, L) = \text{Right}(SA_1, 3 \cdot (L-1) + RF(\text{Right}(SA_1, 1)) \cap \text{Left}(SB_2, BT), \quad (1)$$

$$BT = \begin{vmatrix} RF(\text{Right}(SA_1, 1)) = \\ RF(\text{Left}(SB_2, 1)) \to 3 \cdot (L-1) + 3 - RF(\text{Left}(SB_2, 1)) \\ RF(\text{Right}(SA_1, 1)) \neq RF(\text{Left}(SB_2, 1)) \to 3 - RF(\text{Right}(SA_1, 1)) + \\ LRF(\text{Shift}(SB_2, 3 - RF(\text{Right}(SA_1, 1)))) \end{vmatrix}$$

wherein X is a fusion of genes A and B, $SA_1$ is a transcript sequence of A to the left of the fusion breakpoint, $SA_2$ is a transcript sequence of A to the right of the fusion breakpoint, $SB_1$ is a transcript sequences of B to the left of the fusion breakpoint, $SB_2$ is a transcript sequence of B to the right of the fusion breakpoint, $SA_1 \cap SB_2$ is a fusion transcript sequence, $SA_1 \cap SA_2$ is a transcript sequence of gene A, $SB_1 \cap SB_2$ is a transcript sequence of gene B, L is the peptide length, Right and Left return a given number of bases to rightmost or leftmost, Shift skips a given number of bases on the left, RF is a position of a base in open reading frame, and LRF is the length of ORF. Fusion X yields a joint set of mutant peptides $\{S(X,L_i)\}$ where peptide length $L_i$ varies in some predefined range $L_{min} \ldots L_{max}$.

Algorithm for HLA Genotyping

In some embodiments, HLA genotyping is calculated in silico from genome, exome, transcriptome, and/or HLA sequencing data. In some embodiments, a set of predicted HLA alleles that a patient may have is generated using computation algorithm (2), $$CA_k \in CA, \sum_i CA_k \in A_{ij} \geq \frac{|H|}{2} \quad (2)$$

wherein $H_i$ is a HLA genotyping algorithm, $A_{ij}$ is a set of HLA alleles predicted by algorithm $H_i$, and CA is a set of HLA alleles. In some embodiments, $A_{ij}$ should have 4-digit precision (e.g., HLA-A0201). In some embodiments, the set of HLA alleles CA is used for matching patient and vaccine.

Algorithms for Predicting MHC-Peptide Binding

Algorithms are available for predicting MHC-peptide binding affinity and (algorithms available at cancerimmunity.org/resources/webtools/ or cbs.dtu.dk/services/). In some embodiments, MHC-peptide binding was predicted with NetMHC and NetMHCpan programs (NetMHC (ncbi.nlm.nih.gov/pubmed/26258412, NetMHCpan ncbi.nlm.nih.gov/pubmed/25588790).

In some embodiments, MHC molecules of class I consist of a heavy chain and a light chain and bind to peptides comprising 8 to 11 amino acids. In some embodiments, MHC molecule of class I bind to peptides comprising 9 or 10 amino acids. In some embodiments, long peptides or entire proteins are degraded in the cell, bound to MHC proteins, and presented to cytotoxic T-cells.

In some embodiments, HLA proteins bind peptides comprising 8 to 14 amino acids. In some embodiments, peptides with predicted $IC_{50} < 500$ nM are considered to bind to HLA proteins. In some embodiments, peptides with predicted $IC_{50} < 50$ nM are considered as strong binders to HLA proteins. In some embodiments, peptides with predicted $IC_{50} > 500$ nM are considered as non-binders to HLA proteins. In some embodiments, non-binding peptides are filtered out from a list of peptides. In some embodiments, a population coverage for each long peptide is calculated using only those HLA proteins that can bind its short derivatives. In some embodiments, a long peptide comprising 30 amino acids can be shortened into peptides comprising 9 amino acids for predicting binding to HLA proteins. In some embodiments, mutant peptides are compared to wild type counterparts for binding affinity.

Algorithm for Calculating Population Coverage of Fusion-Derived Peptides

In some embodiments, a population coverage of fusion-derived peptides is calculated. In some embodiments, a population coverage of fusion-derived peptides is an estimate of how many patients will be eligible candidates for vaccination with the fusion-derived peptide. In some embodiments, a population coverage of fusion-derived peptides is calculated from the incidence of the corresponding gene fusion. In some embodiments, a population coverage of fusion-derived peptides is calculated from the allele frequency of HLA proteins that bind to the fusion-derived peptide. In some embodiments, a population coverage of fusion-derived peptides is calculated using computation algorithm (3), $$P = \Sigma_i Q(F_i)(1 - \Sigma_j (1 - Q((A_{ij}))^2 \quad (3)$$

wherein $A_{ij'} \cap_k (A_{ijk})$, $A_{ij'}$ is a set of alleles matching peptides yielded by fusion $F_i$, $F_i$ is a set of fusions yielding a set of peptides $D_{ij}$ comprising the given peptide vaccine, $A_{ijk}$ is the HLA alleles that can bind peptide $D_{ij}$, $Q(A_{ijk})$ is the allele frequency of allele $A_{ijk}$, $Q(F_i)$ is the incidence rate of fusion $F_i$, and P is the probability that a patient will be a candidate for treatment with the peptide vaccine.

DEFINITIONS

"Fusion transcript" refers to a product of fusion gene. Fusion transcript and chimeric transcript are used interchangeably.

"Fusion protein" or "chimeric protein" refers to a product of a fusion transcript and may emerge from genomic rearrangement, read through transcript, or trans-splicing. Fusion protein and chimeric protein are used interchangeably.

"Fusion variant" refers to a variant at particular breakpoints in fusion partner genes. "Fusion exonic variant" refers to a variant at breakpoints leading to fusion of the same partner gene exons.

"Point of junction" and "breakpoint" refer to the point at which two genes, transcripts, or proteins are fused together.

"Administering" or "administration" means providing a material to a subject in a manner that is pharmacologically useful.

"At risk" patients are patients that a health practitioner believes has a chance of having a disease, disorder or condition as provided herein.

"HLA proteins" refers to human leukocyte antigen (HLA) proteins that bind peptides resulting from proteolytic cleavage of protein antigens and representing potential T-cell epitopes, transporting them to the cell surface and presenting them there to specific cells, in particular cytotoxic T-lymphocytes or T-helper cells. HLA proteins are products of HLA genes that are classified into two gene groups coding for different proteins, namely proteins of HLA class I and proteins of HLA class II. HLA class I proteins and HLA class II proteins are specialized for different antigen sources. HLA class I proteins present endogenously synthesized antigens, for example viral proteins and tumor antigens. HLA class II proteins present protein antigens originating from exogenous sources, for example bacterial products. "HLA protein" and "MHC protein" are used interchangeably.

"Vaccine" refers to a composition for generating immunity for the prophylaxis and/or treatment of diseases. Vaccines are compositions comprising antigens and are intended to be used in humans or animals for generating specific defense and protective substance by vaccination.

"Peptide" refers to a series of residues, typically L-amino acids, connected one to the other, typically by peptide bonds between the α-amino and carboxyl groups of adjacent amino acids. Peptides can be a variety of lengths, either in neutral (uncharged) forms or in forms which are salts, and either free of modifications or containing modifications, subject to the condition that the modification not destroy the biological activity of the peptide as described herein. It should be appreciated that a "peptide sequence" or "sequence" may be used to refer to a "peptide" having a particular sequence in the present disclosure in some contexts. In some embodiments, a "long peptide" refers to a peptide comprising about 11-30 amino acid residues corresponding to the fusion breakpoint. In some embodiments, the long peptide is processed into a neoantigenic peptide comprising about 8-11 amino acid residues.

"Neoantigen" refers to a tumor antigen which is produced from tumor-specific mutations in expressed genes. "Fusion-derived", "fusion-specific", and "neoantigen" are used interchangeably. "Neoantigenic peptides" refers to peptides that comprise tumor-specific amino acid sequences (e.g., that contain a fusion junction that is only found in cancer cells due to the genetic rearrangement that is only present in the cancer cells). "Fusion-derived peptide", "fusion-specific peptide", and "neoantigenic peptide" are used interchangeably.

"$IC_{50}$" refers to the concentration of gene fusion peptide necessary for inhibiting binding of a standard peptide to the HLA protein by fifty percent.

"Patient coverage" refers to the percentage of patients (e.g., in a population, for example in a population that is being treated or evaluated) that have a gene fusion corresponding to a fusion-specific neoantigen present in the vaccine library and that have HLA proteins capable of binding the fusion-specific neoantigen.

"Pulsing" refers to the process of antigen loading onto a cell, wherein the antigen may be a nucleic acid or a peptide.

EXAMPLES

Example 1: Therapeutic Cancer Vaccines Comprising Fusion-Specific Peptides

A therapeutic cancer vaccine should guide the immune response and be readily combine with other therapies. Therapeutic cancer vaccines can be composed of processed tumor cells, peptides, whole proteins, DNA, or mRNA. Vaccine antigens include tumor-associated antigens (TAA), differentiation antigens, or cancer-testis antigens. However, many antigens that are present in cancer cells are also present in peripheral organs, thus specifically targeting cancer cells is difficult. The first and only FDA approved therapeutic cancer vaccine called "Provenge" showed modest efficacy in prostate cancer (ncbi.nlm.nih.gov/pubmed/16809734).

Advances in sequencing technologies and bioinformatics algorithms have made it possible to identify mutations in whole cancer genomes. However, "de novo" identification of mutations from whole genome (WGS), whole exome (WES) or RNA sequencing data is expensive and time consuming. Many patients are in need of immediate treatment, especially patients with aggressive tumors like lung cancer, advanced melanoma, or acute leukemia.

Fusion genes have a higher reoccurrence rate than the reoccurrence rates of missense mutations or frameshift mutations. Highly mutated genes including TP53, PIK3CA, EGFR, KRAS, BRAF, and NRAS can be found across different tumor types, yet the reoccurrence rate of mutations in these genes is low. Moreover, recurrent fusion genes and recurrent driver mutations are often mutually exclusive. Thus, recurrent fusions are attractive as a source of neoantigens for the construction of "off-the-shelf" vaccine libraries for at least two reasons: high recurrence rate and the ability to drive cancer (ncbi.nlm.nih.gov/pubmed/25500544). The following examples provide a background for the construction and methods of use of a therapeutic cancer vaccine library comprising fusion-specific vaccines.

Murine Neoantigen Peptide Vaccines

In one study (ncbi.nlm.nih.gov/pubmed/25428507), neoantigenic peptides were identified and used for vaccination of mice. The study showed that two 3-methylcholanthrene-induced sarcoma cell lines d42m1-T3 and F244 were effectively rejected with anti-PD-1 and/or anti-CTLA-4 therapies. The immunological nature of the rejection was confirmed with multiple experimental approaches including depleting CD4+ and CD8+ T-cells with mouse antibodies, performing experiments in mice lacking T, B, natural killer T-cells or dendritic cells, and generating immunological memory in the mice.

The study identified neoantigens responsible for the checkpoint blockade therapy-mediated tumor rejection using a genomic approach. The approach was initially established for identifying TSA responsible for spontaneous rejection of d42m1 sarcomas (ncbi.nlm.nih.gov/pubmed/22318521). The study included features including mutation calling from exome sequencing data, translating mutations to corresponding protein sequences, predicting peptide-MHC class I binding affinity for each epitope, prioritizing epitopes, and filtering out epitopes with lower expression level and lower binding affinity in comparison to the wild-type peptides. Two mutant epitopes for murine MHC H-2Kb were identified in this study: ITYTWTRL (SEQ ID NO: 612) (A506T mutation in alpha-1,3-glucosyltransferase) and VGFNFRTL (SEQ ID NO: 613) (G1254V mutation in laminin alpha subunit 4). Both epitopes were shown to be targets of CD8+ T-cells generated as a consequence of anti-PD1 treatment by experiments including MHC tetramer-binding assays, mass spectrometry detection of epitopes, and ELISPOT assays. Mice were vaccinated with two peptide vaccines based on the identified mutant epitopes and 9/10 mice rejected their tumors and survived. As a negative control, mice were vaccinated with human papillomavirus 28-mer peptides and only 1/10 mice survived. In multiple experiments of mice vaccination, the survival rate for mice vaccinated with therapeutic neoantigenic vaccines was 85% while the survival rate of mice vaccinated with human papillomavirus peptides was only 10%.

In another study (ncbi.nlm.nih.gov/pubmed/25901682), a bioinformatics approach was used to detect tumor-specific mutations from cancer exome sequencing data for B16F10 tumor (melanoma) and colon carcinoma model CT26 in three independent mouse models with different MHC backgrounds. Mutant epitopes were prioritized using both MHC class I and class II prediction algorithms. A considerable fraction of detected mutations produced immunogenic neoantigens which can be recognized by both CD8+ and CD4+ T-cells. Vaccination with the identified immunogenic neoantigens produced anti-tumor activity and complete tumor rejection. About two-thirds of the mice vaccinated with the neoantigenic peptides were alive at day 100 while all untreated mice died at day 65. Interestingly, depletion experiments showed that CD4+ instead of CD8+ T-cells played a major role in anti-cancer response efficacy. Also, immunization with neoantigens encoded by mRNA elicited higher anti-tumor activity than immunization with peptides only. Taken together, this study showed that both MHC class I and class II restricted epitopes can be selected based on binding affinity and can display high anti-tumor potency.

In another study (ncbi.nlm.nih.gov/pubmed/25428506), neoepitopes were identified using whole-exome and transcriptome sequencing analysis with mass spectrometry. This approach identified neoepitopes in MC-38 and TRAMP-C1 mouse tumor cell lines using mutation calling from sequencing data, identification of expressed neoantigens using RNA-sequencing data, prediction of MHC class I binding interactions, and filtering of immunogenic epitopes. Six epitopes were predicted to bind with an $IC_{50}$ less than 500 nM. Immunization of C57BL/6 mice with peptides encoding all six mutated epitopes elicited CD8+ T-cell responses in three out of six mice. Vaccination with long peptides encoding mutant epitopes had therapeutic and preventive effects. Subsequent challenging of vaccinated mice with MC-38 tumor cells didn't result in tumor spreading or growth compared to mice immunized with adjuvant only which experienced tumor spreading and growth.

As described herein, bioinformatics pipelines for detecting and prioritizing neoantigens in whole cancer exomes and/or transcriptomes have made it possible to select targets for vaccination using solely in silico simulation steps. Computational pipelines validated in mice models have improved mouse survival rates and inspired confidence in the potential success of vaccination with personalized neoantigenic vaccines in humans.

Average Bioinformatics Pipelines for Neoantigen Prediction

The following two examples illustrate a non-limiting schematic pipeline used for neoantigen generation from sequencing data (FIG. 1).

In one study (ncbi.nlm.nih.gov/pubmed/24894089), epitope-MHC class I binding prediction algorithms were applied to a large set of neoantigens which had been known to induce strong anti-tumor activity or long-term cancer control. The study analyzed 40 epitopes previously identified as cytotoxic T-cell targets in the literature including 35 epitopes resulting from missense mutations and 5 epitopes resulting from frame-shift mutations. All epitopes were restricted by HLA class I alleles and were present in non-small cell lung cancer, melanoma, renal cell carcinoma, bladder cancer, B-cell acute lymphoblastic leukemia, multiple myeloma, and chronic lymphocytic leukemia. All epitopes were neoantigens that had been identified from cloning, mass spectrometry experiments, genomic mutations, and epitope-binding predictions. Using artificial neural network based prediction algorithms, 27 of 31 of the epitopes recognized by T-cells were predicted to have binding affinity of less than 500 nM to MHC class I proteins. Two-thirds of the patients experienced spontaneous complete tumor regression or tumor regression following therapy. Thus, in silico peptide-MHC class I binding predictions provided a reliable tool to identify neoantigens from exome and/or transcriptome data, and inclusion of such neoantigens in vaccine formulations provided tumor regression in patients.

In another study (ncbi.nlm.nih.gov/pubmed/24891321), neoantigens in human cancer genomes were identified using bioinformatics. A bioinformatics pipeline was applied to 91 whole exomes obtained from chronic lymphocytic leukemias (CLL) biopsies from a group of patients who developed durable remission after allo-HSCT. On average 20 neoantigens derived from 16 missense mutations were predicted to bind HLA class I proteins and more than 50% of all neoantigen were confirmed to bind HLA proteins with biochemical studies. The general steps of the computational pipeline were DNA sequencing, mutation calling, peptide-MHC class I predictions, and experimental validation of binding peptides. From a total of 1838 detected mutations, 3 general classes of mutations were identified including missense, frameshift and splice site mutations. The most abundant class of mutations were missense mutations which represented more than 90% of all detected mutations in cancer genomes (or exomes). A computational pipeline was applied to 2488 whole exome sequences from 13 tumor types and to a large set of HLA alleles. The analysis revealed that one point mutation produced on average 1 to 5 neoantigens and 1 frameshift mutation produced 4 neoantigens with an $IC_{50}<50$ nM. Neoantigens derived from frameshift mutations and gene fusions are expected to be more specific and more immunogenic because there is no corresponding wild type peptide. The study demonstrated that neoantigens derived from frameshift mutations and from gene fusions can be predicted using computational methods.

Vaccines Comprising Modified Fusion-Derived Peptides

The Wilms tumor gene 1 (WT1) can be used as a biomarker in different cancer types including acute myeloid leukemia (AML). In the clinical trial NCT00398138, WT1-positive patients with AML were treated with synthetic analogs of WT1 protein fragments in combination with adjuvants. Synthetic peptide analogs of WT1 protein fragments were designed to bind HLA molecules better than wild-type counterparts and were shown to more effectively induce a WT1-specific T-cell response compared to wild-type counterparts.

Anchor-modified peptides derived from PASD1 were shown to induce a cytotoxic T-cell response against tumor cells in AML patients. Interestingly, their non-modified wild-type analogs demonstrated no detectable binding to HLA proteins. These two examples demonstrate that neoantigenic peptide modifications can lead to an increase in peptide immunogenicity.

Vaccines Based on Fusion-Derived Neoantigens

The Philadelphia chromosome is the result of a translocation between chromosomes 22 and 9. This translocation is present in several cancers types and most notably the translocation is present in ~95% of chronic myelogenous leukemia (CML) cases. The translocation produces a fusion between BCR and ABL1 genes. The ABL1 kinase is constitutively active in the BCR/ABL1 fusion protein and this upregulation of activity leads to dysregulation of cell division and development of cancer.

The sequence spanning the BCR/ABL1 breakpoint is absent in normal tissues and is present only in cancer cells, thus it may be recognized and attacked by the immune system. In a series of recent studies, peptides spanning the BCR/ABL breakpoint were shown to stimulate the immune response.

Cancer specific gene fusions have been used as neoantigens in several anti-cancer vaccines (Table 1). The EWS/

FLI1 gene fusion is present in more than 85% of Ewing's sarcoma tumors (ncbi.nlm.nih.gov/pubmed/17250957) and the PAX-3/FKHR gene fusion is present in 55% of patients with alveolar rhabdomyosarcoma (ARMS) (ncbi.nlm.nih.gov/pubmed/12039929).

TABLE 1

List of fusions used as neoantigens in anti-cancer vaccines.

| Gene Fusion | Patent |
|---|---|
| BCR/ABL-1 [1-5] | google.com.ar/patents/US5997869 |
| EWS/FLI-1 (ncbi.nlm.nih.gov/pubmed/12039929) | google.com.ar/patents/US5997869 |
| PAX-3/FKHR (ncbi.nlm.nih.gov/pubmed/12039929) | google.com.ar/patents/US5997869 |
| TMPRSS2|ERG (ncbi.nlm.nih.gov/pubmed/24149465) | |

Example 2: Follicular Lymphoma (FL) Gene Fusions are Present in Multiple Cancer Types Detection of recurrent chimeric transcripts was performed on 34 follicular lymphoma (FL) transcriptome samples from SRP048820 (ncbi.nlm.nih.gov/pubmed/25607463) and SRP056293 (ncbi.nlm.nih.gov/pmc/articles/PMC4676270/). Transcriptome samples included read through transcripts, products of trans-splicing, and chimeric transcripts formed as a result of genomic rearrangements. Chimeric transcripts were identified as recurrent if present in one or more of the FL transcriptome samples. Chimeric transcripts were identified as present in the sample if detected using two or more software programs, wherein the software programs were ChimeraScan, SOAPFuse, and Integrate.

An average of 28-29 fusion candidates were detected per sample. A total of 308 fusion candidates were detected with 149 of the fusion candidates found in more than one sample. A number of gene fusions present in the FL samples are also found in other cancer types including gastric, colon, breast, and prostate cancers (Table 2).

Neoantigenic peptides for each recurrent fusion protein having a predicted IC50 less than 500 nM to HLA class I proteins were selected. The prediction analysis can be performed using various length peptides, for example a peptide with 9 amino acids corresponding to 9 amino acids of the fusion junction. HLA class I alleles that bind to peptides with an $IC_{50}$ less than 500 nM are identified as binding (Table 3). All fusion-derived peptides were novel and could be placed into a vaccine library. Patients are eligible for vaccination if they have a gene fusion corresponding to a fusion-derived peptide in the library and if the patient has at least one MHC class I alleles capable of binding to the fusion-derived peptide in the library. Methods of selecting a patient for vaccination and vaccine compositions are described herein.

TABLE 2

Recurrent Fusions Detected in Follicular Lymphoma (FL) Samples

| Gene Fusion | Breakpoint Coordinates | Number of Samples Fusion/Total | Non-FL Cancer Type (References) |
|---|---|---|---|
| DUS4L/BCAP29 | chr7: 107217037 chr7: 107221204 | 4/34 | Gastric Cancer (ncbi.nlm.nih.gov/pubmed/24240688) |
| RRM2/C2orf48 | chr2: 10269281 chr2: 10281981 | 2/34 | BT474 and SKBR3 cell lines (ncbi.nlm.nih.gov/pubmed/23956304) |
| PRKAA1/TTC33 | chr5: 40764616 chr5: 40747121 | 13/34 | Colon, Kidney, Stomach, Breast, Ovary, Uterus Cancers (ncbi.nlm.nih.gov/pubmed/23226102) |
| MTG1/LOC619207 | chr10: 135216277 chr10: 135269741 | 8/34 | Breast Cancer (ncbi.nlm.nih.gov/pubmed/22496456) |
| CIRBP/C19orf24 | chr19: 1274439 chr19: 1277182 | 14/34 | Prostate Cancer (google.com/patents/WO2012149522A1?cl=en) |

TABLE 3

Predicted HLA Alleles of Recurrent Fusion-Derived Peptides.

| Gene Fusion | Fusion Sequence | Number of peptides (9 AA) | HLA class I alleles (IC50 < 500 nM) |
|---|---|---|---|
| DUS4L/BCAP29 | VWRITGTDGVKKKMTLQWAAV (SEQ ID NO.: 404) | 13 | HLA-A*02:01, HLA-A*02:02, HLA-A*02:03, HLA-A*02:06, HLA-A*02:11, HLA-A*02:12, HLA-A*02:16, HLA-A*02:19, HLA-A*02:50, HLA-A*11:01, HLA-B*15:03, HLA-B*27:20, HLA-B*39:01 |
| RRM2/C2orf48 | RLMLELGFSKVLGDREVQSRWSPGPRGDSTPVREMETNHPPSVRG (SEQ ID NO.: 405) | 37 | HLA-A*02:01, HLA-A*02:02, HLA-A*02:03, HLA-A*02:06, HLA-A*02:11, HLA-A*02:12, HLA-A*02:16, HLA-A*02:19, HLA-A*02:50, HLA-A*30:01, HLA-A*31:01, HLA-A*32:07, HLA-A*33:01, HLA-A*68:01, HLA-B*07:02, HLA-B*15:03, HLA-B*18:01, HLA-B*27:20, HLA-B*40:01, HLA-B*40:02, HLA-B*40:13, HLA-B*42:01, HLA-B*44:02, HLA-B*45:01, |

TABLE 3-continued

Predicted HLA Alleles of Recurrent Fusion-Derived Peptides.

| Gene Fusion | Fusion Sequence | Number of peptides (9 AA) | HLA class I alleles (IC50 < 500 nM) |
|---|---|---|---|
| | | | HLA-B*73:01, HLA-C*03:03, HLA-C*07:01, HLA-C*12:03 |
| PRKAA1/ TTC33 | TYLLDFRSIDEWLPLGG RGKLVRRSQRSLPSSLK LKLLMRRM (SEQ ID NO.: 406) | 34 | HLA-A*02:03, HLA-A*02:06, HLA-A*02:11, HLA-A*02:16, HLA-A*02:50, HLA-A*03:01, HLA-A*11:01, HLA-A*30:01, HLA-A*31:01, HLA-A*32:07, HLA-A*32:15, HLA-A*33:01, HLA-A*68:23, HLA-B*07:02, HLA-B*08:01, HLA-B*15:01, HLA-B*15:03, HLA-B*15:17, HLA-B*27:05, HLA-B*27:20, HLA-B*35:01, HLA-B*39:01, HLA-B*40:13, HLA-B*42:01, HLA-B*53:01, HLA-B*57:01, HLA-B*58:01 HLA-C*03:03, HLA-C*12:03, HLA-C*15:02 |
| MTG1/ LOC619207 | LYTLNKHQRFGWTRCSE AGVQTQHVRRSGVGPTP RGMGIRVQPGVDAGRGL CRVQAAGLRPCRGRPQV CPAAWRDGPALASQRVL PGQRVLPLGVQPWLMVP EPVPPRMGGGRAVLQRH FPGAPAGEGPQSLRGTP RDQKREWGGPPLCPACG GGHGVLPGAGVRPCAPG PPPGRGRRQEVPGLQGY RAHHPQLQTGQQLPQRL RPAAGRRGGLLR (SEQ ID NO.: 407) | 208 | HLA-A*31:01, HLA-B*27:20, HLA-C*06:02 |
| CIRBP/ C19orf24 | non-coding | 0 | — |

Example 3: Fusion-Derived Peptides Having High Percentages of Patient Population Coverage Two fusion transcripts can be found in solitary fibrous tumors. The transcripts are formed from fusion of exon 4 of the Nab2 gene (5' partner gene) with exon 2 of the Stat6 gene (3' partner gene) and exon 6 of the Nab2 gene (5' partner gene) with exon 16 of the Stat6 gene (3' partner gene). The amino acid sequence of the Nab2/Stat6 fusion protein is shown below. A novel amino acid sequence is generated when exon 4 of Nab2 is fused with exon 2 of Stat6 because of the presence of an untranslated region at the beginning of exon 2 of Stat6. Exon 6 of the Nab2 gene is fused with exon 16 of the Stat6 gene in frame.

```
Nab2/Stat6 (Nab2 exon 4 to Stat6 exon 2)
fusion protein (COSF1547)
                                    (SEQ ID NO.: 408)
MHRAPSPTAEQPPGGGDSARRTLQPRLKPSARAMALPRTLGELQLYR

VLQRANLLSYYETFIQQGGDDVQQLCEAGEEEFLEIMALVGMATKPL

HVRRLQKALREWATNPGLFSQPVPAVPVSS1PLFKISETAGTRKGSM

SNGHGSPGEKAGSARSFSPKSPLELGEKLSPLPGGPGAGDPRIWPGR

STPESDVGAGGEEEAGSPPFSPPAGGGVPEGTGAGGLAAGGTGGGPD

RLEPEMVRMVVESVERIFRSFPRGDAGEVTSLLKLNKKLARSVGHIF

EMDDNDSQKEEEIRKYSIIYGRFDSKRREGKQLSLHELTINEAAAQF

CMRDNTLLLRRVELFSLSRQVARESTYLSSLKGSRLHPEELGGPPLK

KLKQEATSKSQIMSLWGLVSKMPPEKVQRLYVDFPQHLRHLLGDWLE
```
```
-continued

SQPWEFLVGSDAFCCNLASALLSDTVQHLQASVGEQGEGSTILQHIS

TLESIYQRDPLKLVATFRQILQGEKKAVMEQFRHLPMPFHWKQEELK

FKTGLRRLQHRVGEIHLLREALQKGAEAGQVSLHSLIETPANGTGPS

EALAMLLQETTGELEAAKALVLKRIQIWKRQQQLAGNGAPFEESLAP

LQERCESLVDIYSQLQQEVGAAGGELEPKTRASLTGRLDEVLRTLVT

SCFLVEKQPPQVLKTQTKFQAGVRFLLGLRFLGAPAKPPLVRADMVT

EKQARELSVPQGPGAGAESTGEIINNTVPLENSIPGNCCSALFKNLL

LKKIKRCERKGTESVTEEKCAVLFSASFTLGPGKLPIQLQALSLPLV

VIVHGNQDNNAKATILWDNAFSEMDRVPFVVAERVPWEKMCETLNLK

FMAEVGTNRGLLPEHFLFLAQKIFNDNSLSMEAFQHRSVSWSQFNKE

ILLGRGFTFWQWFDGVLDLTKRCLRSYWSDRLIIGFISKQYVTSLLL

NEPDGTFLLRFSDSEIGGITIAHVIRGQDGSPQIENIQPFSAKDLSI

RSLGDRIRDLAQLKNLYPKKPKDEAFRSHYKPEQMGKDGRGYVPATI

KMTVERDQPLPTPELQMPTMVPSYDLGMAPDSSMSMQLGPDMVPQVY

PPHSHSIPPYQGLSPEESVNVLSAFQEPHLQMPPSLGQMSLPFDQPH

PQGLLPCQPQEHAVSSPDPLLCSDVTMVEDSCLSQPVTAFPQGTWIG

EDIFPPLLPPTEQDLTKLLLEGQGESGGGSLGAQPLLQPSHYGQSGI

SMSHMDLRANPSW
```

Nab2/Stat6 (Nab2 exon 6 to Stat6 exon 16)
fusion protein (COSF1561)
(SEQ ID NO.: 409)
MHRAPSPTAEQPPGGGDSARRTLQPRLKPSARAMALPRTLGELQLYR

VLQRANLLSYYETFIQQGGDDVQQLCEAGEEEFLEIMALVGMATKPL

HVRRLQKALREWATNPGLFSQPVPAVPVSSIPLFKISETAGTRKGSM

SNGHGSPGEKAGSARSFSPKSPLELGEKLSPLPGGPGAGDPRIWPGR

STPESDVGAGGEEEAGSPPFSPPAGGGVPEGTGAGGLAAGGTGGGPD

RLEPEMVRMVVESVERIFRSFPRGDAGEVTSLLKLNKKLARSVGHIF

EMDDNDSQKEEEIRKYSIIYGRFDSKRREGKQLSLHELTINEAAAQF

CMRDNTLLLRRVELFSLSRQVARESTYLSSLKGSRLHPEELGGPPLK

KLKQEVGEQSHPEIQQPPPGPESYVPPYRPSLEEDSASLSGESLDGH

LQAVGSCPRLTPPPADLPLALPAHGLWSRHILQQTLMDEGLRLARLV

SHDRVGRLSPCVPAKPPLAGSPQIENIQPFSAKDLSIRSLGDRIRDL

AQLKNLYPKKPKDEAFRSHYKPEQMGKDGRGYVPATIKMTVERDQPL

PTPELQMPTMVPSYDLGMAPDSSMSMQLGPDMVPQVYPPHSHSIPPY

QGLSPEESVNVLSAFQEPHLQMPPSLGQMSLPFDQPHPQGLLPCQPQ

EHAVSSPDPLLCSDVTMVEDSCLSQPVTAFPQGTWIGEDIFPPLLPP

TEQDLTKLLLEGQGESGGGSLGAQPLLQPSHYGQSGISMSHMDLRAN

PSW

In the case of COSF1547, a long peptide having a sequence GPPLKKLKQEATSKSQIMSLWGLVSKM (SEQ ID NO.: 410) was used for generating neoantigenic peptides (8-11 amino acids) for predicting peptide binding to MHC class I proteins. The example below contains predicted neoantigenic peptides having 9 amino acids.

| | |
|---|---|
| GP<u>PLKKLKQEATSKSQIMSLWGLVS</u>KM | SEQ ID NO.: 410 |
| PLKKLKQE<u>A</u> | SEQ ID NO.: 411 |
| LKKLKQE<u>AT</u> | SEQ ID NO.: 412 |
| KKLKQE<u>ATS</u> | SEQ ID NO.: 413 |
| KLKQE<u>ATSK</u> | SEQ ID NO.: 414 |
| LKQE<u>ATSKS</u> | SEQ ID NO.: 415 |
| KQE<u>ATSKSQ</u> | SEQ ID NO.: 416 |
| QE<u>ATSKSQI</u> | SEQ ID NO.: 417 |
| E<u>ATSKSQIM</u> | SEQ ID NO.: 418 |
| <u>ATSKSQIMS</u> | SEQ ID NO.: 419 |
| <u>T</u>SKSQIMSL | SEQ ID NO.: 420 |
| <u>S</u>KSQIMSLW | SEQ ID NO.: 421 |
| <u>K</u>SQIMSLWG | SEQ ID NO.: 422 |
| <u>S</u>QIMSLWGL | SEQ ID NO.: 423 |
| <u>Q</u>IMSLWGLV | SEQ ID NO.: 424 |
| <u>I</u>MSLWGLVS | SEQ ID NO.: 425 |

In the case of COSF1561, a long peptide having a sequence PCVPAKPPLAGSPQIENIQP (SEQ ID NO: 614) was used for generating neoantigenic peptides having 8-11 amino acids for predicting peptide binding to MHC class I proteins.

A set of neoantigenic peptides comprising 8-11 amino acids was generated for all available MHC class I alleles using prediction algorithms described herein and filtering out of all epitopes with IC$_{50}$>500 nM. Those MHC class I proteins that are able to effectively bind Nab/Stat6 fusion-derived neoepitopes are listed in the Table 4.

For Nab2/Stat6 COSF1547, the allele coverage was calculated to be 94% meaning that 94% of the population can effectively present neoantigenic peptides derived from the long peptide spanning the Nab2/Stat6 fusion breakpoint. The Nab2/Stat6 COSF1547 fusion incidence rate is around 34% in solitary fibrous tumors. The patient coverage of the fusion-derived long peptide from Nab2/Stat6 COSF1547 is around 32%. For COSF1561, patient coverage of the fusion-derived long peptide is about 20%.

Both recurrent Nab2/Stat6 fusion-derived long peptides spanning fusion breakpoints are original and placed into the vaccine library. Results for another less frequent Nab2/Stat6 fusion (COSF1561, exon 6 of Nab2 to exon 17 of Stat6) are also shown in Table 4.

TABLE 4

Nab/Stat6 fusion-derived peptides predicted to bind HLA alleles.

| Fusion | Long peptide spanning fusion breakpoint and yielding neoantigens | 8-11-mer neoantigenic peptides (SEQ ID NO.) | HLA class I alleles that bind neoantigens (IC50 < 500 nM) |
|---|---|---|---|
| Nab2/Stat6 COSF1547 | GPPLKKLKQEATSKSQIMSLW GLVSKM (SEQ ID NO.: 426) | ATSKSQIM (429)<br>EATSKSQI (430)<br>IMSLWGLV (431)<br>KSQIMSLW (432)<br>QIMSLWGL (433)<br>SKSQIMSL (434)<br>EATSKSQIM (435)<br>KLKQEATSK (436)<br>QEATSKSQI (437)<br>QIMSLWGLV (438)<br>SQIMSLWGL (439)<br>TSKSQIMSL (440)<br>ATSKSQIMSL (441)<br>IMSLWGLVSK (442)<br>KKLKQEATSK (443) | HLA-A*02:01<br>HLA-A*02:02<br>HLA-A*02:03<br>HLA-A*02:06<br>HLA-A*02:11<br>HLA-A*02:17<br>HLA-A*03:01<br>HLA-A*11:01<br>HLA-A*30:01<br>HLA-A*32:01<br>HLA-A*68:01<br>HLA-A*68:02<br>HLA-A*69:01<br>HLA-B*15:01<br>HLA-B*15:03 |

TABLE 4-continued

Nab/Stat6 fusion-derived peptides predicted to bind HLA alleles.

| Fusion | Long peptide spanning fusion breakpoint and yielding neoantigens | 8-11-mer neoantigenic peptides (SEQ ID NO.) | HLA class I alleles that bind neoantigens (IC50 < 500 nM) |
|---|---|---|---|
| | | KQEATSKSQI (444) | HLA-B*15:17 |
| | | KSQIMSLWGL (445) | HLA-B*35:01 |
| | | QEATSKSQIM (446) | HLA-B*39:01 |
| | | SQIMSLWGLV (447) | HLA-B*40:01 |
| | | TSKSQIMSLW (448) | HLA-B*40:02 |
| | | ATSKSQIMSLW (449) | HLA-B*44:02 |
| | | EATSKSQIMSL (450) | HLA-B*45:01 |
| | | IMSLWGLVSKM (451) | HLA-B*48:01 |
| | | KQEATSKSQIM (452) | HLA-B*57:01 |
| | | KSQIMSLWGLV (453) | HLA-B*58:01 |
| | | LKQEATSKSQI (454) | HLA-C*03:03 |
| | | QEATSKSQIMS (455) | HLA-C*12:03 |
| | | QIMSLWGLVSK (456) | HLA-C*15:02 |
| | | SQIMSLWGLVS (457) | |
| Nab2/Stat6 COSF1561 | PCVPAKPPLAGSPQIENIQP (SEQ ID NO.: 427) | PLAGSPQI (458) | HLA-A*02:11 |
| | | PPLAGSPQI (459) | HLA-B*07:02 |
| | | KPPLAGSPQI (460) | HLA-B*15:17 |
| | | LAGSPQIENI (461) | HLA-B*42:01 |
| | | GSPQIENIQPF (462) | HLA-C*03:03 |
| | | PLAGSPQIENI (463) | HLA-C*12:03 |
| Nab2/Stat6 COSF1561 | PCVPAKPPLAAEQMGKDGRGY (SEQ ID NO.: 428) | AEQMGKDG (464) | HLA-A*03:01 |
| | | LAAEQMGK (465) | HLA-A*68:01 |
| | | PPLAAEQM (466) | HLA-B*07:02 |
| | | KPPLAAEQM (467) | HLA-B*35*01 |
| | | PLAAEQMGK (468) | HLA-B*42:01 |
| | | VPAKPPLAA (469) | HLA-B*44:02 |
| | | AEQMGKDGRGY (470) | HLA-B*44:03 |
| | | LAAEQMGKDGR (471) | HLA-B*45:01 |
| | | PAKPPLAAEQM (472) | HLA-C*03:03 |
| | | | HLA-C*12:03 |

Example 4: Prostate Cancer Vaccine Compositions Comprising TMPRSS2/ERG Fusion Peptides In total, 8 exonic variants of the TMPRSS2/ERG fusion from the COSMIC database were analyzed. The majority of the discovered antigenic peptides were not previously published. The TMPRSS2/ERG fusion is specific to prostate cancer and has quite a high incidence rate. The major protein coding exonic variant is estimated to be found in over 10% of cases. Further analysis showed that a vaccine based on TMPRSS2/ERG fusion-derived neoantigens can be used for about 20,000 prostate cancer patients a year in the USA.

TABLE 5

Population coverage of TMPRSS2/ERG fusion peptides.

| Long peptide spanning fusion breakpoint and yielding neoantigens (number of neoantigens) | HLA class I alleles that bind neoantigens (IC50 < 500 nM) | Population covered by the alleles |
|---|---|---|
| DGVSHCPGGEDENRCGSLISCE (3) (SEQ ID NO.: 473) | B*40:01, B*40:02, C*12:03 | 18% |
| FLVGAALAAGLLWKFRSLISCE (13) (SEQ ID NO.: 474) | A*02:01, A*02:02, A*02:03, A*02:06, A*02:11, A*02:17, A*30:01, A*31:01, A*33:01, A*68:01, B*08:01, B*15:03, C*03:03, C*12:03 | 73% |
| FLVGAALAAGLLWKFRTLLMNAVWPKAGRW (22) (SEQ ID NO.: 475) | A*02:01, A*02:02, A*02:03, A*02:06, A*02:11, A*02:17, A*03:01, A*11:01, A*24:03, A*30:01, A*31:01, A*32:01, A*33:01, A*68:01, A*69:01, B*08:01, B*15:03, B*15:17, B*27:05, B*39:01, B*57:01, B*58:01, C*03:03, C*12:03, C*14:02, C*15:02 | 92% |
| MALNSEALSVVSEDQSLFEC (9) (SEQ ID NO.: 476) | A*02:01, A*02:02, A*02:03, A*02:06, A*02:11, A*02:17, A*68:02, A*69:01, B*15:03, B*15:17, B*35:01, B*40:02, B*45:01, B*53:01, C*03:03, C*12:03, C*14:02, C*15:02 | 67% |
| MALNSPSGSEQLVDGLAY (SEQ ID NO.: 477) | A*01:01, A*02:02, A*02:11, A*02:17, A*26:01, A*29:02, A*68:02, B*07:02, B*15:01, B*15:03, | 88% |

TABLE 5-continued

Population coverage of TMPRSS2/ERG fusion peptides.

| Long peptide spanning fusion breakpoint and yielding neoantigens (number of neoantigens) | HLA class I alleles that bind neoantigens (IC50 < 500 nM) | Population covered by the alleles |
|---|---|---|
| | B*15:17, B*18:01, B*35:01, B*40:01, B*40:02, B*42:01, B*44:02, B*44:03, B*45:01, C*03:03, C*15:02 | |
| MALNSVIPGSLETRGKPC (10) (SEQ ID NO.: 478) | A*02:01, A*02:02, A*02:03, A*02:06, A*02:11, A*11:01, A*30:01, A*31:01, A*68:01, A*69:01, B*15:01, B*15:03, B*15:17, B*35:01, C*03:03, C*12:03, C*14:02 | 78% |
| VCTQPKSPSGTVCTSRSLISCE (5) (SEQ ID NO.: 479) | A*31:01, A*68:02, B*15:17, C*03:03 | 17% |
| VCTQPKSPSGTVCTSSYSRIFGDPRKAVLT (60) (SEQ ID NO.: 480) | A*02:01, A*02:02, A*02:03, A*02:11, A*03:01, A*11:01, A*29:02, A*30:01, A*30:02, A*31:01, A*32:01, A*33:01, A*68:01, A*68:02, B*07:02, B*15:01, B*15:03, B*15:17, B*35:01, B*42:01, B*44:03, B*53:01, B*57:01, B*58:01, C*03:03, C*05:01, C*07:02, C*08:02, C*12:03, C*14:02, C*15:02 | 98% |

Example 5: Universal Cancer Vaccine Compositions Comprising ETV6/NTRK3 Fusion Peptides Four exonic variants of the ETV6/NTRK3 fusion from the COSMIC database were analyzed to predict neoantigen peptides. All of the predicted neoantigen peptides were not previously published. According to the COSMIC database, this fusion was found in congenital (infantile) fibrosarcoma, mesoblastic nephroma, breast ductal secretory carcinoma, mammary analogue secretory carcinoma of salivary glands, thyroid carcinoma, and intestine carcinoma. This demonstrated that neoantigen vaccines based on a single fusion can target a wide spectrum of tumor types.

TABLE 6

ETV6/NTRK3 fusion-derived peptides predicted to bind HLA alleles.

| Long peptide spanning fusion breakpoint and yielding neoantigens (number of neoantigens) | HLA class I alleles that bind neoantigens (IC50 < 500 nM) | Population covered by the alleles |
|---|---|---|
| IHTQPEVILHQNHEEDVQHIKRRDIVLKRE (8) (SEQ ID NO.: 481) | A*02:02, A*02:03, A*02:11, A*33:01, A*68:01, B*15:03, B*40:01, B*44:02, C*06:02, C*07:01, C*12:03 | 68% |
| IHTQPEVILHQNHEEGPVAVISGEEDSASP (10) (SEQ ID NO.: 482) | A*02:02, A*02:03, A*02:11, A*02:17, B*15:03, B*15:09, B*39:01, B*40:01, B*40:02, B*45:01, C*07:01, C*12:03, C*14:02 | 48% |
| VSPPEEHAMPIGRIADVQHIKRRDIVLKRE (14) (SEQ ID NO.: 483) | A*02:03, A*02:06, A*02:11, A*03:01, A*11:01, A*30:01, A*31:01, A*33:01, A*68:01, A*68:02, B*07:02, B*08:01, B*27:05, B*35:01, B*42:01, B*58:01, C*03:03, C*06:02, C*07:01, C*12:03, C*15:02 | 92% |
| VSPPEEHAMPIGRIADVQHIKRRDIVLKRE (11) (SEQ ID NO.: 484) | A*02:02, A*02:03, A*02:06, A*02:11, A*02:17, A*30:01, A*32:01, A*68:02, A*69:01, B*07:02, B*15:01, B*15:17, B*27:05, B*35:01, B*39:01, B*42:01, B*58:01, C*03:03, C*12:03, C*14:02, C*15:02 | 66% |

Example 6: Identification of Novel Peptides in Previously Studied Gene Fusion (FUS/ERG)

FUS/ERG fusion can be found, for example, in acute myeloid leukaemia and occurs due to fusion of exon 7 of the FUS gene with exon 11 of the ERG gene. The amino acid sequence of the FUS/ERG fusion protein is shown below.

```
FUS/ERG (Fus exon 7 to exon 11 of Erg) fusion
protein (COSF315)
                                  (SEQ ID NO.: 485)
MASNDYTQQATQSYGAYPTQPGQGYSQQSSQPYGQQSYSGYSQSTDTSGY

GQSSYSSYGQSQNTGYGTQSTPQGYGSTGGYGSSQSSQSSYGQQSSYPGY

GQQPAPSSTSGSYGSSSQSSSYGQPQSGSYSQQPSYGGQQQSYGQQQSYN

PPQGYGQQNQYNSSSGGGGGGGGGGNYGQDQSSMSSGGGSGGGYGNQDQS

GGGGSGGYGQQDRGGRGRGGSGGGGGGGGGGYNRSSGGYEPRGRGGGRGG

RGGMGGSDRGGFNKFGGSGQIQLWQFLLELLSDSSNSSCITWEGTNGEFK

MTDPDEVARRWGERKSKPNMNYDKLSRALRYYYDKNIMTKVHGKRYAYKF

DFHGIAQALQPHPPESSLYKYPSDLPYMGSYHAHPQKMNFVAPHPPALPV

TSSSFFAAPNPYWNSPTGGIYPNTRLPTSHMPSHLGTYY
```

The fusion-derived long peptide having the sequence SDRGGFNKFGGSGQIQLWQF (SEQ ID NO: 615) was used for generating neoantigenic peptides (8-11 amino acids) for predicting peptide binding to MHC class I proteins. Results are shown in the Table 7. In the case of acute myeloid leukaemia, patient coverage of the fusion-derived long peptide is about 10%. Recurrent FUS/ERG fusion-derived long peptides are original and placed into the vaccine library.

TABLE 7

FUS/ERG fusion-derived peptides predicted to bind HLA alleles.

| Fusion | Long peptide spanning fusion breakpoint and yielding neoantigens | neoantigenic peptides (8-11 amino acids) (SEQ ID NO.) | HLA class I alleles that bind neoantigens (IC50 < 500 nM) |
|---|---|---|---|
| FUS/ERG COSF315 | GPPLKKLKQEATSKSQIMSLW GLVSKM (SEQ ID NO.: 486) | GSGQIQLW (487) KFGGSGQI (488) FGGSGQIQL (489) GGSGQIQLW (490) KFGGSGQIQL (491) KFGGSGQIQLW (492) NKFGGSGQIQL (493) | HLA-A*24:02 HLA-A*24:03 HLA-B*15:17 HLA-B*39:01 HLA-B*57:01 HLA-B*58:01 HLA-C*03:03 HLA-C*14:02 |

Example 7: Peptides Corresponding to Multiple Gene Fusion Junctions Increase Patient Coverage FUS/DDIT3 fusions can be found, for example, in myxoid-round cell liposarcoma. The most frequent subtypes of this fusion are formed due to junction of exon 5 of Fus with exon 2 of DDIT3, exon 7 of Fus with exon 2 of DDIT3, and exon 8 of Fus with exon 2 of DDIT3. The amino acid sequences of the FUS/DDIT3 fusion proteins are shown below. In each fusion protein, a stop codon occurs soon after the breakpoint due to a frameshift. Neoantigens predictions were calculated using long peptides having 10 amino acids to the left and all amino acids to the right from the fusion junction.

```
FUS/DDIT3 (Fus exon 5 to exon 2 of DDIT3) fusion
protein (COSF300)
                                  (SEQ ID NO.: 494)
MASNDYTQQATQSYGAYPTQPGQGYSQQSSQPYGQQSYSGYSQSTDTSGY

GQSSYSSYGQSQNTGYGTQSTPQGYGSTGGYGSSQSSQSSYGQQSSYPGY

GQQPAPSSTSGSYGSSSQSSSYGQPQSGSYSQQPSYGGQQQSYGQQQSYN

PPQGYGQQNQYNSSSGGGGGGGGGGVFKKEVYLHTSPHLKAD

FUS/DDIT3 (Fus exon 7 to exon 2 of DDIT3) fusion
protein (COSF302)
                                  (SEQ ID NO.: 495)
MASNDYTQQATQSYGAYPTQPGQGYSQQSSQPYGQQSYSGYSQSTDTSGY

GQSSYSSYGQSQNTGYGTQSTPQGYGSTGGYGSSQSSQSSYGQQSSYPGY

GQQPAPSSTSGSYGSSSQSSSYGQPQSGSYSQQPSYGGQQQSYGQQQSYN

PPQGYGQQNQYNSSSGGGGGGGGGGNYGQDQSSMSSGGGSGGGYGNQDQS
```

-continued

GGGGSGGYGQQDRGGRGRGGSGGGGGGGGGGGYNRSSGGYEPRGRGGGRGG

RGGMGGSDRGGFNKFGVFKKEVYLHTSPHLKAD

FUS/DDIT3 (Fus exon 8 to exon 2 of DDIT3) fusion
protein (COSF301)
(SEQ ID NO.: 496)
MASNDYTQQATQSYGAYPTQPGQGYSQQSSQPYGQQSYSGYSQSTDTSGY

GQSSYSSYGQSQNTGYGTQSTPQGYGSTGGYGSSQSSQSSYGQQSSYPGY

GQQPAPSSTSGSYGSSSQSSSYGQPQSGSYSQQPSYGGQQQSYGQQQSYN

PPQGYGQQNQYNSSSGGGGGGGGGGNYGQDQSSMSSGGGSGGGYGNQDQS

GGGGSGGYGQQDRGGRGRGGSGGGGGGGGGGYNRSSGGYEPRGRGGGRGG

RGGMGGSDRGGFNKFGGPRDQGSRHDSVFKKEVYLHTSPHLKAD

Fusion-derived long peptides that were used for generating neoantigenic peptides having 8-11 amino acids for predicting peptide binding to MHC class I are shown in Table 8. Patient coverage with three fusion-derived long peptides is around 50% for myxoid-round cell liposarcoma. Recurrent FUS/DDIT3 fusion-derived peptides spanning fusion breakpoints are original and placed into vaccine library.

TABLE 8

FUS/DDIT3 fusion-derived peptides predicted to bind HLA alleles.

| Fusion | Long peptide spanning fusion breakpoint and yielding neoantigens | neoantigenic peptides (8-11 amino acids) | HLA class I alleles that bind (IC50 < 500 nM) |
|---|---|---|---|
| FUS/DDIT3 COSF300 | SGGGGGGGGGGVFKKEVYLHTS PHLKAD (SEQ ID NO.: 497) | HTSPHLKA (498) KEVYLHTS (499) VFKKEVYL (500) VYLHTSPH (501) YLHTSPHL (502) EVYLHTSPH (503) GVFKKEVYL (504) KEVYLHTSP (505) VYLHTSPHL (506) YLHTSPHLK (507) EVYLHTSPHL (508) YLHTSPHLKA (509) EVYLHTSPHLK (510) KEVYLHTSPHL (511) GVFKKEVY (512) | HLA-A*02:01, HLA-A*02:02, HLA-A*02:03, HLA-A*02:06, HLA-A*02:11, HLA-A*02:17, HLA-A*03:01, HLA-A*11:01, HLA-A*23:01, HLA-A*24:02, HLA-A*24:03, HLA-A*26:01, HLA-A*29:02, HLA-A*30:01, HLA-A*33:01, HLA-A*66:01, HLA-A*68:01, HLA-A*68:02, HLA-A*69:01, HLA-B*15:01, HLA-B*15:03, HLA-B*15:03, HLA-B*40:01, HLA-B*40:02, HLA-B*44:03, HLA-B*45:01, HLA-C*03:03, HLA-C*12:03, HLA-C*14:02 |
| FUS/DDIT3 COSF302 | SDRGGENKFGVEKKEVYLHTS PHLKAD (SEQ ID NO.: 513) | FNKFGVFK (514) GFNKFGVF (515) GVFKKEVY (516) HTSPHLKA (517) KEVYLHTS (518) NKFGVFKK (519) VFKKEVYL (520) VYLHTSPH (521) YLHTSPHL (522) EVYLHTSPH (523) FNKFGVFKK (524) GFNKFGVFK (525) GGFNKFGVF (526) GVFKKEVYL (527) KEVYLHTSP (528) VYLHTSPHL (529) YLHTSPHLK (530) EVYLHTSPHL (531) FGVFKKEVYL (532) GFNKFGVFKK (533) YLHTSPHLKA (534) EVYLHTSPHLK (535) FNKFGVFKKEV (536) GGFNKFGVFKK (537) KEVYLHTSPHL (538) KFGVFKKEVYL (539) NKFGVFKKEVY (540) RGGFNKFGVFK (541) | HLA-A*02:01, HLA-A*02:02, HLA-A*02:03, HLA-A*02:06, HLA-A*02:11, HLA-A*02:17, HLA-A*03:01, HLA-A*11:01, HLA-A*23:01, HLA-A*24:02, HLA-A*24:03, HLA-A*26:01, HLA-A*29:02, HLA-A*30:01, HLA-A*31:01, HLA-A*33:01, HLA-A*66:01, HLA-A*68:01, HLA-A*68:02, HLA-A*69:01, HLA-B*15:01, HLA-B*15:03, HLA-B*40:01, HLA-B*40:02, HLA-B*44:03, HLA-B*45:01, HLA-C*03:03, HLA-C*12:03, HLA-C*14:02 |
| FUS/DDIT3 COSF301 | PRDQGSRHDSVFKKEVYLHTS PHLKAD (SEQ ID NO.: 542) | DSVFKKEV (543) GSRHDSVF (544) HTSPHLKA (545) KEVYLHTS (546) SRHDSVFK (547) SVFKKEVY (548) VFKKEVYL (549) VYLHTSPH (550) YLHTSPHL (551) EVYLHTSPH (552) GSRHDSVFK (553) | HLA-A*02:01, HLA-A*02:02, HLA-A*02:03, HLA-A*02:06, HLA-A*02:11, HLA-A*02:17, HLA-A*03:01, HLA-A*11:01, HLA-A*23:01, HLA-A*24:02, HLA-A*24:03, HLA-A*26:01, HLA-A*29:02, HLA-A*30:01, HLA-A*33:01, HLA-A*66:01, HLA-A*68:01, HLA-A*68:02, HLA-A*69:01, HLA-B*15:01, HLA-B*15:03, HLA-B*15:17, |

TABLE 8-continued

FUS/DDIT3 fusion-derived peptides predicted to bind HLA alleles.

| Fusion | Long peptide spanning fusion breakpoint and yielding neoantigens | neoantigenic peptides (8-11 amino acids) | HLA class I alleles that bind (IC50 < 500 nM) |
|---|---|---|---|
| | | KEVYLHTSP (554) | HLA-B*27:05, HLA-B*40:01, |
| | | QGSRHDSVF (555) | HLA-B*40:02, HLA-B*44:03, |
| | | SRHDSVFKK (556) | HLA-B*45:01, HLA-C*03:03, |
| | | SVFKKEVYL (557) | HLA-C*06:02, HLA-C*07:01, |
| | | VYLHTSPHL (558) | HLA-C*12:03, HLA-C*14:02, |
| | | YLHTSPHLK (559) | HLA-C*15:02 |
| | | DQGSRHDSVF (560) | |
| | | EVYLHTSPHL (561) | |
| | | GSRHDSVFKK (562) | |
| | | RHDSVFKKEV (563) | |
| | | YLHTSPHLKA (564) | |
| | | EVYLHTSPHLK (565) | |
| | | KEVYLHTSPHL (566) | |
| | | RDQGSRHDSVF (567) | |
| | | SRHDSVFKKEV (568) | |

Example 8: Identification of Novel Peptides in Previously Studied Gene Fusion (BCR/ABL1)

Figure 4:
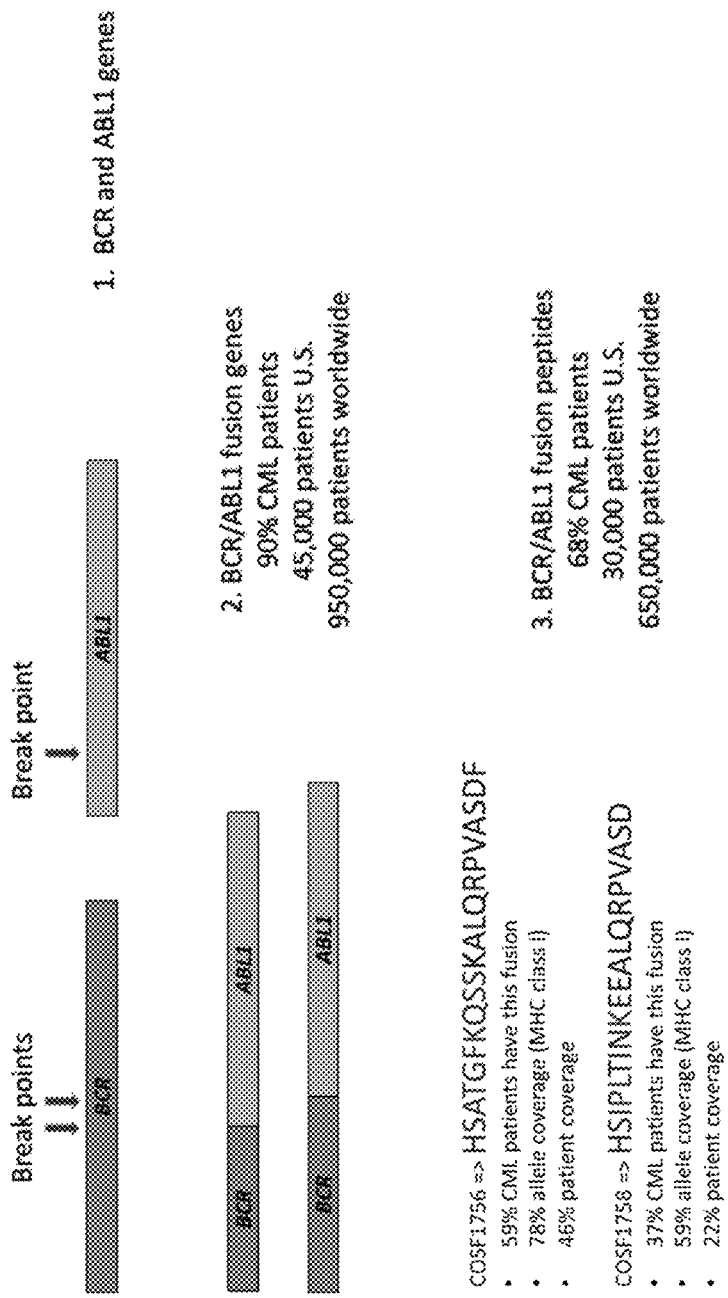
FIG. 4 shows a non-limiting example of a therapeutic cancer vaccine comprising BCR/ABL1 fusion peptides. The method described in the specification is applied to identification of BCR/ABL1 fusion peptides for the treatment of CML. Three breakpoints in BCR and ABL1 genes are marked with arrows (1). Fusion at these breakpoints yields two BCR/ABL1 gene fusions that are present in 90% of CML patients which comprises 45,000 patients in the U.S. and 950,00 patients worldwide (2). The method discloses two BCR/ABL1 fusion peptides selected based on allele coverage and patient coverage that are present in 68% of CML patients which means that 30,000 patients in the U.S. and 650,000 patients worldwide are eligible for treatment with a cancer vaccine comprising these two peptides (3). The sequences correspond to SEQ ID NOs: 610 to 611 from top to bottom, respectively.

While the BCR/ABL1 fusion and its immunogenic properties have been described, the most comprehensive neoantigens were discovered by the disclosed method, namely two fusion peptides that are present in 68% of patients (FIG. 4). In this non-limiting example, the method described in the specification is applied to identification of BCR/ABL1 fusion peptides for the treatment of CML. Three breakpoints in BCR and ABL1 genes are marked with arrows in FIG. 4. Fusion at these breakpoints yields two BCR/ABL1 gene fusions that are present in 90% of CML patients which comprises 45,000 patients in the U.S. and 950,00 patients worldwide (2). The method discloses two BCR/ABL1 fusion peptides selected based on allele coverage and patient coverage that are present in 68% of CML patients which means that 30,000 patients in the U.S. and 650,000 patients worldwide are eligible for treatment with a cancer vaccine comprising these two peptides shown in FIG. 4. The sequences correspond to SEQ ID NOs: 610 to 611 from top to bottom, respectively.

The COSMIC database contains over 18 exonic variants of the BCR/ABL1 fusion that were analyzed and yielded neoantigen peptides. Half of the fusion exonic variants yielded peptides that were not previously published. According to COSMIC, the fusion variants are found in CML and ALL (including T-ALL and B-ALL).

TABLE 9

BCR/ABL1 fusion-derived peptides predicted to bind HLA alleles.

| Long peptide spanning fusion breakpoint and yielding neoantigens (number of neoantigens) | HLA class I alleles that bind neoantigens (IC50 < 500 nM) | Population covered by the alleles |
|---|---|---|
| ASEETYLSHLEALLLKPFSGQ (6) (SEQ ID NO.: 569) | A*03:01, A*11:01, A*23:01, A*24:03, A*30:01, A*68:01, B*15:01, B*15:03, B*18:01, B*35:01, B*40:01, B*40:02, B*44:02, B*44:03, C*14:02 | 79% |
| EITPRRQSMTVKKGEKPFSGQ (6) (SEQ ID NO.: 570) | A*11:01, A*68:01, B*15:01, B*15:03, B*15:17, C*03:03, C*14:02 | 37% |
| EITPRRQSMTVKKGESYTFLISSDYERAEW (17) (SEQ ID NO.: 571) | A*23:01, A*25:01, A*26:01, A*29:02, A*30:01, A*30:02, A*32:01, A*68:01, B*15:01, B*15:03, B*15:17, B*35:01, B*40:01, B*40:02, B*44:02, B*44:03, B*45:01, B*57:01, B*58:01, C*03:03 | 77% |
| GVATDIQALKAAFDVKALQRPVASDFEPQG (14) (SEQ ID NO.: 572) | A*02:02, A*02:03, A*02:11, A*03:01, A*11:01, A*30:01, A*31:01, A*68:01, A*68:02, B*15:01, B*15:03, B*15:17, B*39:01, B*58:01, C*03:03, C*12:03 | 64% |
| GVATDIQALKAAFDVRPSPCEDRHWPGLAL (15) (SEQ ID NO.: 573) | A*31:01, A*68:01, B*15:01, B*15:03, B*15:09, B*15:17, B*35:01, B*38:01, B*39:01, B*40:01, B*40:02, B*42:01, B*48:01, B*53:01, B*58:01, C*03:03, C*06:02, C*07:01, C*07:02, C*12:03, C*14:02 | 88% |

TABLE 9-continued

BCR/ABL1 fusion-derived peptides predicted to bind HLA alleles.

| Long peptide spanning fusion breakpoint and yielding neoantigens (number of neoantigens) | HLA class I alleles that bind neoantigens (IC50 < 500 nM) | Population covered by the alleles |
|---|---|---|
| KLQTVHSIPLTINKEAGSIEALQRPVASD F (14) (SEQ ID NO.: 574) | A*02:11, A*02:17, A*11:01, A*68:01, A*68:02, B*15:03, B*15:17, B*35:01, B*39:01, B*40:01, B*40:02, B*42:01, B*45:01, C*03:03, C*12:03, C*15:02 | 53% |
| KLQTVHSIPLTINKEEALQRPVASDFEPQ G (11) (SEQ ID NO.: 575) | A*31:01, A*68:01, B*07:02, B*15:17, B*35:01, B*40:02, B*42:01, B*44:02, B*45:01, C*03:03, C*14:02 | 64% |
| KLQTVHSIPLTINKEGEKLRVLGYNHNGE W (10) (SEQ ID NO.: 576) | A*11:01, A*31:01, A*68:01, B*15:17, B*40:02, B*44:02, B*44:03, C*03:03, C*15:02 | 54% |
| KTRVYRDTAEPNWNEKPFSGQ (5) (SEQ ID NO.: 577) | A*68:01, B*15:03, B*35:01, B*42:01, B*53:01, C*03:03, C*12:03 | 32% |
| KTRVYRDTAEPNWNELDPQALQDRDWQRT V (5) (SEQ ID NO.: 578) | A*68:02, A*69:01, B*39:01, B*40:01, B*40:02, B*44:02, C*03:03, C*12:03 | 45% |
| LNVIVHSATGFKQSSKALQRPVASDFEPQ G (17) (SEQ ID NO.: 579) | A*02:11, A*03:01, A*11:01, A*30:01, A*31:01, A*68:01, A*68:02, B*15:03, B*15:09, B*15:17, B*39:01, B*58:01, C*03:03, C*12:03, C*14:02, C*15:02 | 63% |
| LNVIVHSATGFKQSSSEKLRVLGYNHNGE W (18) (SEQ ID NO.: 580) | A*01:01, A*11:01, A*30:01, A*31:01, A*68:01, B*15:01, B*15:03, B*15:09, B*15:17, B*18:01, B*39:01, B*44:02, B*44:03, C*03:03, C*06:02, C*07:01, C*15:02 | 88% |
| QIWPNDGEGAFHGDAEALQRPVASDFEPQ G (11) (SEQ ID NO.: 581) | A*24:03, A*68:02, B*15:09, B*35:01, B*38:01, B*39:01, B*40:01, B*40:02, B*44:02, B*45:01, C*03:03, C*06:02, C*07:01, C*07:02, C*12:03, C*14:02 | 88% |
| QIWPNDGEGAFHGDAGEKLRVLGYNHNGE W (7) (SEQ ID NO.: 582) | A*24:03, B*15:09, B*15:17, B*38:01, B*39:01, B*44:02, B*44:03, C*03:03, C*06:02, C*07:01, C*12:03, C*14:02 | 74% |
| QWSHQQRVGDLFQKLNLRARSNKDAKDPT T (8) (SEQ ID NO.: 583) | A*02:06, A*02:11, A*03:01, A*11:01, A*30:01, A*31:01, A*33:01, A*68:01, B*15:03 | 50% |
| RKQTGVFGVKIAVVTKSPSAASSI (10) (SEQ ID NO.: 584) | A*02:03, A*02:06, A*11:01, A*30:01, A*31:01, B*15:03, B*15:17, B*39:01, C*03:03, C*12:03, C*14:02, C*15:02 | 41% |
| SNKDAKDPTTKNSLEKALQRPVASDFEPQ G (10) (SEQ ID NO.: 585) | A*02:02, A*02:03, A*02:11, A*03:01, A*11:01, A*30:01, A*68:01, A*69:01, B*15:03, B*15:17, B*39:01, B*40:02, B*44:02, B*58:01, C*03:03, C*12:03, C*14:02, C*15:02 | 68% |
| SRDALVSGALESTKATKAKPFSGQ (SEQ ID NO.: 586) | A*03:01, A*11:01, A*30:01, A*31:01, A*68:01, B*15:01, B*15:03, B*15:17, B*57:01, B*58:01, C*03:03, C*14:02 | 63% |

Example 9: Method Validation Using EWSR1/FLI1 Gene Fusion

The EWSR1/FLI1 fusion can be found, for example, in Ewing's sarcoma. Two most frequent types of EWSR1/FLI1 fusions occur due to junction of exon 7 of the EWSR1 gene with exon 5 or exon 6 of the FLI1 gene. The amino acid sequences of the fusion proteins are shown below.

Fusion-derived peptides having 8-10 amino acids corresponding to the fusion junction were used for predicting peptide binding to MHC class I proteins. Results are shown in Table 10. Some of the immunogenic EWSR1/FLI1 derived peptides were previously disclosed by patent application U.S. Pat. No. 5,997,869A and were also successfully discovered using methods described herein.

```
EWSR1/FLI1 (EWSR1 exon 7 to exon 6 of FLI1) fusion
protein (COSF166)
                                      (SEQ ID NO.: 587)
MASTDYSTYSQAAAQQGYSAYTAQPTQGYAQTTQAYGQQSYGTYGQPTDV

SYTQAQTTATYGQTAYATSYGQPPTGYTTPTAPQAYSQPVQGYGTGAYDT

TTATVTTTQASYAAQSAYGTQPAYPAYGQQPAATAPTRPQDGNKPTETSQ

PQSSTGGYNQPSLGYGQSNYSYPQVPGSYPMQPVTAPPSYPPTSYSSTQP

TSYDQSSYSQQNTYGQPSSYGQQSSYGQQSSYGQQPPTSYPPQTGSYSQA

PSQYSQQSSSYGQQNPSYDSVRRGAWGNNMNSGLNKSPPLGGAQTISKNT

EQRPQPDPYQILGPTSSRLANPGSGQIQLWQFLLELLSDSANASCITWEG

TNGEFKMTDPDEVARRWGERKSKPNMNYDKLSRALRYYYDKNIMTKVHGK

RYAYKFDFHGIAQALQPHPTESSMYKYPSDISYMPSYHAHQQKVNFVPPH

PSSMPVTSSSFFGAASQYWTSPTGGIYPNPNVPRHPNTHVPSHLGSYY

EWSR1/FLI1 (EWSR1 exon 7 to exon 5 of FLI1) fusion
protein (CO5F168)
                                      (SEQ ID NO.: 588)
MASTDYSTYSQAAAQQGYSAYTAQPTQGYAQTTQAYGQQSYGTYGQPTDV

SYTQAQTTATYGQTAYATSYGQPPTGYTTPTAPQAYSQPVQGYGTGAYDT

TTATVTTTQASYAAQSAYGTQPAYPAYGQQPAATAPTRPQDGNKPTETSQ

PQSSTGGYNQPSLGYGQSNYSYPQVPGSYPMQPVTAPPSYPPTSYSSTQP

TSYDQSSYSQQNTYGQPSSYGQQSSYGQQSSYGQQPPTSYPPQTGSYSQA

PSQYSQQSSSYGQQSSLLAYNTTSHTDQSSRLSVKEDPSYDSVRRGAWGN

NMNSGLNKSPPLGGAQTISKNTEQRPQPDPYQILGPTSSRLANPGSGQIQ

LWQFLLELLSDSANASCITWEGTNGEFKMTDPDEVARRWGERKSKPNMNY

DKSLRALRYYDKNIMTKVHGKRYAYKFDFHGIAQALQPHPTESSMYKYPS

DISYMPSYHAHQQKVNFVPPHPSSMPVTSSSFFGAASQYWTSPTGGIYPN

PNVPRHPNTHVPSHLGSYY
```

TABLE 10

EWSR1/FLI1 fusion-derived peptides predicted to bind HLA alleles.

| Fusion | Long peptide spanning fusion breakpoint and yielding | 8-11-mer neoantigenic peptides | HLA class I alleles that bind neoantigens |
|---|---|---|---|
| EWSR1/FLI1 COSF166 | SQQSSSYGQQNPSYDSVRRG (SEQ ID NO.: 589) | SSYGQQNPSY (591) SYGQQNPSY (592) SSYGQQNPSY (593) YGQQNPSY (594) NPSYDSVR (595) QQNPSYDSV (596) NPSYDSVRR (597) YGQQNPSY (598) QQNPSYDSVR (599) | HLA-A*11:01 HLA-A*29:02 HLA-A*31:01 HLA-A*68:01 HLA-B*15:01 HLA-B*35:01 HLA-C*12:03 |
| EWSR1/FLI1 COSF168 | SQQSSSYGQQSSLLAYNTTS (SEQ ID NO.: 590) | GQQSSLLAY (600) QQSSLLAY (601) SSSYGQQSSL (602) SSYGQQSSL (603) SSYGQQSSL (604) SSYGQQSSLL (605) SYGQQSSL (606) SYGQQSSLL (607) YGQQSSLL (608) YGQQSSLLAY (609) | HLA-A*24:02 HLA-A*29:02 HLA-B*15:01 HLA-B*35:01 HLA-C*03:03 HLA-C*06:02 HLA-C*07:01 HLA-C*07:02 |

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A method comprising:
   a) obtaining information relating to a TMPRSS2/ERG gene fusion in a biological sample from a subject having or suspected of having cancer;
   b) obtaining information relating to one or more HLA alleles of the subject having or suspected of having cancer;
   c) selecting two or more two or more TMPRSS2/ERG fusion-derived neoantigen peptides from a library consisting of a plurality of containers, each respective container of the plurality containing a respective fusion-derived neoantigen peptide consisting of a respective sequence set forth in SEQ ID NOs: 1-403, wherein each selected TMPRSS2/ERG fusion-derived neoantigen peptide consists of an amino acid sequence selected from the group consisting of SEQ ID NOs: 374-381;
   d) determining binding of the selected TMPRSS2/ERG fusion-derived neoantigen peptides of (c) to the one or more HLA alleles of the subject;
   e) selecting at least one of the TMPRSS2/ERG fusion-derived neoantigen peptides for administration to the subject when the TMPRSS2/ERG fusion-derived neoantigen peptide is determined to bind to the one or more HLA alleles of the subject; and
   f) administering a peptide vaccine comprising the selected TMPRSS2/ERG fusion-derived neoantigen peptide of (e) to the subject; and
   g) monitoring tumor growth or formation in the subject after administering the one or more fusion peptides of (f) to the subject.

2. The method of claim 1, wherein the information relating to one or more HLA alleles of the subject are obtained from patient data obtained from the subject or by analysis of the biological sample from the subject.

3. The method of claim 1, wherein the biological sample is a tissue sample or fluid sample taken from the subject.

4. The method of claim 1, wherein the biological sample is analyzed by DNA sequencing, RNA sequencing, and/or protein sequencing.

5. The method of claim 1, wherein the peptide vaccine comprises one or more adjuvants.

6. The method of claim 1, wherein the peptide vaccine is administered to the subject at least once.

* * * * *

SEQUENCE LISTING

<160> NUMBER OF SEQ ID NOS: 615

<210> SEQ ID NO 1
<211> LENGTH: 30
<212> TYPE: PRT
<213> ORGANISM: Artificial Sequence
<220> FEATURE:

```
<223> OTHER INFORMATION: Synthetic Polypeptide

<400> SEQUENCE: 1

Ala Ile Lys Ser Lys Asn Val Asp Val Asn Val Lys Asp Glu Glu Thr
1               5                   10                  15

Glu Val Lys Ser Glu Glu Gly Pro Gly Trp Thr Ile Leu Arg
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 2

Glu Ala Pro Leu Asn Pro Lys Ala Asn Arg Glu Lys Met Thr Gln Asp
1               5                   10                  15

Pro Leu Leu Gly Met Leu Asp Gly Arg Glu Asp Leu Glu Arg
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 3

Glu Ala Pro Leu Asn Pro Lys Ala Asn Arg Glu Lys Met Thr Gln Pro
1               5                   10                  15

Ile Ser Gly Ile Pro Ser Pro Asp Glu Ser Pro Lys Arg Ala
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 4

Glu Ala Pro Leu Asn Pro Lys Ala Asn Arg Glu Lys Met Thr Gln Leu
1               5                   10                  15

Lys Ser Glu Leu Asp Met Leu Val Gly Lys Cys Arg Glu Glu
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 5

Pro Arg Ala Val Phe Pro Ser Ile Val Gly Arg Pro Arg His Gln Leu
1               5                   10                  15

Lys Ser Glu Leu Asp Met Leu Val Gly Lys Cys Arg Glu Glu
            20                  25                  30

<210> SEQ ID NO 6
<211> LENGTH: 30
<212> TYPE: PRT
<213> ORGANISM: Artificial Sequence
```

<220> FEATURE:
<223> OTHER INFORMATION: Synthetic Polypeptide

<400> SEQUENCE: 6

Gln Thr Lys Val Leu Ser Ala Ser Gln Ala Phe Ala Ala Gln Arg Asp
1               5                   10                  15

Ser Ile Thr Gln His Lys Val Cys Ala Pro Glu Asn Tyr Leu
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 7

Asn Asp Lys Leu Gln Lys Glu Leu Asn Val Leu Lys Ser Glu Gln Asp
1               5                   10                  15

Leu Ile Arg Asp Gln Gly Phe Arg Gly Asp Gly Gly Ser Thr
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 8

Gln Glu Arg Glu Arg Asp Pro Gln Gln Glu Gln Glu Arg Glu Arg Ile
1               5                   10                  15

Asp Asp Val Ile Asp Glu Ile Ile Ser Leu Glu Ser Ser Tyr
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 9

Gln Glu Arg Glu Arg Asp Pro Gln Gln Glu Gln Glu Arg Glu Arg Leu
1               5                   10                  15

Pro Val Ser Gly Asn Leu Leu Asp Val Tyr Ser Ser Gln Gly
            20                  25                  30

<210> SEQ ID NO 10
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 10

Ser Ser Gln Lys Ala His Gly Ile Leu Ala Arg Arg Pro Ser Tyr Arg
1               5                   10                  15

Thr His Gly

<210> SEQ ID NO 11
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 11

Met Ser Val Pro Thr Pro Ile Tyr Gln Thr Ser Ser Gly Gln Tyr Ser
1               5                   10                  15

Ser Phe Arg Gln Asp His Pro Ser Ser Met Gly Val Tyr Gly
            20                  25                  30

<210> SEQ ID NO 12
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 12

Arg Asn Val Gln Asp Phe Lys Arg Ala Ser Glu Glu Ile Thr Lys Thr
1               5                   10                  15

Thr Gln Asp Gly Leu Asp Trp Leu Ile Ser Thr
            20                  25

<210> SEQ ID NO 13
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 13

Thr Pro Ala Gln Leu Tyr Thr Leu Gln Pro Lys Leu Pro Ile Thr Val
1               5                   10                  15

Tyr Arg Arg Lys His Gln Glu Leu Gln Ala Met Gln Met Glu
            20                  25                  30

<210> SEQ ID NO 14
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 14

Thr Gln Leu Pro His Ile Pro Val Ala Val Arg Val Gly Cys Leu Gln
1               5                   10                  15

Tyr Tyr Arg Thr Asp Ser Asp Asn Gln Ala Ile Leu Ser Glu
            20                  25                  30

<210> SEQ ID NO 15
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 15

Lys Thr Arg Val Tyr Arg Asp Thr Ala Glu Pro Asn Trp Asn Glu Lys
1               5                   10                  15

Pro Phe Ser Gly Gln
            20

<210> SEQ ID NO 16
<211> LENGTH: 24
<212> TYPE: PRT

<213> ORGANISM: Artificial Sequence
<220> FEATURE:
<223> OTHER INFORMATION: Synthetic Polypeptide

<400> SEQUENCE: 16

Arg Lys Gln Thr Gly Val Phe Gly Val Lys Ile Ala Val Val Thr Lys
1               5                   10                  15

Ser Pro Ser Ala Ala Ser Ser Ile
            20

<210> SEQ ID NO 17
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 17

Glu Ile Thr Pro Arg Arg Gln Ser Met Thr Val Lys Lys Gly Glu Ser
1               5                   10                  15

Tyr Thr Phe Leu Ile Ser Ser Asp Tyr Glu Arg Ala Glu Trp
            20                  25                  30

<210> SEQ ID NO 18
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 18

Lys Leu Gln Thr Val His Ser Ile Pro Leu Thr Ile Asn Lys Glu Ala
1               5                   10                  15

Gly Ser Ile Glu Ala Leu Gln Arg Pro Val Ala Ser Asp Phe
            20                  25                  30

<210> SEQ ID NO 19
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 19

Lys Thr Arg Val Tyr Arg Asp Thr Ala Glu Pro Asn Trp Asn Glu Leu
1               5                   10                  15

Asp Pro Gln Ala Leu Gln Asp Arg Asp Trp Gln Arg Thr Val
            20                  25                  30

<210> SEQ ID NO 20
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 20

Gln Trp Ser His Gln Gln Arg Val Gly Asp Leu Phe Gln Lys Leu Asn
1               5                   10                  15

Leu Arg Ala Arg Ser Asn Lys Asp Ala Lys Asp Pro Thr Thr
            20                  25                  30

<210> SEQ ID NO 21
<211> LENGTH: 24

```
<212> TYPE: PRT
<213> ORGANISM: Artificial Sequence
<220> FEATURE:
<223> OTHER INFORMATION: Synthetic Polypeptide

<400> SEQUENCE: 21

Ser Arg Asp Ala Leu Val Ser Gly Ala Leu Glu Ser Thr Lys Ala Thr
1               5                   10                  15

Lys Ala Lys Pro Phe Ser Gly Gln
            20

<210> SEQ ID NO 22
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 22

Ser Asn Lys Asp Ala Lys Asp Pro Thr Thr Lys Asn Ser Leu Glu Lys
1               5                   10                  15

Ala Leu Gln Arg Pro Val Ala Ser Asp Phe Glu Pro Gln Gly
            20                  25                  30

<210> SEQ ID NO 23
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 23

Ala Ser Glu Glu Thr Tyr Leu Ser His Leu Glu Ala Leu Leu Leu Lys
1               5                   10                  15

Pro Phe Ser Gly Gln
            20

<210> SEQ ID NO 24
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 24

Glu Ile Thr Pro Arg Arg Gln Ser Met Thr Val Lys Lys Gly Glu Lys
1               5                   10                  15

Pro Phe Ser Gly Gln
            20

<210> SEQ ID NO 25
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 25

Lys Leu Gln Thr Val His Ser Ile Pro Leu Thr Ile Asn Lys Glu Gly
1               5                   10                  15

Glu Lys Leu Arg Val Leu Gly Tyr Asn His Asn Gly Glu Trp
            20                  25                  30

<210> SEQ ID NO 26
```

```
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 26

Gly Val Ala Thr Asp Ile Gln Ala Leu Lys Ala Ala Phe Asp Val Arg
1               5                   10                  15

Pro Ser Pro Cys Glu Asp Arg His Trp Pro Gly Leu Ala Leu
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 27

Gly Val Ala Thr Asp Ile Gln Ala Leu Lys Ala Ala Phe Asp Val Lys
1               5                   10                  15

Ala Leu Gln Arg Pro Val Ala Ser Asp Phe Glu Pro Gln Gly
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 28

Gln Ile Trp Pro Asn Asp Gly Glu Gly Ala Phe His Gly Asp Ala Gly
1               5                   10                  15

Glu Lys Leu Arg Val Leu Gly Tyr Asn His Asn Gly Glu Trp
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 29

Leu Asn Val Ile Val His Ser Ala Thr Gly Phe Lys Gln Ser Ser Ser
1               5                   10                  15

Glu Lys Leu Arg Val Leu Gly Tyr Asn His Asn Gly Glu Trp
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 30

Leu Asn Val Ile Val His Ser Ala Thr Gly Phe Lys Gln Ser Ser Lys
1               5                   10                  15

Ala Leu Gln Arg Pro Val Ala Ser Asp Phe Glu Pro Gln Gly
            20                  25                  30
```

```
<210> SEQ ID NO 31
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 31

Lys Leu Gln Thr Val His Ser Ile Pro Leu Thr Ile Asn Lys Glu Glu
1               5                   10                  15

Ala Leu Gln Arg Pro Val Ala Ser Asp Phe Glu Pro Gln Gly
            20                  25                  30

<210> SEQ ID NO 32
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 32

Gln Ile Trp Pro Asn Asp Gly Glu Gly Ala Phe His Gly Asp Ala Glu
1               5                   10                  15

Ala Leu Gln Arg Pro Val Ala Ser Asp Phe Glu Pro Gln Gly
            20                  25                  30

<210> SEQ ID NO 33
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 33

Gln Ile Trp Pro Asn Asp Gly Glu Gly Ala Phe His Gly Asp Ala Asp
1               5                   10                  15

Tyr Glu Leu Leu Thr Glu Asn Asp Met Leu Pro Asn Met Arg
            20                  25                  30

<210> SEQ ID NO 34
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 34

Gln Ile Trp Pro Asn Asp Gly Glu Gly Ala Phe His Gly Asp Ala Val
1               5                   10                  15

Leu Gln Glu Arg Ile Pro Trp Val Pro Pro Glu Cys Ile Glu
            20                  25                  30

<210> SEQ ID NO 35
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 35

Ala Pro Asn Val His Ile Asn Thr Ile Glu Pro Val Asn Ile Asp Asn
1               5                   10                  15

Asp Leu Arg Leu Gln Met Glu Ala Gln Arg Ile Cys Leu Ser
            20                  25                  30
```

<210> SEQ ID NO 36
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 36

```
Arg Tyr Val Lys Ser Cys Leu Gln Lys Lys Gln Arg Lys Pro Phe Ser
1               5                   10                  15

Ser Ala Leu Pro Gly Pro Asp Met Ser Met Lys Pro Ser Ala
            20                  25                  30
```

<210> SEQ ID NO 37
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 37

```
Ser Ser Ser Glu Ser Ser Ser Asp Ser Glu Asp Ser Glu Thr Ala
1               5                   10                  15

Ser Ala Leu Pro Gly Pro Asp Met Ser Met Lys Pro Ser Ala
            20                  25                  30
```

<210> SEQ ID NO 38
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 38

```
Ser Glu Phe Arg Glu Gly Val Arg Lys Ile Ala Arg Glu Gln Lys Val
1               5                   10                  15

Tyr Arg Arg Lys His Gln Glu Leu Gln Ala Met Gln Met Glu
            20                  25                  30
```

<210> SEQ ID NO 39
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 39

```
Leu Gln Glu Glu Asn Arg Asp Leu Arg Lys Ala Ser Val Thr Ile Glu
1               5                   10                  15

Asp Pro Lys Trp Glu Phe Pro Arg Lys Asn Leu Val Leu Gly
            20                  25                  30
```

<210> SEQ ID NO 40
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 40

```
Glu Glu Glu Phe Leu Thr Asn Glu Leu Ser Arg Lys Leu Met Gln Glu
1               5                   10                  15

Asp Pro Lys Trp Glu Phe Pro Arg Lys Asn Leu Val Leu Gly
            20                  25                  30
```

```
<210> SEQ ID NO 41
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 41

Ser Arg His Ser Leu Glu Gln Lys Pro Thr Asp Ala Pro Pro Lys Val
1               5                   10                  15

Trp His Arg Arg Leu Lys Asn Gln Lys Ser Ala Lys Glu Gly
            20                  25                  30

<210> SEQ ID NO 42
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 42

Ser Arg His Ser Leu Glu Gln Lys Pro Thr Asp Ala Pro Pro Lys Ala
1               5                   10                  15

Gly Val Pro Asn Lys Pro Gly Ile Pro Lys Leu Leu Glu Gly
            20                  25                  30

<210> SEQ ID NO 43
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 43

Ser Arg His Ser Leu Glu Gln Lys Pro Thr Asp Ala Pro Pro Lys Asp
1               5                   10                  15

Asp Phe Trp Ile Pro Glu Thr Ser Phe Ile Leu Thr Ile Ile
            20                  25                  30

<210> SEQ ID NO 44
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 44

Val His Pro Asp Ala Leu Asn Arg Phe Gly Lys Thr Ala Leu Gln Leu
1               5                   10                  15

His Val His Ala Cys Leu Leu Thr Arg Lys Gln Glu Asp Cys
            20                  25                  30

<210> SEQ ID NO 45
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 45

Val His Pro Asp Ala Leu Asn Arg Phe Gly Lys Thr Ala Leu Gln Leu
1               5                   10                  15

His Val His Ala Cys Leu Leu Thr Arg Lys Gln Glu Asp Cys
```

<210> SEQ ID NO 46
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 46

Val His Pro Asp Ala Leu Asn Arg Phe Gly Lys Thr Ala Leu Gln Leu
1               5                   10                  15

His Val His Ala Cys Leu Leu Thr Arg Lys Gln Glu Asp Cys
            20                  25                  30

<210> SEQ ID NO 47
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 47

Leu Ala Glu Asn Ile Thr Gln Glu Arg Asp Ser Leu Met Cys Leu Asp
1               5                   10                  15

Leu Ile Arg Asp Gln Gly Phe Arg Gly Asp Gly Gly Ser Thr
            20                  25                  30

<210> SEQ ID NO 48
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 48

Thr Gln Glu Glu Glu Asp Glu Ile Leu Pro Arg Lys Asp Tyr Glu Lys
1               5                   10                  15

Thr Leu Gly Arg Arg Asp Ser Ser Asp Asp Trp Glu Ile Pro
            20                  25                  30

<210> SEQ ID NO 49
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 49

Glu Glu Arg Ser Val Leu Asn Asn Gln Leu Leu Glu Met Lys Lys Ser
1               5                   10                  15

Thr Leu Pro Thr Gln Glu Glu Ile Glu Asn Leu Pro Ala Phe
            20                  25                  30

<210> SEQ ID NO 50
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 50

Arg Lys Glu Glu Glu Gln Ala Thr Glu Thr Gln Pro Ile Val Tyr Val
1               5                   10                  15

```
Tyr Arg Arg Lys His Gln Glu Leu Gln Ala Met Gln Met Glu
        20                  25                  30

<210> SEQ ID NO 51
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 51

Ala Met Pro Tyr Phe Ile Gln Val Met Lys Glu Tyr Leu Thr Lys Gly
1               5                  10                  15

Val Tyr Arg Arg Lys His Gln Glu Leu Gln Ala Met Gln Met
        20                  25                  30

<210> SEQ ID NO 52
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 52

Ala Met Pro Tyr Phe Ile Gln Val Met Lys Glu Tyr Leu Thr Lys Cys
1               5                  10                  15

Thr Ala Gly Ser Thr Arg Ser Cys Lys Pro Cys Arg Trp Ser
        20                  25                  30

<210> SEQ ID NO 53
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 53

Cys Val Ala Tyr Glu Arg Gly Gln Cys Asp Leu Glu Leu Ile Asn Leu
1               5                  10                  15

Pro Val Ser Gly Asn Leu Leu Asp Val Tyr Ser Ser Gln Gly
        20                  25                  30

<210> SEQ ID NO 54
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 54

Gly Lys Ala Gly Glu Arg Gly Val Pro Gly Pro Pro Gly Ala Val Gly
1               5                  10                  15

Asp Pro Ile Pro Glu Glu Leu Tyr Glu Met Leu Ser Asp His
        20                  25                  30

<210> SEQ ID NO 55
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 55

Gly Pro Ser Gly Pro Arg Gly Leu Pro Gly Pro Pro Gly Ala Pro Gly
1               5                  10                  15
```

```
Asp Pro Ile Pro Glu Glu Leu Tyr Glu Met Leu Ser Asp His
            20                  25                  30

<210> SEQ ID NO 56
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 56

Gly Ala Pro Gly Ala Lys Gly Ala Arg Gly Ser Ala Gly Pro Pro Gly
1               5                   10                  15

Asp Pro Ile Pro Glu Glu Leu Tyr Glu Met Leu Ser Asp His
            20                  25                  30

<210> SEQ ID NO 57
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 57

Gly Pro Ser Gly Pro Ala Gly Pro Thr Gly Ala Arg Gly Ala Pro Gly
1               5                   10                  15

Asp Pro Ile Pro Glu Glu Leu Tyr Glu Met Leu Ser Asp His
            20                  25                  30

<210> SEQ ID NO 58
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 58

Gly Pro Pro Gly Pro Ala Gly Pro Ala Gly Pro Pro Gly Pro Ile Gly
1               5                   10                  15

Asp Pro Ile Pro Glu Glu Leu Tyr Glu Met Leu Ser Asp His
            20                  25                  30

<210> SEQ ID NO 59
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 59

Gly Pro Pro Gly Pro Arg Gly Arg Thr Gly Asp Ala Gly Pro Val Gly
1               5                   10                  15

Asp Pro Ile Pro Glu Glu Leu Tyr Glu Met Leu Ser Asp His
            20                  25                  30

<210> SEQ ID NO 60
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 60

Gly Pro Ala Gly Pro Pro Gly Phe Pro Gly Ala Val Gly Ala Lys Gly
```

```
                1               5                  10                  15
Asp Pro Ile Pro Glu Glu Leu Tyr Glu Met Leu Ser Asp His
                20                  25                  30

<210> SEQ ID NO 61
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 61

Gly Pro Arg Gly Ala Asn Gly Ala Pro Gly Asn Asp Gly Ala Lys Gly
1               5                  10                  15

Asp Pro Ile Pro Glu Glu Leu Tyr Glu Met Leu Ser Asp His
                20                  25                  30

<210> SEQ ID NO 62
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 62

Gly Lys Pro Gly Arg Pro Gly Glu Arg Gly Pro Pro Gly Pro Gln Gly
1               5                  10                  15

Asp Pro Ile Pro Glu Glu Leu Tyr Glu Met Leu Ser Asp His
                20                  25                  30

<210> SEQ ID NO 63
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 63

Tyr Asp Glu Lys Ser Thr Gly Gly Ile Ser Val Pro Gly Pro Met Gly
1               5                  10                  15

Asp Pro Ile Pro Glu Glu Leu Tyr Glu Met Leu Ser Asp His
                20                  25                  30

<210> SEQ ID NO 64
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 64

Gly Pro Gln Gly Pro Gly Gly Pro Gly Pro Lys Gly Asn Ser Gly
1               5                  10                  15

Asp Pro Ile Pro Glu Glu Leu Tyr Glu Met Leu Ser Asp His
                20                  25                  30

<210> SEQ ID NO 65
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 65
```

Gly Leu Pro Gly Thr Ala Gly Leu Pro Gly Met Lys Gly His Arg Gly
1               5                   10                  15

Asp Pro Ile Pro Glu Glu Leu Tyr Glu Met Leu Ser Asp His
            20                  25                  30

<210> SEQ ID NO 66
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 66

Gly Asn Pro Gly Ala Asp Gly Gln Pro Gly Ala Lys Gly Ala Asn Gly
1               5                   10                  15

Asp Pro Ile Pro Glu Glu Leu Tyr Glu Met Leu Ser Asp His
            20                  25                  30

<210> SEQ ID NO 67
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 67

Lys Arg His Val Trp Phe Gly Glu Ser Met Thr Asp Gly Phe Gln Gly
1               5                   10                  15

Asp Pro Ile Pro Glu Glu Leu Tyr Glu Met Leu Ser Asp His
            20                  25                  30

<210> SEQ ID NO 68
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 68

Arg Thr Cys Arg Asp Leu Lys Met Cys His Ser Asp Trp Lys Ser Gly
1               5                   10                  15

Gly Pro His Ser Arg Gly Ala Leu
            20

<210> SEQ ID NO 69
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 69

Gly Phe Gln Gly Pro Pro Gly Glu Pro Gly Glu Pro Gly Ala Ser Gly
1               5                   10                  15

Asp Pro Ile Pro Glu Glu Leu Tyr Glu Met Leu Ser Asp His
            20                  25                  30

<210> SEQ ID NO 70
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 70

Gly Glu Pro Gly Ser Pro Gly Glu Asn Gly Ala Pro Gly Gln Met Gly
1               5                   10                  15

Asp Pro Ile Pro Glu Glu Leu Tyr Glu Met Leu Ser Asp His
            20                  25                  30

<210> SEQ ID NO 71
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 71

Gly His Arg Gly Phe Ser Gly Leu Gln Gly Pro Pro Gly Pro Pro Gly
1               5                   10                  15

Asp Pro Ile Pro Glu Glu Leu Tyr Glu Met Leu Ser Asp His
            20                  25                  30

<210> SEQ ID NO 72
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 72

Gly Pro Ile Gly Pro Pro Gly Pro Ala Gly Ala Pro Gly Asp Lys Gly
1               5                   10                  15

Asp Pro Ile Pro Glu Glu Leu Tyr Glu Met Leu Ser Asp His
            20                  25                  30

<210> SEQ ID NO 73
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 73

Gly Gln Ala Gly Val Met Gly Phe Pro Gly Pro Lys Gly Ala Ala Gly
1               5                   10                  15

Asp Pro Ile Pro Glu Glu Leu Tyr Glu Met Leu Ser Asp His
            20                  25                  30

<210> SEQ ID NO 74
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 74

Pro Pro Gly Pro Pro Gly Pro Pro Gly Pro Pro Gly Leu Gly Gly Gly
1               5                   10                  15

Asp Pro Ile Pro Glu Glu Leu Tyr Glu Met Leu Ser Asp His
            20                  25                  30

<210> SEQ ID NO 75
<211> LENGTH: 30
<212> TYPE: PRT
<213> ORGANISM: Artificial Sequence
<220> FEATURE:
<223> OTHER INFORMATION: Synthetic Polypeptide

```
<400> SEQUENCE: 75

Gly Lys Asp Gly Glu Ala Gly Ala Gln Gly Pro Pro Gly Pro Ala Gly
1               5                   10                  15

Asp Pro Ile Pro Glu Glu Leu Tyr Glu Met Leu Ser Asp His
            20                  25                  30

<210> SEQ ID NO 76
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 76

Gly Gln Arg Gly Glu Arg Gly Phe Pro Gly Leu Pro Gly Pro Ser Gly
1               5                   10                  15

Asp Pro Ile Pro Glu Glu Leu Tyr Glu Met Leu Ser Asp His
            20                  25                  30

<210> SEQ ID NO 77
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 77

Gly Pro Pro Gly Leu Ala Gly Pro Pro Gly Glu Ser Gly Arg Glu Gly
1               5                   10                  15

Asp Pro Ile Pro Glu Glu Leu Tyr Glu Met Leu Ser Asp His
            20                  25                  30

<210> SEQ ID NO 78
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 78

Gly Pro Ala Gly Pro Val Gly Pro Val Gly Ala Arg Gly Pro Ala Gly
1               5                   10                  15

Asp Pro Ile Pro Glu Glu Leu Tyr Glu Met Leu Ser Asp His
            20                  25                  30

<210> SEQ ID NO 79
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 79

Gly Val Pro Gly Asp Leu Gly Ala Pro Gly Pro Ser Gly Ala Arg Gly
1               5                   10                  15

Asp Pro Ile Pro Glu Glu Leu Tyr Glu Met Leu Ser Asp His
            20                  25                  30

<210> SEQ ID NO 80
<211> LENGTH: 30
<212> TYPE: PRT
<213> ORGANISM: Artificial Sequence
<220> FEATURE:
<223> OTHER INFORMATION: Synthetic Polypeptide
```

```
<400> SEQUENCE: 80

Gly Leu Pro Gly Glu Arg Gly Arg Pro Gly Ala Pro Gly Pro Ala Gly
1               5                   10                  15

Asp Pro Ile Pro Glu Glu Leu Tyr Glu Met Leu Ser Asp His
            20                  25                  30

<210> SEQ ID NO 81
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 81

Gly Pro Ala Gly Glu Lys Gly Ser Pro Gly Ala Asp Gly Pro Ala Gly
1               5                   10                  15

Asp Pro Ile Pro Glu Glu Leu Tyr Glu Met Leu Ser Asp His
            20                  25                  30

<210> SEQ ID NO 82
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 82

Gly Ala Arg Gly Asn Asp Gly Ala Thr Gly Ala Ala Gly Pro Pro Gly
1               5                   10                  15

Asp Pro Ile Pro Glu Glu Leu Tyr Glu Met Leu Ser Asp His
            20                  25                  30

<210> SEQ ID NO 83
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 83

Gly Glu Pro Gly Pro Pro Gly Pro Ala Gly Ala Ala Gly Pro Ala Gly
1               5                   10                  15

Asp Pro Ile Pro Glu Glu Leu Tyr Glu Met Leu Ser Asp His
            20                  25                  30

<210> SEQ ID NO 84
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 84

Gly Ala Pro Gly Ser Lys Gly Asp Thr Gly Ala Lys Gly Glu Pro Gly
1               5                   10                  15

Asp Pro Ile Pro Glu Glu Leu Tyr Glu Met Leu Ser Asp His
            20                  25                  30

<210> SEQ ID NO 85
<211> LENGTH: 30
<212> TYPE: PRT
<213> ORGANISM: Artificial Sequence
<220> FEATURE:
```

<223> OTHER INFORMATION: Synthetic Polypeptide

<400> SEQUENCE: 85

Gly Ala Glu Gly Ser Pro Gly Arg Asp Gly Ser Pro Gly Ala Lys Gly
1               5                   10                  15

Asp Pro Ile Pro Glu Glu Leu Tyr Glu Met Leu Ser Asp His
            20                  25                  30

<210> SEQ ID NO 86
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 86

Gly Glu Ala Gly Arg Pro Gly Glu Ala Gly Leu Pro Gly Ala Lys Gly
1               5                   10                  15

Asp Pro Ile Pro Glu Glu Leu Tyr Glu Met Leu Ser Asp His
            20                  25                  30

<210> SEQ ID NO 87
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 87

Gly Phe Pro Gly Ala Ala Gly Arg Val Gly Pro Pro Gly Pro Ser Gly
1               5                   10                  15

Asp Pro Ile Pro Glu Glu Leu Tyr Glu Met Leu Ser Asp His
            20                  25                  30

<210> SEQ ID NO 88
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 88

Gly Pro Ala Gly Pro Pro Gly Glu Ala Gly Lys Pro Gly Glu Gln Gly
1               5                   10                  15

Asp Pro Ile Pro Glu Glu Leu Tyr Glu Met Leu Ser Asp His
            20                  25                  30

<210> SEQ ID NO 89
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 89

Gly Glu Gln Gly Pro Ser Gly Ala Ser Gly Pro Ala Gly Pro Arg Gly
1               5                   10                  15

Asp Pro Ile Pro Glu Glu Leu Tyr Glu Met Leu Ser Asp His
            20                  25                  30

<210> SEQ ID NO 90
<211> LENGTH: 30
<212> TYPE: PRT
<213> ORGANISM: Artificial Sequence

```
<220> FEATURE:
<223> OTHER INFORMATION: Synthetic Polypeptide

<400> SEQUENCE: 90

Gly Pro Val Gly Pro Ala Gly Lys Ser Gly Asp Arg Gly Glu Thr Gly
1               5                   10                  15

Asp Pro Ile Pro Glu Glu Leu Tyr Glu Met Leu Ser Asp His
            20                  25                  30

<210> SEQ ID NO 91
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 91

Gly Glu Arg Gly Ala Ala Gly Leu Pro Gly Pro Lys Gly Asp Arg Gly
1               5                   10                  15

Asp Pro Ile Pro Glu Glu Leu Tyr Glu Met Leu Ser Asp His
            20                  25                  30

<210> SEQ ID NO 92
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 92

Thr His Gly Gln Glu Glu Gly Gln Val Glu Gly Gln Asp Glu Asp Arg
1               5                   10                  15

Trp Thr Trp

<210> SEQ ID NO 93
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 93

Thr His Gly Gln Glu Glu Gly Gln Val Glu Gly Gln Asp Glu Asp Thr
1               5                   10                  15

Lys Asn Thr Ile Lys
            20

<210> SEQ ID NO 94
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 94

Thr Leu Leu Leu Leu Ala Val Thr Leu Cys Leu Ala Thr Cys Gln Tyr
1               5                   10                  15

Trp Pro Lys Trp Glu Gly Leu Asp Ser Thr Leu Phe His Glu
            20                  25                  30

<210> SEQ ID NO 95
<211> LENGTH: 30
<212> TYPE: PRT
<213> ORGANISM: Artificial Sequence
```

<220> FEATURE:
<223> OTHER INFORMATION: Synthetic Polypeptide

<400> SEQUENCE: 95

Thr Leu Leu Leu Leu Ala Val Thr Leu Cys Leu Ala Thr Cys Gln Cys
1               5                   10                  15

Cys Leu Leu Val Leu Pro Trp Pro Tyr Leu Ala Pro Arg Met
            20                  25                  30

<210> SEQ ID NO 96
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 96

Ala Pro Ser Ala Leu Ser Ser Ser Pro Leu Leu Thr Ala Pro His Arg
1               5                   10                  15

Lys

<210> SEQ ID NO 97
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 97

Ala Pro Ser Ala Leu Ser Ser Ser Pro Leu Leu Thr Ala Pro His Val
1               5                   10                  15

Thr Met Ala Lys Ile Asn Pro Pro
            20

<210> SEQ ID NO 98
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 98

Glu Leu Ser Glu Pro Gly Asp Gly Glu Ala Leu Met Tyr His Thr Ala
1               5                   10                  15

Leu Gly Thr Lys Asp His Val Met Thr Pro Asn Arg Ile Ile
            20                  25                  30

<210> SEQ ID NO 99
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 99

Glu Leu Ser Glu Pro Gly Asp Gly Glu Ala Leu Met Tyr His Thr Ala
1               5                   10                  15

Leu Gly Thr Lys Asp His Val Met Thr Pro
            20                  25

<210> SEQ ID NO 100
<211> LENGTH: 30
<212> TYPE: PRT
<213> ORGANISM: Artificial Sequence -continued

```
<220> FEATURE:
<223> OTHER INFORMATION: Synthetic Polypeptide

<400> SEQUENCE: 100

Thr Arg Ala Phe Glu Gln Leu Met Thr Asp Leu Thr Leu Ser Arg Leu
1               5                   10                  15

Gln Gly Ser Leu Lys Arg Lys Gln Val Val Asn Leu Ser Pro
            20                  25                  30

<210> SEQ ID NO 101
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 101

Ser Pro Pro Trp Asp Gln Asp Arg Arg Met Met Phe Pro Pro Pro Gly
1               5                   10                  15

Ile Leu Thr Asn Val Ile
            20

<210> SEQ ID NO 102
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 102

Pro Pro Pro Ser Gly Ile Ala Thr Leu Val Ser Gly Ile Ala Gly Val
1               5                   10                  15

Tyr Arg Arg Lys His Gln Glu Leu Gln Ala Met Gln Met Glu
            20                  25                  30

<210> SEQ ID NO 103
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 103

Asp Cys Val Leu Val Leu Leu Leu Met Pro Arg Leu Ile Cys Lys Cys
1               5                   10                  15

Thr Ala Gly Ser Thr Arg Ser Cys Lys Pro Cys Arg Trp Ser
            20                  25                  30

<210> SEQ ID NO 104
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 104

Arg His Leu Val Phe Pro Leu Leu Glu Phe Leu Ser Val Lys Glu Leu
1               5                   10                  15

Val Met Tyr Gln Ile Pro Phe Ala Arg Val Val Cys Leu Val
            20                  25                  30

<210> SEQ ID NO 105
<211> LENGTH: 26
<212> TYPE: PRT
```

<213> ORGANISM: Artificial Sequence
<220> FEATURE:
<223> OTHER INFORMATION: Synthetic Polypeptide

<400> SEQUENCE: 105

Arg His Leu Val Phe Pro Leu Leu Glu Phe Leu Ser Val Lys Glu Val
1               5                   10                  15

Arg Gly Gly Glu Met Leu Ile Ala Leu Asn
            20                  25

<210> SEQ ID NO 106
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 106

Asn Lys Tyr Ile Met Ser Asn Ser Gly Asp Tyr Glu Ile Leu Tyr Leu
1               5                   10                  15

Tyr Arg Arg Lys His Gln Glu Leu Gln Ala Met Gln Met Glu
            20                  25                  30

<210> SEQ ID NO 107
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 107

Ile Leu Arg Gly Thr Phe Asn Asp Gly Phe Gln Ile Glu Val Gln Cys
1               5                   10                  15

Thr Ala Gly Ser Thr Arg Ser Cys Lys Pro Cys Arg Trp Ser
            20                  25                  30

<210> SEQ ID NO 108
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 108

His Thr Asp Gly Asn Glu Gln Leu Ser Val Met Arg Tyr Ser Ile Val
1               5                   10                  15

Tyr Arg Arg Lys His Gln Glu Leu Gln Ala Met Gln Met Glu
            20                  25                  30

<210> SEQ ID NO 109
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 109

Val Thr Lys Thr Ala Asp Lys His Lys Asp Val Ile Ile Asn Gln Val
1               5                   10                  15

Ser Pro Thr Pro Glu Pro His Leu Pro Leu Ser Leu Ile Leu
            20                  25                  30

<210> SEQ ID NO 110
<211> LENGTH: 30

```
<212> TYPE: PRT
<213> ORGANISM: Artificial Sequence
<220> FEATURE:
<223> OTHER INFORMATION: Synthetic Polypeptide

<400> SEQUENCE: 110

Ser Glu Asp His Val Ala Ser Val Lys Lys Ser Val Ser Ser Lys Val
1               5                   10                  15

Tyr Arg Arg Lys His Gln Glu Leu Gln Ala Met Gln Met Glu
            20                  25                  30

<210> SEQ ID NO 111
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 111

Ile Ile Leu Trp Asp His Asp Leu Asn Pro Glu Arg Glu Ile Glu Cys
1               5                   10                  15

Thr Ala Gly Ser Thr Arg Ser Cys Lys Pro Cys Arg Trp Ser
            20                  25                  30

<210> SEQ ID NO 112
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 112

Trp Ser Lys Thr Thr Val Glu Pro Thr Pro Gly Lys Gly Pro Lys Val
1               5                   10                  15

Tyr Arg Arg Lys His Gln Glu Leu Gln Ala Met Gln Met Glu
            20                  25                  30

<210> SEQ ID NO 113
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 113

Val Thr Lys Thr Ala Asp Lys His Lys Asp Val Ile Ile Asn Gln Val
1               5                   10                  15

Tyr Arg Arg Lys His Gln Glu Leu Gln Ala Met Gln Met Glu
            20                  25                  30

<210> SEQ ID NO 114
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 114

Ser Thr Ser Thr Gln Ser Lys Ser Ser Gly Ser Ala His Phe Gly
1               5                   10                  15

Pro Pro Arg Met Gln Trp Arg Ser Pro Pro Gly
            20                  25

<210> SEQ ID NO 115
```

```
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 115

Glu Cys Glu Gln Ala Glu Arg Leu Gly Ala Val Asp Glu Ser Leu Arg
1               5                   10                  15

Lys Tyr Ile Phe Lys Pro Arg Thr Val
            20                  25

<210> SEQ ID NO 116
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 116

Ala Leu Arg Met Glu Glu Asp Ser Ile Arg Leu Pro Ala His Leu Pro
1               5                   10                  15

Lys Asn Arg Gly Ile Ala Ile Pro Val Asp Leu Asp Ser Gln
            20                  25                  30

<210> SEQ ID NO 117
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 117

Ile His Thr Gln Pro Glu Val Ile Leu His Gln Asn His Glu Glu Gly
1               5                   10                  15

Arg Lys His Pro Tyr Ser Trp Glu Cys Met Cys Gln Lys Tyr
            20                  25                  30

<210> SEQ ID NO 118
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 118

Ile His Thr Gln Pro Glu Val Ile Leu His Gln Asn His Glu Glu Val
1               5                   10                  15

Leu Gln Glu Arg Ile Pro Trp Val Pro Pro Glu Cys Ile Glu
            20                  25                  30

<210> SEQ ID NO 119
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 119

Val Ser Pro Pro Glu Glu His Ala Met Pro Ile Gly Arg Ile Ala Asp
1               5                   10                  15

Tyr Glu Leu Leu Thr Glu Asn Asp Met Leu Pro Asn Met Arg
            20                  25                  30
```

```
<210> SEQ ID NO 120
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 120

Val Ser Pro Pro Glu Glu His Ala Met Pro Ile Gly Arg Ile Ala Asp
1               5                   10                  15

Lys Ser Asn Leu Leu Val Phe Arg Thr Asn Gly Val Ser Asp
            20                  25                  30

<210> SEQ ID NO 121
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 121

Val Ser Pro Pro Glu Glu His Ala Met Pro Ile Gly Arg Ile Ala Asp
1               5                   10                  15

Val Gln His Ile Lys Arg Arg Asp Ile Val Leu Lys Arg Glu
            20                  25                  30

<210> SEQ ID NO 122
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 122

Ile His Thr Gln Pro Glu Val Ile Leu His Gln Asn His Glu Glu Gly
1               5                   10                  15

Pro Val Ala Val Ile Ser Gly Glu Glu Asp Ser Ala Ser Pro
            20                  25                  30

<210> SEQ ID NO 123
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 123

Val Ser Pro Pro Glu Glu His Ala Met Pro Ile Gly Arg Ile Ala Gly
1               5                   10                  15

Pro Val Ala Val Ile Ser Gly Glu Glu Asp Ser Ala Ser Pro
            20                  25                  30

<210> SEQ ID NO 124
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 124

Ile His Thr Gln Pro Glu Val Ile Leu His Gln Asn His Glu Glu Asp
1               5                   10                  15

Val Gln His Ile Lys Arg Arg Asp Ile Val Leu Lys Arg Glu
            20                  25                  30
```

-continued

<210> SEQ ID NO 125
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 125

Ala Pro Ser Gln Tyr Ser Gln Gln Ser Ser Tyr Gly Gln Gln Ile
1               5                   10                  15

Ala Ile Ala Pro Asn Gly Ala Leu Gln Leu Ala Ser Pro Gly
            20                  25                  30

<210> SEQ ID NO 126
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 126

Ala Pro Ser Gln Tyr Ser Gln Gln Ser Ser Tyr Gly Gln Gln Lys
1               5                   10                  15

Lys Leu Leu Glu Asn Val Ala Glu Arg Arg Lys Asn Met
            20                  25

<210> SEQ ID NO 127
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 127

Gly Met Gly Ser Ala Gly Glu Arg Gly Gly Phe Asn Lys Pro Gly Glu
1               5                   10                  15

Lys Phe

<210> SEQ ID NO 128
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 128

Gly Gly Met Ser Arg Gly Gly Arg Gly Gly Arg Gly Gly Met Gly
1               5                   10                  15

Lys Ile Leu Lys Asp Leu Ser Ser Glu Asp Thr Arg Gly Arg
            20                  25                  30

<210> SEQ ID NO 129
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 129

Ala Pro Ser Gln Tyr Ser Gln Gln Ser Ser Tyr Gly Gln Gln Ile
1               5                   10                  15

Ala Ile Thr Gln Gly Gly Ala Ile Gln Leu Ala Asn Asn Gly
            20                  25                  30

<210> SEQ ID NO 130
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 130

Asn Lys Pro Gly Gly Pro Met Asp Glu Gly Pro Asp Leu Asp Leu Val
1               5                   10                  15

Phe Lys Lys Glu Val Tyr Leu His Thr Ser Pro His Leu Lys
            20                  25                  30

<210> SEQ ID NO 131
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 131

Leu Pro Pro Arg Glu Gly Arg Gly Met Pro Pro Pro Leu Arg Gly Val
1               5                   10                  15

Phe Lys Lys Glu Val Tyr Leu His Thr Ser Pro His Leu Lys
            20                  25                  30

<210> SEQ ID NO 132
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 132

Ala Pro Ser Gln Tyr Ser Gln Gln Ser Ser Tyr Gly Gln Gln Met
1               5                   10                  15

Phe Lys Lys Glu Val Tyr Leu His Thr Ser Pro His Leu Lys
            20                  25                  30

<210> SEQ ID NO 133
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 133

Ala Pro Ser Gln Tyr Ser Gln Gln Ser Ser Tyr Gly Gln Gln Thr
1               5                   10                  15

Ala Gln Pro Ser Pro Ser Thr Val Pro Lys Thr Glu Asp Gln
            20                  25                  30

<210> SEQ ID NO 134
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 134

Ala Pro Ser Gln Tyr Ser Gln Gln Ser Ser Tyr Gly Gln Gln Asn
1               5                   10                  15

Pro Tyr Gln Ile Leu Gly Pro Thr Ser Ser Arg Leu Ala Asn
            20                  25                  30

```
<210> SEQ ID NO 135
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 135

Asn Lys Pro Gly Gly Pro Met Asp Glu Gly Pro Asp Leu Asp Leu Asp
1               5                   10                  15

Leu Pro Tyr Glu Pro Pro Arg Arg Ser Ala Trp Thr Gly His
            20                  25                  30

<210> SEQ ID NO 136
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 136

Ala Pro Ser Gln Tyr Ser Gln Gln Ser Ser Tyr Gly Gln Gln Ser
1               5                   10                  15

Ser Gly Gln Ile Gln Leu Trp Gln Phe Leu Leu Glu Leu Leu
            20                  25                  30

<210> SEQ ID NO 137
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 137

Ala Pro Ser Gln Tyr Ser Gln Gln Ser Ser Tyr Gly Gln Gln Asn
1               5                   10                  15

Leu Pro Tyr Glu Pro Pro Arg Arg Ser Ala Trp Thr Gly His
            20                  25                  30

<210> SEQ ID NO 138
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 138

Ala Pro Ser Gln Tyr Ser Gln Gln Ser Ser Tyr Gly Gln Gln Arg
1               5                   10                  15

Asp Ile Lys Gln Glu Pro Gly Met Tyr Arg Glu Gly Pro Thr
            20                  25                  30

<210> SEQ ID NO 139
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 139

Asn Lys Pro Gly Gly Pro Met Asp Glu Gly Pro Asp Leu Asp Leu Asp
1               5                   10                  15

Pro Val Gly Asp Gly Leu Phe Lys Asp Gly Lys Asn Pro Ser
```

```
            20                  25                  30

<210> SEQ ID NO 140
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 140

Ala Pro Ser Gln Tyr Ser Gln Gln Ser Ser Ser Tyr Gly Gln Gln Asn
1               5                   10                  15

Pro Val Gly Asp Gly Leu Phe Lys Asp Gly Lys Asn Pro Ser
            20                  25                  30

<210> SEQ ID NO 141
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 141

Gly Gly Met Ser Arg Gly Gly Arg Gly Gly Arg Gly Gly Met Gly
1               5                   10                  15

Ile Pro Val Thr Ala Ser Leu Pro Pro Leu Glu Trp Pro Leu
            20                  25                  30

<210> SEQ ID NO 142
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 142

Tyr Glu Asp Pro Pro Thr Ala Lys Ala Ala Val Glu Trp Phe Asp Asp
1               5                   10                  15

Met Pro Cys Val Gln Ala Gln Tyr Ser Pro Ser Pro Pro Gly
            20                  25                  30

<210> SEQ ID NO 143
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 143

Ala Pro Ser Gln Tyr Ser Gln Gln Ser Ser Ser Tyr Gly Gln Gln Arg
1               5                   10                  15

Pro Met Asp Glu Gly Pro Asp Leu Asp Leu Gly Pro Pro Val
            20                  25                  30

<210> SEQ ID NO 144
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 144

Gly Met Gly Ser Ala Gly Glu Arg Gly Gly Phe Asn Lys Pro Gly Gly
1               5                   10                  15
```

```
Pro Pro Val Asp Pro Asp Glu Asp Ser Asp Asn Ser Ala Ile
            20                  25                  30

<210> SEQ ID NO 145
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 145

Leu Pro Pro Arg Glu Gly Arg Gly Met Pro Pro Leu Arg Gly Asp
1               5                   10                  15

Met Pro Cys Val Gln Ala Gln Tyr Ser Pro Ser Pro Pro Gly
            20                  25                  30

<210> SEQ ID NO 146
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 146

Asn Lys Pro Gly Gly Pro Met Asp Glu Gly Pro Asp Leu Asp Leu Asp
1               5                   10                  15

Met Pro Cys Val Gln Ala Gln Tyr Ser Pro Ser Pro Pro Gly
            20                  25                  30

<210> SEQ ID NO 147
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 147

Tyr Glu Asp Pro Pro Thr Ala Lys Ala Ala Val Glu Trp Phe Asp Glu
1               5                   10                  15

Pro Thr Ala Glu Glu Gly Ser Pro Ala Ser Pro Gly Pro Glu
            20                  25                  30

<210> SEQ ID NO 148
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 148

Ala Pro Ser Gln Tyr Ser Gln Gln Ser Ser Tyr Gly Gln Gln Lys
1               5                   10                  15

Pro Thr Ala Glu Glu Gly Ser Pro Ala Ser Pro Gly Pro Glu
            20                  25                  30

<210> SEQ ID NO 149
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 149

Ala Pro Ser Gln Tyr Ser Gln Gln Ser Ser Tyr Gly Gln Gln Ser
1               5                   10                  15
```

```
Gly Arg Asp Gly Ile Ser Thr Ser Lys Arg Gln Lys Ser
            20                  25
```

<210> SEQ ID NO 150
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 150

```
Gly Gly Met Ser Arg Gly Gly Arg Gly Gly Arg Gly Gly Met Gly
1               5                   10                  15

Arg Lys Arg Arg Asn Phe Asn Lys Gln Ala Thr Glu Ile Leu
            20                  25                  30
```

<210> SEQ ID NO 151
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 151

```
Ala Pro Ser Gln Tyr Ser Gln Gln Ser Ser Tyr Gly Gln Gln Asn
1               5                   10                  15

Val Lys Trp Gly Lys Leu Arg Asp Tyr Gln Val Arg Gly Leu
            20                  25                  30
```

<210> SEQ ID NO 152
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 152

```
Gly Gly Met Ser Arg Gly Gly Arg Gly Gly Arg Gly Gly Met Gly
1               5                   10                  15

Gly Thr Asn Leu Gly Lys Lys Lys Gln His Ile Cys His Ile
            20                  25                  30
```

<210> SEQ ID NO 153
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 153

```
Tyr Gly Gln Thr Ala Tyr Ala Thr Ser Tyr Gly Gln Pro Pro Thr Glu
1               5                   10                  15

Gly Thr Ser Thr Gly Tyr Thr Thr Pro Thr Ala Pro Gln Ala
            20                  25                  30
```

<210> SEQ ID NO 154
<211> LENGTH: 28
<212> TYPE: PRT
<213> ORGANISM: Artificial Sequence
<220> FEATURE:
<223> OTHER INFORMATION: Synthetic Polypeptide

<400> SEQUENCE: 154

```
Ala Tyr Pro Ala Tyr Gly Gln Gln Pro Ala Ala Thr Ala Pro Thr Ser
```

```
                1               5                  10                  15
Ser Ala Gly Glu Arg Gly Gly Phe Asn Lys Pro Gly
            20                  25

<210> SEQ ID NO 155
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 155

Ala Tyr Pro Ala Tyr Gly Gln Gln Pro Ala Ala Thr Ala Pro Thr Ser
1               5                  10                  15

Tyr Ser Ser Thr Gln Pro Thr Ser Tyr Asp Gln Ser Ser Tyr
            20                  25                  30

<210> SEQ ID NO 156
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 156

Ala Pro Ser Gln Tyr Ser Gln Gln Ser Ser Ser Tyr Gly Gln Gln Asn
1               5                  10                  15

Glu Lys Lys Asp Ile Asp His Glu Thr Val Val Glu Glu Gln
            20                  25                  30

<210> SEQ ID NO 157
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 157

Gly Gly Met Ser Arg Gly Gly Arg Gly Gly Gly Arg Gly Gly Met Gly
1               5                  10                  15

Arg His Arg Pro Trp Gly
            20

<210> SEQ ID NO 158
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 158

Leu Arg Leu Gln Asp Tyr Glu Glu Lys Thr Lys Lys Ala Glu Arg Asp
1               5                  10                  15

Asp Phe Trp Ile Pro Glu Thr Ser Phe Ile Leu Thr Ile Ile
            20                  25                  30

<210> SEQ ID NO 159
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 159
```

-continued

Thr Ser Ser Leu His Gly Ser Ser Leu His Arg Pro Ser Thr Glu Asp
1               5                   10                  15

Leu Ile Arg Asp Gln Gly Phe Arg Gly Asp Gly Gly Ser Thr
            20                  25                  30

<210> SEQ ID NO 160
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 160

Met Gly Cys Ile Gly Ser Arg Thr Val Gly Ser Thr Thr Gly Leu Ser
1               5                   10                  15

Ala Thr Pro Pro Ala Ser Leu Pro Gly
            20                  25

<210> SEQ ID NO 161
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 161

Ser Thr Glu Gln Thr Arg Thr Asp Phe Ser Trp Asp Gly Ile Asn Asp
1               5                   10                  15

Leu Ile Arg Asp Gln Gly Phe Arg Gly Asp Gly Gly Ser Thr
            20                  25                  30

<210> SEQ ID NO 162
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 162

Met Ala Ser Ser Gly Glu Arg Thr Pro Ser Asn Ala Leu Asp Pro Arg
1               5                   10                  15

Trp Arg Ser Leu Trp
            20

<210> SEQ ID NO 163
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 163

Arg Leu Ser Glu Ala Arg Leu Ser Gln Arg Asp Leu Ser Pro Thr Asp
1               5                   10                  15

Leu Ile Arg Asp Gln Gly Phe Arg Gly Asp Gly Gly Ser Thr
            20                  25                  30

<210> SEQ ID NO 164
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 164

```
Ala Thr Leu Cys Thr Ala Arg Pro Ser Pro Thr Leu Pro Glu Gln Asp
1               5                   10                  15

Trp Pro Lys Trp Glu Gly Leu Asp Ser Thr Leu Phe His Glu
            20                  25                  30

<210> SEQ ID NO 165
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 165

Ala Thr Leu Cys Thr Ala Arg Pro Ser Pro Thr Leu Pro Glu Gln Gly
1               5                   10                  15

Cys Leu Leu Val Leu Pro Trp Pro Tyr Leu Ala Pro Arg Met
            20                  25                  30

<210> SEQ ID NO 166
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 166

Leu Val Glu Asp Leu Asp Arg Ile Val Ala Leu Thr Ser Asn Gln Gly
1               5                   10                  15

Leu Leu Glu Ser Ser Ala Glu Lys Ala Pro Val Ser Val Ser
            20                  25                  30

<210> SEQ ID NO 167
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 167

Ala Arg Asp Ile His His Ile Asp Tyr Tyr Lys Lys Thr Thr Asn Leu
1               5                   10                  15

Asp Ala Lys Lys Ser Pro Leu Ala Leu Leu Ala Gln Thr Cys
            20                  25                  30

<210> SEQ ID NO 168
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 168

Leu Val Glu Asp Leu Asp Arg Val Leu Thr Val Thr Ser Thr Asp Asn
1               5                   10                  15

Val Met Glu Gln Phe Asn Pro Gly Leu Arg Asn Leu Ile Asn
            20                  25                  30

<210> SEQ ID NO 169
<211> LENGTH: 30
<212> TYPE: PRT
<213> ORGANISM: Artificial Sequence
<220> FEATURE:
<223> OTHER INFORMATION: Synthetic Polypeptide
```

<400> SEQUENCE: 169

Leu Val Glu Asp Leu Asp Arg Val Leu Thr Val Thr Ser Thr Asp Phe
1               5                   10                  15

Lys Glu Ser Ala Leu Arg Lys Gln Ser Leu Tyr Leu Lys Phe
            20                  25                  30

<210> SEQ ID NO 170
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 170

Leu Val Glu Asp Leu Asp Arg Val Leu Thr Val Thr Ser Thr Asp Val
1               5                   10                  15

Pro Gly Pro Pro Pro Gly Val Pro Ala Pro Gly Gly Pro Pro
            20                  25                  30

<210> SEQ ID NO 171
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 171

Leu Val Glu Asp Leu Asp Arg Val Leu Thr Val Thr Ser Thr Asp Val
1               5                   10                  15

Lys Ala Thr Gln Glu Glu Asn Arg Glu Leu Arg Ser Arg Cys
            20                  25                  30

<210> SEQ ID NO 172
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 172

Arg Lys Ala Gly Asp Phe His Arg Asn Asp Ser Ile Tyr Glu Glu Pro
1               5                   10                  15

Gln Gln Val Val Gln Lys Lys Pro Ala Gln Glu Glu Thr Glu
            20                  25                  30

<210> SEQ ID NO 173
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 173

Tyr Phe Lys Asp Lys Gly Asp Ser Asn Ser Ser Ala Gly Trp Lys Val
1               5                   10                  15

Met Gly Leu Leu Thr Asn His Gly Gly Val Pro His Gln Pro
            20                  25                  30

<210> SEQ ID NO 174
<211> LENGTH: 30
<212> TYPE: PRT
<213> ORGANISM: Artificial Sequence
<220> FEATURE:
<223> OTHER INFORMATION: Synthetic Polypeptide -continued

<400> SEQUENCE: 174

Gln Tyr Asn Ser Ser Gly Gly Gly Gly Gly Gly Gly Gly Gly Val
1               5                   10                  15

Ala Ile Ala Pro Asn Gly Ala Leu Gln Leu Ala Ser Pro Gly
            20                  25                  30

<210> SEQ ID NO 175
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 175

Glu Pro Arg Gly Arg Gly Gly Gly Arg Gly Gly Arg Gly Gly Met Gly
1               5                   10                  15

Pro Ser Gly Pro Pro Ala Phe Ala Ala His Pro Ser Glu Gln
            20                  25                  30

<210> SEQ ID NO 176
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 176

Glu Pro Arg Gly Arg Gly Gly Gly Arg Gly Gly Arg Gly Gly Met Gly
1               5                   10                  15

Asn Cys Arg Asp Gln Ala Leu Trp Ser
            20                  25

<210> SEQ ID NO 177
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 177

Glu Pro Arg Gly Arg Gly Gly Gly Arg Gly Gly Arg Gly Gly Met Gly
1               5                   10                  15

Pro Gln Trp Thr Thr Cys Ile Cys Arg Pro Pro Leu Arg Ala
            20                  25                  30

<210> SEQ ID NO 178
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 178

Glu Pro Arg Gly Arg Gly Gly Gly Arg Gly Gly Arg Gly Gly Met Gly
1               5                   10                  15

Cys Leu Pro Ser Gly Pro Pro Ala Phe Ala Ala His Pro Ser
            20                  25                  30

<210> SEQ ID NO 179
<211> LENGTH: 30
<212> TYPE: PRT
<213> ORGANISM: Artificial Sequence
<220> FEATURE:

<223> OTHER INFORMATION: Synthetic Polypeptide

<400> SEQUENCE: 179

Gln Tyr Asn Ser Ser Gly Gly Gly Gly Gly Gly Gly Gly Gly Ala
1               5                   10                  15

Pro Val Asp His Leu His Leu Pro Pro Thr Pro Pro Ser Ser
            20                  25                  30

<210> SEQ ID NO 180
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 180

Gln Tyr Asn Ser Ser Gly Gly Gly Gly Gly Gly Gly Gly Gly Glu
1               5                   10                  15

Thr Ala Gly Ile Arg Pro Ser Gly Pro Asp Arg Gly Gly Glu
            20                  25                  30

<210> SEQ ID NO 181
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 181

Gly Gly Met Gly Gly Ser Asp Arg Gly Gly Phe Asn Lys Phe Gly Ala
1               5                   10                  15

Pro Val Asp His Leu His Leu Pro Pro Thr Pro Pro Ser Ser
            20                  25                  30

<210> SEQ ID NO 182
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 182

Gln Tyr Asn Ser Ser Gly Gly Gly Gly Gly Gly Gly Gly Gly Val
1               5                   10                  15

Phe Lys Lys Glu Val Tyr Leu His Thr Ser Pro His Leu Lys
            20                  25                  30

<210> SEQ ID NO 183
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 183

Glu Pro Arg Gly Arg Gly Gly Gly Arg Gly Gly Arg Gly Gly Met Gly
1               5                   10                  15

Val Gln Glu Gly Ser Val Ser Ser Tyr Ile Thr Thr Pro Glu
            20                  25                  30

<210> SEQ ID NO 184
<211> LENGTH: 30
<212> TYPE: PRT
<213> ORGANISM: Artificial Sequence

```
<220> FEATURE:
<223> OTHER INFORMATION: Synthetic Polypeptide

<400> SEQUENCE: 184

Gly Gly Met Gly Gly Ser Asp Arg Gly Gly Phe Asn Lys Phe Gly Val
1               5                   10                  15

Phe Lys Lys Glu Val Tyr Leu His Thr Ser Pro His Leu Lys
            20                  25                  30

<210> SEQ ID NO 185
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 185

Gly Tyr Gly Gln Ser Ser Tyr Ser Ser Tyr Gly Gln Ser Gln Asn Met
1               5                   10                  15

Phe Lys Lys Glu Val Tyr Leu His Thr Ser Pro His Leu Lys
            20                  25                  30

<210> SEQ ID NO 186
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 186

Phe Asn Arg Gly Gly Asn Gly Arg Gly Arg Gly Arg Gly Val
1               5                   10                  15

Phe Lys Lys Glu Val Tyr Leu His Thr Ser Pro His Leu Lys
            20                  25                  30

<210> SEQ ID NO 187
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 187

Ile Glu Ser Val Ala Asp Tyr Phe Lys Gln Ile Gly Ile Ile Lys Thr
1               5                   10                  15

Asp Pro Thr Ala Glu Met Ala Ala Glu Ser Leu Pro Phe Ser
            20                  25                  30

<210> SEQ ID NO 188
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 188

Asn Lys Phe Gly Gly Pro Arg Asp Gln Gly Ser Arg His Asp Ser Val
1               5                   10                  15

Phe Lys Lys Glu Val Tyr Leu His Thr Ser Pro His Leu Lys
            20                  25                  30

<210> SEQ ID NO 189
<211> LENGTH: 27
<212> TYPE: PRT
```

```
<213> ORGANISM: Artificial Sequence
<220> FEATURE:
<223> OTHER INFORMATION: Synthetic Polypeptide

<400> SEQUENCE: 189

Glu Pro Arg Gly Arg Gly Gly Arg Gly Gly Arg Gly Gly Met Gly
1               5                   10                  15

Gly Ser Asp Arg Gly Gly Phe Asn Lys Phe Gly
            20                  25

<210> SEQ ID NO 190
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 190

Gly Gly Met Gly Gly Ser Asp Arg Gly Gly Phe Asn Lys Phe Gly Asp
1               5                   10                  15

Leu Pro Tyr Glu Pro Pro Arg Arg Ser Ala Trp Thr Gly His
            20                  25                  30

<210> SEQ ID NO 191
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 191

Asn Lys Phe Gly Gly Pro Arg Asp Gln Gly Ser Arg His Asp Ser Ala
1               5                   10                  15

Ala Gln Pro Ser Pro Ser Thr Val Pro Lys Thr Glu Asp Gln
            20                  25                  30

<210> SEQ ID NO 192
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 192

Gln Tyr Asn Ser Ser Ser Gly Gly Gly Gly Gly Gly Gly Gly Gly Asp
1               5                   10                  15

Leu Pro Tyr Glu Pro Pro Arg Arg Ser Ala Trp Thr Gly His
            20                  25                  30

<210> SEQ ID NO 193
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 193

Gly Gly Met Gly Gly Ser Asp Arg Gly Gly Phe Asn Lys Phe Gly Asp
1               5                   10                  15

Pro Tyr Gln Ile Leu Gly Pro Thr Ser Ser Arg Leu Ala Asn
            20                  25                  30

<210> SEQ ID NO 194
<211> LENGTH: 30
```

<212> TYPE: PRT
<213> ORGANISM: Artificial Sequence
<220> FEATURE:
<223> OTHER INFORMATION: Synthetic Polypeptide

<400> SEQUENCE: 194

Gly Gly Met Gly Gly Ser Asp Arg Gly Gly Phe Asn Lys Phe Gly Gly
1               5                   10                  15

Ser Gly Gln Ile Gln Leu Trp Gln Phe Leu Leu Glu Leu Leu
            20                  25                  30

<210> SEQ ID NO 195
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 195

Glu Pro Arg Gly Arg Gly Gly Arg Gly Gly Arg Gly Gly Met Gly
1               5                   10                  15

Gln Trp Pro Asp Pro Ala Leu Ala Val Pro Pro Gly Ala Pro
            20                  25                  30

<210> SEQ ID NO 196
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 196

Phe Asp Asp Pro Pro Ser Ala Lys Ala Ala Ile Asp Trp Phe Asp Asp
1               5                   10                  15

Pro Val Gly Asp Gly Leu Phe Lys Asp Gly Lys Asn Pro Ser
            20                  25                  30

<210> SEQ ID NO 197
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 197

Arg Ala Glu Asn Ala Cys Val Pro Pro Phe Thr Ile Glu Val Lys Lys
1               5                   10                  15

Thr Leu Gly Arg Arg Asp Ser Ser Asp Asp Trp Glu Ile Pro
            20                  25                  30

<210> SEQ ID NO 198
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 198

Pro Leu Glu Gly Asp Met Ser Ser Pro Asn Ser Thr Gly Ile Gln Ile
1               5                   10                  15

Met Phe Glu Thr Phe Asn Thr Pro Ala Met Tyr Val Ala Ile
            20                  25                  30

<210> SEQ ID NO 199

```
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 199

Met Ile Pro His Pro Gln Ser Arg Gly Pro Phe Pro Thr Cys Gln Ile
1               5                   10                  15
Met Phe Glu Thr Phe Asn Thr Pro Ala Met Tyr Val Ala Ile
            20                  25                  30

<210> SEQ ID NO 200
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 200

Gly Lys Pro Arg Asn Val Ala Leu Ile Thr Gly Ile Thr Gly Gln Pro
1               5                   10                  15
Leu His Ile Cys Gln Pro
            20

<210> SEQ ID NO 201
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 201

Glu Asp Gly Glu Lys Ala Ala Arg Glu Val Lys Leu Leu Leu Leu Gly
1               5                   10                  15
Ser Thr Thr Gly Leu Ser Ala Thr Pro Pro Ala Ser Leu Pro
            20                  25                  30

<210> SEQ ID NO 202
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 202

Gln Lys Leu Met Gly Gln Ile His Gln Leu Arg Ser Glu Leu Gln Glu
1               5                   10                  15
Asp Pro Lys Trp Glu Phe Pro Arg Lys Asn Leu Val Leu Gly
            20                  25                  30

<210> SEQ ID NO 203
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 203

Gly Ala Arg Leu Ala Ala Lys Tyr Leu Asp Lys Glu Leu Ala Gly Ser
1               5                   10                  15
Thr Leu Pro Thr Gln Glu Glu Ile Glu Asn Leu Pro Ala Phe
            20                  25                  30
```

<210> SEQ ID NO 204
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 204

Gly Ala Ser Cys Lys Asp Thr Ser Gly Glu Ile Lys Val Leu Gln Val
1               5                   10                  15

Trp His Arg Arg Leu Lys Asn Gln Lys Ser Ala Lys Glu Gly
            20                  25                  30

<210> SEQ ID NO 205
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 205

Leu Ile Asn Ile Met Ile Glu Pro Gln Ala Thr Arg Lys Ala Gln Asp
1               5                   10                  15

Ala Ile Arg Ser His Ser Glu Ser Ala Ser Pro Ser Ala Leu
            20                  25                  30

<210> SEQ ID NO 206
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 206

Glu Val Leu Arg Asn Leu Ser Ser Pro Gly Trp Glu Asn Ile Ser Ser
1               5                   10                  15

Leu Leu Phe Val Ser Lys Phe Phe Glu His His Pro Ile Pro
            20                  25                  30

<210> SEQ ID NO 207
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 207

Met Thr Val Asp His Leu Lys Met Leu His Thr Ala Gly Gly Lys Ala
1               5                   10                  15

Phe Asn Asn Pro Arg Pro Gly Gln Leu Gly Arg Leu Leu Pro
            20                  25                  30

<210> SEQ ID NO 208
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 208

Val Val Ala Ser Thr Ile Ser Gly Lys Ser Gln Ile Glu Glu Thr Val
1               5                   10                  15

Tyr Arg Arg Lys His Gln Glu Leu Gln Ala Met Gln Met Glu
            20                  25                  30

<210> SEQ ID NO 209
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 209

Lys Lys His Tyr Glu Leu Ala Gly Val Ala Glu Gly Trp Glu Val
1               5                   10                  15

Tyr Arg Arg Lys His Gln Glu Leu Gln Ala Met Gln Met Glu
            20                  25                  30

<210> SEQ ID NO 210
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 210

His Gly Ala Thr Thr Cys Leu Arg Ala Pro Pro Glu Pro Ala Asp Leu
1               5                   10                  15

Tyr Arg Arg Lys His Gln Glu Leu Gln Ala Met Gln Met Glu
            20                  25                  30

<210> SEQ ID NO 211
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 211

Ser Asp Ser Ala Gln Gly Ser Asp Val Ser Leu Thr Ala Cys Lys Asp
1               5                   10                  15

Asp Phe Trp Ile Pro Glu Thr Ser Phe Ile Leu Thr Ile Ile
            20                  25                  30

<210> SEQ ID NO 212
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 212

Glu Ala Thr Gly Glu Lys Arg Pro Arg Gly Arg Pro Arg Lys Trp Val
1               5                   10                  15

Thr Val Lys Val Pro Gln Lys Asn Ser
            20                  25

<210> SEQ ID NO 213
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 213

Pro Lys Gly Ser Lys Asn Lys Ser Pro Ser Lys Ala Ala Gln Lys Val
1               5                   10                  15

His Gln Glu Arg Leu Tyr Gln Glu Tyr Asn Phe Ser Lys Ala
            20                  25                  30

```
<210> SEQ ID NO 214
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 214

Glu Ala Thr Gly Glu Lys Arg Pro Arg Gly Arg Pro Arg Lys Trp Asn
1               5                   10                  15

Phe Phe Arg Leu Asn Tyr Leu Glu Val Cys His
            20                  25

<210> SEQ ID NO 215
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 215

Glu Ala Thr Gly Glu Lys Arg Pro Arg Gly Arg Pro Arg Lys Trp Val
1               5                   10                  15

Val Val Ser Thr Thr Val Asn Val Asp Gly His Val Leu Ala
            20                  25                  30

<210> SEQ ID NO 216
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 216

Glu Ala Thr Gly Glu Lys Arg Pro Arg Gly Arg Pro Arg Lys Trp Leu
1               5                   10                  15

Gln Lys His Asp Lys Glu Asp Phe Pro Ala Ser Trp Arg Ser
            20                  25                  30

<210> SEQ ID NO 217
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 217

Glu Ala Thr Gly Glu Lys Arg Pro Arg Gly Arg Pro Arg Lys Trp Gly
1               5                   10                  15

Ser Val Lys Ser Ala Gly Pro Thr Thr Ala Arg Glu Gln Val
            20                  25                  30

<210> SEQ ID NO 218
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 218

Pro Arg Lys Trp Pro Gln Gln Val Val Gln Lys Lys Pro Ala Gln Ser
1               5                   10                  15

Trp Tyr Leu Gly
```

```
                    20

<210> SEQ ID NO 219
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 219

Glu Ala Thr Gly Glu Lys Arg Pro Arg Gly Arg Pro Arg Lys Trp Ser
1               5                   10                  15

Trp Tyr Leu Gly
            20

<210> SEQ ID NO 220
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 220

Glu Ala Thr Gly Glu Lys Arg Pro Arg Gly Arg Pro Arg Lys Trp Val
1               5                   10                  15

Ile Leu Thr Asn Gln Ile Thr Thr His Leu Ser Gly Ala Leu
            20                  25                  30

<210> SEQ ID NO 221
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 221

Glu Ala Thr Gly Glu Lys Arg Pro Arg Gly Arg Pro Arg Lys Trp Leu
1               5                   10                  15

Ser Ala Ser Leu Ala Val Val His Met Glu Pro Ala Met Asn
            20                  25                  30

<210> SEQ ID NO 222
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 222

Glu Ala Thr Gly Glu Lys Arg Pro Arg Gly Arg Pro Arg Lys Trp Gly
1               5                   10                  15

Thr Lys Pro Ala Ser Tyr Met Pro
            20

<210> SEQ ID NO 223
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 223

Glu Ala Thr Gly Glu Lys Arg Pro Arg Gly Arg Pro Arg Lys Trp Ala
1               5                   10                  15
```

```
Glu Tyr Phe Tyr Glu Phe Leu Ser Leu Arg Ser Leu Asp Lys
            20                  25                  30
```

<210> SEQ ID NO 224
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 224

```
Glu Ala Thr Gly Glu Lys Arg Pro Arg Gly Arg Pro Arg Lys Trp Leu
1               5                   10                  15

Phe Lys Leu Val Ser His Val Leu Glu Asn Arg Met Gly Trp
            20                  25                  30
```

<210> SEQ ID NO 225
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 225

```
Pro Arg Lys Trp Pro Gln Gln Val Val Gln Lys Lys Pro Ala Gln Gly
1               5                   10                  15

Thr Lys Pro Ala Ser Tyr Met Pro
            20
```

<210> SEQ ID NO 226
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 226

```
Met Glu Ser Gln Arg Gly Arg Asn Cys Asn Glu Lys Pro Thr Asn Val
1               5                   10                  15

Arg
```

<210> SEQ ID NO 227
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 227

```
Lys Ala Asn Ala Ala Arg Ser Gln Leu Glu Thr Tyr Lys Arg Gln Glu
1               5                   10                  15

Asp Pro Lys Trp Glu Phe Pro Arg Lys Asn Leu Val Leu Gly
            20                  25                  30
```

<210> SEQ ID NO 228
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 228

```
Ser Arg Ser Pro Pro Ala Glu Asn Glu Val Ser Thr Pro Met Gln Lys
1               5                   10                  15
```

```
Lys Lys Gly Gly Arg Gly Leu Met Thr Glu Asn Thr Met Arg
            20                  25                  30

<210> SEQ ID NO 229
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 229

Ser Val Glu Gly Val Val Arg Ile Leu Leu Glu His Tyr Tyr Lys Ala
1               5                   10                  15

Trp Lys Lys Arg Trp Phe Ile Leu Arg Ser Gly Arg Met Ser
            20                  25                  30

<210> SEQ ID NO 230
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 230

Ser Phe Arg Ala Ile Ile Arg Asp Leu Asn Ser Leu Phe Thr Pro Asp
1               5                   10                  15

Cys Arg Leu Leu Trp Asp Tyr Val Tyr Gln Leu Leu Ser Asp
            20                  25                  30

<210> SEQ ID NO 231
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 231

Asn Ile Ile Phe Gln Phe Thr Lys Cys Cys Pro Pro Lys Pro Lys Glu
1               5                   10                  15

Thr Gly Ser Asp Phe Ser Met Phe Glu Ala Leu Arg Asp Thr
            20                  25                  30

<210> SEQ ID NO 232
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 232

Ser Pro Lys Asp Phe Asn Lys Tyr Phe Leu Thr Phe Ala Val Glu Glu
1               5                   10                  15

Ala Glu Ser Gly Asn Ile Ser Gln Lys Ser Asp Glu Glu Asp
            20                  25                  30

<210> SEQ ID NO 233
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 233

Pro Pro Ile Thr Pro Ser Ser Phe Arg Ser Ser Thr Pro Thr Gly
1               5                   10                  15
```

```
Pro Pro Arg Met Gln Trp Arg Ser Pro Pro Gly
            20                  25
```

<210> SEQ ID NO 234
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 234

```
Pro Pro Ile Thr Pro Ser Ser Ser Phe Arg Ser Ser Thr Pro Thr Glu
1               5                   10                  15

Pro Thr Gln Ile Tyr Arg Phe Leu Arg Thr Arg Asn Leu Ile
            20                  25                  30
```

<210> SEQ ID NO 235
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 235

```
Asp Leu Ala Glu Ile Gly Ile Ala Val Gly Asn Asn Asp Val Lys Glu
1               5                   10                  15

Asp Pro Lys Trp Glu Phe Pro Arg Lys Asn Leu Val Leu Gly
            20                  25                  30
```

<210> SEQ ID NO 236
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 236

```
Val Arg Ser Lys Asn Met Ala Arg Arg Gly His Ser Ala Gln Ile Asp
1               5                   10                  15

Pro Leu Cys Asp Glu Leu Cys Arg Thr Val Ile Ala Ala Ala
            20                  25                  30
```

<210> SEQ ID NO 237
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 237

```
Leu Arg Lys Leu Phe Val Gln Asp Leu Ala Thr Arg Val Lys Lys Glu
1               5                   10                  15

Asp Pro Lys Trp Glu Phe Pro Arg Lys Asn Leu Val Leu Gly
            20                  25                  30
```

<210> SEQ ID NO 238
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 238

```
Phe Leu Glu Asn Asn Leu Glu Gln Leu Thr Lys Val His Lys Gln Glu
```

```
                  1               5                  10                  15
Asp Pro Lys Trp Glu Phe Pro Arg Lys Asn Leu Val Leu Gly
                 20                  25                  30

<210> SEQ ID NO 239
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 239

Val Arg Ser Lys Asn Met Ala Arg Arg Gly His Ser Ala Gln Ile Asp
1               5                   10                  15
Val Ala Glu Glu Ala Gly Cys Pro Leu Ser Cys Ala Val Ser
                 20                  25                  30

<210> SEQ ID NO 240
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 240

Glu Asn Glu Lys Glu Leu Ala Ala Cys Gln Leu Arg Ile Ser Gln Glu
1               5                   10                  15
Asp Pro Lys Trp Glu Phe Pro Arg Lys Asn Leu Val Leu Gly
                 20                  25                  30

<210> SEQ ID NO 241
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 241

Glu Ile Leu Thr Arg Ala His Glu Arg Glu Phe Gly Ser Val Asp Val
1               5                   10                  15
Tyr Arg Arg Lys His Gln Glu Leu Gln Ala Met Gln Met Glu
                 20                  25                  30

<210> SEQ ID NO 242
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 242

Thr Leu Glu Gly Glu Leu His Asp Leu Arg Gly Gln Val Ala Lys Thr
1               5                   10                  15
Leu Thr Ala His Leu Glu Thr Arg Trp Arg Arg Thr Lys
                 20                  25                  30

<210> SEQ ID NO 243
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 243
```

Thr Ser Ser Gly Ala Gly Phe Phe Leu Pro Gln His Asp Ser Ser Val
1               5                   10                  15

Trp His Arg Arg Leu Lys Asn Gln Lys Ser Ala Lys Glu Gly
            20                  25                  30

<210> SEQ ID NO 244
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 244

Arg Gly Gly Arg Gly Gly Arg Glu Phe Ala Asp Phe Glu Tyr Arg Asp
1               5                   10                  15

Leu Ile Arg Asp Gln Gly Phe Arg Gly Asp Gly Gly Ser Thr
            20                  25                  30

<210> SEQ ID NO 245
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 245

Arg Lys Asp Glu Glu Leu Thr Ser Ser Gln Arg Asp Leu Ala Val Arg
1               5                   10                  15

Asp Leu Lys Leu Asp Asn Ile Leu Leu Asp Ala Glu Gly His
            20                  25                  30

<210> SEQ ID NO 246
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 246

Gln Lys Lys Lys Ala Lys Ser Gln Gln Tyr Lys Gly His Lys Lys Arg
1               5                   10                  15

Thr Gly Trp Ala Pro Pro Thr Phe Leu Leu Tyr Gln Phe Ala
            20                  25                  30

<210> SEQ ID NO 247
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 247

Ser His His Ser Ser His Lys Lys Arg Lys Asn Lys Asn Arg His Arg
1               5                   10                  15

Pro Pro Gln Asp Ala Met Ala Gln Pro Pro Arg Leu Ser Arg
            20                  25                  30

<210> SEQ ID NO 248
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 248

```
Val Leu His Pro Met Asp Ala Ala Gln Arg Ser Gln His Ile Lys Lys
1               5                   10                  15

Thr Leu Gly Arg Arg Asp Ser Ser Asp Asp Trp Glu Ile Pro
            20                  25                  30

<210> SEQ ID NO 249
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 249

Lys Asn Leu Leu Glu Phe Ala Glu Thr Leu Gln Phe Ile Asp Ser Phe
1               5                   10                  15

Leu Asn Thr Ser Ser Asn His Glu Asn Ser Asp Leu Glu Met
            20                  25                  30

<210> SEQ ID NO 250
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 250

Ala Phe Thr Val Pro Lys Asn Arg Ser Leu Ala Ser Pro Leu Gln Ser
1               5                   10                  15

Trp Tyr Leu Gly
            20

<210> SEQ ID NO 251
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 251

Ala Phe Thr Val Pro Lys Asn Arg Ser Leu Ala Ser Pro Leu Gln Pro
1               5                   10                  15

Asn Gly Ser Gly Gln Val Val Gly Lys Val Pro Gly His Phe
            20                  25                  30

<210> SEQ ID NO 252
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 252

Ala Phe Thr Val Pro Lys Asn Arg Ser Leu Ala Ser Pro Leu Gln Ser
1               5                   10                  15

Ser Gln Leu Glu Leu His Leu His Leu His Arg Cys His Phe
            20                  25                  30

<210> SEQ ID NO 253
<211> LENGTH: 30
<212> TYPE: PRT
<213> ORGANISM: Artificial Sequence
<220> FEATURE:
<223> OTHER INFORMATION: Synthetic Polypeptide
```

```
<400> SEQUENCE: 253

Leu Met Ser Thr Glu Asn Glu Leu Lys Gly Gln Gln Val Leu Pro Leu
1               5                   10                  15

Arg Ile Cys Asp Trp Thr Met Asn Gln Asn Gly Arg His Leu
            20                  25                  30

<210> SEQ ID NO 254
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 254

Ala Phe Thr Val Pro Lys Asn Arg Ser Leu Ala Ser Pro Leu Gln Pro
1               5                   10                  15

Thr Gln Pro Gln Ala His Leu Lys Pro Ile Asp Met Trp Asp
            20                  25                  30

<210> SEQ ID NO 255
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 255

Ala Phe Thr Val Pro Lys Asn Arg Ser Leu Ala Ser Pro Leu Gln Leu
1               5                   10                  15

Arg Ile Cys Asp Trp Thr Met Asn Gln Asn Gly Arg His Leu
            20                  25                  30

<210> SEQ ID NO 256
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 256

Leu Met Ser Thr Glu Asn Glu Leu Lys Gly Gln Gln Val Leu Pro Pro
1               5                   10                  15

Asn Gly Ser Gly Gln Val Val Gly Lys Val Pro Gly His Phe
            20                  25                  30

<210> SEQ ID NO 257
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 257

Phe Gln Glu Asn Gly Pro Pro Leu Leu Lys Lys Ile Lys Gln Glu Ser
1               5                   10                  15

Trp Tyr Leu Gly
            20

<210> SEQ ID NO 258
<211> LENGTH: 30
<212> TYPE: PRT
<213> ORGANISM: Artificial Sequence
<220> FEATURE:
<223> OTHER INFORMATION: Synthetic Polypeptide
```

<400> SEQUENCE: 258

Phe Gln Glu Asn Gly Pro Pro Leu Leu Lys Lys Ile Lys Gln Glu Leu
1               5                   10                  15

Arg Ile Cys Asp Trp Thr Met Asn Gln Asn Gly Arg His Leu
            20                  25                  30

<210> SEQ ID NO 259
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 259

Leu Met Ser Thr Glu Asn Glu Leu Lys Gly Gln Gln Val Leu Pro Ser
1               5                   10                  15

Trp Tyr Leu Gly
            20

<210> SEQ ID NO 260
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 260

Glu Ala Leu Asn His Arg Ile Val Gln Gln Ala Lys Glu Met Thr Val
1               5                   10                  15

Trp His Arg Arg Leu Lys Asn Gln Lys Ser Ala Lys Glu Gly
            20                  25                  30

<210> SEQ ID NO 261
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 261

Phe Asp Ser Lys Arg Arg Glu Gly Lys Gln Leu Ser Leu His Glu Ala
1               5                   10                  15

Thr Ser Lys Ser Gln Ile Met Ser Leu Trp Gly Leu Val Ser
            20                  25                  30

<210> SEQ ID NO 262
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 262

Asp Ser Ala Ser Leu Ser Gly Glu Ser Leu Asp Gly His Leu Gln Ala
1               5                   10                  15

Glu Gln Met Gly Lys Asp Gly Arg Gly Tyr Val Pro Ala Thr
            20                  25                  30

<210> SEQ ID NO 263
<211> LENGTH: 30
<212> TYPE: PRT
<213> ORGANISM: Artificial Sequence
<220> FEATURE:

<223> OTHER INFORMATION: Synthetic Polypeptide

<400> SEQUENCE: 263

Gln Val Ala Arg Glu Ser Thr Tyr Leu Ser Ser Leu Lys Gly Ser Arg
1               5                   10                  15

Gln Pro Pro Ser Pro Arg Ser Cys Leu Cys Gly Val Trp Ser
            20                  25                  30

<210> SEQ ID NO 264
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 264

Gln Val Ala Arg Glu Ser Thr Tyr Leu Ser Ser Leu Lys Gly Ser Arg
1               5                   10                  15

Pro Gln Val Tyr Pro Pro His Ser His Ser Ile Pro Pro Tyr
            20                  25                  30

<210> SEQ ID NO 265
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 265

Asp Ser Ala Ser Leu Ser Gly Glu Ser Leu Asp Gly His Leu Gln Gly
1               5                   10                  15

Thr Asn His Phe Leu Pro Gln Ser Ser Arg Cys Leu Pro Trp
            20                  25                  30

<210> SEQ ID NO 266
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 266

Pro Glu Glu Leu Gly Gly Pro Pro Leu Lys Lys Leu Lys Gln Glu Gly
1               5                   10                  15

Pro Thr Thr Ser Tyr Pro Arg Ala Pro Asp Ala Tyr His Gly
            20                  25                  30

<210> SEQ ID NO 267
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 267

Phe Asp Ser Lys Arg Arg Glu Gly Lys Gln Leu Ser Leu His Glu Cys
1               5                   10                  15

Leu Cys Thr Ala
            20

<210> SEQ ID NO 268
<211> LENGTH: 30
<212> TYPE: PRT
<213> ORGANISM: Artificial Sequence

```
<220> FEATURE:
<223> OTHER INFORMATION: Synthetic Polypeptide

<400> SEQUENCE: 268

Gln Val Ala Arg Glu Ser Thr Tyr Leu Ser Ser Leu Lys Gly Ser Arg
1               5                   10                  15

Asp Gln Pro Leu Pro Thr Pro Glu Leu Gln Met Pro Thr Met
            20                  25                  30

<210> SEQ ID NO 269
<211> LENGTH: 29
<212> TYPE: PRT
<213> ORGANISM: Artificial Sequence
<220> FEATURE:
<223> OTHER INFORMATION: Synthetic Polypeptide

<400> SEQUENCE: 269

Pro Glu Glu Leu Gly Gly Pro Pro Leu Lys Lys Leu Lys Gln Glu Gly
1               5                   10                  15

Val Pro Gly Arg Leu Arg Arg Leu Leu Leu Gln Leu Gly
            20                  25

<210> SEQ ID NO 270
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 270

Gln Val Ala Arg Glu Ser Thr Tyr Leu Ser Ser Leu Lys Gly Ser Arg
1               5                   10                  15

Pro His Leu Gln Met Pro Pro Ser Leu Gly Gln Met Ser Leu
            20                  25                  30

<210> SEQ ID NO 271
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 271

Asp Ser Ala Ser Leu Ser Gly Glu Ser Leu Asp Gly His Leu Gln Gly
1               5                   10                  15

Ser Pro Gln Ile Glu Asn Ile Gln Pro Phe Ser Ala Lys Asp
            20                  25                  30

<210> SEQ ID NO 272
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 272

Gln Val Ala Arg Glu Ser Thr Tyr Leu Ser Ser Leu Lys Gly Ser Ser
1               5                   10                  15

<210> SEQ ID NO 273
<211> LENGTH: 30
<212> TYPE: PRT
<213> ORGANISM: Artificial Sequence
<220> FEATURE:
<223> OTHER INFORMATION: Synthetic Polypeptide
```

<400> SEQUENCE: 273

Pro Glu Glu Leu Gly Gly Pro Pro Leu Lys Lys Leu Lys Gln Glu Ala
1               5                   10                  15

Thr Ser Lys Ser Gln Ile Met Ser Leu Trp Gly Leu Val Ser
            20                  25                  30

<210> SEQ ID NO 274
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 274

Pro Glu Glu Leu Gly Gly Pro Pro Leu Lys Lys Leu Lys Gln Glu Ser
1               5                   10                  15

Ile Tyr Gln Arg Asp Pro Leu Lys Leu Val Ala Thr Phe Arg
            20                  25                  30

<210> SEQ ID NO 275
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 275

Phe Asp Ser Lys Arg Arg Glu Gly Lys Gln Leu Ser Leu His Glu Phe
1               5                   10                  15

Arg His Leu Pro Met Pro Phe His Trp Lys Gln Glu Glu Leu
            20                  25                  30

<210> SEQ ID NO 276
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 276

Val Gly Arg Leu Ser Pro Cys Val Pro Ala Lys Pro Pro Leu Ala Ala
1               5                   10                  15

Glu Gln Met Gly Lys Asp Gly Arg Gly Tyr Val Pro Ala Thr
            20                  25                  30

<210> SEQ ID NO 277
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 277

Val Gly Arg Leu Ser Pro Cys Val Pro Ala Lys Pro Pro Leu Ala Gly
1               5                   10                  15

Asn Leu Gln Val Pro Asp His Val Ser Val Gly Ser Gly Leu
            20                  25                  30

<210> SEQ ID NO 278
<211> LENGTH: 30
<212> TYPE: PRT
<213> ORGANISM: Artificial Sequence
<220> FEATURE:

<223> OTHER INFORMATION: Synthetic Polypeptide

<400> SEQUENCE: 278

Val Gly Arg Leu Ser Pro Cys Val Pro Ala Lys Pro Pro Leu Ala Gly
1               5                   10                  15
Ser Pro Gln Ile Glu Asn Ile Gln Pro Phe Ser Ala Lys Asp
            20                  25                  30

<210> SEQ ID NO 279
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 279

Pro Glu Glu Leu Gly Gly Pro Pro Leu Lys Leu Lys Gln Glu Phe
1               5                   10                  15
Leu Phe Ser Val Ser Ser Glu Leu Gln Gly Gly Thr Trp Val
            20                  25                  30

<210> SEQ ID NO 280
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 280

Val Gly Arg Leu Ser Pro Cys Val Pro Ala Lys Pro Pro Leu Ala Gly
1               5                   10                  15
Thr Asn His Phe Leu Pro Gln Ser Ser Arg Cys Leu Pro Trp
            20                  25                  30

<210> SEQ ID NO 281
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 281

Pro Ser Arg Lys Pro Leu Asp Ser Arg Val Leu Asn Ala Val Lys Tyr
1               5                   10                  15
Tyr Gly Thr Ala Ala Asn Asp Ile Gly Asp Thr Thr Asn Arg
            20                  25                  30

<210> SEQ ID NO 282
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 282

Lys Gly Glu Thr Ile Thr Gly Leu Leu Gln Glu Phe Asp Val Gln Glu
1               5                   10                  15
Ala Leu Ser Val Val Ser Glu Asp Gln Ser Leu Phe Glu Cys
            20                  25                  30

<210> SEQ ID NO 283
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 283

```
Asp Val Asp Leu Ala Glu Val Lys Pro Leu Val Glu Lys Gly Glu Glu
1               5                   10                  15
Ala Leu Ser Val Val Ser Glu Asp Gln Ser Leu Phe Glu Cys
            20                  25                  30
```

<210> SEQ ID NO 284
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 284

```
Pro Ile Ala Met Ala Leu Ala Asn Val Val Pro Cys Ser Gln Trp Val
1               5                   10                  15
Phe Thr Lys Tyr Gly Lys Cys Tyr Met Phe Asn Ser Gly Glu
            20                  25                  30
```

<210> SEQ ID NO 285
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 285

```
Pro Pro Thr Trp Pro Lys Pro Leu Val Pro Ala Ile Pro Ile Cys Ser
1               5                   10                  15
Ser Ala Gly Glu Arg Gly Gly Phe Asn Lys Pro Gly Gly Pro
            20                  25                  30
```

<210> SEQ ID NO 286
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 286

```
Met Arg Arg Gln Gln Glu Gly Phe Lys Gly Thr Phe Pro Asp Ala Leu
1               5                   10                  15
Pro Val Ser Gly Asn Leu Leu Asp Val Tyr Ser Ser Gln Gly
            20                  25                  30
```

<210> SEQ ID NO 287
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 287

```
Gly Glu Val Asp Ala Asp Cys Met Asp Val Asn Val Arg Gly Pro Ala
1               5                   10                  15
Gly Pro Ser Arg Thr Gly Tyr Leu His Pro Pro Ser Pro Gly
            20                  25                  30
```

<210> SEQ ID NO 288
<211> LENGTH: 30
<212> TYPE: PRT

```
<213> ORGANISM: Artificial Sequence
<220> FEATURE:
<223> OTHER INFORMATION: Synthetic Polypeptide

<400> SEQUENCE: 288

Lys Cys Gly Ser Gly Pro Val His Ile Ser Gly Gln His Leu Val Val
1               5                   10                  15

Tyr Arg Arg Lys His Gln Glu Leu Gln Ala Met Gln Met Glu
            20                  25                  30

<210> SEQ ID NO 289
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 289

Val Ala Pro Pro Thr Thr Ala Ala Ser Ser Val Glu Glu Pro Glu Gly
1               5                   10                  15

His Arg Glu Ser Asn Ser Arg Leu Pro Gly Pro Pro Glu Gly
            20                  25                  30

<210> SEQ ID NO 290
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 290

Phe Met Asp Asn Pro Phe Glu Phe Asn Pro Glu Asp Pro Ile Pro Asp
1               5                   10                  15

Lys Leu Lys Cys Thr Lys Glu Glu His Leu Cys Thr Gln Arg
            20                  25                  30

<210> SEQ ID NO 291
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 291

Pro Gln Tyr Phe Arg Gln Gly His Asn Cys His Lys Pro Asp Thr Tyr
1               5                   10                  15

Cys Arg Leu Leu Trp Asp Tyr Val Tyr Gln Leu Leu Ser Asp
            20                  25                  30

<210> SEQ ID NO 292
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 292

Met Asp Arg Asp Leu Ser Tyr Asn Leu Leu Glu Asp Leu Pro Ser Phe
1               5                   10                  15

Ser Val

<210> SEQ ID NO 293
<211> LENGTH: 30
<212> TYPE: PRT
```

```
<213> ORGANISM: Artificial Sequence
<220> FEATURE:
<223> OTHER INFORMATION: Synthetic Polypeptide

<400> SEQUENCE: 293

Ser Asn Pro Met Asn Pro Thr Ile Gly Asn Gly Leu Ser Pro Gln Asn
1               5                   10                  15
Ser Ile Arg His Asn Leu Ser Leu His Ser Lys Phe Ile Arg
            20                  25                  30

<210> SEQ ID NO 294
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 294

Ser Asn Pro Met Asn Pro Thr Ile Gly Asn Gly Leu Ser Pro Gln Phe
1               5                   10                  15
Thr Ala Asp Leu Asp Gln Phe Asp Gln Leu Leu Pro Thr Leu
            20                  25                  30

<210> SEQ ID NO 295
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 295

Tyr Gln Leu Ser Glu Thr Ser Tyr Gln Pro Thr Ser Ile Pro Gln Gly
1               5                   10                  15
Leu Pro Glu Leu Glu Leu Glu Ala Ile Asp Asn Gln Phe Gly
            20                  25                  30

<210> SEQ ID NO 296
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 296

Ser Asn Pro Met Asn Pro Thr Ile Gly Asn Gly Leu Ser Pro Gln Pro
1               5                   10                  15
Gly Ser Glu Leu Asp Asn Leu Glu Glu Ile Leu Asp Asp Leu
            20                  25                  30

<210> SEQ ID NO 297
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 297

Pro Ser Asn His Met Asn Pro Val Ser Asn Gly Leu Ser Pro Gln Asn
1               5                   10                  15
Ser Ile Arg His Asn Leu Ser Leu His Ser Lys Phe Ile Arg
            20                  25                  30

<210> SEQ ID NO 298
<211> LENGTH: 30
```

<212> TYPE: PRT
<213> ORGANISM: Artificial Sequence
<220> FEATURE:
<223> OTHER INFORMATION: Synthetic Polypeptide

<400> SEQUENCE: 298

Leu Gly Arg Asn Leu Ser Thr His Gln Thr Tyr Pro Val Val Ala Gly
1               5                   10                  15

Arg Glu Met Val Gly Pro Thr Leu Pro Gly Tyr Pro Pro His
            20                  25                  30

<210> SEQ ID NO 299
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 299

Ala Gly Ser Pro Asp Thr Glu Ser Pro Val Leu Val Asn Asp Tyr Arg
1               5                   10                  15

Glu Asn Val Ile Glu Tyr Lys His Cys Leu Ile Thr Lys Asn
            20                  25                  30

<210> SEQ ID NO 300
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 300

Ala Gly Ser Pro Asp Thr Glu Ser Pro Val Leu Val Asn Asp Tyr Glu
1               5                   10                  15

Ile Glu Leu Ser Ser Leu Arg Glu Ala Leu Ser Phe Val Ser
            20                  25                  30

<210> SEQ ID NO 301
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 301

Leu Glu Lys Ile Ile Lys Cys Asn Arg Ser Thr Glu Ile Ser Ser Val
1               5                   10                  15

Leu Gln Glu Arg Ile Pro Trp Val Pro Pro Glu Cys Ile Glu
            20                  25                  30

<210> SEQ ID NO 302
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 302

Lys Lys Arg Asn Ser Thr Gln Leu Lys Ser Arg Val Lys Asn Ile Asn
1               5                   10                  15

Lys Ser Asn Leu Leu Val Phe Arg Thr Asn Gly Val Ser Asp
            20                  25                  30

<210> SEQ ID NO 303

```
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 303

Asn Ser Glu Leu Thr Pro Ser Glu Ser Leu Ala Thr Thr Asp Asp Glu
1               5                   10                  15

Ile Glu Leu Ser Ser Leu Arg Glu Ala Leu Ser Phe Val Ser
            20                  25                  30

<210> SEQ ID NO 304
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 304

Arg Gln Ile Lys Ala Ile Met Lys Glu Val Ile Pro Phe Leu Lys Glu
1               5                   10                  15

Asp Pro Lys Trp Glu Phe Pro Arg Lys Asn Leu Val Leu Gly
            20                  25                  30

<210> SEQ ID NO 305
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 305

Gly Val Ala Cys Glu Pro Leu Pro Asp Arg Tyr Thr Val Ser Glu Glu
1               5                   10                  15

Ser Asn Gly Trp Lys
            20

<210> SEQ ID NO 306
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 306

Leu Gln Pro Met Ala Gly Thr Cys Pro Ala Pro Glu Ile His Ala Ile
1               5                   10                  15

Glu Arg Leu Glu Val Ser Ser Leu Ala Gln Thr Ser Ser Ala
            20                  25                  30

<210> SEQ ID NO 307
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 307

Asp Ser Glu Arg Leu Gln Tyr Glu Lys Lys Leu Lys Ser Thr Lys Cys
1               5                   10                  15

Thr Ala Gly Ser Thr Arg Ser Cys Lys Pro Cys Arg Trp Ser
            20                  25                  30
```

```
<210> SEQ ID NO 308
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 308

Tyr Lys Lys Met Gln Asp Thr Val Val Leu Ala Gln Gly Lys Lys Val
 1               5                  10                  15

Tyr Arg Arg Lys His Gln Glu Leu Gln Ala Met Gln Met Glu
            20                  25                  30

<210> SEQ ID NO 309
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 309

Leu Val Cys Lys Met Lys Gly Glu Gly Val Glu Ile Val Asp Arg Val
 1               5                  10                  15

Trp His Arg Arg Leu Lys Asn Gln Lys Ser Ala Lys Glu Gly
            20                  25                  30

<210> SEQ ID NO 310
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 310

Lys Glu Pro Val Lys Ile Ala Ala Pro Glu Leu His Lys Gly Asp Val
 1               5                  10                  15

Gln Thr His Leu Glu Asn Pro Thr Arg Tyr His Leu Gln Gln
            20                  25                  30

<210> SEQ ID NO 311
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 311

Pro Gln Glu Ile Ala Pro Asp Ala Ser Phe Ile Asp Asp Glu Ala Val
 1               5                  10                  15

Gln Thr His Leu Glu Asn Pro Thr Arg Tyr His Leu Gln Gln
            20                  25                  30

<210> SEQ ID NO 312
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 312

Asp Ser Glu Glu Asp Glu Pro Thr Lys Lys Lys Thr Ile Leu Gln Leu
 1               5                  10                  15

Pro Val Ser Gly Asn Leu Leu Asp Val Tyr Ser Ser Gln Gly
            20                  25                  30
```

<210> SEQ ID NO 313
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 313

Lys Glu Pro Val Lys Ile Ala Ala Pro Glu Leu His Lys Gly Asp Ile
1               5                   10                  15

Asp Asp Val Ile Asp Glu Ile Ile Ser Leu Glu Ser Ser Tyr
            20                  25                  30

<210> SEQ ID NO 314
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 314

Lys Leu Trp Gly Ile Asp Arg Asp Ser Tyr Arg Arg Ile Leu Met Glu
1               5                   10                  15

Asp Pro Lys Trp Glu Phe Pro Arg Lys Asn Leu Val Leu Gly
            20                  25                  30

<210> SEQ ID NO 315
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 315

Ser Pro Trp Pro Leu Leu Gly Ser Ala Gln Gly Gln Phe Ser Ala Val
1               5                   10                  15

His Pro Asn Val Ser Gln Gly Cys Gln Gly Gly Cys Ala Thr
            20                  25                  30

<210> SEQ ID NO 316
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 316

Thr Gly Leu Pro Gly Pro Pro Leu Ile Thr Arg Thr Lys Cys Ala Val
1               5                   10                  15

His Pro Asn Val Ser Gln Gly Cys Gln Gly Gly Cys Ala Thr
            20                  25                  30

<210> SEQ ID NO 317
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 317

Phe Gly Glu Lys Leu Phe Ser Gly Val Leu Met Asp Leu Ser Lys Ser
1               5                   10                  15

Thr Leu Pro Thr Gln Glu Glu Ile Glu Asn Leu Pro Ala Phe
            20                  25                  30

```
<210> SEQ ID NO 318
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 318

Ala Thr Ser Ile Leu Glu Tyr Pro Ile Glu Pro Ser Gly Val Leu Gly
1               5                   10                  15

Pro Ala Ser Val Ile Ser Asn Asp Asp Ser Ala Ser Pro
            20                  25                  30

<210> SEQ ID NO 319
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 319

Glu Ala Ser Ser Leu Lys Tyr Leu Ala Glu Glu Phe Ser Ile Pro Glu
1               5                   10                  15

Pro Thr Gly Glu Pro Ser Pro Lys Arg Pro Arg Gly Arg Pro
            20                  25                  30

<210> SEQ ID NO 320
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 320

Glu Ala Ser Ser Leu Lys Tyr Leu Ala Glu Glu Phe Ser Ile Pro Lys
1               5                   10                  15

Ala Glu Ala Thr Gly Glu Lys Arg Pro Arg Gly Arg Pro Arg
            20                  25                  30

<210> SEQ ID NO 321
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 321

His Met Val Ser Thr Thr Leu Pro Val Asp Ser Arg Met Ile Glu Ser
1               5                   10                  15

Thr Ala Asn Pro Glu Thr Pro Asn Ser Thr Ile Ser Arg Glu
            20                  25                  30

<210> SEQ ID NO 322
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 322

Asp Gly Tyr Gln Gly Ser Gln Thr Phe His Gly Ala Pro Leu Thr Val
1               5                   10                  15

Tyr Arg Arg Lys His Gln Glu Leu Gln Ala Met Gln Met Glu
```

```
                 20                  25                  30

<210> SEQ ID NO 323
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 323

Ala Ser Tyr Asp Asp Pro Tyr Lys Lys Ala Val Ala Met Ser Lys Arg
1               5                  10                  15

<210> SEQ ID NO 324
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 324

Asp Ser Met Glu Asn Gln Val Ser Val Asp Ala Phe Lys Ile Leu Asp
1               5                  10                  15

Met Glu Ala Gln Gln Val Asn Glu Ala Glu Ser Ala Arg Glu
            20                  25                  30

<210> SEQ ID NO 325
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 325

Asp Ser Met Glu Asn Gln Val Ser Val Asp Ala Phe Lys Ile Leu Lys
1               5                  10                  15

Cys Glu Arg Leu Leu Leu Tyr Leu Tyr Cys His Glu Leu Ser
            20                  25                  30

<210> SEQ ID NO 326
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 326

Glu His Arg Lys Glu Leu Gly Pro Tyr Val Phe Arg Glu Ala Gln Val
1               5                  10                  15

Asn Lys Leu Glu Leu Glu Leu Glu Ser Ala Lys Gln Lys Phe
            20                  25                  30

<210> SEQ ID NO 327
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 327

Phe Ile Gln Lys Ile Arg Tyr Thr Asn Ala Arg Asp Arg Asn Gln Asp
1               5                  10                  15

Leu Ile Arg Asp Gln Gly Phe Arg Gly Asp Gly Ser Thr
            20                  25                  30
```

<210> SEQ ID NO 328
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 328

Thr Val Gln Gly Ser Asn Ile Phe Glu Arg Thr Glu Val Leu Ala Asp
1               5                   10                  15

Asp Phe Trp Ile Pro Glu Thr Ser Phe Ile Leu Thr Ile Ile
            20                  25                  30

<210> SEQ ID NO 329
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 329

Thr Val Gln Gly Ser Asn Ile Phe Glu Arg Thr Glu Val Leu Ala Ala
1               5                   10                  15

Gly Val Pro Asn Lys Pro Gly Ile Pro Lys Leu Leu Glu Gly
            20                  25                  30

<210> SEQ ID NO 330
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 330

Gly Gln Glu Ser Asp Asp Phe Glu Leu Ser Gly Ser Gly Asp Leu Asp
1               5                   10                  15

Asp Phe Trp Ile Pro Glu Thr Ser Phe Ile Leu Thr Ile Ile
            20                  25                  30

<210> SEQ ID NO 331
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 331

Gly Gln Glu Ser Asp Asp Phe Glu Leu Ser Gly Ser Gly Asp Leu Val
1               5                   10                  15

Trp His Arg Arg Leu Lys Asn Gln Lys Ser Ala Lys Glu Gly
            20                  25                  30

<210> SEQ ID NO 332
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 332

Gly Gln Glu Ser Asp Asp Phe Glu Leu Ser Gly Ser Gly Asp Leu Ala
1               5                   10                  15

Gly Val Pro Asn Lys Pro Gly Ile Pro Lys Leu Leu Glu Gly
            20                  25                  30

```
<210> SEQ ID NO 333
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 333

Pro Gly His Met His Thr Gln Val Pro Pro Tyr Pro Gln Pro Gln Leu
1               5                   10                  15

Tyr Arg Arg Lys His Gln Glu Leu Gln Ala Met Gln Met Glu
            20                  25                  30

<210> SEQ ID NO 334
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 334

Gly Thr Leu Pro Ala Ala Ser Glu Leu Pro Ala Ser Gln Arg Thr Val
1               5                   10                  15

Tyr Arg Arg Lys His Gln Glu Leu Gln Ala Met Gln Met Glu
            20                  25                  30

<210> SEQ ID NO 335
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 335

Gly Thr Leu Pro Ala Ala Ser Glu Leu Pro Ala Ser Gln Arg Thr Val
1               5                   10                  15

Leu Gln Glu Arg Ile Pro Trp Val Pro Pro Glu Cys Ile Glu
            20                  25                  30

<210> SEQ ID NO 336
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 336

Met Ala Ala Thr Asp Leu Glu Arg Phe Ser Asn Ser Tyr Asn Asn Ser
1               5                   10                  15

Gln Ala Pro Ser Pro Gly Leu Gly Ser
            20                  25

<210> SEQ ID NO 337
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 337

Val Pro Pro Ala Thr Met Ser Gly Ser Met Met Gly Ser Asp Met Leu
1               5                   10                  15

Pro Val Ser Gly Asn Leu Leu Asp Val Tyr Ser Ser Gln Gly
```

```
              20                  25                  30

<210> SEQ ID NO 338
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 338

Val Pro Pro Ala Thr Met Ser Gly Ser Met Met Gly Ser Asp Met Ile
1               5                   10                  15

Asp Asp Val Ile Asp Glu Ile Ile Ser Leu Glu Ser Ser Tyr
              20                  25                  30

<210> SEQ ID NO 339
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 339

Arg Gln Arg Glu Glu Ser Tyr Ser Arg Met Gly Tyr Met Asp Pro Ile
1               5                   10                  15

Asp Asp Val Ile Asp Glu Ile Ile Ser Leu Glu Ser Ser Tyr
              20                  25                  30

<210> SEQ ID NO 340
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 340

Leu Glu Asp Met Arg Ser Asn Asn Val Glu Asp Cys Lys Met Met Val
1               5                   10                  15

Ile His Pro Lys Thr Asp Glu Gln Arg Cys Arg Leu Gln Glu
              20                  25                  30

<210> SEQ ID NO 341
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 341

Val Cys Ser Leu Asp Ile Leu Ser Ser Ala Phe Gln Leu Val Gly Asp
1               5                   10                  15

Asp Phe Trp Ile Pro Glu Thr Ser Phe Ile Leu Thr Ile Ile
              20                  25                  30

<210> SEQ ID NO 342
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 342

Val Cys Ser Leu Asp Ile Leu Ser Ser Ala Phe Gln Leu Val Gly Ala
1               5                   10                  15
```

```
Gly Val Pro Asn Lys Pro Gly Ile Pro Lys Leu Leu Glu Gly
            20                  25                  30

<210> SEQ ID NO 343
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 343

Ile Leu Pro Tyr Thr Leu Ala Ser Leu Tyr His Arg Glu Lys Gln Leu
1               5                   10                  15

Ile Ala Met Asp Ser Ala Ile Thr Leu Trp Gln Phe Leu Leu
            20                  25                  30

<210> SEQ ID NO 344
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 344

Leu Ser Ser Ile Arg Pro Pro Arg Leu Glu Gly Glu Asn Thr Gln Asp
1               5                   10                  15

Leu Ile Arg Asp Gln Gly Phe Arg Gly Asp Gly Gly Ser Thr
            20                  25                  30

<210> SEQ ID NO 345
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 345

Leu Ser Ser Ile Arg Pro Pro Arg Leu Glu Gly Glu Asn Thr Gln Lys
1               5                   10                  15

Thr Leu Gly Arg Arg Asp Ser Ser Asp Asp Trp Glu Ile Pro
            20                  25                  30

<210> SEQ ID NO 346
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 346

Pro Thr Ala Asn Leu Asp Gln Lys Asp Lys Gln Phe Val Ala Lys Asp
1               5                   10                  15

Leu Ile Arg Asp Gln Gly Phe Arg Gly Asp Gly Gly Ser Thr
            20                  25                  30

<210> SEQ ID NO 347
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 347

Ser Lys Lys Glu Val Pro Ile His Arg Val Ala Asp Ile Ser Gly Lys
1               5                   10                  15
```

```
Thr Leu Gly Arg Arg Asp Ser Ser Asp Asp Trp Glu Ile Pro
            20                  25                  30
```

<210> SEQ ID NO 348
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 348

```
Ser Lys Lys Glu Val Pro Ile His Arg Val Ala Asp Ile Ser Gly Asp
1               5                   10                  15

Leu Ile Arg Asp Gln Gly Phe Arg Gly Asp Gly Gly Ser Thr
            20                  25                  30
```

<210> SEQ ID NO 349
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 349

```
Tyr Ser His Lys Leu Phe Asn Gly Ser Met Glu Ala Phe Ile Lys Arg
1               5                   10                  15

Pro Arg Gly Gln Arg Asp Ser Ser Tyr Tyr Trp Glu Ile Glu
            20                  25                  30
```

<210> SEQ ID NO 350
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 350

```
Lys Gln Thr Leu Gly Glu Gly Glu Arg Ala Glu Cys Gly Thr Thr Arg
1               5                   10                  15

Met Gln Phe Glu Val Thr Ala Asn Gln Pro His Leu Gln Pro
            20                  25                  30
```

<210> SEQ ID NO 351
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 351

```
Gly Pro Pro Gln Pro Pro Gln Gln Arg Pro Tyr Gly Tyr Asp Gln Glu
1               5                   10                  15

Trp Val Ser Lys Ser Pro Ser His Leu Ser Cys Val Ile Asn
            20                  25                  30
```

<210> SEQ ID NO 352
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 352

```
Gly Pro Pro Gln Pro Pro Gln Gln Arg Pro Tyr Gly Tyr Asp Gln Leu
```

```
Asn Ile Leu Arg
            20
```

<210> SEQ ID NO 353
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 353

```
Gln Tyr Pro Gly Gln Gln Gly Tyr Pro Gly Gln Gln Gln Gly Tyr Val
1               5                   10                  15
Glu His Pro Gln Met Thr Phe Gly Arg Leu His Arg Ile Ile
            20                  25                  30
```

<210> SEQ ID NO 354
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 354

```
Gln Tyr Pro Gly Gln Gln Gly Tyr Pro Gly Gln Gln Gln Gly Tyr Gly
1               5                   10                  15
Phe Lys Val Thr Leu Pro Pro Phe Met Cys Asn Lys Gln Ala
            20                  25                  30
```

<210> SEQ ID NO 355
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 355

```
Gly Pro Pro Gln Pro Pro Gln Gln Arg Pro Tyr Gly Tyr Asp Gln Ile
1               5                   10                  15
Met Pro Lys Lys Pro Ala Glu Asp Glu Asn Asp Ser Lys Gly
            20                  25                  30
```

<210> SEQ ID NO 356
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 356

```
Thr Ala Pro Ser Ala Gln Gln Arg Pro Tyr Gly Tyr Glu Gln Ile
1               5                   10                  15
Met Pro Lys Lys Pro Ala Glu Asp Glu Asn Asp Ser Lys Gly
            20                  25                  30
```

<210> SEQ ID NO 357
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 357

```
Gly Asp Gly Met Pro Val Gly Pro Val Pro Pro Gly Phe Phe Gln Arg
1               5                   10                  15

Glu Asn Val Ile Glu Tyr Lys His Cys Leu Ile Thr Lys Asn
            20                  25                  30
```

<210> SEQ ID NO 358
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 358

```
Glu Thr Cys Glu His Ser Ser Glu Ala Lys Ala Phe His Asp Tyr Arg
1               5                   10                  15

Glu Asn Val Ile Glu Tyr Lys His Cys Leu Ile Thr Lys Asn
            20                  25                  30
```

<210> SEQ ID NO 359
<211> LENGTH: 26
<212> TYPE: PRT
<213> ORGANISM: Artificial Sequence
<220> FEATURE:
<223> OTHER INFORMATION: Synthetic Polypeptide

<400> SEQUENCE: 359

```
Asn Ile Thr Leu Gly Glu Pro Pro Gly Phe Leu His Ser Trp Trp Cys
1               5                   10                  15

Glu Lys Met Ser Leu Asn Ile Asn Thr Val
            20                  25
```

<210> SEQ ID NO 360
<211> LENGTH: 23
<212> TYPE: PRT
<213> ORGANISM: Artificial Sequence
<220> FEATURE:
<223> OTHER INFORMATION: Synthetic Polypeptide

<400> SEQUENCE: 360

```
His Pro Gln Met Thr Phe Gly Arg Leu His Arg Ile Ile Pro Lys Gly
1               5                   10                  15

Gln Tyr Gly Asn Tyr Gln Gln
            20
```

<210> SEQ ID NO 361
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 361

```
Tyr Pro Lys Lys Pro Lys Asp Glu Ala Phe Arg Ser His Tyr Lys Gln
1               5                   10                  15

Phe Glu Glu Gly Leu Leu Asp Arg Cys Pro Ala Pro Gly Pro
            20                  25                  30
```

<210> SEQ ID NO 362
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 362

Thr Glu Leu Asn Gln Gly Asp Met Lys Pro Pro Ser Tyr Asp Ser Val
1               5                   10                  15

Tyr Arg Arg Lys His Gln Glu Leu Gln Ala Met Gln Met Glu
                20                  25                  30

<210> SEQ ID NO 363
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 363

Cys Thr Glu Lys Gly Thr Trp Arg Glu Ser Thr Leu Thr Cys Thr Val
1               5                   10                  15

Leu Leu Gln Ile Leu
                20

<210> SEQ ID NO 364
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 364

Arg Phe Ala Lys Lys Met Asp Lys Met Val Gln Lys Lys Asn Ala Ile
1               5                   10                  15

Gly Gln Asn Gly Lys Asp Trp Ile Pro Leu Ser Ser Thr Lys
                20                  25                  30

<210> SEQ ID NO 365
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 365

His Glu Gly Leu Ser Pro Thr Pro Phe Met Asn Ser Asn Leu Met Asp
1               5                   10                  15

Met Pro Cys Val Gln Ala Gln Tyr Ser Pro Ser Pro Pro Gly
                20                  25                  30

<210> SEQ ID NO 366
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 366

Gly Tyr Lys Ile Leu Ile Pro Lys Gly Ser Tyr Gly Arg Val Lys Val
1               5                   10                  15

Ser

<210> SEQ ID NO 367
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 367

```
Ser Tyr Leu Pro Gly Gly Thr Thr Gly Leu Gln Leu Pro Ser Thr Pro
1               5                   10                  15

Val Asp Arg Glu Pro Val Asp Arg Glu Pro Val Val Cys His
            20                  25                  30

<210> SEQ ID NO 368
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 368

Ser Pro Met Ala Leu Leu Thr Ile Gly Ser Ser Ser Glu Lys Glu Pro
1               5                   10                  15

Val Asp Arg Glu Pro Val Asp Arg Glu Pro Val Val Cys His
            20                  25                  30

<210> SEQ ID NO 369
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 369

Gln Pro Pro Tyr Thr Gly Ala Gln Thr Gln Ala Gly Gln Ile Glu Val
1               5                   10                  15

Tyr Arg Arg Lys His Gln Glu Leu Gln Ala Met Gln Met Glu
            20                  25                  30

<210> SEQ ID NO 370
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 370

Lys Asn Val Met Ser Ala Phe Gly Leu Thr Asp Asp Gln Val Ser Val
1               5                   10                  15

Tyr Arg Arg Lys His Gln Glu Leu Gln Ala Met Gln Met Glu
            20                  25                  30

<210> SEQ ID NO 371
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 371

Glu Pro Pro Gly Glu Pro Gly Pro Ser Thr Asn Ile Pro Glu Asn Val
1               5                   10                  15

Tyr Arg Arg Lys His Gln Glu Leu Gln Ala Met Gln Met Glu
            20                  25                  30

<210> SEQ ID NO 372
<211> LENGTH: 30
<212> TYPE: PRT
<213> ORGANISM: Artificial Sequence
<220> FEATURE:
<223> OTHER INFORMATION: Synthetic Polypeptide
```

<400> SEQUENCE: 372

Gln Ala Pro Pro Gln Gln Pro Gln Gln Tyr Gly Ile Gln Tyr Ser Asp
1               5                   10                  15

Met Pro Cys Val Gln Ala Gln Tyr Ser Pro Ser Pro Gly
            20                  25                  30

<210> SEQ ID NO 373
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 373

Lys Asn Val Met Ser Ala Phe Gly Leu Thr Asp Asp Gln Val Ser Asp
1               5                   10                  15

Thr Asn Ser Thr Ser Gly Asp Pro Val Glu Lys Lys Asp Glu
            20                  25                  30

<210> SEQ ID NO 374
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 374

Met Ala Leu Asn Ser Glu Ala Leu Ser Val Val Ser Glu Asp Gln Ser
1               5                   10                  15

Leu Phe Glu Cys
            20

<210> SEQ ID NO 375
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 375

Met Ala Leu Asn Ser Pro Ser Gly Ser Glu Gln Leu Val Asp Gly Leu
1               5                   10                  15

Ala Tyr

<210> SEQ ID NO 376
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 376

Phe Leu Val Gly Ala Ala Leu Ala Ala Gly Leu Leu Trp Lys Phe Arg
1               5                   10                  15

Thr Leu Leu Met Asn Ala Val Trp Pro Lys Ala Gly Arg Trp
            20                  25                  30

<210> SEQ ID NO 377
<211> LENGTH: 22
<212> TYPE: PRT
<213> ORGANISM: Artificial Sequence
<220> FEATURE:
<223> OTHER INFORMATION: Synthetic Polypeptide

```
<400> SEQUENCE: 377

Phe Leu Val Gly Ala Ala Leu Ala Ala Gly Leu Leu Trp Lys Phe Arg
1               5                   10                  15

Ser Leu Ile Ser Cys Glu
            20

<210> SEQ ID NO 378
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 378

Asp Gly Val Ser His Cys Pro Gly Gly Glu Asp Glu Asn Arg Cys Gly
1               5                   10                  15

Ser Leu Ile Ser Cys Glu
            20

<210> SEQ ID NO 379
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 379

Met Ala Leu Asn Ser Val Ile Pro Gly Ser Leu Glu Thr Arg Gly Lys
1               5                   10                  15

Pro Cys

<210> SEQ ID NO 380
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 380

Val Cys Thr Gln Pro Lys Ser Pro Ser Gly Thr Val Cys Thr Ser Arg
1               5                   10                  15

Ser Leu Ile Ser Cys Glu
            20

<210> SEQ ID NO 381
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 381

Val Cys Thr Gln Pro Lys Ser Pro Ser Gly Thr Val Cys Thr Ser Ser
1               5                   10                  15

Tyr Ser Arg Ile Phe Gly Asp Pro Arg Lys Ala Val Leu Thr
            20                  25                  30

<210> SEQ ID NO 382
<211> LENGTH: 20
<212> TYPE: PRT
<213> ORGANISM: Artificial Sequence
<220> FEATURE:
<223> OTHER INFORMATION: Synthetic Polypeptide
```

```
<400> SEQUENCE: 382

Met Ala Leu Asn Ser Leu Arg Tyr Leu Thr Met Met Ser Ser Leu Tyr
1               5                   10                  15

Gln Thr Ile Arg
            20

<210> SEQ ID NO 383
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 383

Val Cys Thr Gln Pro Lys Ser Pro Ser Gly Thr Val Cys Thr Ser Arg
1               5                   10                  15

Gly Ser Leu Phe Pro Gln Lys Leu Leu Asn Ala Glu Thr Ser
            20                  25                  30

<210> SEQ ID NO 384
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 384

Lys Gly Glu Pro His His Glu Leu Pro Pro Gly Ser Thr Lys Arg Val
1               5                   10                  15

Pro Ala Ser Val Gln Leu His Thr Ala Val Glu Met His His
            20                  25                  30

<210> SEQ ID NO 385
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 385

Asp Ala Gln Ala Gly Lys Glu Pro Gly Gly Ser Arg Ala His Ser Ser
1               5                   10                  15

Pro Gly Gln Cys Ala Ala Ala His Gly Gly Gly Asp Ala Pro
            20                  25                  30

<210> SEQ ID NO 386
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 386

Gln Pro Lys Lys Lys Pro Leu Asp Gly Glu Tyr Phe Thr Leu Gln Ser
1               5                   10                  15

Arg Pro Val Cys Ser Cys Thr Arg Arg Trp Arg Cys Thr Thr
            20                  25                  30

<210> SEQ ID NO 387
<211> LENGTH: 30
<212> TYPE: PRT
<213> ORGANISM: Artificial Sequence
<220> FEATURE:
<223> OTHER INFORMATION: Synthetic Polypeptide
```

```
<400> SEQUENCE: 387

Glu Arg Ser Val Ala Lys Leu Glu Lys Thr Ile Asp Asp Leu Glu Val
1               5                   10                  15

Tyr Arg Arg Lys His Gln Glu Leu Gln Ala Met Gln Met Glu
            20                  25                  30

<210> SEQ ID NO 388
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 388

Glu Arg Ser Val Ala Lys Leu Glu Lys Thr Ile Asp Asp Leu Glu Asp
1               5                   10                  15

Thr Asn Ser Thr Ser Gly Asp Pro Val Glu Lys Lys Asp Glu
            20                  25                  30

<210> SEQ ID NO 389
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 389

Glu Arg Ser Val Ala Lys Leu Glu Lys Thr Ile Asp Asp Leu Glu Val
1               5                   10                  15

Trp His Arg Arg Leu Lys Asn Gln Lys Ser Ala Lys Glu Gly
            20                  25                  30

<210> SEQ ID NO 390
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 390

Leu Gln Lys Leu Glu Glu Ala Glu Lys Ala Ala Asp Glu Ser Glu Ser
1               5                   10                  15

Thr Leu Pro Thr Gln Glu Glu Ile Glu Asn Leu Pro Ala Phe
            20                  25                  30

<210> SEQ ID NO 391
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 391

Pro Arg Met Gln Gly Pro Ile Gln Gln Pro Ser Ile Ser His Gln Glu
1               5                   10                  15

Asp Pro Lys Trp Glu Phe Pro Arg Lys Asn Leu Val Leu Gly
            20                  25                  30

<210> SEQ ID NO 392
<211> LENGTH: 30
<212> TYPE: PRT
<213> ORGANISM: Artificial Sequence
<220> FEATURE:
```

```
<223> OTHER INFORMATION: Synthetic Polypeptide

<400> SEQUENCE: 392

Gln Leu Glu Glu Lys Gln Gln Gln Pro Thr Arg Glu Leu Leu Gln Glu
1               5                   10                  15

Asp Pro Lys Trp Glu Phe Pro Arg Lys Asn Leu Val Leu Gly
            20                  25                  30

<210> SEQ ID NO 393
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 393

Lys Lys Gly Lys Thr Ala Gln Gly Leu Ser Pro Val Asp Gln Arg Glu
1               5                   10                  15

Asp Pro Lys Trp Glu Phe Pro Arg Lys Asn Leu Val Leu Gly
            20                  25                  30

<210> SEQ ID NO 394
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 394

Val Ile Ser Ala Glu Asn Trp Lys Pro Ala Thr Lys Thr Asp Gln Gly
1               5                   10                  15

Leu Leu Lys Met Thr Glu Tyr Lys Leu Val Val Val Gly Ala
            20                  25                  30

<210> SEQ ID NO 395
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 395

Arg Asn Glu Leu Leu Gly Asp Asp Gly Asn Ser Ser Glu Asn Gln Ser
1               5                   10                  15

Asn Lys Val Pro Val Val Gln His Pro His His Val His Pro
            20                  25                  30

<210> SEQ ID NO 396
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 396

Met Arg Ser Tyr Lys Gln Glu Met Gly Lys Leu Glu Thr Asp Phe Ser
1               5                   10                  15

Asn Lys Val Pro Val Val Gln His Pro His His Val His Pro
            20                  25                  30

<210> SEQ ID NO 397
<211> LENGTH: 30
<212> TYPE: PRT
<213> ORGANISM: Artificial Sequence
```

<220> FEATURE:
<223> OTHER INFORMATION: Synthetic Polypeptide

<400> SEQUENCE: 397

Met Arg Ser Tyr Lys Gln Glu Met Gly Lys Leu Glu Thr Asp Phe Tyr
1               5                   10                  15
Leu Gln Met Lys Trp Pro Leu Leu Asp Val Gln Ala Gly Ser
            20                  25                  30

<210> SEQ ID NO 398
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 398

Met Val Ala Asn Val Glu Lys Gln Leu Glu Glu Ala Lys Glu Leu Ser
1               5                   10                  15
Asn Lys Val Pro Val Val Gln His Pro His His Val His Pro
            20                  25                  30

<210> SEQ ID NO 399
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 399

Leu Arg Asp Asn Leu Thr Leu Trp Thr Ser Asp Met Gln Gly Asp Ala
1               5                   10                  15
Tyr Pro Ala Leu Gly Pro Gly Val Thr Ala Asn Pro Gly Thr
            20                  25                  30

<210> SEQ ID NO 400
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 400

Leu Arg Asp Asn Leu Thr Leu Trp Thr Ser Asp Met Gln Gly Asp Ala
1               5                   10                  15
Tyr Pro Val Leu Gly Pro Gly Val Thr Ala Asn Pro Gly Thr
            20                  25                  30

<210> SEQ ID NO 401
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 401

Ile Lys Thr Leu Glu Gly Glu Phe Ser Val Thr Met Trp Ser Ser Gly
1               5                   10                  15
Pro Met Asp Glu Gly Pro Asp Leu Asp Leu Gly Pro Pro Val
            20                  25                  30

<210> SEQ ID NO 402
<211> LENGTH: 30
<212> TYPE: PRT

<213> ORGANISM: Artificial Sequence
<220> FEATURE:
<223> OTHER INFORMATION: Synthetic Polypeptide

<400> SEQUENCE: 402

Phe Gly Ser Thr Arg Gly Ser Leu Asp Lys Pro Asp Ser Phe Met Gly
1               5                   10                  15

Glu Tyr Ser Val Gly Asn Lys His Arg Asp Pro Phe Glu Ala
            20                  25                  30

<210> SEQ ID NO 403
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 403

Gln Cys Lys Thr Glu Thr Gln Glu Ser Gln Ala Phe Gln Glu Arg Gly
1               5                   10                  15

Ser Thr Thr Gly Leu Ser Ala Thr Pro Pro Ala Ser Leu Pro
            20                  25                  30

<210> SEQ ID NO 404
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 404

Val Trp Arg Ile Thr Gly Thr Asp Gly Val Lys Lys Met Thr Leu
1               5                   10                  15

Gln Trp Ala Ala Val
            20

<210> SEQ ID NO 405
<211> LENGTH: 45
<212> TYPE: PRT
<213> ORGANISM: Artificial Sequence
<220> FEATURE:
<223> OTHER INFORMATION: Synthetic Polypeptide

<400> SEQUENCE: 405

Arg Leu Met Leu Glu Leu Gly Phe Ser Lys Val Leu Gly Asp Arg Glu
1               5                   10                  15

Val Gln Ser Arg Trp Ser Pro Gly Pro Arg Gly Asp Ser Thr Pro Val
            20                  25                  30

Arg Glu Met Glu Thr Asn His Pro Pro Ser Val Arg Gly
        35                  40                  45

<210> SEQ ID NO 406
<211> LENGTH: 42
<212> TYPE: PRT
<213> ORGANISM: Artificial Sequence
<220> FEATURE:
<223> OTHER INFORMATION: Synthetic Polypeptide

<400> SEQUENCE: 406

Thr Tyr Leu Leu Asp Phe Arg Ser Ile Asp Glu Trp Leu Pro Leu Gly
1               5                   10                  15

Gly Arg Gly Lys Leu Val Arg Arg Ser Gln Arg Ser Leu Pro Ser Ser
            20                  25                  30

```
Leu Lys Leu Lys Leu Leu Met Arg Arg Met
        35                  40
```

<210> SEQ ID NO 407
<211> LENGTH: 216
<212> TYPE: PRT
<213> ORGANISM: Artificial Sequence
<220> FEATURE:
<223> OTHER INFORMATION: Synthetic Polypeptide

<400> SEQUENCE: 407

```
Leu Tyr Thr Leu Asn Lys His Gln Arg Phe Gly Trp Thr Arg Cys Ser
1               5                   10                  15

Glu Ala Gly Val Gln Thr Gln His Val Arg Arg Ser Gly Val Gly Pro
            20                  25                  30

Thr Pro Arg Gly Met Gly Ile Arg Val Gln Pro Gly Val Asp Ala Gly
        35                  40                  45

Arg Gly Leu Cys Arg Val Gln Ala Ala Gly Leu Arg Pro Cys Arg Gly
    50                  55                  60

Arg Pro Gln Val Cys Pro Ala Ala Trp Arg Asp Gly Pro Ala Leu Ala
65                  70                  75                  80

Ser Gln Arg Val Leu Pro Gly Gln Arg Val Leu Pro Leu Gly Val Gln
                85                  90                  95

Pro Trp Leu Met Val Pro Glu Pro Val Pro Pro Arg Met Gly Gly Gly
            100                 105                 110

Arg Ala Val Leu Gln Arg His Phe Pro Gly Ala Pro Ala Gly Glu Gly
        115                 120                 125

Pro Gln Ser Leu Arg Gly Thr Pro Arg Asp Gln Lys Arg Glu Trp Gly
    130                 135                 140

Gly Pro Pro Leu Cys Pro Ala Cys Gly Gly His Gly Val Leu Pro
145                 150                 155                 160

Gly Ala Gly Val Arg Pro Cys Ala Pro Gly Pro Pro Gly Arg Gly
                165                 170                 175

Arg Arg Gln Glu Val Pro Gly Leu Gln Gly Tyr Arg Ala His His Pro
            180                 185                 190

Gln Leu Gln Thr Gly Gln Gln Leu Pro Gln Arg Leu Arg Pro Ala Ala
        195                 200                 205

Gly Arg Arg Gly Gly Leu Leu Arg
    210                 215
```

<210> SEQ ID NO 408
<211> LENGTH: 1235
<212> TYPE: PRT
<213> ORGANISM: Artificial Sequence
<220> FEATURE:
<223> OTHER INFORMATION: Synthetic Polypeptide

<400> SEQUENCE: 408

```
Met His Arg Ala Pro Ser Pro Thr Ala Glu Gln Pro Gly Gly Gly
1               5                   10                  15

Asp Ser Ala Arg Arg Thr Leu Gln Pro Arg Leu Lys Pro Ser Ala Arg
            20                  25                  30

Ala Met Ala Leu Pro Arg Thr Leu Gly Glu Leu Gln Leu Tyr Arg Val
        35                  40                  45

Leu Gln Arg Ala Asn Leu Leu Ser Tyr Tyr Glu Thr Phe Ile Gln Gln
    50                  55                  60

Gly Gly Asp Asp Val Gln Gln Leu Cys Glu Ala Gly Glu Glu Glu Phe
65                  70                  75                  80
```

```
Leu Glu Ile Met Ala Leu Val Gly Met Ala Thr Lys Pro Leu His Val
                85                  90                  95

Arg Arg Leu Gln Lys Ala Leu Arg Glu Trp Ala Thr Asn Pro Gly Leu
            100                 105                 110

Phe Ser Gln Pro Val Pro Ala Val Pro Val Ser Ser Ile Pro Leu Phe
        115                 120                 125

Lys Ile Ser Glu Thr Ala Gly Thr Arg Lys Gly Ser Met Ser Asn Gly
    130                 135                 140

His Gly Ser Pro Gly Glu Lys Ala Gly Ser Ala Arg Ser Phe Ser Pro
145                 150                 155                 160

Lys Ser Pro Leu Glu Leu Gly Glu Lys Leu Ser Pro Leu Pro Gly Gly
                165                 170                 175

Pro Gly Ala Gly Asp Pro Arg Ile Trp Pro Gly Arg Ser Thr Pro Glu
            180                 185                 190

Ser Asp Val Gly Ala Gly Gly Glu Glu Ala Gly Ser Pro Pro Phe
        195                 200                 205

Ser Pro Pro Ala Gly Gly Val Pro Glu Gly Thr Gly Ala Gly Gly
    210                 215                 220

Leu Ala Ala Gly Gly Thr Gly Gly Pro Asp Arg Leu Glu Pro Glu
225                 230                 235                 240

Met Val Arg Met Val Val Glu Ser Val Glu Arg Ile Phe Arg Ser Phe
                245                 250                 255

Pro Arg Gly Asp Ala Gly Glu Val Thr Ser Leu Leu Lys Leu Asn Lys
            260                 265                 270

Lys Leu Ala Arg Ser Val Gly His Ile Phe Glu Met Asp Asp Asn Asp
        275                 280                 285

Ser Gln Lys Glu Glu Glu Ile Arg Lys Tyr Ser Ile Ile Tyr Gly Arg
    290                 295                 300

Phe Asp Ser Lys Arg Arg Glu Gly Lys Gln Leu Ser Leu His Glu Leu
305                 310                 315                 320

Thr Ile Asn Glu Ala Ala Ala Gln Phe Cys Met Arg Asp Asn Thr Leu
                325                 330                 335

Leu Leu Arg Arg Val Glu Leu Phe Ser Leu Ser Arg Gln Val Ala Arg
            340                 345                 350

Glu Ser Thr Tyr Leu Ser Ser Leu Lys Gly Ser Arg Leu His Pro Glu
        355                 360                 365

Glu Leu Gly Gly Pro Pro Leu Lys Lys Leu Lys Gln Glu Ala Thr Ser
    370                 375                 380

Lys Ser Gln Ile Met Ser Leu Trp Gly Leu Val Ser Lys Met Pro Pro
385                 390                 395                 400

Glu Lys Val Gln Arg Leu Tyr Val Asp Phe Pro Gln His Leu Arg His
                405                 410                 415

Leu Leu Gly Asp Trp Leu Glu Ser Gln Pro Trp Glu Phe Leu Val Gly
            420                 425                 430

Ser Asp Ala Phe Cys Cys Asn Leu Ala Ser Ala Leu Leu Ser Asp Thr
        435                 440                 445

Val Gln His Leu Gln Ala Ser Val Gly Glu Gln Gly Glu Gly Ser Thr
    450                 455                 460

Ile Leu Gln His Ile Ser Thr Leu Glu Ser Ile Tyr Gln Arg Asp Pro
465                 470                 475                 480

Leu Lys Leu Val Ala Thr Phe Arg Gln Ile Leu Gln Gly Glu Lys Lys
                485                 490                 495
```

```
Ala Val Met Glu Gln Phe Arg His Leu Pro Met Pro Phe His Trp Lys
            500                 505                 510

Gln Glu Glu Leu Lys Phe Lys Thr Gly Leu Arg Arg Leu Gln His Arg
        515                 520                 525

Val Gly Glu Ile His Leu Leu Arg Glu Ala Leu Gln Lys Gly Ala Glu
    530                 535                 540

Ala Gly Gln Val Ser Leu His Ser Leu Ile Glu Thr Pro Ala Asn Gly
545                 550                 555                 560

Thr Gly Pro Ser Glu Ala Leu Ala Met Leu Leu Gln Glu Thr Thr Gly
            565                 570                 575

Glu Leu Glu Ala Ala Lys Ala Leu Val Leu Lys Arg Ile Gln Ile Trp
        580                 585                 590

Lys Arg Gln Gln Gln Leu Ala Gly Asn Gly Ala Pro Phe Glu Glu Ser
    595                 600                 605

Leu Ala Pro Leu Gln Glu Arg Cys Glu Ser Leu Val Asp Ile Tyr Ser
610                 615                 620

Gln Leu Gln Gln Glu Val Gly Ala Ala Gly Glu Leu Glu Pro Lys
625                 630                 635                 640

Thr Arg Ala Ser Leu Thr Gly Arg Leu Asp Glu Val Leu Arg Thr Leu
            645                 650                 655

Val Thr Ser Cys Phe Leu Val Glu Lys Gln Pro Pro Gln Val Leu Lys
        660                 665                 670

Thr Gln Thr Lys Phe Gln Ala Gly Val Arg Phe Leu Leu Gly Leu Arg
    675                 680                 685

Phe Leu Gly Ala Pro Ala Lys Pro Pro Leu Val Arg Ala Asp Met Val
690                 695                 700

Thr Glu Lys Gln Ala Arg Glu Leu Ser Val Pro Gln Gly Pro Gly Ala
705                 710                 715                 720

Gly Ala Glu Ser Thr Gly Glu Ile Ile Asn Asn Thr Val Pro Leu Glu
            725                 730                 735

Asn Ser Ile Pro Gly Asn Cys Cys Ser Ala Leu Phe Lys Asn Leu Leu
        740                 745                 750

Leu Lys Lys Ile Lys Arg Cys Glu Arg Lys Gly Thr Glu Ser Val Thr
    755                 760                 765

Glu Glu Lys Cys Ala Val Leu Phe Ser Ala Ser Phe Thr Leu Gly Pro
770                 775                 780

Gly Lys Leu Pro Ile Gln Leu Gln Ala Leu Ser Leu Pro Leu Val Val
785                 790                 795                 800

Ile Val His Gly Asn Gln Asp Asn Asn Ala Lys Ala Thr Ile Leu Trp
            805                 810                 815

Asp Asn Ala Phe Ser Glu Met Asp Arg Val Pro Phe Val Ala Glu
        820                 825                 830

Arg Val Pro Trp Glu Lys Met Cys Glu Thr Leu Asn Leu Lys Phe Met
    835                 840                 845

Ala Glu Val Gly Thr Asn Arg Gly Leu Leu Pro Glu His Phe Leu Phe
850                 855                 860

Leu Ala Gln Lys Ile Phe Asn Asp Asn Ser Leu Ser Met Glu Ala Phe
865                 870                 875                 880

Gln His Arg Ser Val Ser Trp Ser Gln Phe Asn Lys Glu Ile Leu Leu
            885                 890                 895

Gly Arg Gly Phe Thr Phe Trp Gln Trp Phe Asp Gly Val Leu Asp Leu
        900                 905                 910

Thr Lys Arg Cys Leu Arg Ser Tyr Trp Ser Asp Arg Leu Ile Ile Gly
```

```
                915                 920                 925
Phe Ile Ser Lys Gln Tyr Val Thr Ser Leu Leu Asn Glu Pro Asp
        930                 935                 940
Gly Thr Phe Leu Leu Arg Phe Ser Asp Ser Glu Ile Gly Gly Ile Thr
945                 950                 955                 960
Ile Ala His Val Ile Arg Gly Gln Asp Gly Ser Pro Gln Ile Glu Asn
                965                 970                 975
Ile Gln Pro Phe Ser Ala Lys Asp Leu Ser Ile Arg Ser Leu Gly Asp
                980                 985                 990
Arg Ile Arg Asp Leu Ala Gln Leu Lys Asn Leu Tyr Pro Lys Lys Pro
                995                 1000                1005
Lys Asp Glu Ala Phe Arg Ser His Tyr Lys Pro Glu Gln Met Gly
        1010                1015                1020
Lys Asp Gly Arg Gly Tyr Val Pro Ala Thr Ile Lys Met Thr Val
        1025                1030                1035
Glu Arg Asp Gln Pro Leu Pro Thr Pro Glu Leu Gln Met Pro Thr
        1040                1045                1050
Met Val Pro Ser Tyr Asp Leu Gly Met Ala Pro Asp Ser Ser Met
        1055                1060                1065
Ser Met Gln Leu Gly Pro Asp Met Val Pro Gln Val Tyr Pro Pro
        1070                1075                1080
His Ser His Ser Ile Pro Pro Tyr Gln Gly Leu Ser Pro Glu Glu
        1085                1090                1095
Ser Val Asn Val Leu Ser Ala Phe Gln Glu Pro His Leu Gln Met
        1100                1105                1110
Pro Pro Ser Leu Gly Gln Met Ser Leu Pro Phe Asp Gln Pro His
        1115                1120                1125
Pro Gln Gly Leu Leu Pro Cys Gln Pro Gln Glu His Ala Val Ser
        1130                1135                1140
Ser Pro Asp Pro Leu Leu Cys Ser Asp Val Thr Met Val Glu Asp
        1145                1150                1155
Ser Cys Leu Ser Gln Pro Val Thr Ala Phe Pro Gln Gly Thr Trp
        1160                1165                1170
Ile Gly Glu Asp Ile Phe Pro Pro Leu Leu Pro Pro Thr Glu Gln
        1175                1180                1185
Asp Leu Thr Lys Leu Leu Leu Glu Gly Gln Gly Glu Ser Gly Gly
        1190                1195                1200
Gly Ser Leu Gly Ala Gln Pro Leu Leu Gln Pro Ser His Tyr Gly
        1205                1210                1215
Gln Ser Gly Ile Ser Met Ser His Met Asp Leu Arg Ala Asn Pro
        1220                1225                1230
Ser Trp
        1235

<210> SEQ ID NO 409
<211> LENGTH: 755
<212> TYPE: PRT
<213> ORGANISM: Artificial Sequence
<220> FEATURE:
<223> OTHER INFORMATION: Synthetic Polypeptide

<400> SEQUENCE: 409

Met His Arg Ala Pro Ser Pro Thr Ala Glu Gln Pro Pro Gly Gly Gly
1               5                   10                  15

Asp Ser Ala Arg Arg Thr Leu Gln Pro Arg Leu Lys Pro Ser Ala Arg
```

-continued

```
             20                  25                  30
Ala Met Ala Leu Pro Arg Thr Leu Gly Glu Leu Gln Leu Tyr Arg Val
             35                  40                  45
Leu Gln Arg Ala Asn Leu Leu Ser Tyr Tyr Glu Thr Phe Ile Gln Gln
             50                  55                  60
Gly Gly Asp Asp Val Gln Leu Cys Glu Ala Gly Glu Glu Phe
 65                  70                  75                  80
Leu Glu Ile Met Ala Leu Val Gly Met Ala Thr Lys Pro Leu His Val
                     85                  90                  95
Arg Arg Leu Gln Lys Ala Leu Arg Glu Trp Ala Thr Asn Pro Gly Leu
                    100                 105                 110
Phe Ser Gln Pro Val Pro Ala Val Pro Val Ser Ser Ile Pro Leu Phe
                    115                 120                 125
Lys Ile Ser Glu Thr Ala Gly Thr Arg Lys Gly Ser Met Ser Asn Gly
                    130                 135                 140
His Gly Ser Pro Gly Glu Lys Ala Gly Ser Ala Arg Ser Phe Ser Pro
145                 150                 155                 160
Lys Ser Pro Leu Glu Leu Gly Glu Lys Leu Ser Pro Leu Pro Gly Gly
                    165                 170                 175
Pro Gly Ala Gly Asp Pro Arg Ile Trp Pro Gly Arg Ser Thr Pro Glu
                    180                 185                 190
Ser Asp Val Gly Ala Gly Gly Glu Glu Ala Gly Ser Pro Pro Phe
                    195                 200                 205
Ser Pro Pro Ala Gly Gly Val Pro Glu Gly Thr Gly Ala Gly Gly
                    210                 215                 220
Leu Ala Ala Gly Gly Thr Gly Gly Pro Asp Arg Leu Glu Pro Glu
225                 230                 235                 240
Met Val Arg Met Val Val Glu Ser Val Glu Arg Ile Phe Arg Ser Phe
                    245                 250                 255
Pro Arg Gly Asp Ala Gly Glu Val Thr Ser Leu Leu Lys Leu Asn Lys
                    260                 265                 270
Lys Leu Ala Arg Ser Val Gly His Ile Phe Glu Met Asp Asp Asn Asp
                    275                 280                 285
Ser Gln Lys Glu Glu Glu Ile Arg Lys Tyr Ser Ile Ile Tyr Gly Arg
                    290                 295                 300
Phe Asp Ser Lys Arg Arg Glu Gly Lys Gln Leu Ser Leu His Glu Leu
305                 310                 315                 320
Thr Ile Asn Glu Ala Ala Ala Gln Phe Cys Met Arg Asp Asn Thr Leu
                    325                 330                 335
Leu Leu Arg Arg Val Glu Leu Phe Ser Leu Ser Arg Gln Val Ala Arg
                    340                 345                 350
Glu Ser Thr Tyr Leu Ser Ser Leu Lys Gly Ser Arg Leu His Pro Glu
                    355                 360                 365
Glu Leu Gly Gly Pro Leu Lys Lys Leu Lys Gln Glu Val Gly Glu
                    370                 375                 380
Gln Ser His Pro Glu Ile Gln Gln Pro Pro Gly Pro Glu Ser Tyr
385                 390                 395                 400
Val Pro Pro Tyr Arg Pro Ser Leu Glu Glu Asp Ser Ala Ser Leu Ser
                    405                 410                 415
Gly Glu Ser Leu Asp Gly His Leu Gln Ala Val Gly Ser Cys Pro Arg
                    420                 425                 430
Leu Thr Pro Pro Ala Asp Leu Pro Leu Ala Leu Pro Ala His Gly
                    435                 440                 445
```

```
Leu Trp Ser Arg His Ile Leu Gln Gln Thr Leu Met Asp Glu Gly Leu
    450                 455                 460

Arg Leu Ala Arg Leu Val Ser His Asp Arg Val Gly Arg Leu Ser Pro
465                 470                 475                 480

Cys Val Pro Ala Lys Pro Pro Leu Ala Gly Ser Pro Gln Ile Glu Asn
                485                 490                 495

Ile Gln Pro Phe Ser Ala Lys Asp Leu Ser Ile Arg Ser Leu Gly Asp
            500                 505                 510

Arg Ile Arg Asp Leu Ala Gln Leu Lys Asn Leu Tyr Pro Lys Lys Pro
        515                 520                 525

Lys Asp Glu Ala Phe Arg Ser His Tyr Lys Pro Glu Gln Met Gly Lys
    530                 535                 540

Asp Gly Arg Gly Tyr Val Pro Ala Thr Ile Lys Met Thr Val Glu Arg
545                 550                 555                 560

Asp Gln Pro Leu Pro Thr Pro Glu Leu Gln Met Pro Thr Met Val Pro
                565                 570                 575

Ser Tyr Asp Leu Gly Met Ala Pro Asp Ser Ser Met Ser Met Gln Leu
            580                 585                 590

Gly Pro Asp Met Val Pro Gln Val Tyr Pro Pro His Ser His Ser Ile
        595                 600                 605

Pro Pro Tyr Gln Gly Leu Ser Pro Glu Glu Ser Val Asn Val Leu Ser
    610                 615                 620

Ala Phe Gln Glu Pro His Leu Gln Met Pro Pro Ser Leu Gly Gln Met
625                 630                 635                 640

Ser Leu Pro Phe Asp Gln Pro His Pro Gln Gly Leu Leu Pro Cys Gln
                645                 650                 655

Pro Gln Glu His Ala Val Ser Ser Pro Asp Pro Leu Leu Cys Ser Asp
            660                 665                 670

Val Thr Met Val Glu Asp Ser Cys Leu Ser Gln Pro Val Thr Ala Phe
        675                 680                 685

Pro Gln Gly Thr Trp Ile Gly Glu Asp Ile Phe Pro Pro Leu Leu Pro
    690                 695                 700

Pro Thr Glu Gln Asp Leu Thr Lys Leu Leu Leu Glu Gly Gln Gly Glu
705                 710                 715                 720

Ser Gly Gly Gly Ser Leu Gly Ala Gln Pro Leu Leu Gln Pro Ser His
                725                 730                 735

Tyr Gly Gln Ser Gly Ile Ser Met Ser His Met Asp Leu Arg Ala Asn
            740                 745                 750

Pro Ser Trp
        755

<210> SEQ ID NO 410
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 410

Gly Pro Pro Leu Lys Lys Leu Lys Gln Glu Ala Thr Ser Lys Ser Gln
1               5                   10                  15

Ile Met Ser Leu Trp Gly Leu Val Ser Lys Met
            20                  25

<210> SEQ ID NO 411
```

```
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 411

Pro Leu Lys Lys Leu Lys Gln Glu Ala
1               5

<210> SEQ ID NO 412
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 412

Leu Lys Lys Leu Lys Gln Glu Ala Thr
1               5

<210> SEQ ID NO 413
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 413

Lys Lys Leu Lys Gln Glu Ala Thr Ser
1               5

<210> SEQ ID NO 414
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 414

Lys Leu Lys Gln Glu Ala Thr Ser Lys
1               5

<210> SEQ ID NO 415
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 415

Leu Lys Gln Glu Ala Thr Ser Lys Ser
1               5

<210> SEQ ID NO 416
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 416

Lys Gln Glu Ala Thr Ser Lys Ser Gln
1               5

<210> SEQ ID NO 417
<211> LENGTH: 9
```

-continued

```
<212> TYPE: PRT
<213> ORGANISM: Artificial Sequence
<220> FEATURE:
<223> OTHER INFORMATION: Synthetic Polypeptide

<400> SEQUENCE: 417

Gln Glu Ala Thr Ser Lys Ser Gln Ile
1               5

<210> SEQ ID NO 418
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 418

Glu Ala Thr Ser Lys Ser Gln Ile Met
1               5

<210> SEQ ID NO 419
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 419

Ala Thr Ser Lys Ser Gln Ile Met Ser
1               5

<210> SEQ ID NO 420
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 420

Thr Ser Lys Ser Gln Ile Met Ser Leu
1               5

<210> SEQ ID NO 421
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 421

Ser Lys Ser Gln Ile Met Ser Leu Trp
1               5

<210> SEQ ID NO 422
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 422

Lys Ser Gln Ile Met Ser Leu Trp Gly
1               5

<210> SEQ ID NO 423
<211> LENGTH: 9
<212> TYPE: PRT
```

```
<213> ORGANISM: Artificial Sequence
<220> FEATURE:
<223> OTHER INFORMATION: Synthetic Polypeptide

<400> SEQUENCE: 423

Ser Gln Ile Met Ser Leu Trp Gly Leu
1               5

<210> SEQ ID NO 424
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 424

Gln Ile Met Ser Leu Trp Gly Leu Val
1               5

<210> SEQ ID NO 425
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 425

Ile Met Ser Leu Trp Gly Leu Val Ser
1               5

<210> SEQ ID NO 426
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 426

Gly Pro Pro Leu Lys Lys Leu Lys Gln Glu Ala Thr Ser Lys Ser Gln
1               5                   10                  15

Ile Met Ser Leu Trp Gly Leu Val Ser Lys Met
            20                  25

<210> SEQ ID NO 427
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 427

Pro Cys Val Pro Ala Lys Pro Pro Leu Ala Gly Ser Pro Gln Ile Glu
1               5                   10                  15

Asn Ile Gln Pro
            20

<210> SEQ ID NO 428
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 428

Pro Cys Val Pro Ala Lys Pro Pro Leu Ala Ala Glu Gln Met Gly Lys
1               5                   10                  15
```

Asp Gly Arg Gly Tyr
            20

<210> SEQ ID NO 429
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 429

Ala Thr Ser Lys Ser Gln Ile Met
1               5

<210> SEQ ID NO 430
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 430

Glu Ala Thr Ser Lys Ser Gln Ile
1               5

<210> SEQ ID NO 431
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 431

Ile Met Ser Leu Trp Gly Leu Val
1               5

<210> SEQ ID NO 432
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 432

Lys Ser Gln Ile Met Ser Leu Trp
1               5

<210> SEQ ID NO 433
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 433

Gln Ile Met Ser Leu Trp Gly Leu
1               5

<210> SEQ ID NO 434
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 434

Ser Lys Ser Gln Ile Met Ser Leu
1               5

<210> SEQ ID NO 435
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 435

Glu Ala Thr Ser Lys Ser Gln Ile Met
1               5

<210> SEQ ID NO 436
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 436

Lys Leu Lys Gln Glu Ala Thr Ser Lys
1               5

<210> SEQ ID NO 437
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 437

Gln Glu Ala Thr Ser Lys Ser Gln Ile
1               5

<210> SEQ ID NO 438
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 438

Gln Ile Met Ser Leu Trp Gly Leu Val
1               5

<210> SEQ ID NO 439
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 439

Ser Gln Ile Met Ser Leu Trp Gly Leu
1               5

<210> SEQ ID NO 440
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 440

Thr Ser Lys Ser Gln Ile Met Ser Leu

```
1               5

<210> SEQ ID NO 441
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 441

Ala Thr Ser Lys Ser Gln Ile Met Ser Leu
1               5                   10

<210> SEQ ID NO 442
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 442

Ile Met Ser Leu Trp Gly Leu Val Ser Lys
1               5                   10

<210> SEQ ID NO 443
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 443

Lys Lys Leu Lys Gln Glu Ala Thr Ser Lys
1               5                   10

<210> SEQ ID NO 444
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 444

Lys Gln Glu Ala Thr Ser Lys Ser Gln Ile
1               5                   10

<210> SEQ ID NO 445
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 445

Lys Ser Gln Ile Met Ser Leu Trp Gly Leu
1               5                   10

<210> SEQ ID NO 446
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 446

Gln Glu Ala Thr Ser Lys Ser Gln Ile Met
1               5                   10
```

```
<210> SEQ ID NO 447
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 447

Ser Gln Ile Met Ser Leu Trp Gly Leu Val
1               5                   10

<210> SEQ ID NO 448
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 448

Thr Ser Lys Ser Gln Ile Met Ser Leu Trp
1               5                   10

<210> SEQ ID NO 449
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 449

Ala Thr Ser Lys Ser Gln Ile Met Ser Leu Trp
1               5                   10

<210> SEQ ID NO 450
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 450

Glu Ala Thr Ser Lys Ser Gln Ile Met Ser Leu
1               5                   10

<210> SEQ ID NO 451
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 451

Ile Met Ser Leu Trp Gly Leu Val Ser Lys Met
1               5                   10

<210> SEQ ID NO 452
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 452

Lys Gln Glu Ala Thr Ser Lys Ser Gln Ile Met
1               5                   10
```

<210> SEQ ID NO 453
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 453

Lys Ser Gln Ile Met Ser Leu Trp Gly Leu Val
1               5                   10

<210> SEQ ID NO 454
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 454

Leu Lys Gln Glu Ala Thr Ser Lys Ser Gln Ile
1               5                   10

<210> SEQ ID NO 455
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 455

Gln Glu Ala Thr Ser Lys Ser Gln Ile Met Ser
1               5                   10

<210> SEQ ID NO 456
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 456

Gln Ile Met Ser Leu Trp Gly Leu Val Ser Lys
1               5                   10

<210> SEQ ID NO 457
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 457

Ser Gln Ile Met Ser Leu Trp Gly Leu Val Ser
1               5                   10

<210> SEQ ID NO 458
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 458

Pro Leu Ala Gly Ser Pro Gln Ile
1               5

```
<210> SEQ ID NO 459
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 459

Pro Pro Leu Ala Gly Ser Pro Gln Ile
1               5

<210> SEQ ID NO 460
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 460

Lys Pro Pro Leu Ala Gly Ser Pro Gln Ile
1               5                   10

<210> SEQ ID NO 461
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 461

Leu Ala Gly Ser Pro Gln Ile Glu Asn Ile
1               5                   10

<210> SEQ ID NO 462
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 462

Gly Ser Pro Gln Ile Glu Asn Ile Gln Pro Phe
1               5                   10

<210> SEQ ID NO 463
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 463

Pro Leu Ala Gly Ser Pro Gln Ile Glu Asn Ile
1               5                   10

<210> SEQ ID NO 464
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 464

Ala Glu Gln Met Gly Lys Asp Gly
1               5

<210> SEQ ID NO 465
```

```
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 465

Leu Ala Ala Glu Gln Met Gly Lys
1               5

<210> SEQ ID NO 466
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 466

Pro Pro Leu Ala Ala Glu Gln Met
1               5

<210> SEQ ID NO 467
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 467

Lys Pro Pro Leu Ala Ala Glu Gln Met
1               5

<210> SEQ ID NO 468
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 468

Pro Leu Ala Ala Glu Gln Met Gly Lys
1               5

<210> SEQ ID NO 469
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 469

Val Pro Ala Lys Pro Pro Leu Ala Ala
1               5

<210> SEQ ID NO 470
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 470

Ala Glu Gln Met Gly Lys Asp Gly Arg Gly Tyr
1               5                   10

<210> SEQ ID NO 471
<211> LENGTH: 11
```

```
<212> TYPE: PRT
<213> ORGANISM: Artificial Sequence
<220> FEATURE:
<223> OTHER INFORMATION: Synthetic Polypeptide

<400> SEQUENCE: 471

Leu Ala Ala Glu Gln Met Gly Lys Asp Gly Arg
1               5                   10

<210> SEQ ID NO 472
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 472

Pro Ala Lys Pro Pro Leu Ala Ala Glu Gln Met
1               5                   10

<210> SEQ ID NO 473
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 473

Asp Gly Val Ser His Cys Pro Gly Gly Glu Asp Glu Asn Arg Cys Gly
1               5                   10                  15

Ser Leu Ile Ser Cys Glu
            20

<210> SEQ ID NO 474
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 474

Phe Leu Val Gly Ala Ala Leu Ala Ala Gly Leu Leu Trp Lys Phe Arg
1               5                   10                  15

Ser Leu Ile Ser Cys Glu
            20

<210> SEQ ID NO 475
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 475

Phe Leu Val Gly Ala Ala Leu Ala Ala Gly Leu Leu Trp Lys Phe Arg
1               5                   10                  15

Thr Leu Leu Met Asn Ala Val Trp Pro Lys Ala Gly Arg Trp
            20                  25                  30

<210> SEQ ID NO 476
<211> LENGTH: 20
<212> TYPE: PRT
<213> ORGANISM: Artificial Sequence
<220> FEATURE:
<223> OTHER INFORMATION: Synthetic Polypeptide
```

```
<400> SEQUENCE: 476

Met Ala Leu Asn Ser Glu Ala Leu Ser Val Val Ser Glu Asp Gln Ser
1               5                   10                  15

Leu Phe Glu Cys
            20

<210> SEQ ID NO 477
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 477

Met Ala Leu Asn Ser Pro Ser Gly Ser Glu Gln Leu Val Asp Gly Leu
1               5                   10                  15

Ala Tyr

<210> SEQ ID NO 478
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 478

Met Ala Leu Asn Ser Val Ile Pro Gly Ser Leu Glu Thr Arg Gly Lys
1               5                   10                  15

Pro Cys

<210> SEQ ID NO 479
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 479

Val Cys Thr Gln Pro Lys Ser Pro Ser Gly Thr Val Cys Thr Ser Arg
1               5                   10                  15

Ser Leu Ile Ser Cys Glu
            20

<210> SEQ ID NO 480
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 480

Val Cys Thr Gln Pro Lys Ser Pro Ser Gly Thr Val Cys Thr Ser Ser
1               5                   10                  15

Tyr Ser Arg Ile Phe Gly Asp Pro Arg Lys Ala Val Leu Thr
            20                  25                  30

<210> SEQ ID NO 481
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 481
```

Ile His Thr Gln Pro Glu Val Ile Leu His Gln Asn His Glu Glu Asp
1               5                   10                  15

Val Gln His Ile Lys Arg Arg Asp Ile Val Leu Lys Arg Glu
            20                  25                  30

<210> SEQ ID NO 482
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 482

Ile His Thr Gln Pro Glu Val Ile Leu His Gln Asn His Glu Glu Gly
1               5                   10                  15

Pro Val Ala Val Ile Ser Gly Glu Glu Asp Ser Ala Ser Pro
            20                  25                  30

<210> SEQ ID NO 483
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 483

Val Ser Pro Pro Glu Glu His Ala Met Pro Ile Gly Arg Ile Ala Asp
1               5                   10                  15

Val Gln His Ile Lys Arg Arg Asp Ile Val Leu Lys Arg Glu
            20                  25                  30

<210> SEQ ID NO 484
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 484

Val Ser Pro Pro Glu Glu His Ala Met Pro Ile Gly Arg Ile Ala Asp
1               5                   10                  15

Val Gln His Ile Lys Arg Arg Asp Ile Val Leu Lys Arg Glu
            20                  25                  30

<210> SEQ ID NO 485
<211> LENGTH: 439
<212> TYPE: PRT
<213> ORGANISM: Artificial Sequence
<220> FEATURE:
<223> OTHER INFORMATION: Synthetic Polypeptide

<400> SEQUENCE: 485

Met Ala Ser Asn Asp Tyr Thr Gln Gln Ala Thr Gln Ser Tyr Gly Ala
1               5                   10                  15

Tyr Pro Thr Gln Pro Gly Gln Gly Tyr Ser Gln Gln Ser Ser Gln Pro
            20                  25                  30

Tyr Gly Gln Gln Ser Tyr Ser Gly Tyr Ser Gln Ser Thr Asp Thr Ser
        35                  40                  45

Gly Tyr Gly Gln Ser Ser Tyr Ser Ser Tyr Gly Gln Ser Gln Asn Thr
    50                  55                  60

Gly Tyr Gly Thr Gln Ser Thr Pro Gln Gly Tyr Gly Ser Thr Gly Gly
65                  70                  75                  80

Tyr Gly Ser Ser Gln Ser Ser Gln Ser Ser Tyr Gly Gln Gln Ser Ser
                85                  90                  95

Tyr Pro Gly Tyr Gly Gln Gln Pro Ala Pro Ser Ser Thr Ser Gly Ser
            100                 105                 110

Tyr Gly Ser Ser Gln Ser Ser Tyr Gly Gln Pro Gln Ser Gly
        115                 120                 125

Ser Tyr Ser Gln Gln Pro Ser Tyr Gly Gly Gln Gln Ser Tyr Gly
130                 135                 140

Gln Gln Gln Ser Tyr Asn Pro Pro Gln Gly Tyr Gly Gln Asn Gln
145             150                 155                 160

Tyr Asn Ser Ser Ser Gly Gly Gly Gly Gly Gly Gly Gly Asn
            165                 170                 175

Tyr Gly Gln Asp Gln Ser Ser Met Ser Ser Gly Gly Ser Gly Gly
            180                 185                 190

Gly Tyr Gly Asn Gln Asp Gln Ser Gly Gly Gly Ser Gly Gly Tyr
        195                 200                 205

Gly Gln Gln Asp Arg Gly Gly Arg Gly Arg Gly Gly Ser Gly Gly Gly
    210                 215                 220

Gly Gly Gly Gly Gly Gly Tyr Asn Arg Ser Ser Gly Gly Tyr Glu
225                 230                 235                 240

Pro Arg Gly Arg Gly Gly Arg Gly Arg Gly Met Gly Gly
            245                 250                 255

Ser Asp Arg Gly Gly Phe Asn Lys Phe Gly Gly Ser Gly Gln Ile Gln
            260                 265                 270

Leu Trp Gln Phe Leu Leu Glu Leu Leu Ser Asp Ser Ser Asn Ser Ser
        275                 280                 285

Cys Ile Thr Trp Glu Gly Thr Asn Gly Glu Phe Lys Met Thr Asp Pro
        290                 295                 300

Asp Glu Val Ala Arg Arg Trp Gly Glu Arg Lys Ser Lys Pro Asn Met
305                 310                 315                 320

Asn Tyr Asp Lys Leu Ser Arg Ala Leu Arg Tyr Tyr Asp Lys Asn
                325                 330                 335

Ile Met Thr Lys Val His Gly Lys Arg Tyr Ala Tyr Lys Phe Asp Phe
            340                 345                 350

His Gly Ile Ala Gln Ala Leu Gln Pro His Pro Glu Ser Ser Leu
        355                 360                 365

Tyr Lys Tyr Pro Ser Asp Leu Pro Tyr Met Gly Ser Tyr His Ala His
    370                 375                 380

Pro Gln Lys Met Asn Phe Val Ala Pro His Pro Ala Leu Pro Val
385                 390                 395                 400

Thr Ser Ser Ser Phe Phe Ala Ala Pro Asn Pro Tyr Trp Asn Ser Pro
                405                 410                 415

Thr Gly Gly Ile Tyr Pro Asn Thr Arg Leu Pro Thr Ser His Met Pro
            420                 425                 430

Ser His Leu Gly Thr Tyr Tyr
        435

<210> SEQ ID NO 486
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 486

```
Gly Pro Pro Leu Lys Lys Leu Lys Gln Glu Ala Thr Ser Lys Ser Gln
1               5                   10                  15

Ile Met Ser Leu Trp Gly Leu Val Ser Lys Met
            20                  25

<210> SEQ ID NO 487
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 487

Gly Ser Gly Gln Ile Gln Leu Trp
1               5

<210> SEQ ID NO 488
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 488

Lys Phe Gly Gly Ser Gly Gln Ile
1               5

<210> SEQ ID NO 489
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 489

Phe Gly Gly Ser Gly Gln Ile Gln Leu
1               5

<210> SEQ ID NO 490
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 490

Gly Gly Ser Gly Gln Ile Gln Leu Trp
1               5

<210> SEQ ID NO 491
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 491

Lys Phe Gly Gly Ser Gly Gln Ile Gln Leu
1               5                   10

<210> SEQ ID NO 492
<211> LENGTH: 11
<212> TYPE: PRT
<213> ORGANISM: Artificial Sequence
<220> FEATURE:
<223> OTHER INFORMATION: Synthetic Polypeptide
```

```
<400> SEQUENCE: 492

Lys Phe Gly Gly Ser Gly Gln Ile Gln Leu Trp
1               5                   10

<210> SEQ ID NO 493
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 493

Asn Lys Phe Gly Gly Ser Gly Gln Ile Gln Leu
1               5                   10

<210> SEQ ID NO 494
<211> LENGTH: 191
<212> TYPE: PRT
<213> ORGANISM: Artificial Sequence
<220> FEATURE:
<223> OTHER INFORMATION: Synthetic Polypeptide

<400> SEQUENCE: 494

Met Ala Ser Asn Asp Tyr Thr Gln Gln Ala Thr Gln Ser Tyr Gly Ala
1               5                   10                  15

Tyr Pro Thr Gln Pro Gly Gln Gly Tyr Ser Gln Gln Ser Ser Gln Pro
            20                  25                  30

Tyr Gly Gln Gln Ser Tyr Ser Gly Tyr Ser Gln Ser Thr Asp Thr Ser
        35                  40                  45

Gly Tyr Gly Gln Ser Ser Tyr Ser Ser Tyr Gly Gln Ser Gln Asn Thr
    50                  55                  60

Gly Tyr Gly Thr Gln Ser Thr Pro Gln Gly Tyr Gly Ser Thr Gly Gly
65                  70                  75                  80

Tyr Gly Ser Ser Gln Ser Ser Gln Ser Ser Tyr Gly Gln Gln Ser Ser
                85                  90                  95

Tyr Pro Gly Tyr Gly Gln Gln Pro Ala Pro Ser Ser Thr Ser Gly Ser
            100                 105                 110

Tyr Gly Ser Ser Ser Gln Ser Ser Ser Tyr Gly Gln Pro Gln Ser Gly
        115                 120                 125

Ser Tyr Ser Gln Gln Pro Ser Tyr Gly Gly Gln Gln Ser Tyr Gly
    130                 135                 140

Gln Gln Gln Ser Tyr Asn Pro Pro Gly Tyr Gly Gln Gln Asn Gln
145                 150                 155                 160

Tyr Asn Ser Ser Gly Gly Gly Gly Gly Gly Gly Gly Val Phe
                165                 170                 175

Lys Lys Glu Val Tyr Leu His Thr Ser Pro His Leu Lys Ala Asp
            180                 185                 190

<210> SEQ ID NO 495
<211> LENGTH: 283
<212> TYPE: PRT
<213> ORGANISM: Artificial Sequence
<220> FEATURE:
<223> OTHER INFORMATION: Synthetic Polypeptide

<400> SEQUENCE: 495

Met Ala Ser Asn Asp Tyr Thr Gln Gln Ala Thr Gln Ser Tyr Gly Ala
1               5                   10                  15

Tyr Pro Thr Gln Pro Gly Gln Gly Tyr Ser Gln Gln Ser Ser Gln Pro
```

```
            20                  25                  30
Tyr Gly Gln Gln Ser Tyr Ser Gly Tyr Ser Gln Ser Thr Asp Thr Ser
            35                  40                  45
Gly Tyr Gly Gln Ser Ser Tyr Ser Ser Tyr Gly Gln Ser Gln Asn Thr
        50                  55                  60
Gly Tyr Gly Thr Gln Ser Thr Pro Gln Gly Tyr Gly Ser Thr Gly Gly
 65                  70                  75                  80
Tyr Gly Ser Ser Gln Ser Ser Gln Ser Ser Tyr Gly Gln Gln Ser Ser
                85                  90                  95
Tyr Pro Gly Tyr Gly Gln Gln Pro Ala Pro Ser Ser Thr Ser Gly Ser
            100                 105                 110
Tyr Gly Ser Ser Ser Gln Ser Ser Tyr Gly Gln Pro Gln Ser Gly
            115                 120                 125
Ser Tyr Ser Gln Gln Pro Ser Tyr Gly Gly Gln Gln Ser Tyr Gly
        130                 135                 140
Gln Gln Gln Ser Tyr Asn Pro Pro Gln Gly Tyr Gly Gln Gln Asn Gln
145                 150                 155                 160
Tyr Asn Ser Ser Gly Gly Gly Gly Gly Gly Gly Gly Gly Gly Asn
                165                 170                 175
Tyr Gly Gln Asp Gln Ser Ser Met Ser Gly Gly Ser Gly Gly
            180                 185                 190
Gly Tyr Gly Asn Gln Asp Gln Ser Gly Gly Gly Ser Gly Gly Tyr
        195                 200                 205
Gly Gln Gln Asp Arg Gly Gly Arg Gly Arg Gly Gly Ser Gly Gly
    210                 215                 220
Gly Gly Gly Gly Gly Gly Tyr Asn Arg Ser Ser Gly Gly Tyr Glu
225                 230                 235                 240
Pro Arg Gly Arg Gly Gly Arg Gly Gly Arg Gly Gly Met Gly Gly
                245                 250                 255
Ser Asp Arg Gly Gly Phe Asn Lys Phe Gly Val Phe Lys Lys Glu Val
            260                 265                 270
Tyr Leu His Thr Ser Pro His Leu Lys Ala Asp
        275                 280

<210> SEQ ID NO 496
<211> LENGTH: 294
<212> TYPE: PRT
<213> ORGANISM: Artificial Sequence
<220> FEATURE:
<223> OTHER INFORMATION: Synthetic Polypeptide

<400> SEQUENCE: 496

Met Ala Ser Asn Asp Tyr Thr Gln Gln Ala Thr Gln Ser Tyr Gly Ala
 1               5                  10                  15
Tyr Pro Thr Gln Pro Gly Gln Gly Tyr Ser Gln Gln Ser Ser Gln Pro
            20                  25                  30
Tyr Gly Gln Gln Ser Tyr Ser Gly Tyr Ser Gln Ser Thr Asp Thr Ser
            35                  40                  45
Gly Tyr Gly Gln Ser Ser Tyr Ser Ser Tyr Gly Gln Ser Gln Asn Thr
        50                  55                  60
Gly Tyr Gly Thr Gln Ser Thr Pro Gln Gly Tyr Gly Ser Thr Gly Gly
 65                  70                  75                  80
Tyr Gly Ser Ser Gln Ser Ser Gln Ser Ser Tyr Gly Gln Gln Ser Ser
                85                  90                  95
Tyr Pro Gly Tyr Gly Gln Gln Pro Ala Pro Ser Ser Thr Ser Gly Ser
```

```
                100             105             110
Tyr Gly Ser Ser Ser Gln Ser Ser Tyr Gly Gln Pro Gln Ser Gly
            115                 120             125

Ser Tyr Ser Gln Gln Pro Ser Tyr Gly Gly Gln Gln Ser Tyr Gly
        130                 135             140

Gln Gln Gln Ser Tyr Asn Pro Pro Gln Gly Tyr Gly Gln Asn Gln
145                 150                 155                 160

Tyr Asn Ser Ser Ser Gly Gly Gly Gly Gly Gly Gly Gly Gly Asn
                165                 170                 175

Tyr Gly Gln Asp Gln Ser Ser Met Ser Ser Gly Gly Ser Gly Gly
                180                 185                 190

Gly Tyr Gly Asn Gln Asp Gln Ser Gly Gly Gly Ser Gly Gly Tyr
            195                 200                 205

Gly Gln Gln Asp Arg Gly Gly Arg Gly Arg Gly Gly Ser Gly Gly
            210                 215                 220

Gly Gly Gly Gly Gly Gly Gly Tyr Asn Arg Ser Ser Gly Gly Tyr Glu
225                 230                 235                 240

Pro Arg Gly Arg Gly Gly Gly Arg Gly Gly Arg Gly Gly Met Gly Gly
                    245                 250                 255

Ser Asp Arg Gly Gly Phe Asn Lys Phe Gly Gly Pro Arg Asp Gln Gly
                260                 265                 270

Ser Arg His Asp Ser Val Phe Lys Lys Glu Val Tyr Leu His Thr Ser
            275                 280                 285

Pro His Leu Lys Ala Asp
        290

<210> SEQ ID NO 497
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 497

Ser Gly Gly Gly Gly Gly Gly Gly Gly Val Phe Lys Lys Glu Val
1               5                   10                  15

Tyr Leu His Thr Ser Pro His Leu Lys Ala Asp
            20                  25

<210> SEQ ID NO 498
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 498

His Thr Ser Pro His Leu Lys Ala
1               5

<210> SEQ ID NO 499
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 499

Lys Glu Val Tyr Leu His Thr Ser
1               5
```

<210> SEQ ID NO 500
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 500

Val Phe Lys Lys Glu Val Tyr Leu
1               5

<210> SEQ ID NO 501
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 501

Val Tyr Leu His Thr Ser Pro His
1               5

<210> SEQ ID NO 502
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 502

Tyr Leu His Thr Ser Pro His Leu
1               5

<210> SEQ ID NO 503
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 503

Glu Val Tyr Leu His Thr Ser Pro His
1               5

<210> SEQ ID NO 504
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 504

Gly Val Phe Lys Lys Glu Val Tyr Leu
1               5

<210> SEQ ID NO 505
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 505

Lys Glu Val Tyr Leu His Thr Ser Pro
1               5

<210> SEQ ID NO 506
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 506

Val Tyr Leu His Thr Ser Pro His Leu
1               5

<210> SEQ ID NO 507
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 507

Tyr Leu His Thr Ser Pro His Leu Lys
1               5

<210> SEQ ID NO 508
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 508

Glu Val Tyr Leu His Thr Ser Pro His Leu
1               5                   10

<210> SEQ ID NO 509
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 509

Tyr Leu His Thr Ser Pro His Leu Lys Ala
1               5                   10

<210> SEQ ID NO 510
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 510

Glu Val Tyr Leu His Thr Ser Pro His Leu Lys
1               5                   10

<210> SEQ ID NO 511
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 511

Lys Glu Val Tyr Leu His Thr Ser Pro His Leu
1               5                   10

```
<210> SEQ ID NO 512
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 512

Gly Val Phe Lys Lys Glu Val Tyr
1               5

<210> SEQ ID NO 513
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 513

Ser Asp Arg Gly Gly Phe Asn Lys Phe Gly Val Phe Lys Lys Glu Val
1               5                   10                  15

Tyr Leu His Thr Ser Pro His Leu Lys Ala Asp
            20                  25

<210> SEQ ID NO 514
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 514

Phe Asn Lys Phe Gly Val Phe Lys
1               5

<210> SEQ ID NO 515
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 515

Gly Phe Asn Lys Phe Gly Val Phe
1               5

<210> SEQ ID NO 516
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 516

Gly Val Phe Lys Lys Glu Val Tyr
1               5

<210> SEQ ID NO 517
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 517

His Thr Ser Pro His Leu Lys Ala
1               5
```

<210> SEQ ID NO 518
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 518

Lys Glu Val Tyr Leu His Thr Ser
1               5

<210> SEQ ID NO 519
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 519

Asn Lys Phe Gly Val Phe Lys Lys
1               5

<210> SEQ ID NO 520
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 520

Val Phe Lys Lys Glu Val Tyr Leu
1               5

<210> SEQ ID NO 521
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 521

Val Tyr Leu His Thr Ser Pro His
1               5

<210> SEQ ID NO 522
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 522

Tyr Leu His Thr Ser Pro His Leu
1               5

<210> SEQ ID NO 523
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 523

Glu Val Tyr Leu His Thr Ser Pro His
1               5

```
<210> SEQ ID NO 524
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 524

Phe Asn Lys Phe Gly Val Phe Lys Lys
1               5

<210> SEQ ID NO 525
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 525

Gly Phe Asn Lys Phe Gly Val Phe Lys
1               5

<210> SEQ ID NO 526
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 526

Gly Gly Phe Asn Lys Phe Gly Val Phe
1               5

<210> SEQ ID NO 527
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 527

Gly Val Phe Lys Lys Glu Val Tyr Leu
1               5

<210> SEQ ID NO 528
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 528

Lys Glu Val Tyr Leu His Thr Ser Pro
1               5

<210> SEQ ID NO 529
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 529

Val Tyr Leu His Thr Ser Pro His Leu
1               5
```

<210> SEQ ID NO 530
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 530

Tyr Leu His Thr Ser Pro His Leu Lys
1               5

<210> SEQ ID NO 531
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 531

Glu Val Tyr Leu His Thr Ser Pro His Leu
1               5                   10

<210> SEQ ID NO 532
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 532

Phe Gly Val Phe Lys Lys Glu Val Tyr Leu
1               5                   10

<210> SEQ ID NO 533
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 533

Gly Phe Asn Lys Phe Gly Val Phe Lys Lys
1               5                   10

<210> SEQ ID NO 534
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 534

Tyr Leu His Thr Ser Pro His Leu Lys Ala
1               5                   10

<210> SEQ ID NO 535
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 535

Glu Val Tyr Leu His Thr Ser Pro His Leu Lys
1               5                   10

<210> SEQ ID NO 536

```
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 536

Phe Asn Lys Phe Gly Val Phe Lys Lys Glu Val
1               5                   10

<210> SEQ ID NO 537
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 537

Gly Gly Phe Asn Lys Phe Gly Val Phe Lys Lys
1               5                   10

<210> SEQ ID NO 538
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 538

Lys Glu Val Tyr Leu His Thr Ser Pro His Leu
1               5                   10

<210> SEQ ID NO 539
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 539

Lys Phe Gly Val Phe Lys Lys Glu Val Tyr Leu
1               5                   10

<210> SEQ ID NO 540
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 540

Asn Lys Phe Gly Val Phe Lys Lys Glu Val Tyr
1               5                   10

<210> SEQ ID NO 541
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 541

Arg Gly Gly Phe Asn Lys Phe Gly Val Phe Lys
1               5                   10

<210> SEQ ID NO 542
<211> LENGTH: 27
```

<212> TYPE: PRT
<213> ORGANISM: Artificial Sequence
<220> FEATURE:
<223> OTHER INFORMATION: Synthetic Polypeptide

<400> SEQUENCE: 542

Pro Arg Asp Gln Gly Ser Arg His Asp Ser Val Phe Lys Lys Glu Val
1               5                   10                  15

Tyr Leu His Thr Ser Pro His Leu Lys Ala Asp
            20                  25

<210> SEQ ID NO 543
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 543

Asp Ser Val Phe Lys Lys Glu Val
1               5

<210> SEQ ID NO 544
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 544

Gly Ser Arg His Asp Ser Val Phe
1               5

<210> SEQ ID NO 545
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 545

His Thr Ser Pro His Leu Lys Ala
1               5

<210> SEQ ID NO 546
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 546

Lys Glu Val Tyr Leu His Thr Ser
1               5

<210> SEQ ID NO 547
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 547

Ser Arg His Asp Ser Val Phe Lys
1               5

```
<210> SEQ ID NO 548
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 548

Ser Val Phe Lys Lys Glu Val Tyr
1               5

<210> SEQ ID NO 549
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 549

Val Phe Lys Lys Glu Val Tyr Leu
1               5

<210> SEQ ID NO 550
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 550

Val Tyr Leu His Thr Ser Pro His
1               5

<210> SEQ ID NO 551
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 551

Tyr Leu His Thr Ser Pro His Leu
1               5

<210> SEQ ID NO 552
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 552

Glu Val Tyr Leu His Thr Ser Pro His
1               5

<210> SEQ ID NO 553
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 553

Gly Ser Arg His Asp Ser Val Phe Lys
1               5

<210> SEQ ID NO 554
```

```
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 554

Lys Glu Val Tyr Leu His Thr Ser Pro
1               5

<210> SEQ ID NO 555
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 555

Gln Gly Ser Arg His Asp Ser Val Phe
1               5

<210> SEQ ID NO 556
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 556

Ser Arg His Asp Ser Val Phe Lys Lys
1               5

<210> SEQ ID NO 557
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 557

Ser Val Phe Lys Lys Glu Val Tyr Leu
1               5

<210> SEQ ID NO 558
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 558

Val Tyr Leu His Thr Ser Pro His Leu
1               5

<210> SEQ ID NO 559
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 559

Tyr Leu His Thr Ser Pro His Leu Lys
1               5

<210> SEQ ID NO 560
<211> LENGTH: 10
```

```
<212> TYPE: PRT
<213> ORGANISM: Artificial Sequence
<220> FEATURE:
<223> OTHER INFORMATION: Synthetic Polypeptide

<400> SEQUENCE: 560

Asp Gln Gly Ser Arg His Asp Ser Val Phe
1               5                   10

<210> SEQ ID NO 561
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 561

Glu Val Tyr Leu His Thr Ser Pro His Leu
1               5                   10

<210> SEQ ID NO 562
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 562

Gly Ser Arg His Asp Ser Val Phe Lys Lys
1               5                   10

<210> SEQ ID NO 563
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 563

Arg His Asp Ser Val Phe Lys Lys Glu Val
1               5                   10

<210> SEQ ID NO 564
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 564

Tyr Leu His Thr Ser Pro His Leu Lys Ala
1               5                   10

<210> SEQ ID NO 565
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 565

Glu Val Tyr Leu His Thr Ser Pro His Leu Lys
1               5                   10

<210> SEQ ID NO 566
<211> LENGTH: 11
<212> TYPE: PRT
```

<213> ORGANISM: Artificial Sequence
<220> FEATURE:
<223> OTHER INFORMATION: Synthetic Polypeptide

<400> SEQUENCE: 566

Lys Glu Val Tyr Leu His Thr Ser Pro His Leu
1               5                   10

<210> SEQ ID NO 567
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 567

Arg Asp Gln Gly Ser Arg His Asp Ser Val Phe
1               5                   10

<210> SEQ ID NO 568
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 568

Ser Arg His Asp Ser Val Phe Lys Lys Glu Val
1               5                   10

<210> SEQ ID NO 569
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 569

Ala Ser Glu Glu Thr Tyr Leu Ser His Leu Gly Ala Leu Leu Leu Lys
1               5                   10                  15

Pro Phe Ser Gly Gln
            20

<210> SEQ ID NO 570
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 570

Glu Ile Thr Pro Arg Arg Gln Ser Met Thr Val Lys Lys Gly Glu Lys
1               5                   10                  15

Pro Phe Ser Gly Gln
            20

<210> SEQ ID NO 571
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 571

Glu Ile Thr Pro Arg Arg Gln Ser Met Thr Val Lys Lys Gly Glu Ser
1               5                   10                  15

Tyr Thr Phe Leu Ile Ser Ser Asp Tyr Glu Arg Ala Glu Trp
            20                  25                  30

<210> SEQ ID NO 572
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 572

Gly Val Ala Thr Asp Ile Gln Ala Leu Lys Ala Ala Phe Asp Val Lys
1               5                   10                  15

Ala Leu Gln Arg Pro Val Ala Ser Asp Phe Glu Pro Gln Gly
            20                  25                  30

<210> SEQ ID NO 573
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 573

Gly Val Ala Thr Asp Ile Gln Ala Leu Lys Ala Ala Phe Asp Val Arg
1               5                   10                  15

Pro Ser Pro Cys Glu Asp Arg His Trp Pro Gly Leu Ala Leu
            20                  25                  30

<210> SEQ ID NO 574
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 574

Lys Leu Gln Thr Val His Ser Ile Pro Leu Thr Ile Asn Lys Glu Ala
1               5                   10                  15

Gly Ser Ile Glu Ala Leu Gln Arg Pro Val Ala Ser Asp Phe
            20                  25                  30

<210> SEQ ID NO 575
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 575

Lys Leu Gln Thr Val His Ser Ile Pro Leu Thr Ile Asn Lys Glu Glu
1               5                   10                  15

Ala Leu Gln Arg Pro Val Ala Ser Asp Phe Glu Pro Gln Gly
            20                  25                  30

<210> SEQ ID NO 576
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 576

Lys Leu Gln Thr Val His Ser Ile Pro Leu Thr Ile Asn Lys Glu Gly

```
                1               5                  10                  15
Glu Lys Leu Arg Val Leu Gly Tyr Asn His Asn Gly Glu Trp
            20                  25                  30

<210> SEQ ID NO 577
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 577

Lys Thr Arg Val Tyr Arg Asp Thr Ala Glu Pro Asn Trp Asn Glu Lys
1               5                   10                  15

Pro Phe Ser Gly Gln
            20

<210> SEQ ID NO 578
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 578

Lys Thr Arg Val Tyr Arg Asp Thr Ala Glu Pro Asn Trp Asn Glu Leu
1               5                   10                  15

Asp Pro Gln Ala Leu Gln Asp Arg Asp Trp Gln Arg Thr Val
            20                  25                  30

<210> SEQ ID NO 579
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 579

Leu Asn Val Ile Val His Ser Ala Thr Gly Phe Lys Gln Ser Ser Lys
1               5                   10                  15

Ala Leu Gln Arg Pro Val Ala Ser Asp Phe Glu Pro Gln Gly
            20                  25                  30

<210> SEQ ID NO 580
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 580

Leu Asn Val Ile Val His Ser Ala Thr Gly Phe Lys Gln Ser Ser Ser
1               5                   10                  15

Glu Lys Leu Arg Val Leu Gly Tyr Asn His Asn Gly Glu Trp
            20                  25                  30

<210> SEQ ID NO 581
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 581
```

-continued

Gln Ile Trp Pro Asn Asp Gly Glu Gly Ala Phe His Gly Asp Ala Glu
1               5                   10                  15

Ala Leu Gln Arg Pro Val Ala Ser Asp Phe Glu Pro Gln Gly
            20                  25                  30

<210> SEQ ID NO 582
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 582

Gln Ile Trp Pro Asn Asp Gly Glu Gly Ala Phe His Gly Asp Ala Gly
1               5                   10                  15

Glu Lys Leu Arg Val Leu Gly Tyr Asn His Asn Gly Glu Trp
            20                  25                  30

<210> SEQ ID NO 583
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 583

Gln Trp Ser His Gln Gln Arg Val Gly Asp Leu Phe Gln Lys Leu Asn
1               5                   10                  15

Leu Arg Ala Arg Ser Asn Lys Asp Ala Lys Asp Pro Thr Thr
            20                  25                  30

<210> SEQ ID NO 584
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 584

Arg Lys Gln Thr Gly Val Phe Gly Val Lys Ile Ala Val Val Thr Lys
1               5                   10                  15

Ser Pro Ser Ala Ala Ser Ser Ile
            20

<210> SEQ ID NO 585
<211> LENGTH: 30
<212> TYPE: PRT
<213> ORGANISM: Artificial Sequence
<220> FEATURE:
<223> OTHER INFORMATION: Synthetic Polypeptide

<400> SEQUENCE: 585

Ser Asn Lys Asp Ala Lys Asp Pro Thr Thr Lys Asn Ser Leu Glu Lys
1               5                   10                  15

Ala Leu Gln Arg Pro Val Ala Ser Asp Phe Glu Pro Gln Gly
            20                  25                  30

<210> SEQ ID NO 586
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 586

Ser Arg Asp Ala Leu Val Ser Gly Ala Leu Glu Ser Thr Lys Ala Thr
1               5                   10                  15

Lys Ala Lys Pro Phe Ser Gly Gln
                20

<210> SEQ ID NO 587
<211> LENGTH: 498
<212> TYPE: PRT
<213> ORGANISM: Artificial Sequence
<220> FEATURE:
<223> OTHER INFORMATION: Synthetic Polypeptide

<400> SEQUENCE: 587

Met Ala Ser Thr Asp Tyr Ser Thr Tyr Ser Gln Ala Ala Gln Gln
1               5                   10                  15

Gly Tyr Ser Ala Tyr Thr Ala Gln Pro Thr Gly Tyr Ala Gln Thr
                20                  25                  30

Thr Gln Ala Tyr Gly Gln Gln Ser Tyr Gly Thr Tyr Gly Gln Pro Thr
                35                  40                  45

Asp Val Ser Tyr Thr Gln Ala Gln Thr Thr Ala Thr Tyr Gly Gln Thr
    50                  55                  60

Ala Tyr Ala Thr Ser Tyr Gly Gln Pro Pro Thr Gly Tyr Thr Thr Pro
65                  70                  75                  80

Thr Ala Pro Gln Ala Tyr Ser Gln Pro Val Gln Gly Tyr Gly Thr Gly
                85                  90                  95

Ala Tyr Asp Thr Thr Thr Ala Thr Val Thr Thr Thr Gln Ala Ser Tyr
                100                 105                 110

Ala Ala Gln Ser Ala Tyr Gly Thr Gln Pro Ala Tyr Pro Ala Tyr Gly
                115                 120                 125

Gln Gln Pro Ala Ala Thr Ala Pro Thr Arg Pro Gln Asp Gly Asn Lys
    130                 135                 140

Pro Thr Glu Thr Ser Gln Pro Gln Ser Ser Thr Gly Gly Tyr Asn Gln
145                 150                 155                 160

Pro Ser Leu Gly Tyr Gly Gln Ser Asn Tyr Ser Tyr Pro Gln Val Pro
                165                 170                 175

Gly Ser Tyr Pro Met Gln Pro Val Thr Ala Pro Pro Ser Tyr Pro Pro
                180                 185                 190

Thr Ser Tyr Ser Ser Thr Gln Pro Thr Ser Tyr Asp Gln Ser Ser Tyr
                195                 200                 205

Ser Gln Gln Asn Thr Tyr Gly Gln Pro Ser Ser Tyr Gly Gln Gln Ser
    210                 215                 220

Ser Tyr Gly Gln Gln Ser Ser Tyr Gly Gln Gln Pro Pro Thr Ser Tyr
225                 230                 235                 240

Pro Pro Gln Thr Gly Ser Tyr Ser Gln Ala Pro Ser Gln Tyr Ser Gln
                245                 250                 255

Gln Ser Ser Ser Tyr Gly Gln Gln Asn Pro Ser Tyr Asp Ser Val Arg
                260                 265                 270

Arg Gly Ala Trp Gly Asn Asn Met Asn Ser Gly Leu Asn Lys Ser Pro
                275                 280                 285

Pro Leu Gly Gly Ala Gln Thr Ile Ser Lys Asn Thr Glu Gln Arg Pro
    290                 295                 300

Gln Pro Asp Pro Tyr Gln Ile Leu Gly Pro Thr Ser Ser Arg Leu Ala
305                 310                 315                 320

Asn Pro Gly Ser Gly Gln Ile Gln Leu Trp Gln Phe Leu Leu Glu Leu
                325                 330                 335

```
Leu Ser Asp Ser Ala Asn Ala Ser Cys Ile Thr Trp Glu Gly Thr Asn
                340                 345                 350

Gly Glu Phe Lys Met Thr Asp Pro Asp Glu Val Ala Arg Arg Trp Gly
            355                 360                 365

Glu Arg Lys Ser Lys Pro Asn Met Asn Tyr Asp Lys Leu Ser Arg Ala
        370                 375                 380

Leu Arg Tyr Tyr Asp Lys Asn Ile Met Thr Lys Val His Gly Lys
385                 390                 395                 400

Arg Tyr Ala Tyr Lys Phe Asp Phe His Gly Ile Ala Gln Ala Leu Gln
                405                 410                 415

Pro His Pro Thr Glu Ser Ser Met Tyr Lys Tyr Pro Ser Asp Ile Ser
            420                 425                 430

Tyr Met Pro Ser Tyr His Ala His Gln Gln Lys Val Asn Phe Val Pro
        435                 440                 445

Pro His Pro Ser Ser Met Pro Val Thr Ser Ser Ser Phe Phe Gly Ala
    450                 455                 460

Ala Ser Gln Tyr Trp Thr Ser Pro Thr Gly Gly Ile Tyr Pro Asn Pro
465                 470                 475                 480

Asn Val Pro Arg His Pro Asn Thr His Val Pro Ser His Leu Gly Ser
                485                 490                 495

Tyr Tyr

<210> SEQ ID NO 588
<211> LENGTH: 520
<212> TYPE: PRT
<213> ORGANISM: Artificial Sequence
<220> FEATURE:
<223> OTHER INFORMATION: Synthetic Polypeptide

<400> SEQUENCE: 588

Met Ala Ser Thr Asp Tyr Ser Thr Tyr Ser Gln Ala Ala Ala Gln Gln
1               5                   10                  15

Gly Tyr Ser Ala Tyr Thr Ala Gln Pro Thr Gln Gly Tyr Ala Gln Thr
                20                  25                  30

Thr Gln Ala Tyr Gly Gln Gln Ser Tyr Gly Thr Tyr Gly Gln Pro Thr
            35                  40                  45

Asp Val Ser Tyr Thr Gln Ala Gln Thr Thr Ala Thr Tyr Gly Gln Thr
    50                  55                  60

Ala Tyr Ala Thr Ser Tyr Gly Gln Pro Pro Thr Gly Tyr Thr Thr Pro
65                  70                  75                  80

Thr Ala Pro Gln Ala Tyr Ser Gln Pro Val Gln Gly Tyr Gly Thr Gly
                85                  90                  95

Ala Tyr Asp Thr Thr Thr Ala Thr Val Thr Thr Thr Gln Ala Ser Tyr
                100                 105                 110

Ala Ala Gln Ser Ala Tyr Gly Thr Gln Pro Ala Tyr Pro Ala Tyr Gly
            115                 120                 125

Gln Gln Pro Ala Ala Thr Ala Pro Thr Arg Pro Gln Asp Gly Asn Lys
        130                 135                 140

Pro Thr Glu Thr Ser Gln Pro Gln Ser Ser Thr Gly Gly Tyr Asn Gln
145                 150                 155                 160

Pro Ser Leu Gly Tyr Gly Gln Ser Asn Tyr Ser Tyr Pro Gln Val Pro
                165                 170                 175

Gly Ser Tyr Pro Met Gln Pro Val Thr Ala Pro Pro Ser Tyr Pro Pro
            180                 185                 190
```

```
Thr Ser Tyr Ser Ser Thr Gln Pro Thr Ser Tyr Asp Gln Ser Ser Tyr
        195                 200                 205

Ser Gln Gln Asn Thr Tyr Gly Gln Pro Ser Ser Tyr Gly Gln Gln Ser
        210                 215                 220

Ser Tyr Gly Gln Gln Ser Ser Tyr Gly Gln Gln Pro Pro Thr Ser Tyr
225                 230                 235                 240

Pro Pro Gln Thr Gly Ser Tyr Ser Gln Ala Pro Ser Gln Tyr Ser Gln
            245                 250                 255

Gln Ser Ser Ser Tyr Gly Gln Gln Ser Ser Leu Leu Ala Tyr Asn Thr
            260                 265                 270

Thr Ser His Thr Asp Gln Ser Ser Arg Leu Ser Val Lys Glu Asp Pro
            275                 280                 285

Ser Tyr Asp Ser Val Arg Arg Gly Ala Trp Gly Asn Asn Met Asn Ser
            290                 295                 300

Gly Leu Asn Lys Ser Pro Pro Leu Gly Gly Ala Gln Thr Ile Ser Lys
305                 310                 315                 320

Asn Thr Glu Gln Arg Pro Gln Pro Asp Pro Tyr Gln Ile Leu Gly Pro
                325                 330                 335

Thr Ser Ser Arg Leu Ala Asn Pro Gly Ser Gly Gln Ile Gln Leu Trp
                340                 345                 350

Gln Phe Leu Leu Glu Leu Leu Ser Asp Ser Ala Asn Ala Ser Cys Ile
            355                 360                 365

Thr Trp Glu Gly Thr Asn Gly Glu Phe Lys Met Thr Asp Pro Asp Glu
            370                 375                 380

Val Ala Arg Arg Trp Gly Glu Arg Lys Ser Lys Pro Asn Met Asn Tyr
385                 390                 395                 400

Asp Lys Leu Ser Arg Ala Leu Arg Tyr Tyr Asp Lys Asn Ile Met
                405                 410                 415

Thr Lys Val His Gly Lys Arg Tyr Ala Tyr Lys Phe Asp Phe His Gly
                420                 425                 430

Ile Ala Gln Ala Leu Gln Pro His Pro Thr Glu Ser Ser Met Tyr Lys
            435                 440                 445

Tyr Pro Ser Asp Ile Ser Tyr Met Pro Ser Tyr His Ala His Gln Gln
450                 455                 460

Lys Val Asn Phe Val Pro Pro His Pro Ser Ser Met Pro Val Thr Ser
465                 470                 475                 480

Ser Ser Phe Phe Gly Ala Ala Ser Gln Tyr Trp Thr Ser Pro Thr Gly
                485                 490                 495

Gly Ile Tyr Pro Asn Pro Asn Val Pro Arg His Pro Asn Thr His Val
            500                 505                 510

Pro Ser His Leu Gly Ser Tyr Tyr
            515                 520

<210> SEQ ID NO 589
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 589

Ser Gln Gln Ser Ser Tyr Gly Gln Gln Asn Pro Ser Tyr Asp Ser
1               5                   10                  15

Val Arg Arg Gly
            20
```

```
<210> SEQ ID NO 590
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 590

Ser Gln Gln Ser Ser Ser Tyr Gly Gln Gln Ser Ser Leu Leu Ala Tyr
1               5                   10                  15

Asn Thr Thr Ser
            20

<210> SEQ ID NO 591
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 591

Ser Ser Tyr Gly Gln Gln Asn Pro Ser Tyr
1               5                   10

<210> SEQ ID NO 592
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 592

Ser Tyr Gly Gln Gln Asn Pro Ser Tyr
1               5

<210> SEQ ID NO 593
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 593

Ser Ser Tyr Gly Gln Gln Asn Pro Ser Tyr
1               5                   10

<210> SEQ ID NO 594
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 594

Tyr Gly Gln Gln Asn Pro Ser Tyr
1               5

<210> SEQ ID NO 595
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 595

Asn Pro Ser Tyr Asp Ser Val Arg
```

```
1               5
```

<210> SEQ ID NO 596
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 596

```
Gln Gln Asn Pro Ser Tyr Asp Ser Val
1               5
```

<210> SEQ ID NO 597
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 597

```
Asn Pro Ser Tyr Asp Ser Val Arg Arg
1               5
```

<210> SEQ ID NO 598
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 598

```
Tyr Gly Gln Gln Asn Pro Ser Tyr
1               5
```

<210> SEQ ID NO 599
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 599

```
Gln Gln Asn Pro Ser Tyr Asp Ser Val Arg
1               5                   10
```

<210> SEQ ID NO 600
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 600

```
Gly Gln Gln Ser Ser Leu Leu Ala Tyr
1               5
```

<210> SEQ ID NO 601
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 601

```
Gln Gln Ser Ser Leu Leu Ala Tyr
1               5
```

```
<210> SEQ ID NO 602
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 602

Ser Ser Ser Tyr Gly Gln Gln Ser Ser Leu
1               5                   10

<210> SEQ ID NO 603
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 603

Ser Ser Tyr Gly Gln Gln Ser Ser Leu
1               5

<210> SEQ ID NO 604
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 604

Ser Ser Tyr Gly Gln Gln Ser Ser Leu
1               5

<210> SEQ ID NO 605
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 605

Ser Ser Tyr Gly Gln Gln Ser Ser Leu Leu
1               5                   10

<210> SEQ ID NO 606
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 606

Ser Tyr Gly Gln Gln Ser Ser Leu
1               5

<210> SEQ ID NO 607
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 607

Ser Tyr Gly Gln Gln Ser Ser Leu Leu
1               5
```

<210> SEQ ID NO 608
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 608

Tyr Gly Gln Gln Ser Ser Leu Leu
1               5

<210> SEQ ID NO 609
<211> LENGTH: 10
<212> TYPE: PRT
<213> ORGANISM: Artificial Sequence
<220> FEATURE:
<223> OTHER INFORMATION: Synthetic Polypeptide

<400> SEQUENCE: 609

Tyr Gly Gln Gln Ser Ser Leu Leu Ala Tyr
1               5                   10

<210> SEQ ID NO 610
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 610

His Ser Ala Thr Gly Phe Lys Gln Ser Ser Lys Ala Leu Gln Arg Pro
1               5                   10                  15

Val Ala Ser Asp Phe
            20

<210> SEQ ID NO 611
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 611

His Ser Ile Pro Leu Thr Ile Asn Lys Glu Glu Ala Leu Gln Arg Pro
1               5                   10                  15

Val Ala Ser Asp
            20

<210> SEQ ID NO 612
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 612

Ile Thr Tyr Thr Trp Thr Arg Leu
1               5

<210> SEQ ID NO 613
<211> LENGTH: 8
<212> TYPE: PRT
<213> ORGANISM: Artificial Sequence
<220> FEATURE:
<223> OTHER INFORMATION: Synthetic Polypeptide -continued

```
<400> SEQUENCE: 613

Val Gly Phe Asn Phe Arg Thr Leu
1               5

<210> SEQ ID NO 614
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 614

Pro Cys Val Pro Ala Lys Pro Pro Leu Ala Gly Ser Pro Gln Ile Glu
1               5                   10                  15

Asn Ile Gln Pro
            20

<210> SEQ ID NO 615
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 615

Ser Asp Arg Gly Gly Phe Asn Lys Phe Gly Gly Ser Gly Gln Ile Gln
1               5                   10                  15

Leu Trp Gln Phe
            20
```